United States Patent
Ji et al.

(10) Patent No.: US 12,252,485 B2
(45) Date of Patent: Mar. 18, 2025

(54) HETEROCYCLIC COMPOUND AND ORGANIC LIGHT EMITTING DEVICE COMPRISING SAME

(71) Applicant: LT MATERIALS CO., LTD., Yongin (KR)

(72) Inventors: Hye-Su Ji, Yongin (KR); Hyun-Ju La, Yongin (KR); Won-Jang Jeong, Yongin (KR); Dong-Jun Kim, Yongin (KR)

(73) Assignee: LT MATERIALS CO., LTD., Yongin (KR)

( * ) Notice: Subject to any disclaimer, the term of this patent is extended or adjusted under 35 U.S.C. 154(b) by 765 days.

(21) Appl. No.: 17/606,553

(22) PCT Filed: Jul. 3, 2020

(86) PCT No.: PCT/KR2020/008746
§ 371 (c)(1),
(2) Date: Oct. 26, 2021

(87) PCT Pub. No.: WO2021/010631
PCT Pub. Date: Jan. 21, 2021

(65) Prior Publication Data
US 2022/0213098 A1 Jul. 7, 2022

(30) Foreign Application Priority Data
Jul. 12, 2019 (KR) .................. 10-2019-0084457

(51) Int. Cl.
*H01L 51/54* (2006.01)
*C07D 471/04* (2006.01)
*C07D 519/00* (2006.01)
*C07F 9/28* (2006.01)
*H10K 85/60* (2023.01)
*H10K 50/13* (2023.01)
*H10K 50/16* (2023.01)
*H10K 50/17* (2023.01)
*H10K 50/18* (2023.01)

(52) U.S. Cl.
CPC ......... *C07D 471/04* (2013.01); *C07D 519/00* (2013.01); *C07F 9/28* (2013.01); *H10K 85/622* (2023.02); *H10K 85/624* (2023.02); *H10K 85/626* (2023.02); *H10K 85/654* (2023.02); *H10K 85/6572* (2023.02); *H10K 50/13* (2023.02); *H10K 50/16* (2023.02); *H10K 50/171* (2023.02); *H10K 50/18* (2023.02)

(58) Field of Classification Search
None
See application file for complete search history.

(56) References Cited

U.S. PATENT DOCUMENTS

| | | | |
|---|---|---|---|
| 4,356,429 | A | 10/1982 | Tang |
| 9,005,777 | B2 | 4/2015 | Jung et al. |
| 10,193,078 | B2 | 1/2019 | Ito et al. |
| 10,367,150 | B2 | 7/2019 | Jeong et al. |
| 10,720,585 | B2 | 7/2020 | Park et al. |
| 2017/0117478 | A1 | 4/2017 | Kim et al. |
| 2018/0323379 | A1 | 11/2018 | Kim et al. |
| 2019/0288218 | A1 | 9/2019 | La et al. |
| 2020/0343452 | A1 | 10/2020 | Lee |

FOREIGN PATENT DOCUMENTS

| | | |
|---|---|---|
| CN | 108884090 A | 11/2018 |
| KR | 10-2013-0042900 A | 4/2013 |
| KR | 10-2016-0006196 A | 1/2016 |
| KR | 10-2016-0029662 A | 3/2016 |
| KR | 10-2016-0096782 A | 8/2016 |
| KR | 10-2017-0080453 A | 7/2017 |
| KR | 10-2019-0064236 A | 6/2019 |
| KR | 10-2019-0078117 A | 7/2019 |
| WO | WO2018/101764 A1 | 6/2018 |

OTHER PUBLICATIONS

International Search Report (PCT/ISA/210) issued in PCT/KR2020/008746 mailed on Oct. 13, 2020.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, 1994, vol. 6, No. 9, pp. 677-679.
Yanada et al., "Indium(III)-Catalyzed Tandem Reaction with Alkynylbenzaldehydes and Alkynylanilines to Heteroaromatic Compounds", The Journal of Organic Chemistry, 2008, vol. 73, No. 13, pp. 5135-5138.

*Primary Examiner* — Andrew K Bohaty
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

15 Claims, 3 Drawing Sheets

【FIG. 1】
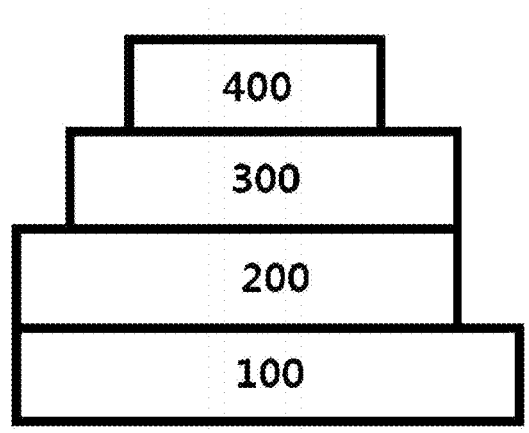
【FIG. 2】
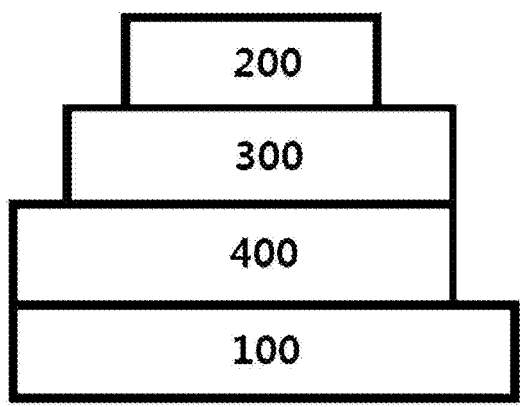

[FIG. 3]
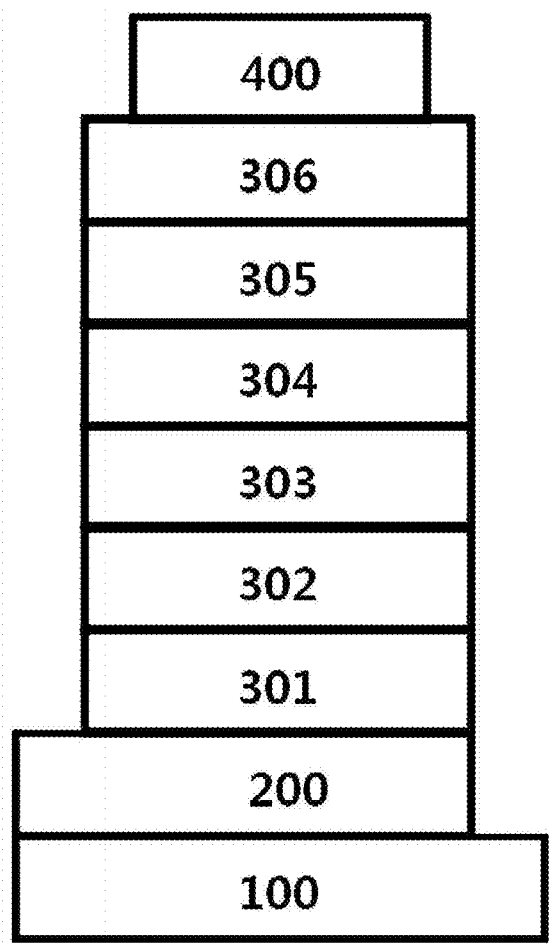

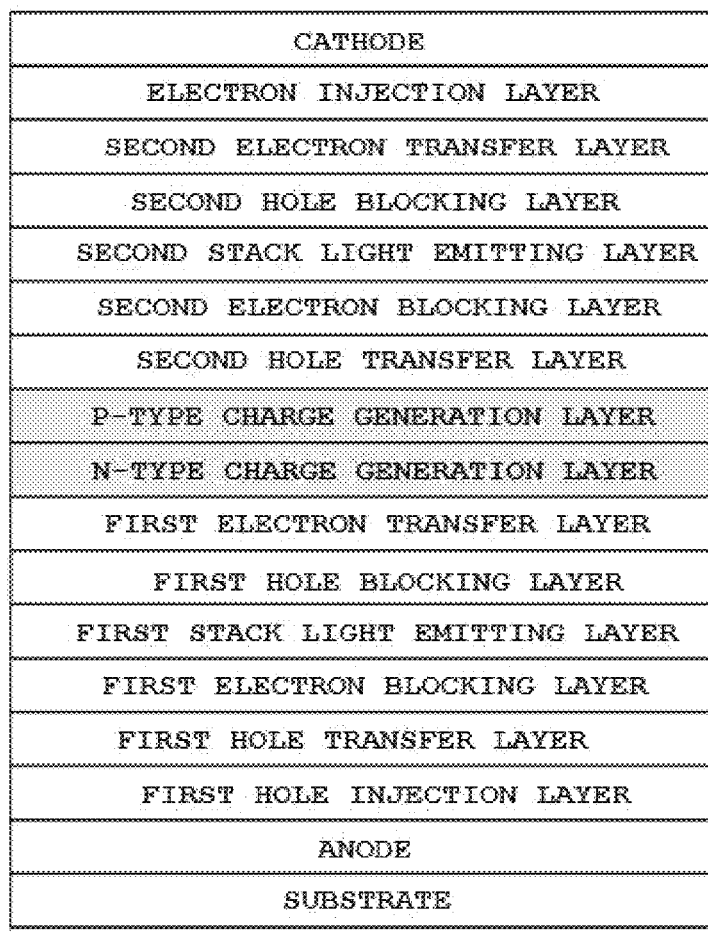
[FIG. 4]

HETEROCYCLIC COMPOUND AND ORGANIC LIGHT EMITTING DEVICE COMPRISING SAME

TECHNICAL FIELD

This application claims priority to and the benefits of Korean Patent Application No. 10-2019-0084457, filed with the Korean Intellectual Property Office on Jul. 12, 2019, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of foiling a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

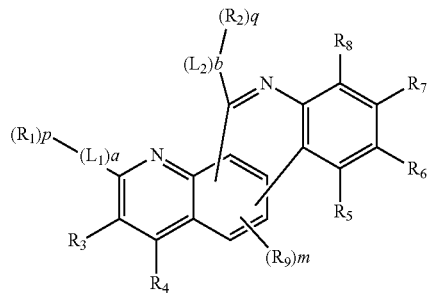

In Chemical Formula 1, $L_1$ and $L_2$ are the same as or different from each other, and each independently a direct bond; a substituted or unsubstituted C6 to C60 arylene group; or a substituted or unsubstituted C2 to C60 heteroarylene group, and a and b are an integer of 0 to 4, $R_1$ is selected from the group consisting of a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, $R_2$ is selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, p and q are an integer of 1 to 5, $R_3$ to $R_9$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, R, R' and R" are a substituted or unsubstituted C1 to C60 alkyl group; a substituted or unsubstituted C6 to C60 aryl group; or a substituted or unsubstituted C2 to C60 heteroaryl group, and m is an integer of 0 or 1.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a hole blocking material, a light emitting material, an electron transfer material, an electron injection material, a charge generation material or the like in an organic light emitting device. Particularly, the compound can be used as a hole blocking layer material or an electron transfer layer material of an organic light emitting device.

When using the compound represented by Chemical Formula 1 in an organic material layer, a driving voltage of a device can be lowered, light efficiency can be enhanced, and lifetime properties of the device can be enhanced by thermal stability of the compound.

Particularly, the compound represented by Chemical Formula 1 has a tetracyclic central skeleton in which two quinoline skeleton structures are fused as a core structure, and by introducing a substituent at a No. 2 position of the fused each quinoline group, an excellent electron transfer ability is obtained, and superior device properties of low driving voltage, high efficiency and long lifetime are obtained.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode Mode for Disclosure Hereinafter, the present application will be described in detail.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent is capable of substituting, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4 methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring group thereof, and the like, but are not limited thereto.

In the present specification, the phosphine oxide group is represented by —P(=O)R$_{101}$R$_{102}$, and R$_{101}$ and R$_{102}$ are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethyl-silyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted, the following structural formulae may be included, however, the structure is not limited thereto.

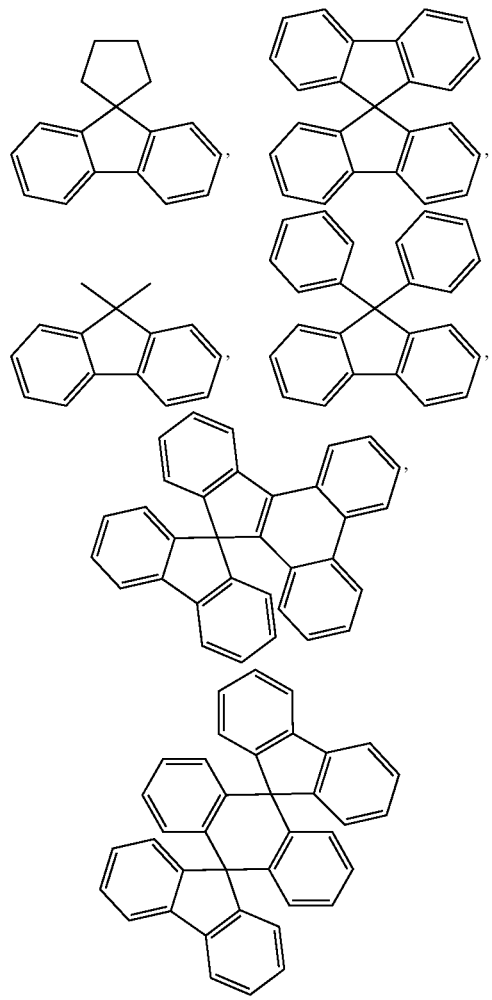

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In one embodiment of the present application, Chemical Formula 1 may be represented by any one of the following Chemical Formula 2 to Chemical Formula 5.

[Chemical Formula 2]

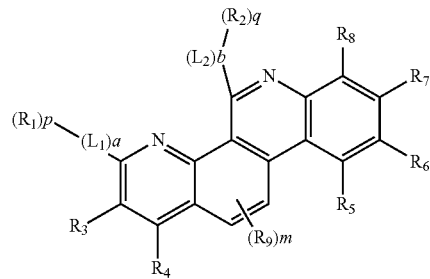

[Chemical Formula 3]

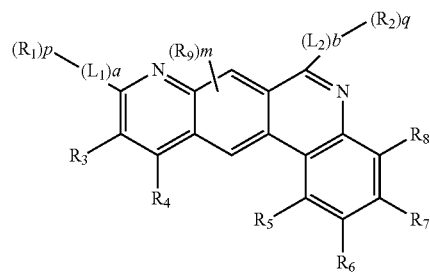

[Chemical Formula 4]

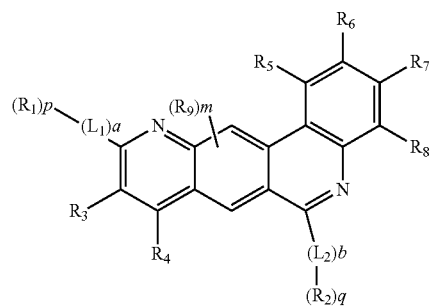

[Chemical Formula 5]

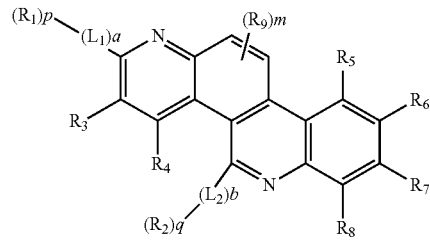

In Chemical Formulae 2 to 5, $R_1$ to $R_9$, $L_1$, $L_2$, m, a, b, p and q have the same definitions as in Chemical Formula 1.

Particularly, in the core structure of Chemical Formula 1, when a ring comprising N of another quinoline group is fused to a benzene ring of the quinoline group and a substituent is included at the No. 2 position of each of the quinolines, an electron transfer ability is enhanced by increasing planarity and conjugation range in the compound. In other words, by the excited hetero-skeleton site being stabilized and efficiently transferring electrons without being decomposed or destroyed, superior driving and light emission efficiency are obtained when using the compound of Chemical Formula 1 in an organic light emitting device.

In addition, by having both p-type and n-type substituents in the core structure such as Chemical Formula 1, more bipolar properties are obtained leading to a uniform molecular arrangement, and thereby inducing efficient electron migration and preventing hole leakage to effectively trap excitons in a light emitting layer, and as a result, light emitting efficiency and lifetime are improved.

In one embodiment of the present application, $R_3$, $R_4$ and $R_9$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other may bond to each other to form a substituted or unsubstituted C6 to C60 aromatic hydrocarbon ring or a substituted or unsubstituted C2 to C60 heterating.

In one embodiment of the present application, R, R' and R" may be a substituted or unsubstituted C1 to C60 alkyl group; a substituted or unsubstituted C6 to C60 aryl group; or a substituted or unsubstituted C2 to C60 heteroaryl group.

In another embodiment, R, R' and R" may be a substituted or unsubstituted C1 to C20 alkyl group; a substituted or unsubstituted C6 to C40 aryl group; or a substituted or unsubstituted C2 to C40 heteroaryl group.

In another embodiment, R, R' and R" may be a phenyl group.

In another embodiment, R, R' and R" may be a methyl group.

In another embodiment, $R_3$, $R_4$ and $R_9$ may be hydrogen.

In one embodiment of the present application, $L_1$ and $L_2$ are the same as or different from each other, and may be each independently a direct bond; a substituted or unsubstituted arylene group; or a substituted or unsubstituted heteroarylene group.

In another embodiment, $L_1$ and $L_2$ are the same as or different from each other, and may be each independently a direct bond; a substituted or unsubstituted C6 to C60 arylene group; or a substituted or unsubstituted C2 to C60 heteroarylene group.

In another embodiment, $L_1$ and $L_2$ are the same as or different from each other, and may be each independently a direct bond; a substituted or unsubstituted C6 to C40 arylene group; or a substituted or unsubstituted C2 to C40 heteroarylene group.

In another embodiment, $L_1$ and $L_2$ are the same as or different from each other, and may be each independently a direct bond; a substituted or unsubstituted C6 to C20 arylene group; or a substituted or unsubstituted C2 to C20 heteroarylene group.

In another embodiment, $L_1$ and $L_2$ are the same as or different from each other, and may be each independently a direct bond; a C6 to C20 arylene group; or a C2 to C20 heteroarylene group unsubstituted or substituted with a C6 to C20 aryl group.

In another embodiment, $L_1$ and $L_2$ are the same as or different from each other, and may be each independently a direct bond; a phenylene group; a biphenylene group; a naphthylene group; a divalent triazine group unsubstituted or substituted with a phenyl group; or a divalent pyrimidine group unsubstituted or substituted with a phenyl group.

In one embodiment of the present application, $L_1$ may be a direct bond; or a phenylene group.

In one embodiment of the present application, $L_2$ may be a phenylene group; a biphenylene group; a naphthylene group; a divalent triazine group unsubstituted or substituted with a phenyl group; or a divalent pyrimidine group unsubstituted or substituted with a phenyl group.

In one embodiment of the present application, $R_1$ may be selected from the group consisting of a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group.

In another embodiment, $R_1$ may be selected from the group consisting of a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, $R_1$ may be a substituted or unsubstituted C6 to C60 aryl group.

In another embodiment, $R_1$ may be a C6 to C40 aryl group. In another embodiment, $R_1$ may be a C6 to C40 monocyclic aryl group.

In another embodiment, $R_1$ may be a C10 to C40 polycyclic aryl group.

In another embodiment, $R_1$ may be a phenyl group; a naphthyl group; a phenanthrenyl group; a triphenylenyl group; a pyrenyl group; a fluoranthenyl group; or a spiro-bifluorenyl group.

In one embodiment of the present application, $R_2$ may be selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group.

In another embodiment, $R_2$ may be selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, $R_2$ may be hydrogen; a substituted or unsubstituted C6 to C60 aryl group; a substituted or unsubstituted C2 to C60 heteroaryl group; or —P(=O)RR'.

In another embodiment, $R_2$ may be hydrogen; a substituted or unsubstituted C6 to C40 aryl group; a substituted or unsubstituted C2 to C40 heteroaryl group; or —P(=O)RR'. In another embodiment, $R_2$ may be hydrogen; a C6 to C40 aryl group unsubstituted or substituted with a C2 to C40 heteroaryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(=O)RR'.

In another embodiment, $R_2$ may be a C6 to C40 aryl group unsubstituted or substituted with a C2 to C40 heteroaryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(=O)RR'.

In another embodiment, $R_2$ may be a phenyl group unsubstituted or substituted with a carbazole group; —P(=O)RR'; a triazine group unsubstituted or substituted with one or more substituents selected from the group consisting of a phenyl group, a biphenyl group, a naphthyl group and a dimethylfluorenyl group; a pyrimidine group unsubstituted or substituted with one or more substituents selected from the group consisting of a phenyl group, a naphthyl group and a biphenyl group; a pyridine group unsubstituted or substituted with a pyridine group; a carbazole group; a dibenzofuran group; a dibenzothiophene group; a phenanthroline group unsubstituted or substituted with a phenyl group; an imidazole group unsubstituted or substituted with an ethyl group or a phenyl group; a quinazoline group unsubstituted or substituted with a phenyl group; or an imidazo[1,2-a]pyridine group unsubstituted or substituted with a phenyl group.

In one embodiment of the present application, $R_1$ and $R_2$ may be substituted again with a C2 to C20 heteroaryl group, and may specifically be substituted with a carbazole group; a dibenzofuran group; or a dibenzothiophene group.

In one embodiment of the present application, by having both p-type and n-type substituents like $R_1$ and $R_2$ in the core structure such as Chemical Formula 1, more bipolar properties are obtained leading to a uniform molecular arrangement, and thereby inducing efficient electron migration and preventing hole leakage to effectively trap excitons in a light emitting layer, and as a result, light emitting efficiency and lifetime are improved.

In one embodiment of the present application, when $R_2$ is hydrogen, at least one of $R_5$ to $R_8$ of Chemical Formula 1 may be represented by -($L_3$)r-($Z_3$)s, $L_3$ is a direct bond; a substituted or unsubstituted C6 to C60 arylene group; or a substituted or unsubstituted C2 to C60 heteroarylene group, $Z_3$ is selected from the group consisting of a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group, r is an integer of 0 to 4, and s is an integer of 1 to 5.

In one embodiment of the present application, $L_3$ may be a direct bond; a substituted or unsubstituted C6 to C60 arylene group; or a substituted or unsubstituted C2 to C60 heteroarylene group.

In another embodiment, $L_3$ may be a direct bond; a substituted or unsubstituted C6 to C60 arylene group; or a substituted or unsubstituted C2 to C60 heteroarylene group.

In another embodiment, $L_3$ may be a direct bond; a substituted or unsubstituted C6 to C40 arylene group; or a substituted or unsubstituted C2 to C40 heteroarylene group.

In another embodiment, $L_3$ may be a direct bond; a substituted or unsubstituted C6 to C20 arylene group; or a substituted or unsubstituted C2 to C20 heteroarylene group.

In another embodiment, $L_3$ may be a direct bond; a C6 to C20 arylene group; or a C2 to C20 heteroarylene group unsubstituted or substituted with a C6 to C20 aryl group.

In another embodiment, $L_3$ may be a direct bond; a phenylene group; a biphenylene group; a naphthylene group; a divalent triazine group unsubstituted or substituted with a phenyl group; or a divalent pyrimidine group unsubstituted or substituted with a phenyl group.

In one embodiment of the present application, $Z_3$ may be selected from the group consisting of a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group.

In another embodiment, $Z_3$ may be selected from the group consisting of a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, $Z_3$ may be a substituted or unsubstituted C6 to C60 aryl group; a substituted or unsubstituted C2 to C60 heteroaryl group; or —P(=O)RR'.

In another embodiment, $Z_3$ may be a substituted or unsubstituted C6 to C40 aryl group; a substituted or unsubstituted C2 to C40 heteroaryl group; or —P(=O)RR'.

In another embodiment, $Z_3$ may be a C6 to C40 aryl group unsubstituted or substituted with a C2 to C40 heteroaryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(=O)RR'.

In another embodiment, $Z_3$ may be a C6 to C40 aryl group unsubstituted or substituted with a C2 to C40 heteroaryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(=O)RR'.

In another embodiment, $Z_3$ may be a phenyl group unsubstituted or substituted with a carbazole group; —P(=O)RR'; a triazine group unsubstituted or substituted with one or more substituents selected from the group consisting of a phenyl group, a biphenyl group, a naphthyl group and a dimethylfluorenyl group; a pyrimidine group unsubstituted or substituted with one or more substituents selected from the group consisting of a phenyl group, a naphthyl group and a biphenyl group; a pyridine group unsubstituted or substituted with a pyridine group; a carbazole group; a dibenzofuran group; a dibenzothiophene group; a phenanthroline group unsubstituted or substituted with a phenyl group; an imidazole group unsubstituted or substituted with an ethyl group or a phenyl group; a quinazoline group unsubstituted or substituted with a phenyl group; or an imidazo[1,2-a]pyridine group unsubstituted or substituted with a phenyl group.

In one embodiment of the present application, $Z_3$ may be substituted again with a C2 to C20 heteroaryl group, and may specifically be substituted with a carbazole group; a dibenzofuran group; or a dibenzothiophene group.

In one embodiment of the present application, when $R_2$ is hydrogen, one of $R_5$ to $R_8$ of Chemical Formula 1 may be represented by -($L_3$)r-($Z_3$)s, and the rest may be hydrogen.

In another embodiment, when $R_2$ is hydrogen, $R_6$ of $R_5$ to $R_8$ of Chemical Formula 1 may be represented by -(L_3)r-(Z_3)s, and $R_5$, $R_7$ and $R^8$ may be hydrogen.

In another embodiment, when $R_2$ is hydrogen, $R_7$ of $R_5$ to $R_8$ of Chemical Formula 1 may be represented by -(L_3)r-(Z_3)s, and $R_5$, $R_6$ and $R_8$ may be hydrogen.

In one embodiment of the present application, Chemical Formula 1 may be represented by any one of the following Chemical Formulae 6 to 8.

[Chemical Formula 6]

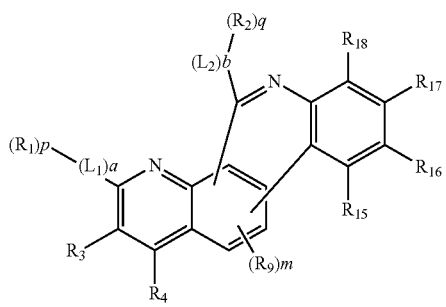

[Chemical Formula 7]

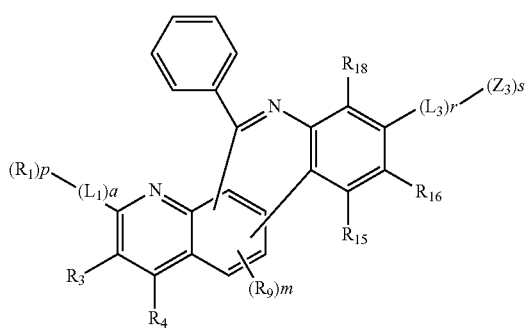

[Chemical Formula 8]

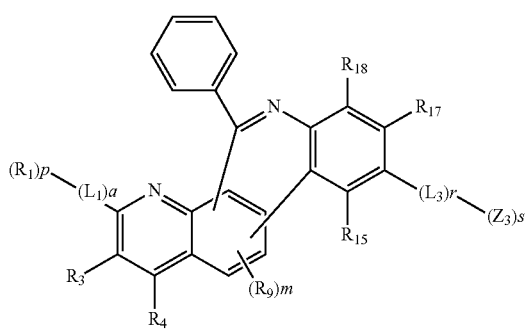

In Chemical Formulae 6 to 8,
$R_1$, $R_2$, $L_1$, $L_2$, a, b, p, q, $R_3$, $R_4$, $R_9$ and m have the same definitions as in Chemical Formula 1,
$R_{15}$ to $R_{18}$ are hydrogen,
$L_3$ is a direct bond; a substituted or unsubstituted C6 to C60 arylene group; or a substituted or unsubstituted C2 to C60 heteroarylene group,
$Z_3$ is selected from the group consisting of a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, r is an integer of 0 to 4,
s is an integer of 1 to 5, and
R, R' and R" have the same definitions as in Chemical Formula 1.

In one embodiment of the present application, Chemical Formula 6 may be represented by any one of the following Chemical Formulae 6-1 to 6-4.

[Chemical Formula 6-1]

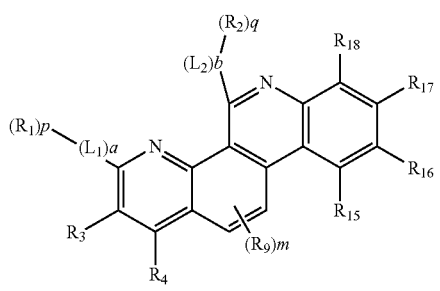

[Chemical Formula 6-2]

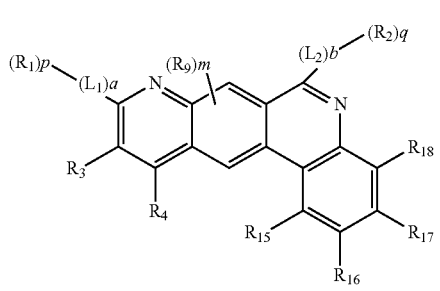

[Chemical Formula 6-3]

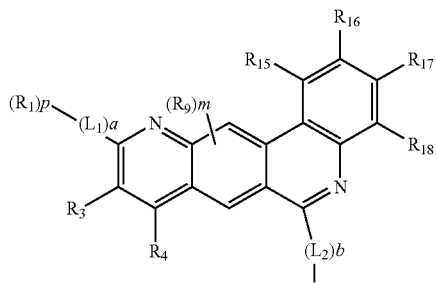

[Chemical Formula 6-4]

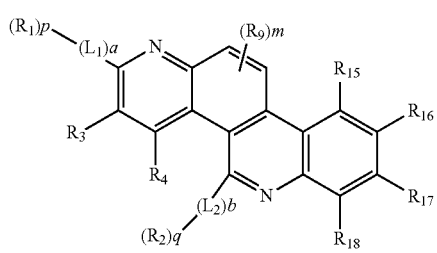

In Chemical Formulae 6-1 to 6-4,
$R_1$ to $R_4$, $R_9$, $R_{15}$ to $R_{18}$, $L_1$, $L_2$, m, a, b, p and q have the same definitions as in Chemical Formula 6.

In one embodiment of the present application, Chemical Formula 7 may be represented by any one of the following Chemical Formulae 7-1 to 7-4.

[Chemical Formula 7-1]

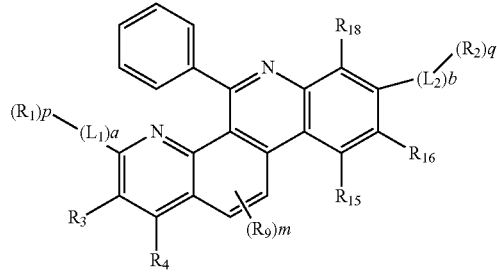

[Chemical Formula 7-2]

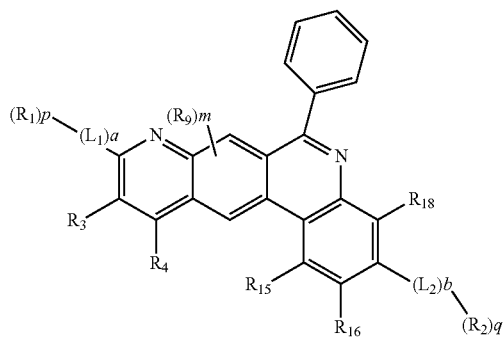

[Chemical Formula 7-3]

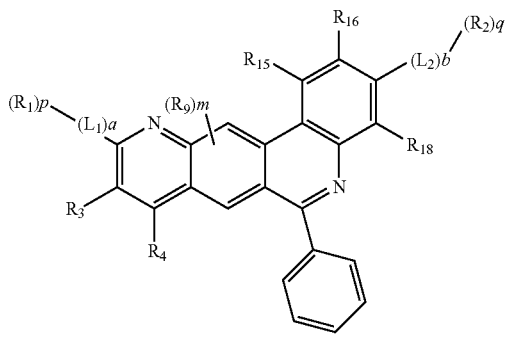

[Chemical Formula 7-4]

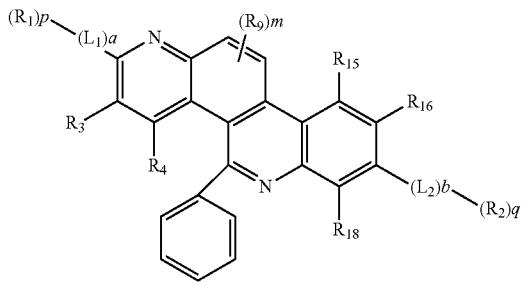

In Chemical Formulae 7-1 to 7-4, $R_1$ to $R_4$, $R_9$, $R_{15}$, $R_{16}$, $R_{18}$, $L_1$, $L_2$, m, a, b, p and q have the same definitions as in Chemical Formula 7.

In one embodiment of the present application, Chemical Formula 8 may be represented by any one of the following Chemical Formulae 8-1 to 8-4.

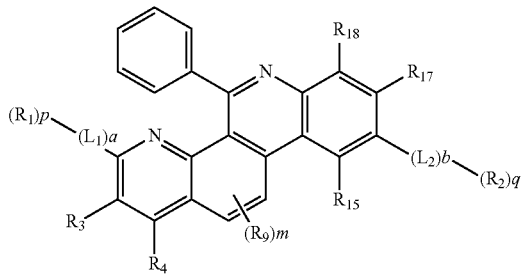

[Chemical Formula 8-2]

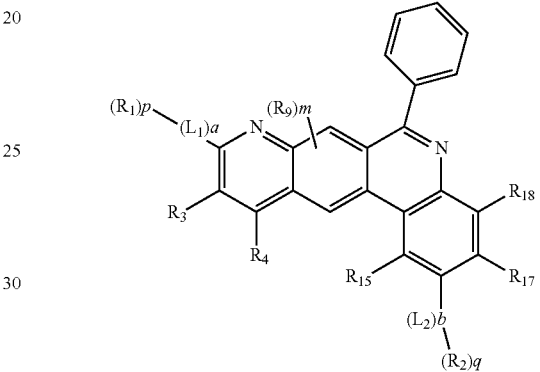

[Chemical Formula 8-3]

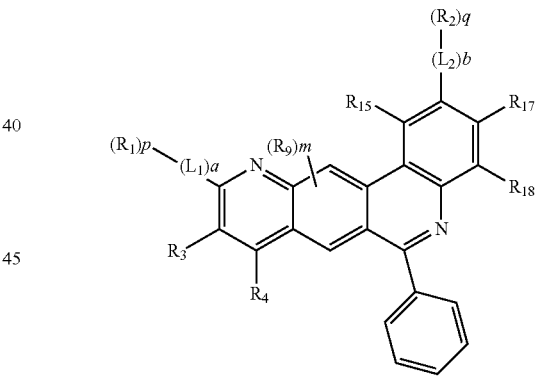

[Chemical Formula 8-4]

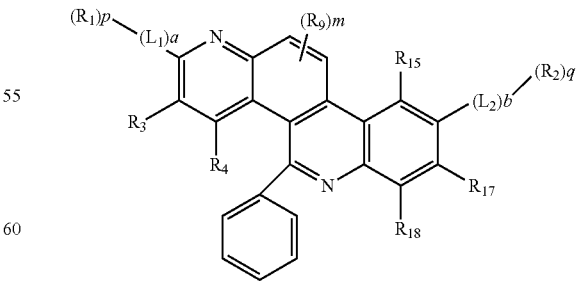

In Chemical Formulae 8-1 to 8-4, $R_1$ to $R_4$, $R_9$, $R_{15}$, $R_{17}$, $R_{18}$, $L_1$, $L_2$, m, a, b, p and q have the same definitions as in Chemical Formula 8.

In the heterocyclic compound provided in one embodiment of the present application, Chemical Formula 1 is represented by any one of the following compounds.
[Chemical Formula 8-1]
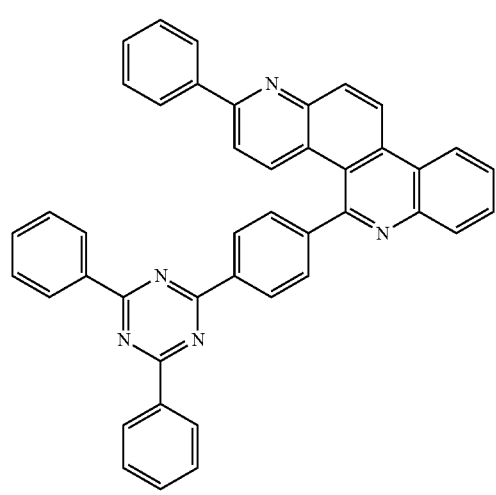
1
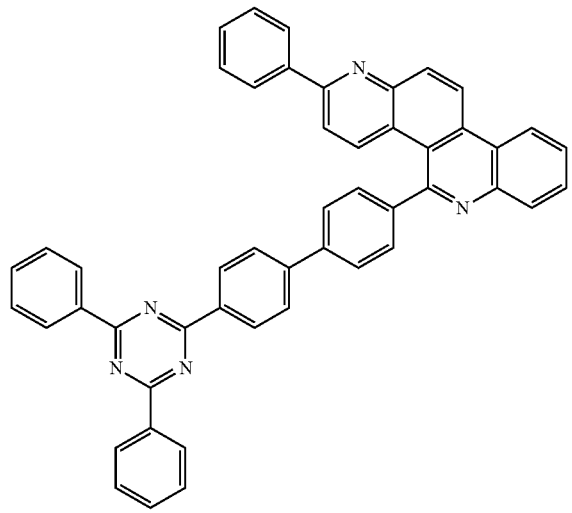
2
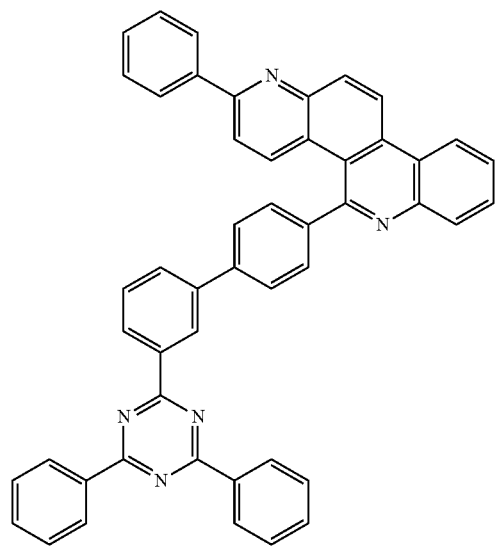
3
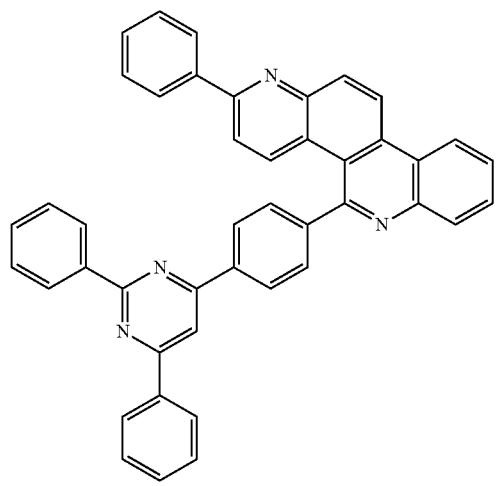
4

-continued
5
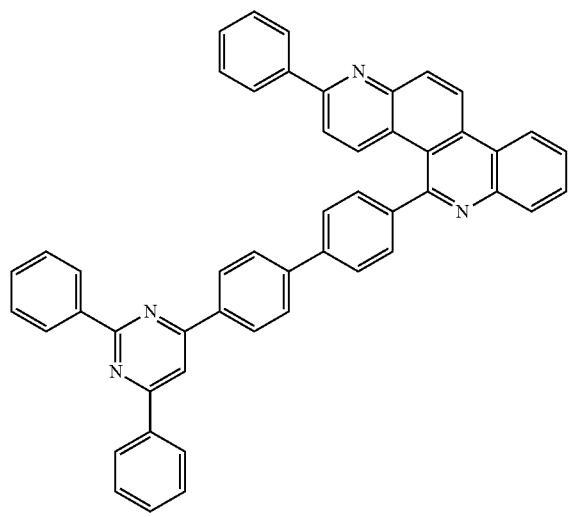
6
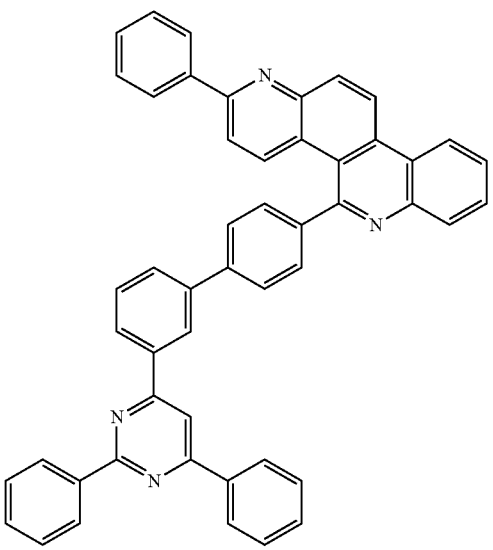
7
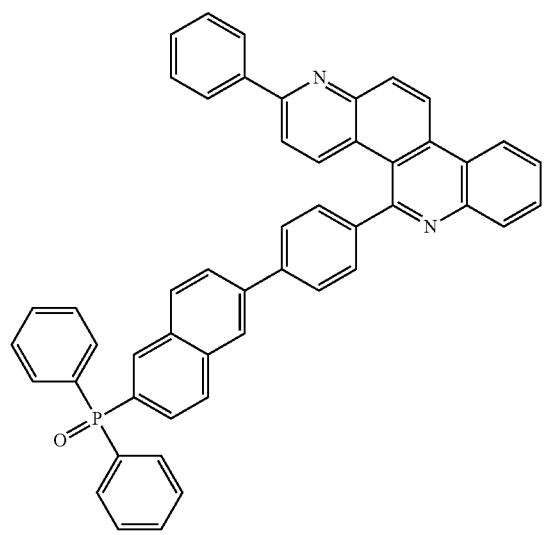
8
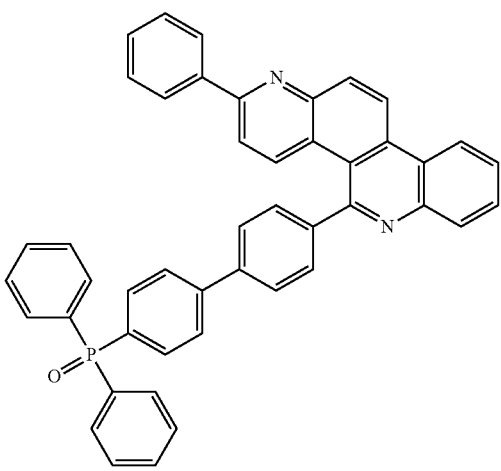
9
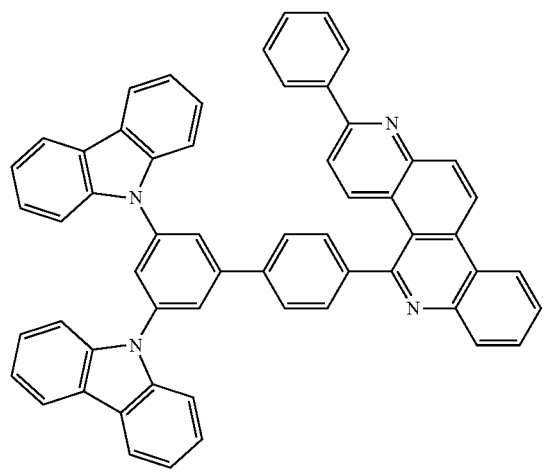
10
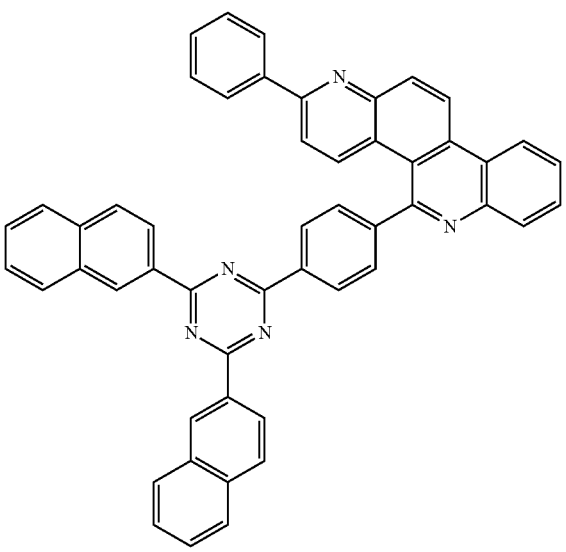

-continued
11
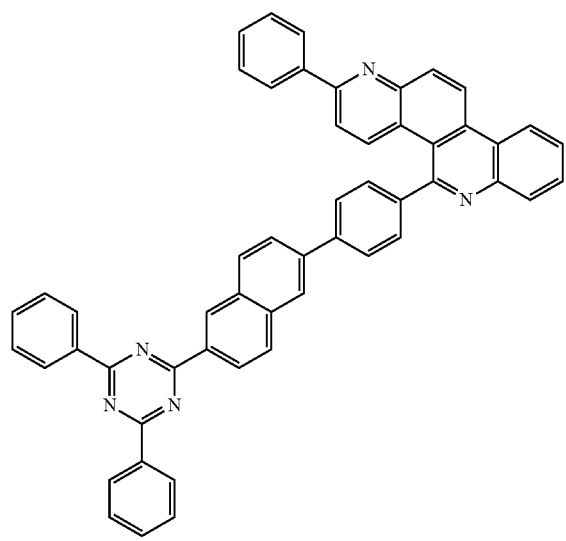
12
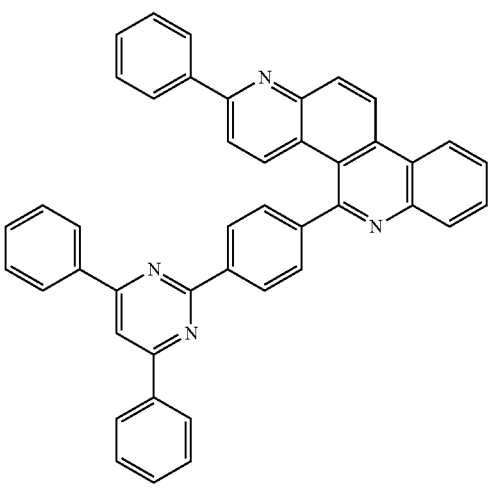
13
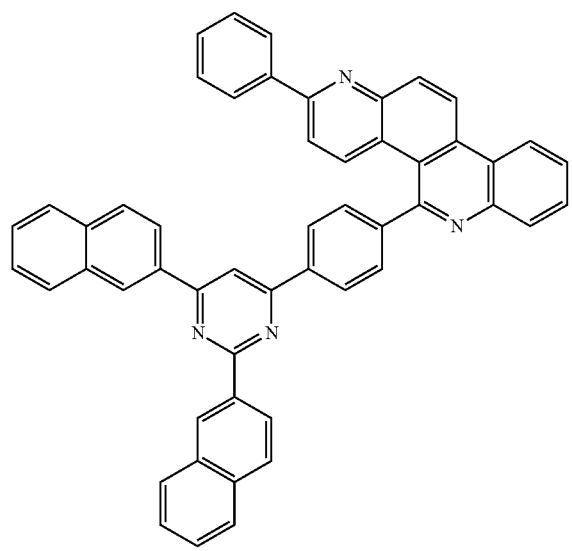
14
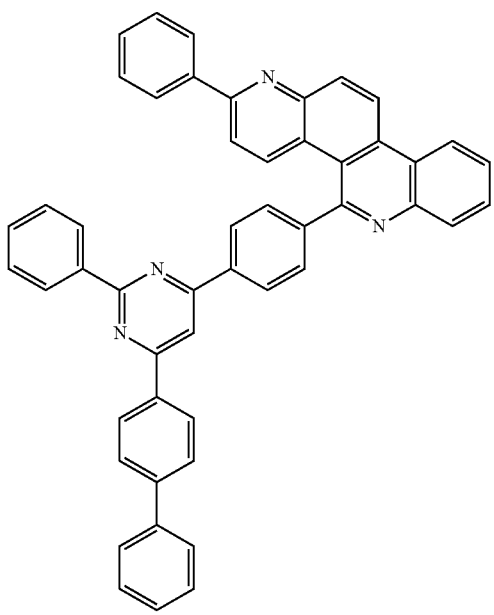

-continued
15
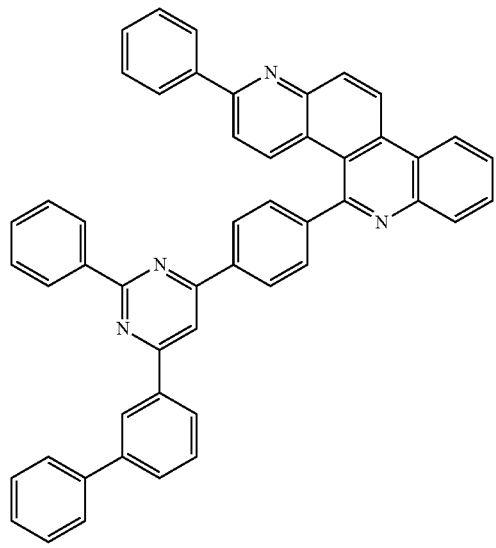
16
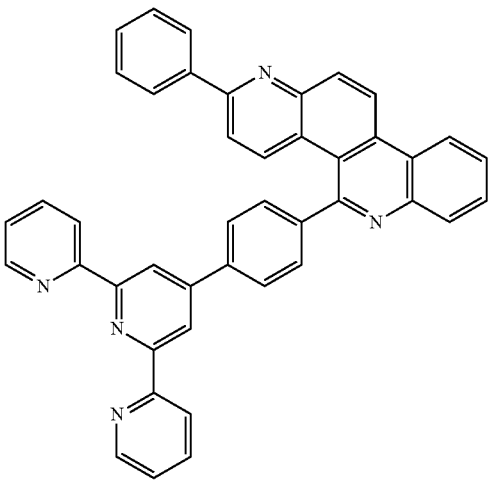
17
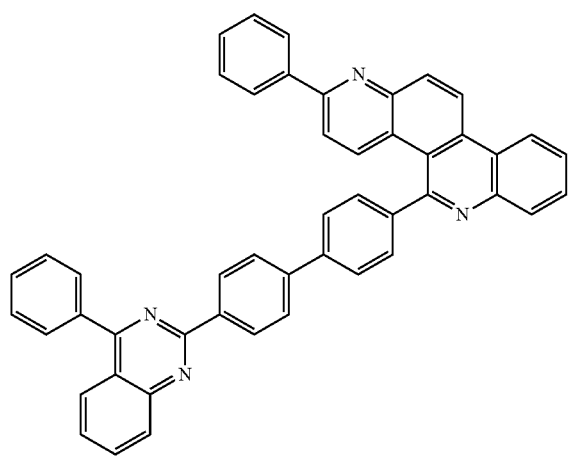
18
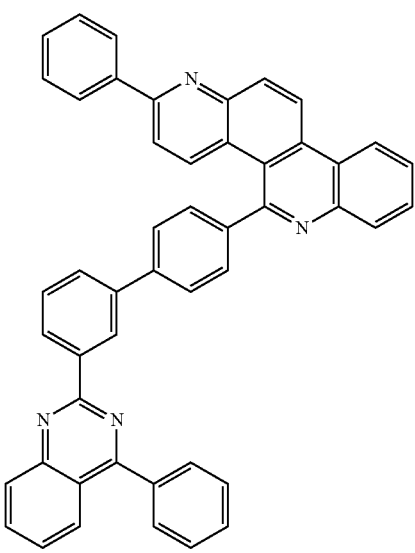
19
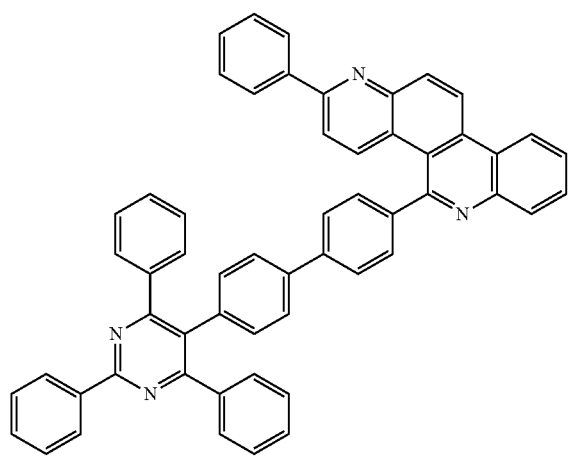
20
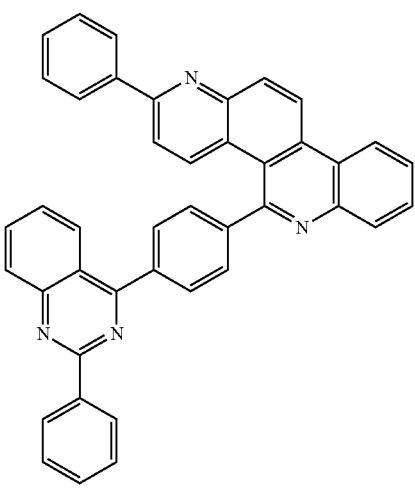

21
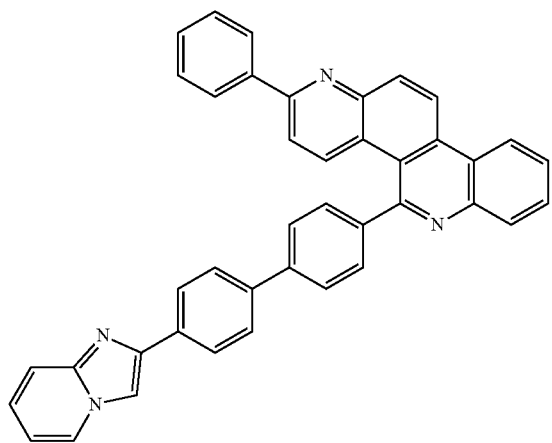
22
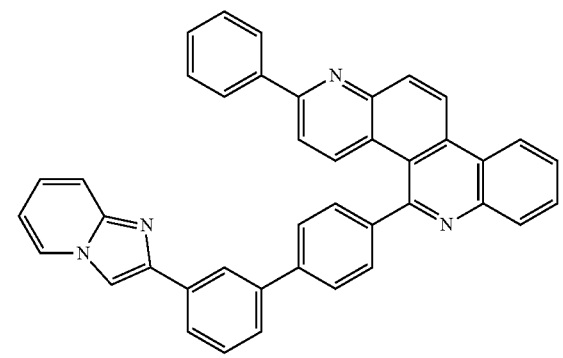
23
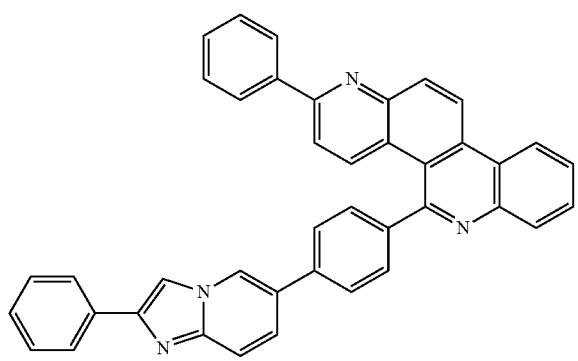
24
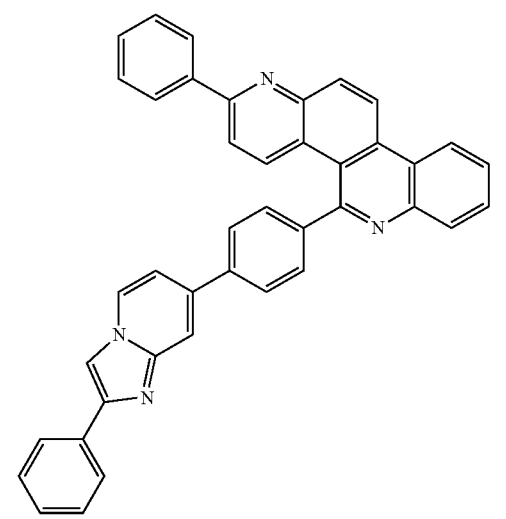
25
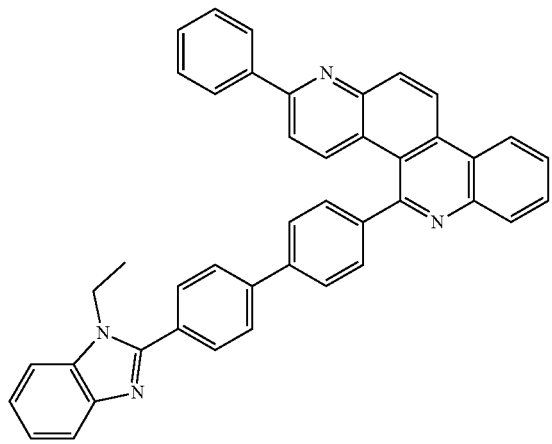
26
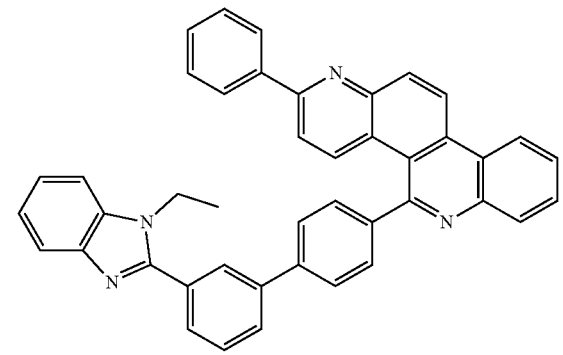

-continued
27
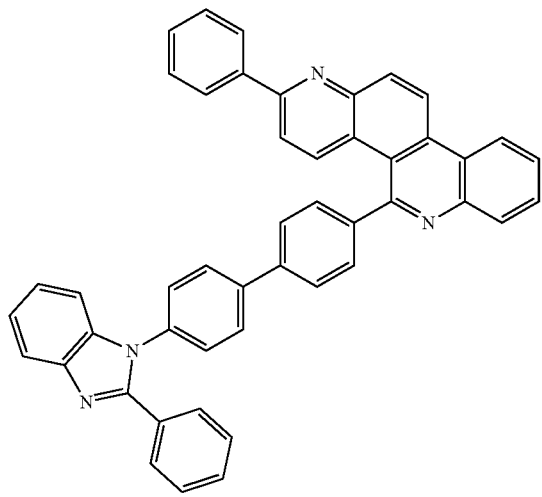
28
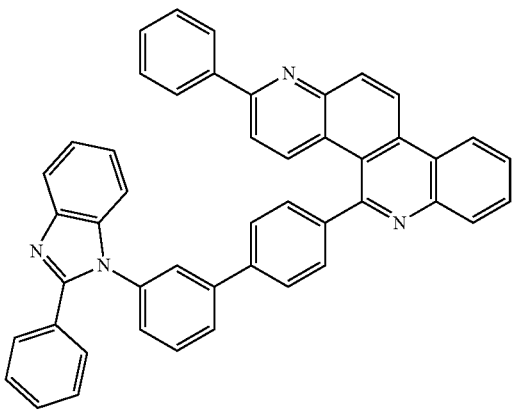
29
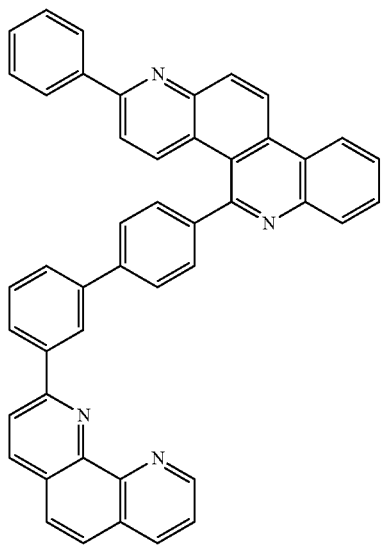
30
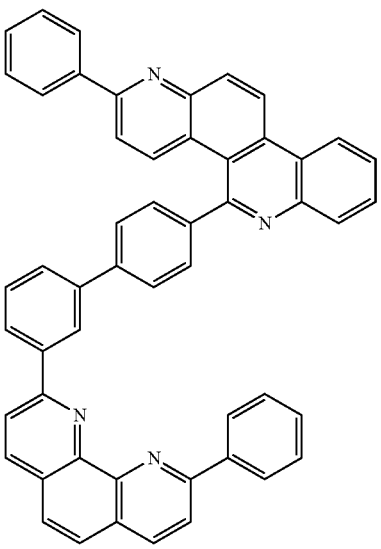
31
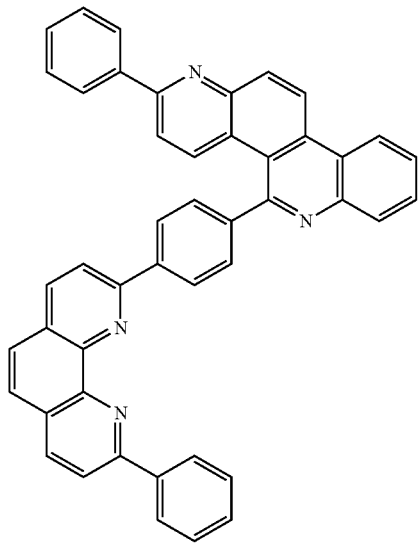
32
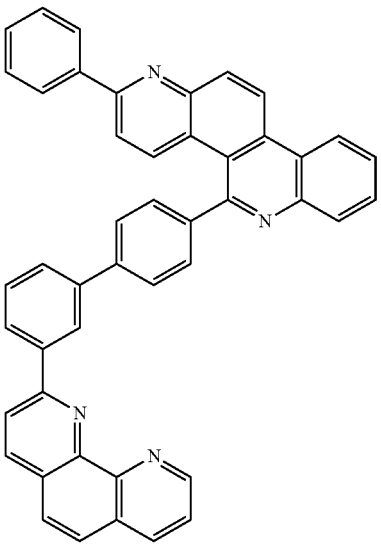

-continued
33
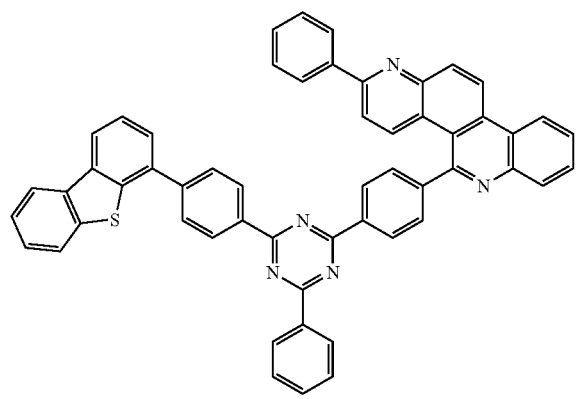
34
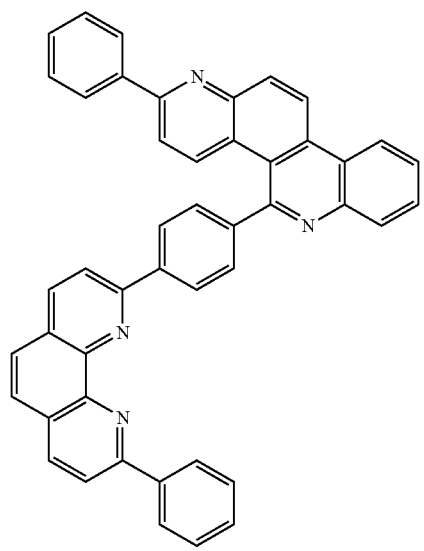
35
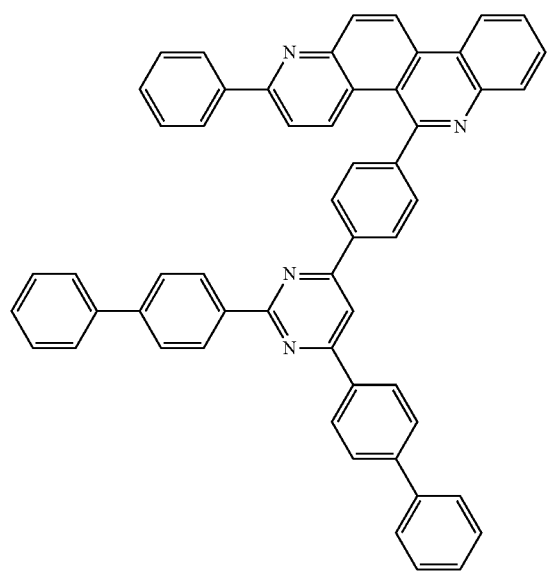
36
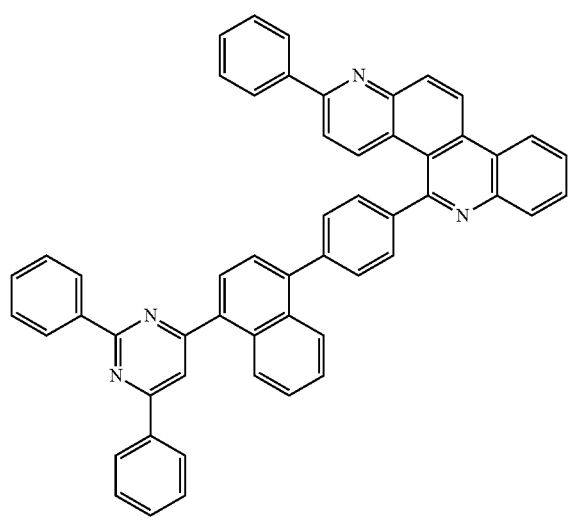

-continued
37
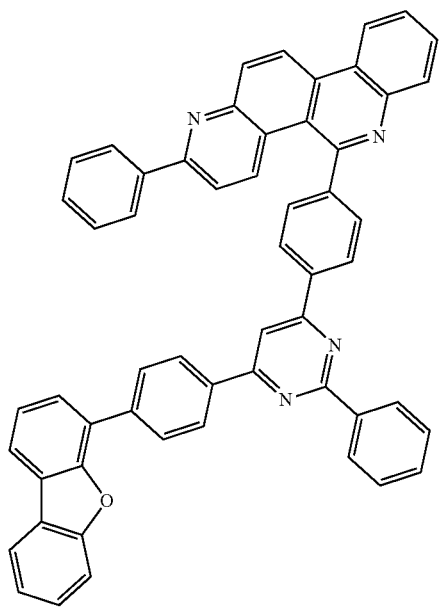
38
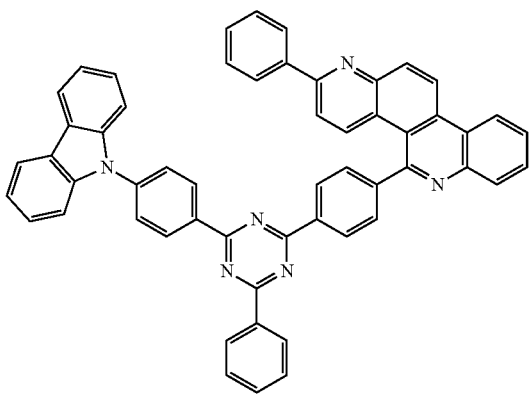
39
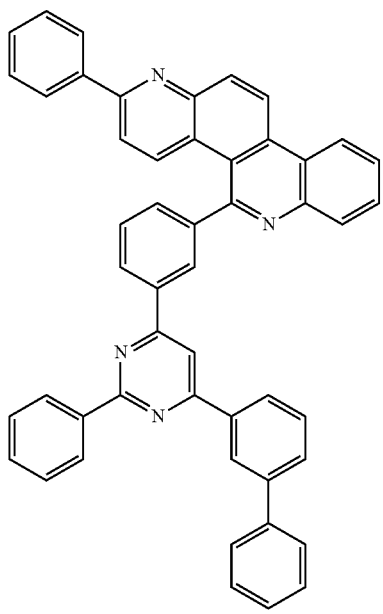
40
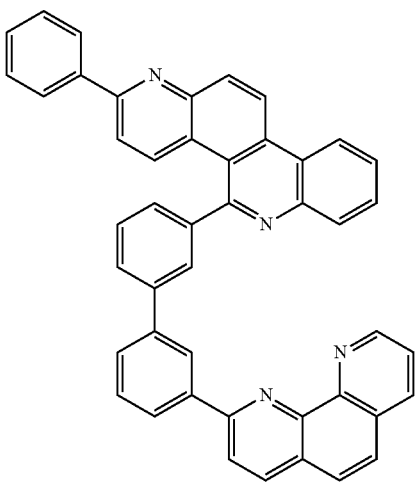

-continued
41
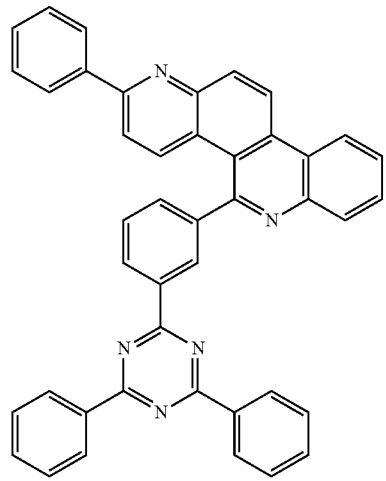
42
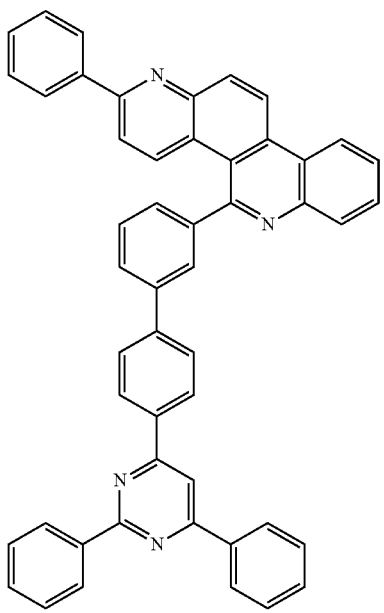
43
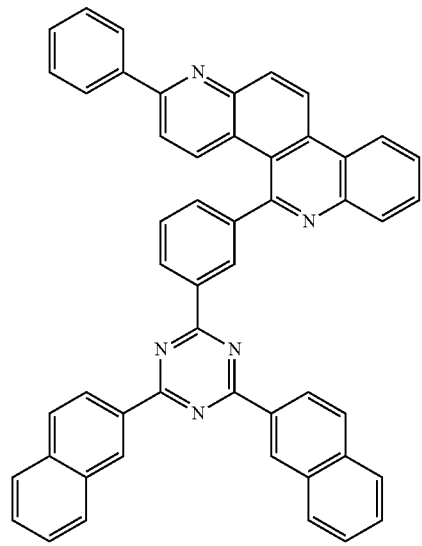
44
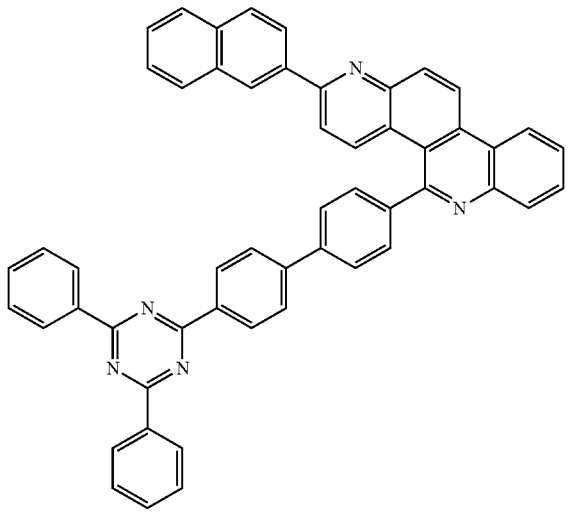

45
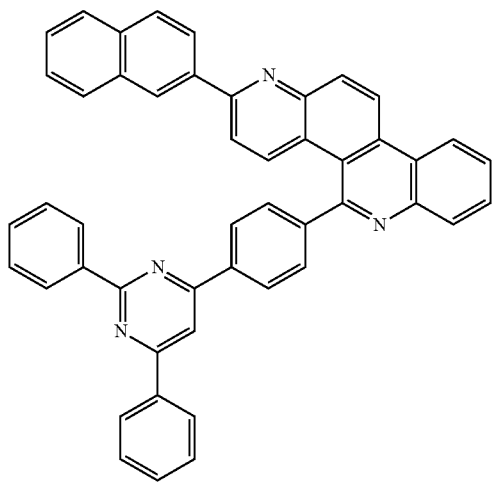
46
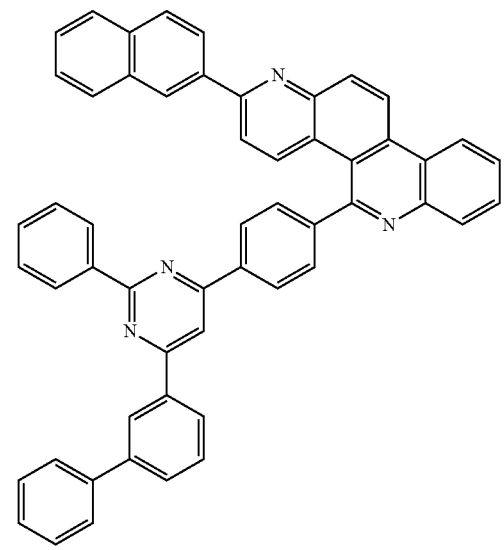
47
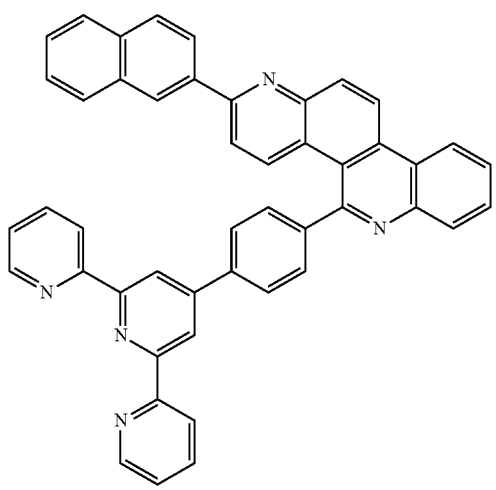
48
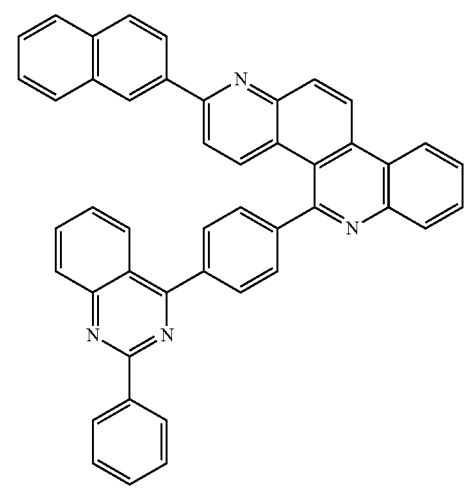
49
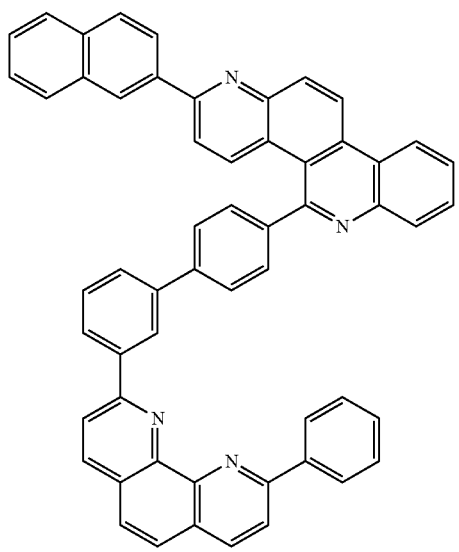
50
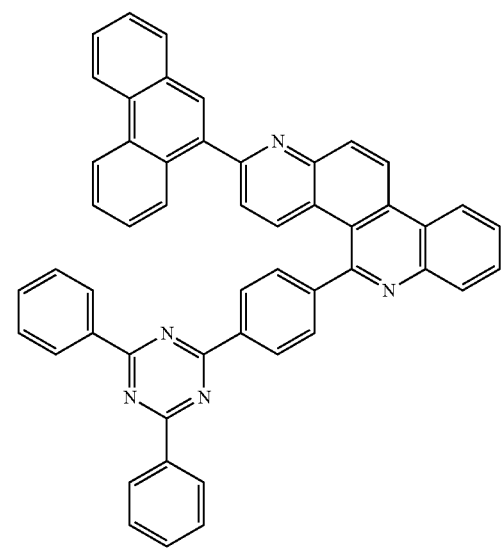

-continued
51
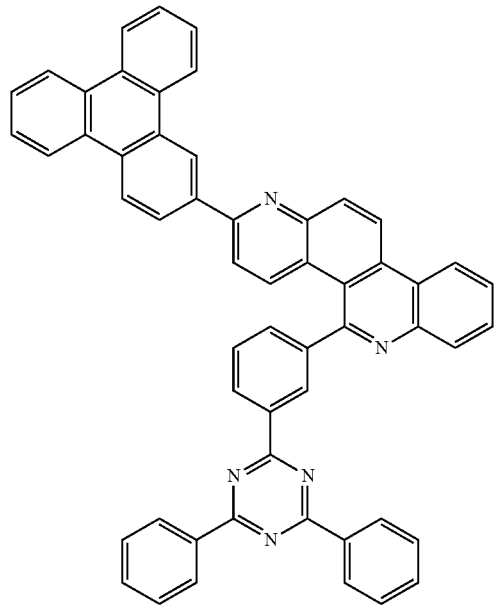
52
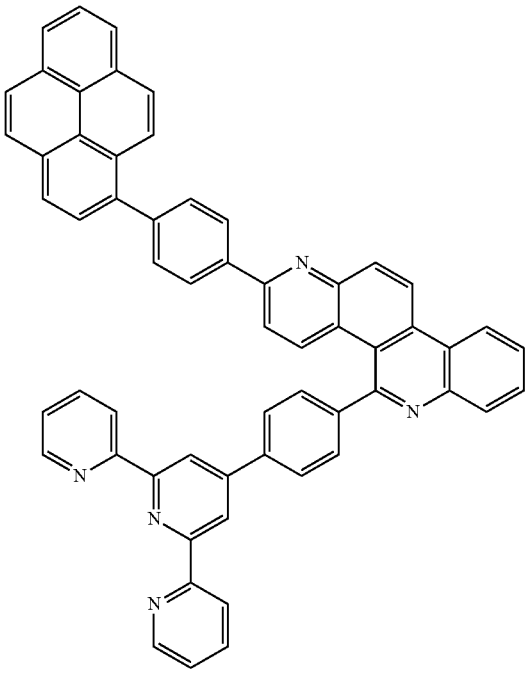
53
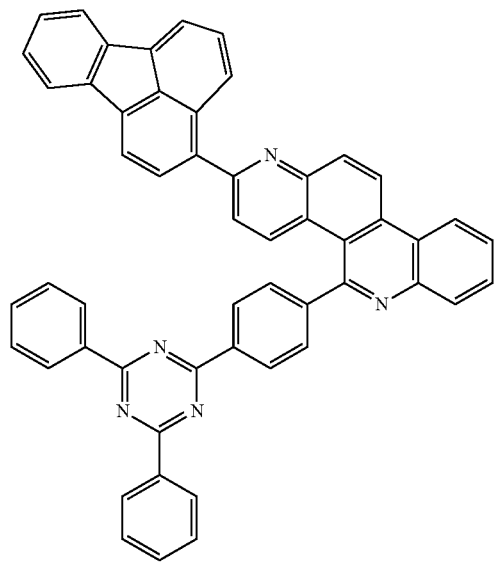
54
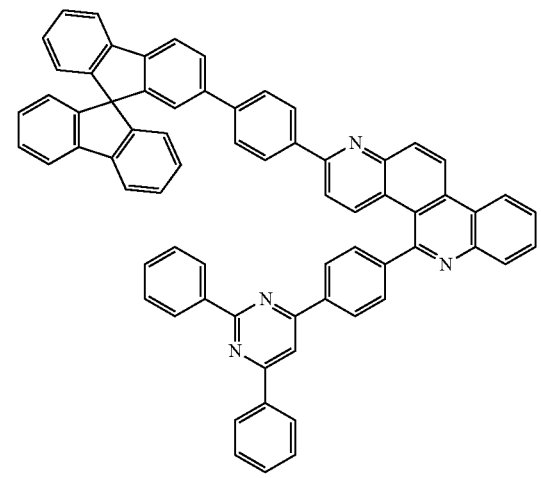
55
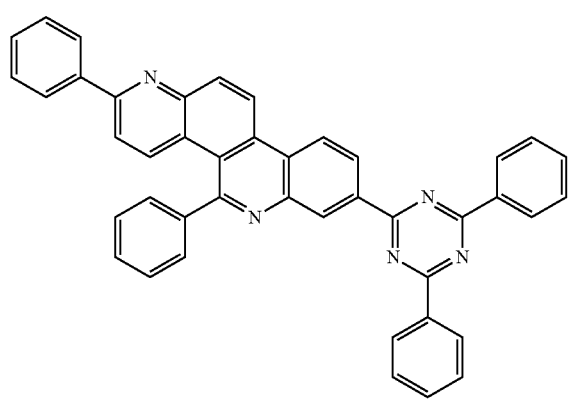
56
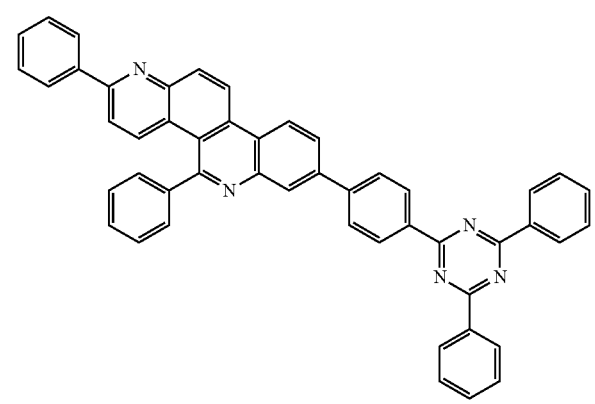

57
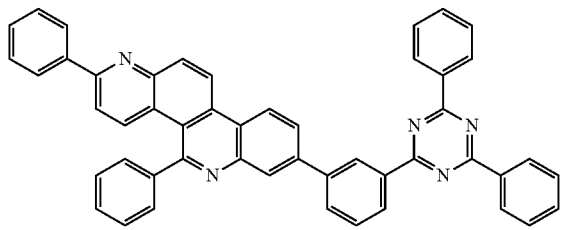
58
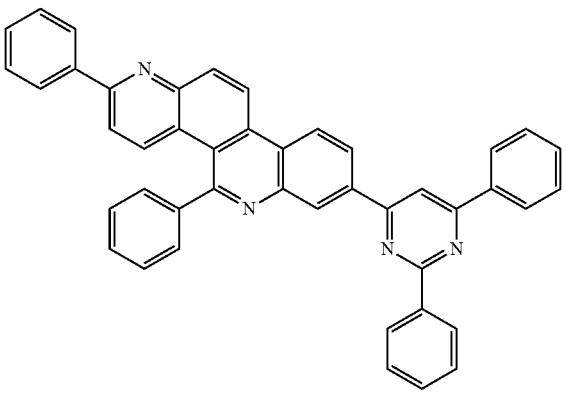
59
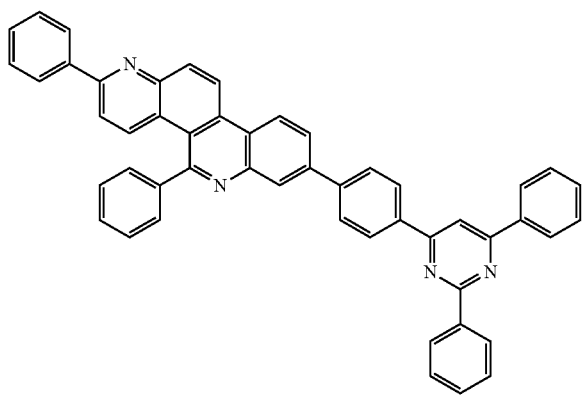
60
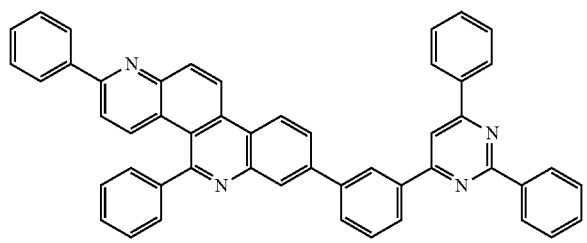
61
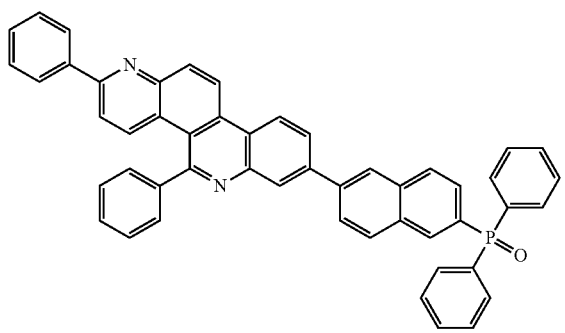
62
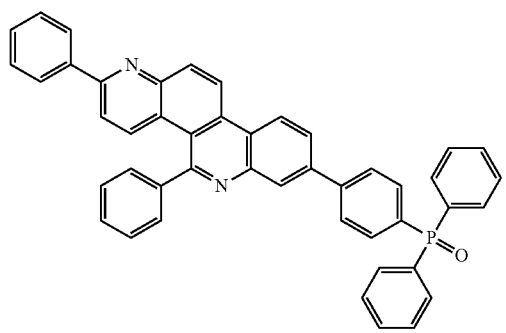
63
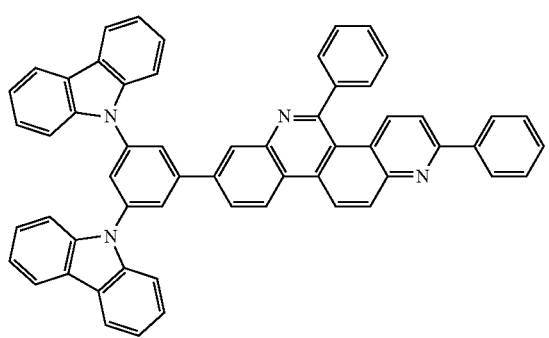
64
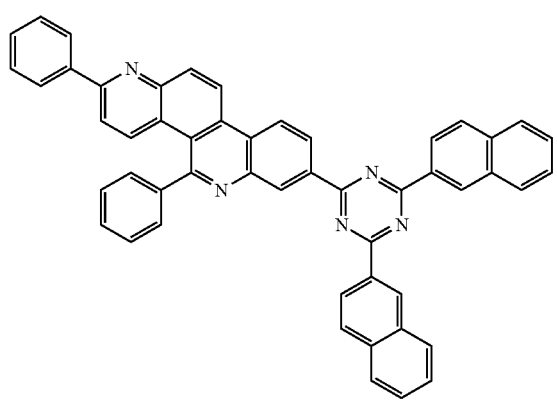

-continued
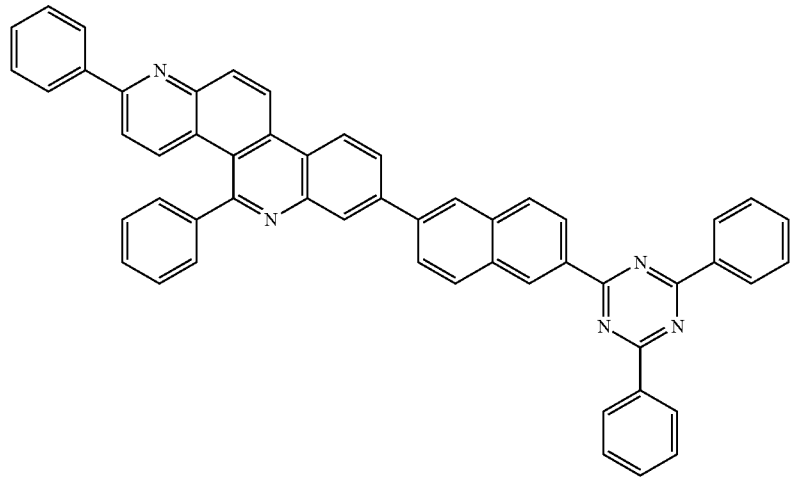
65
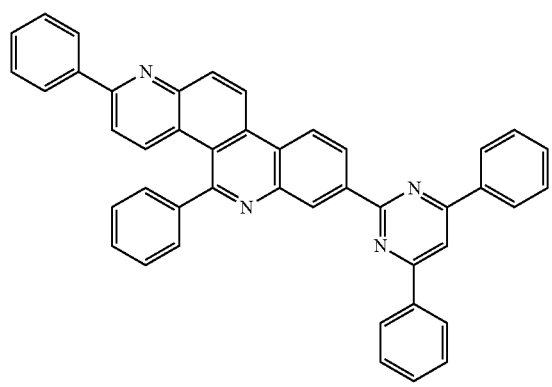
66
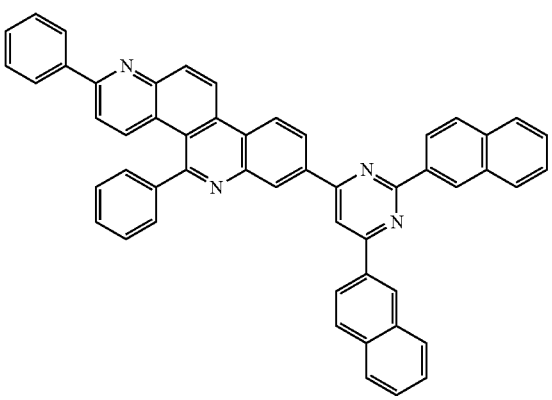
67
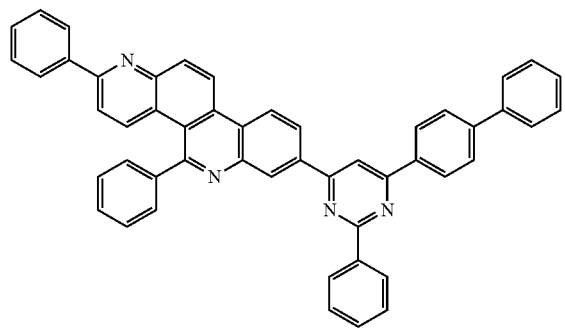
68
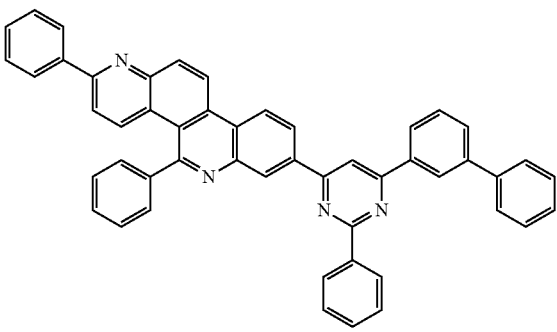
69
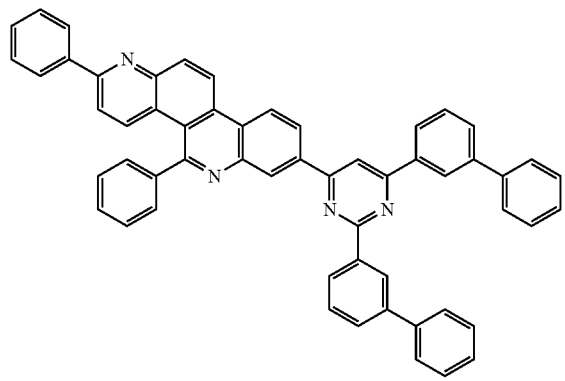
70
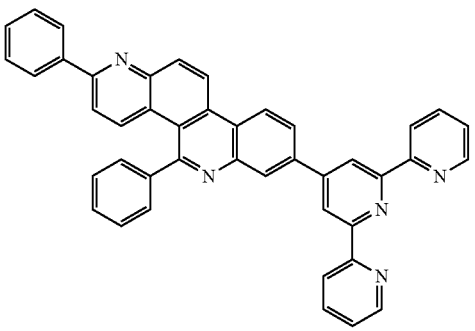
71

-continued
72
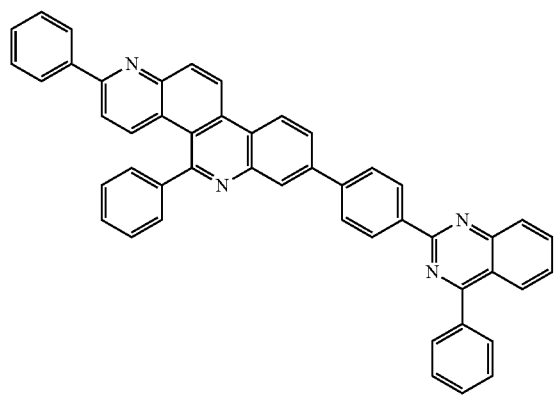
73
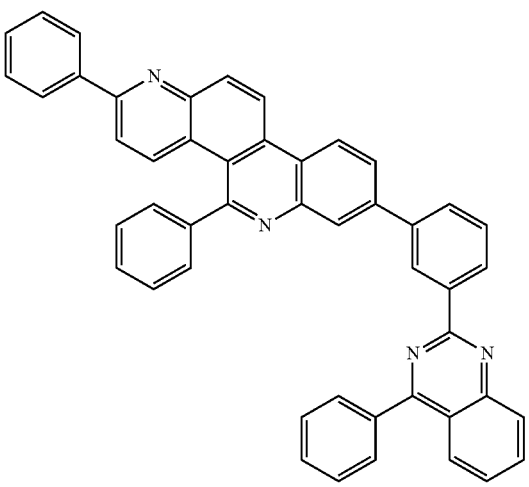
74
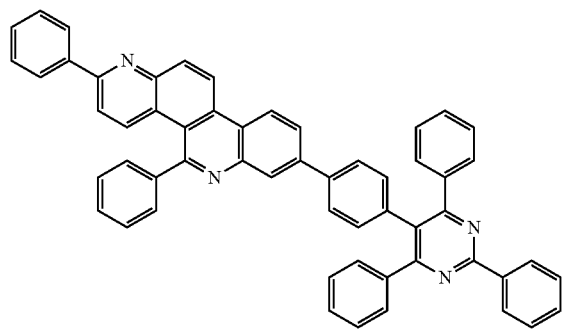
75
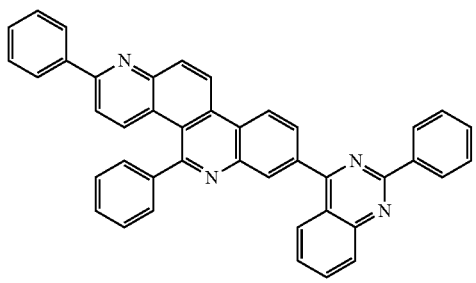
76
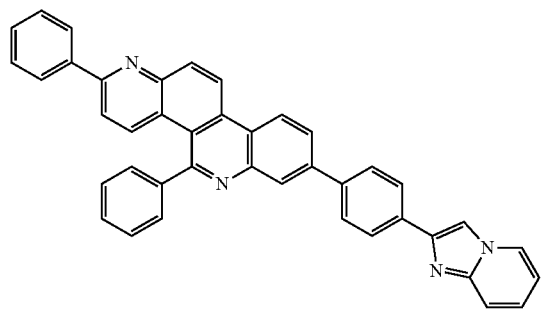
77
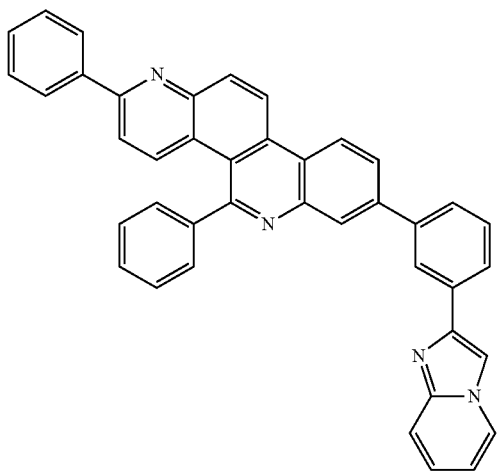

-continued
78
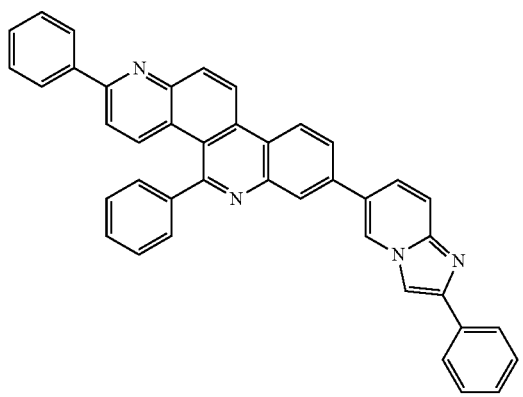
79
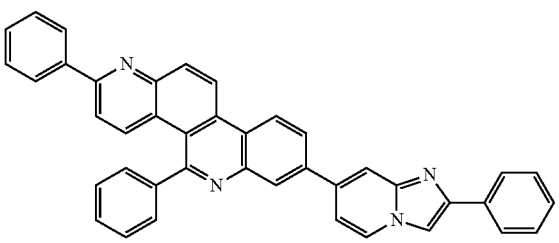
80
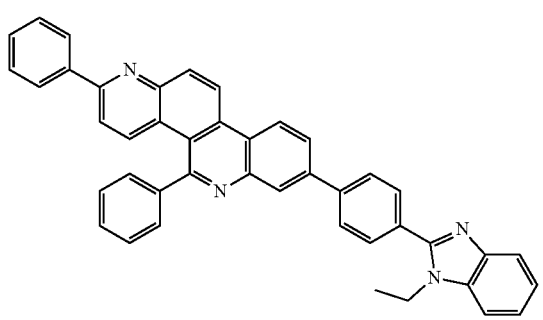
81
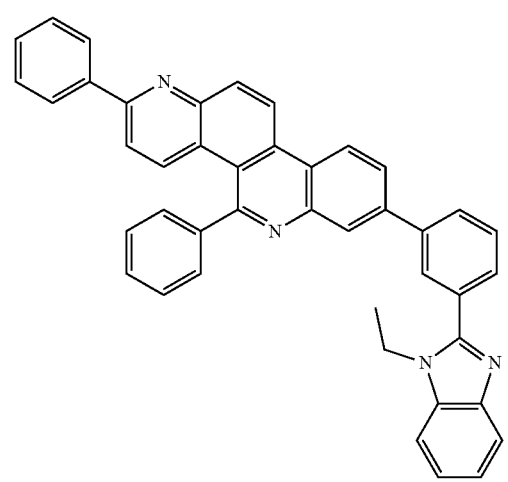
82
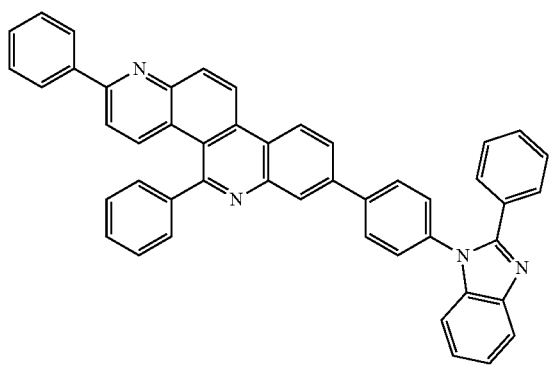
83
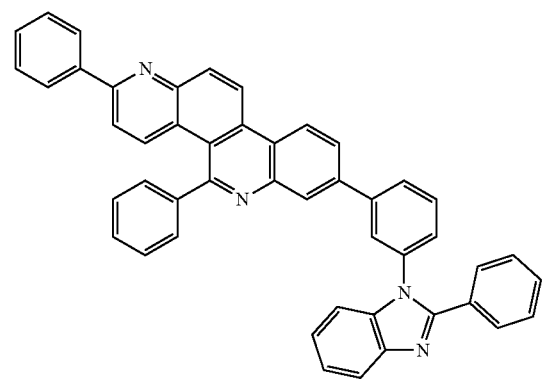
84
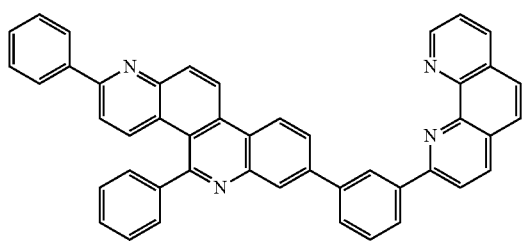
85
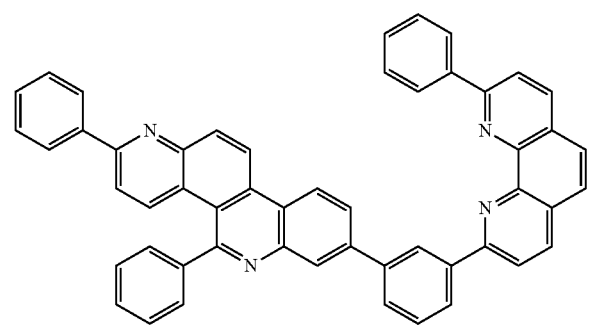

86
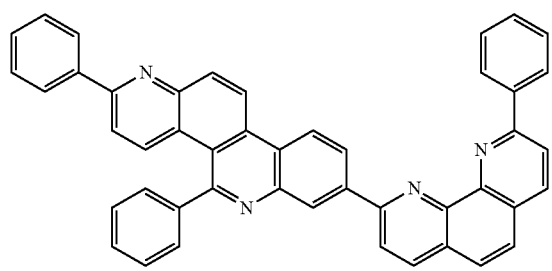
87
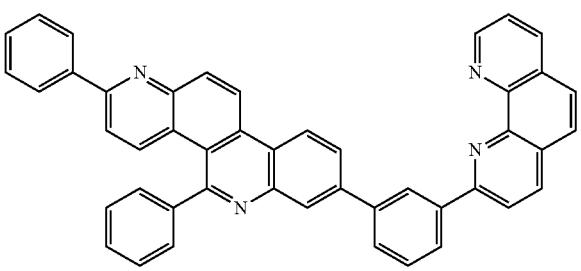
88
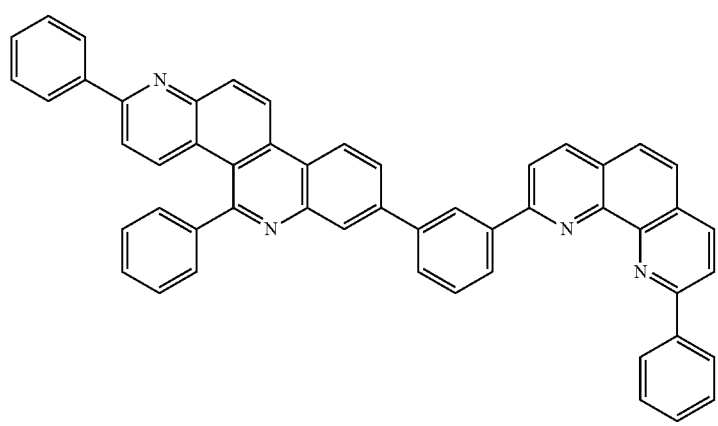
89
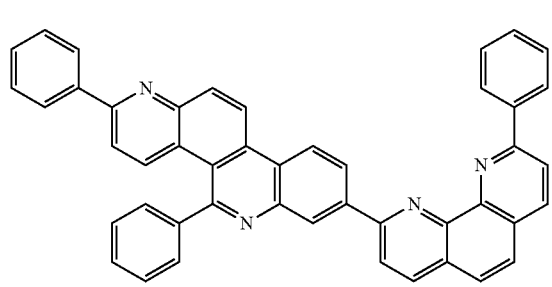
90
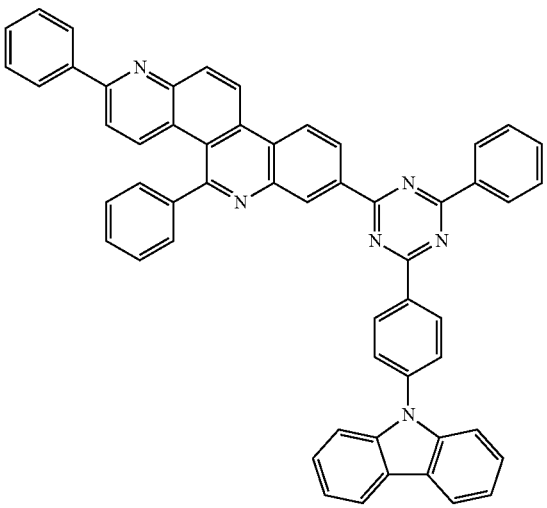

-continued
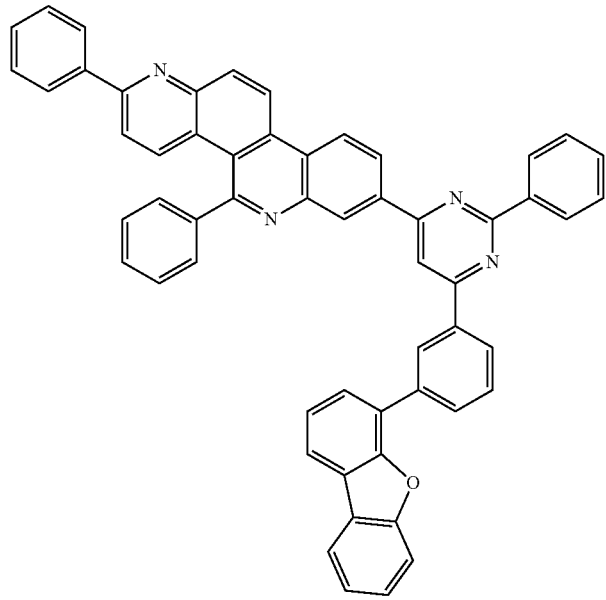
91
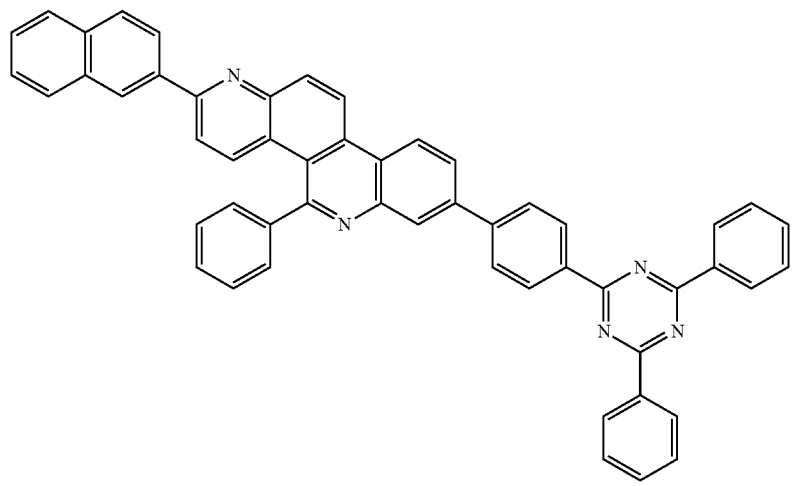
92
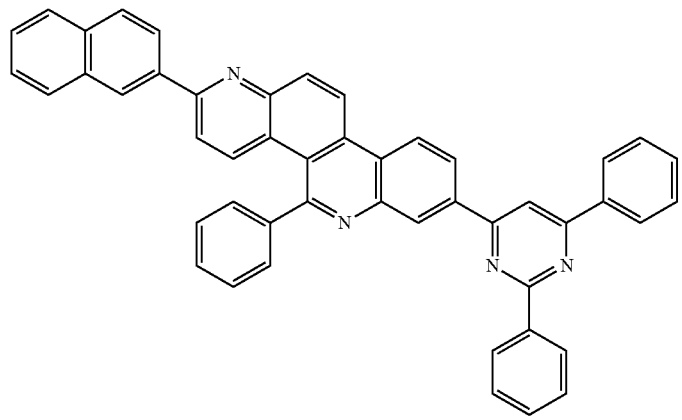
93

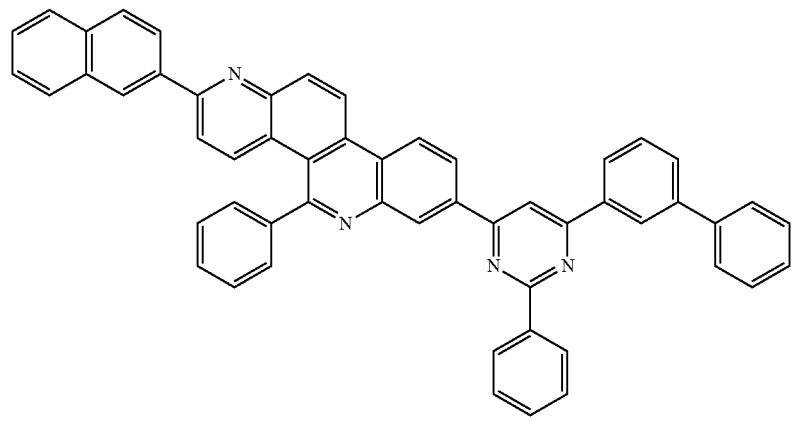
94
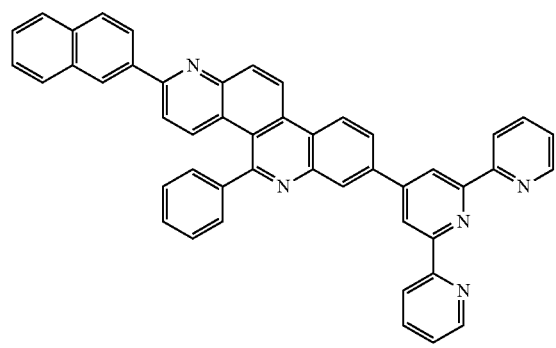
95
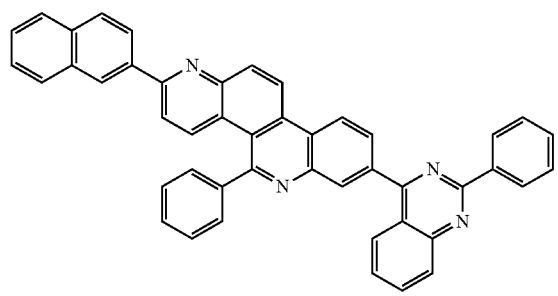
96
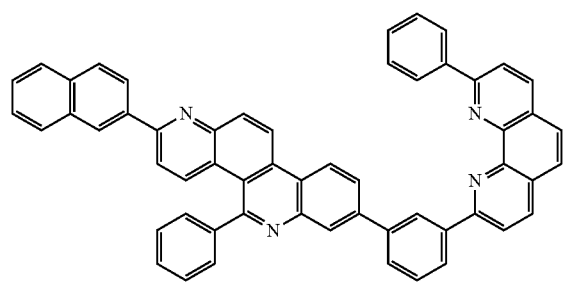
97
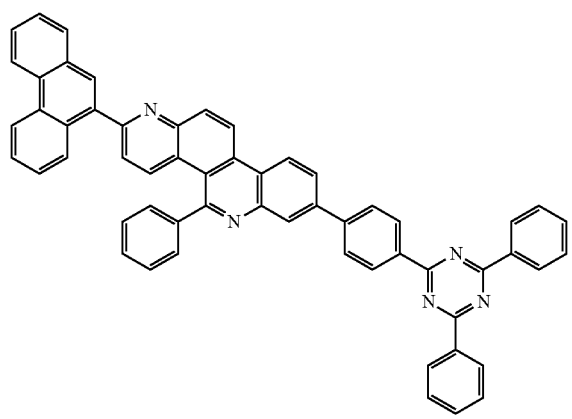
98

-continued
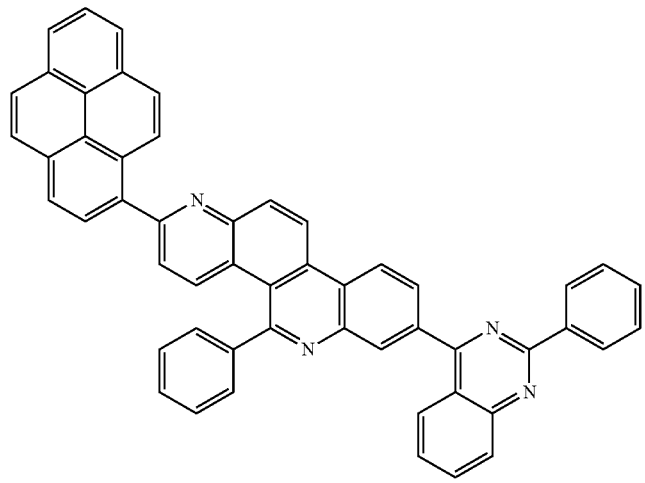
99
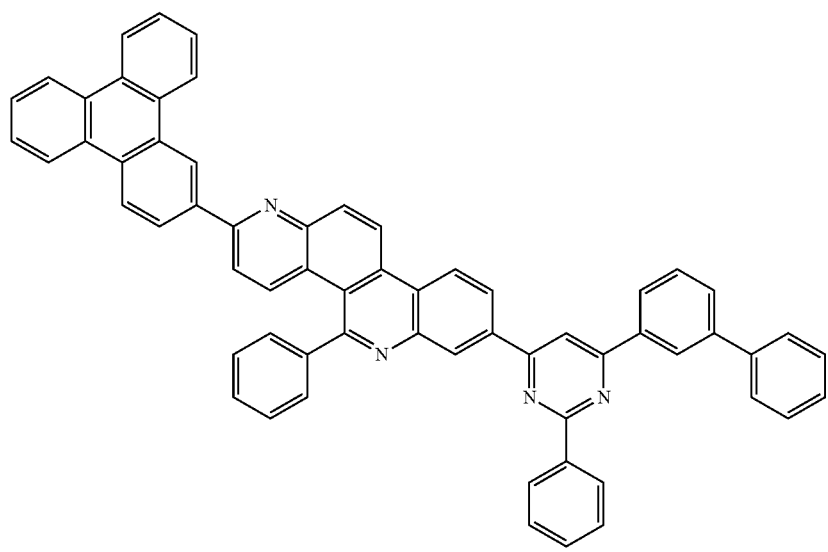
100
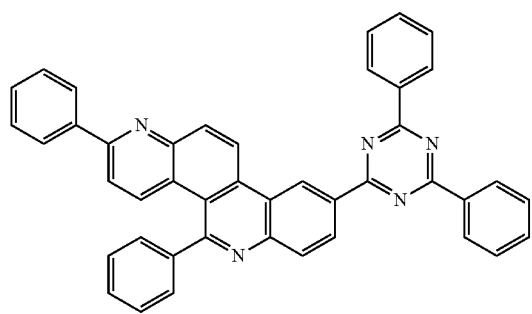
101
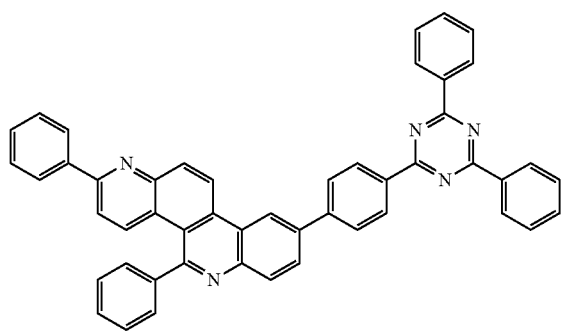
102

-continued
103
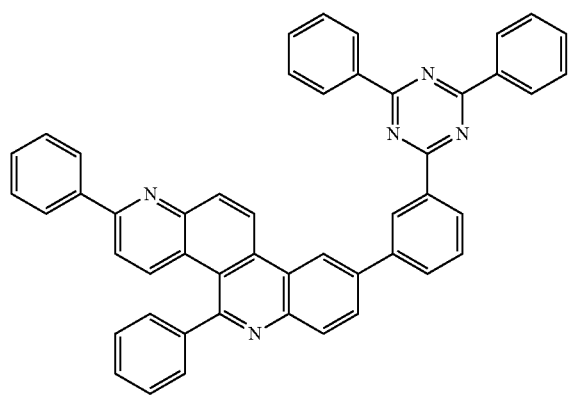
104
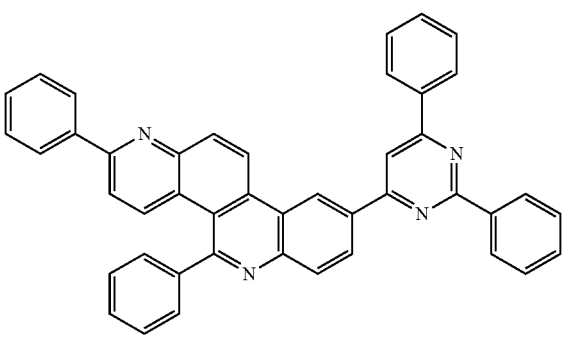
105
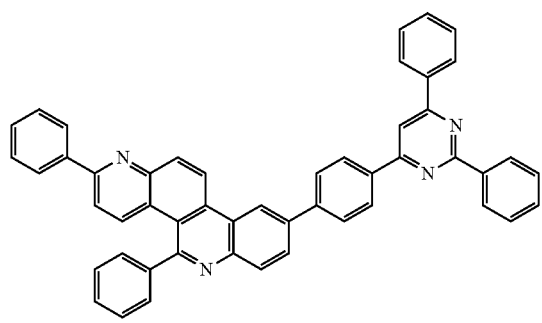
106
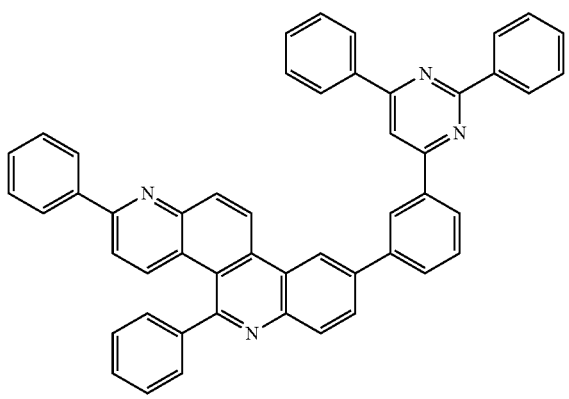
107
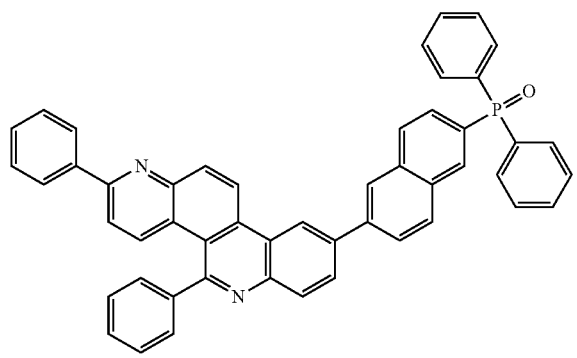
108
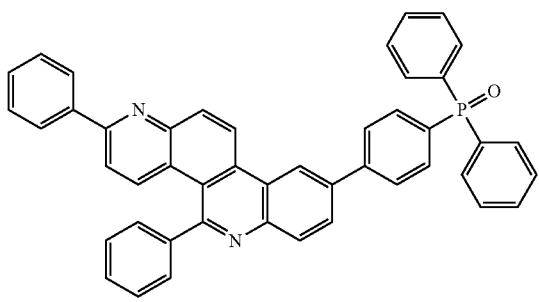
109
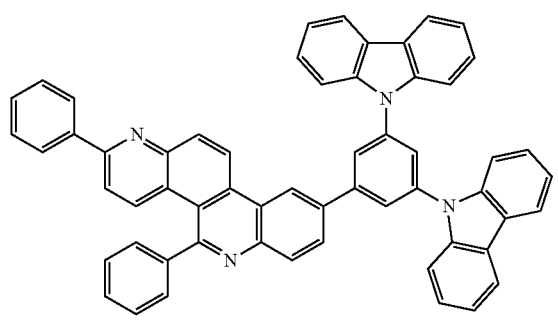
110
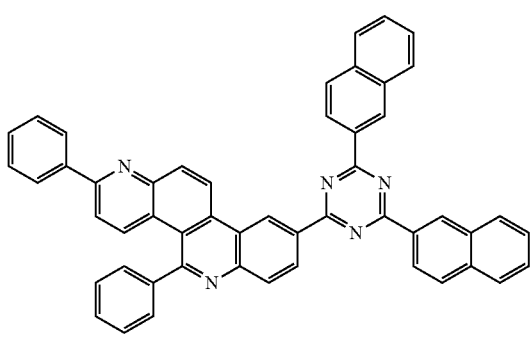

-continued
111
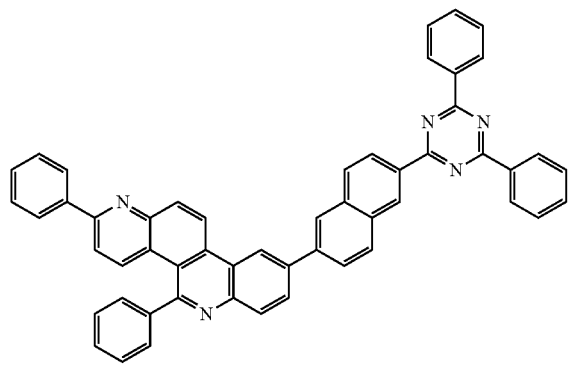
112
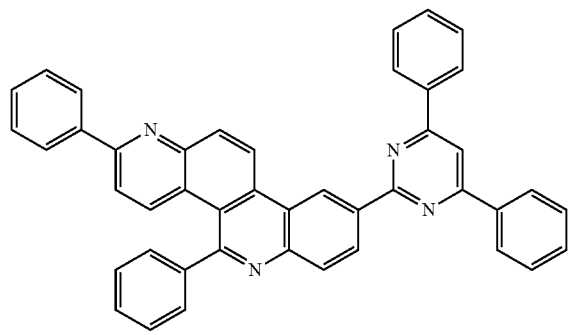
113
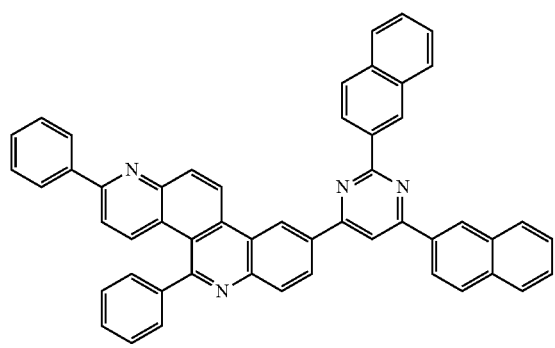
114
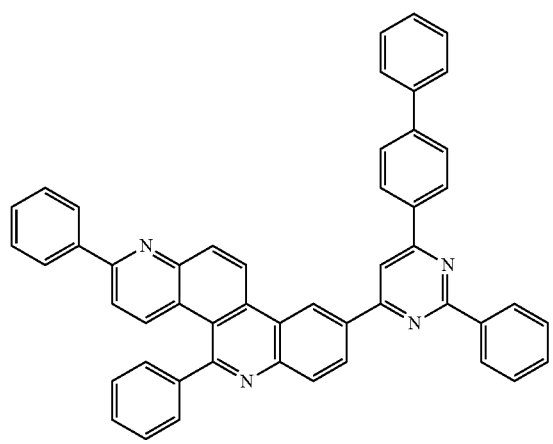
115
116
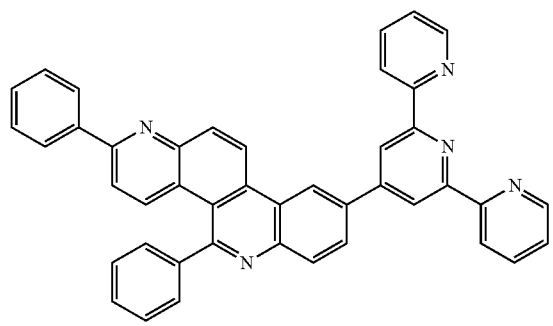
117
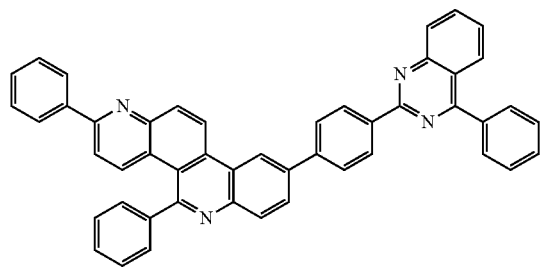
118
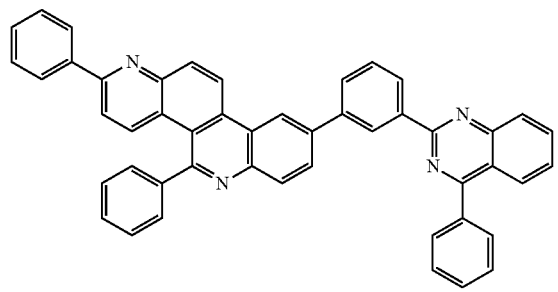

-continued
119
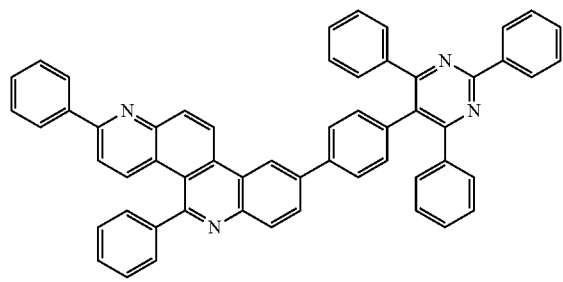
120
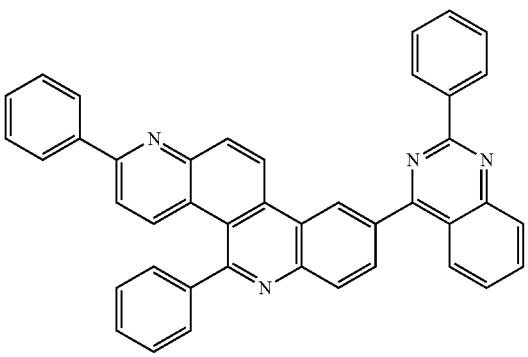
121
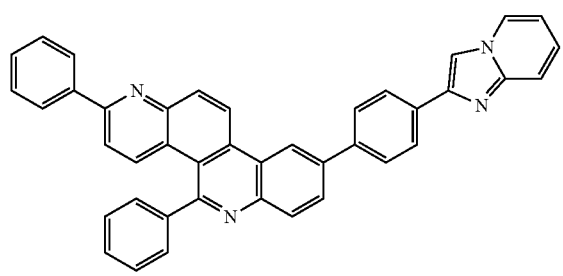
122
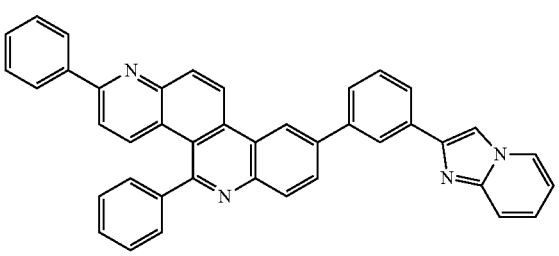
123
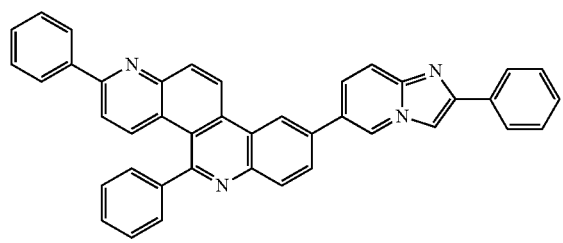
124
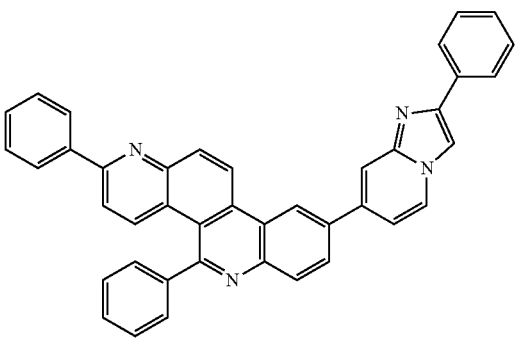
125
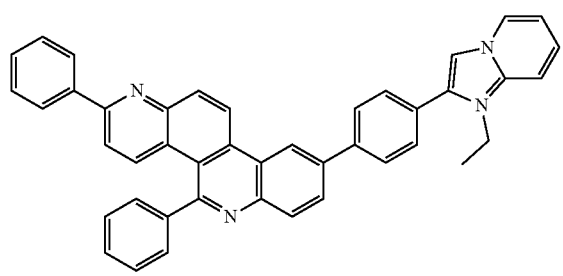
126
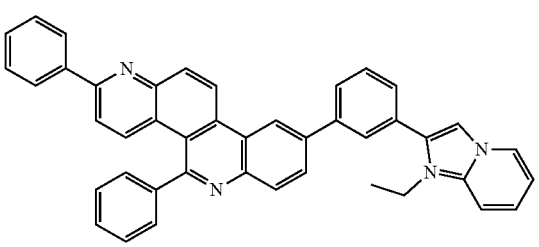
127
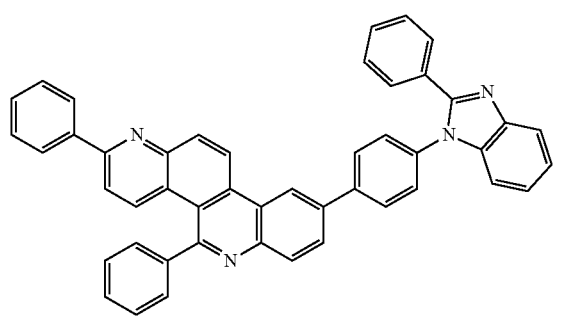
128
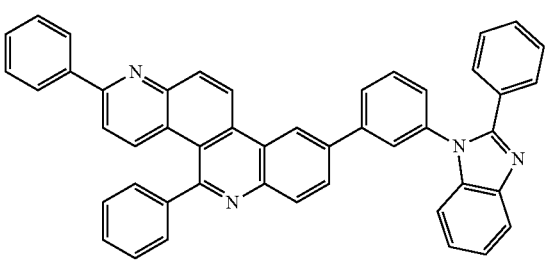

-continued
129
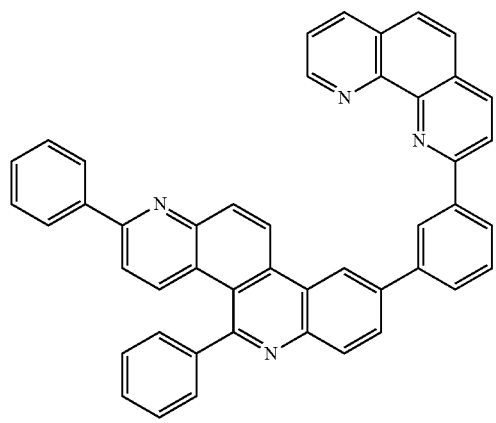
130
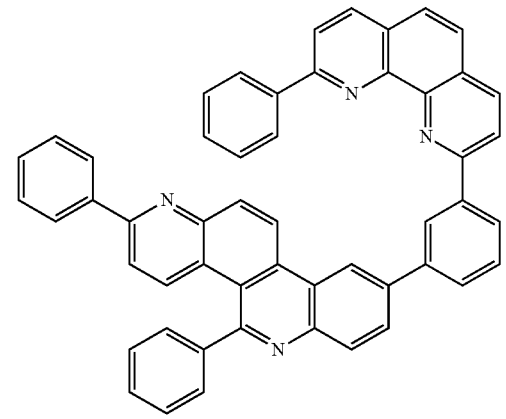
131
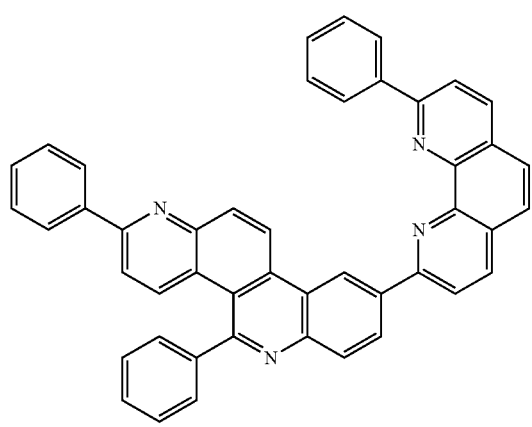
132
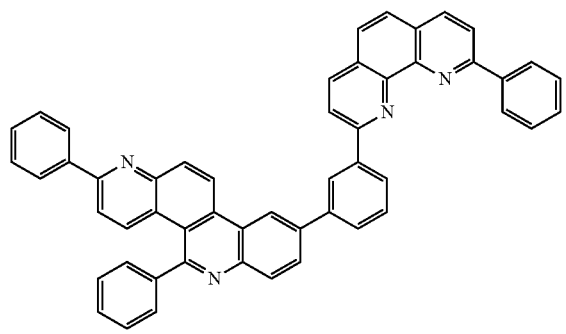
133
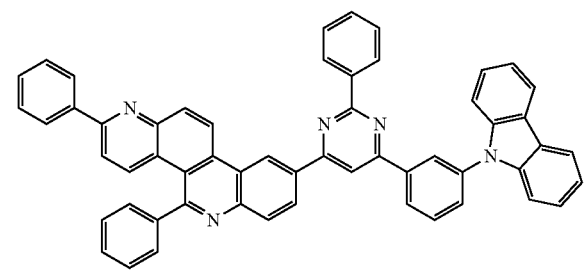
134
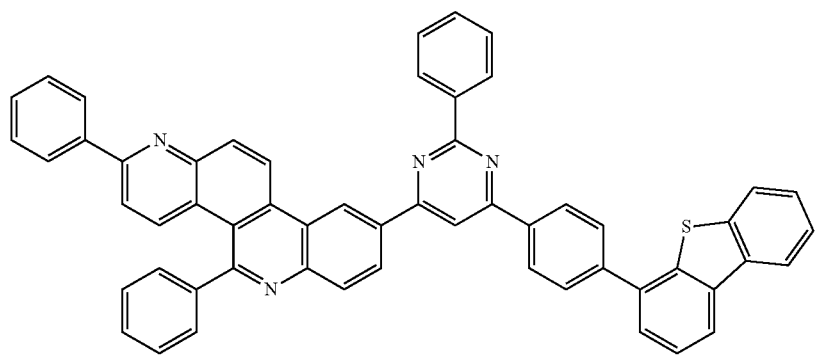
135

-continued
136
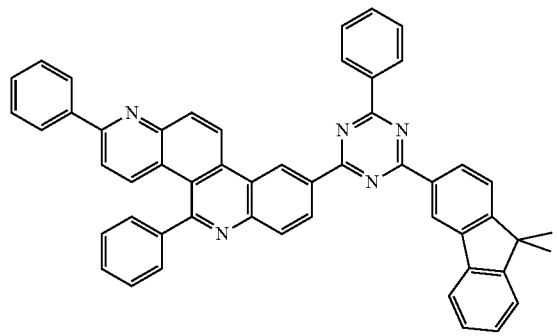
137
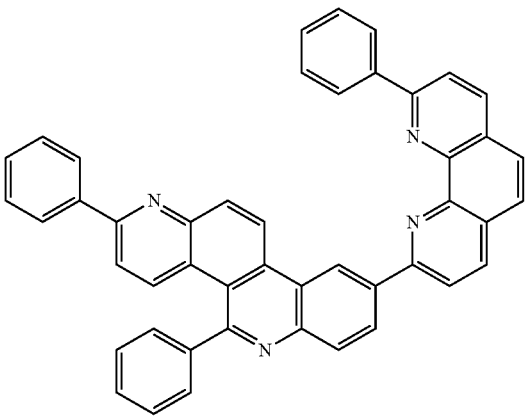
138
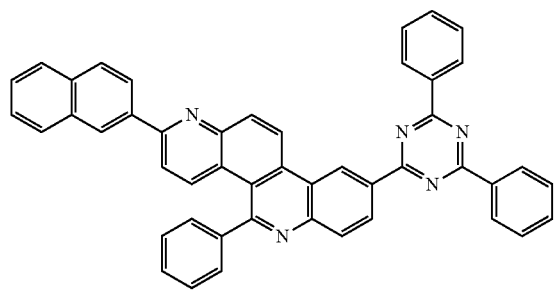
139
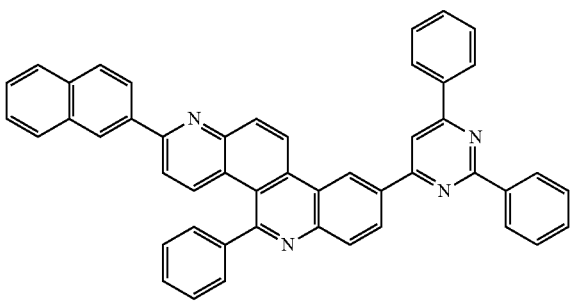
140
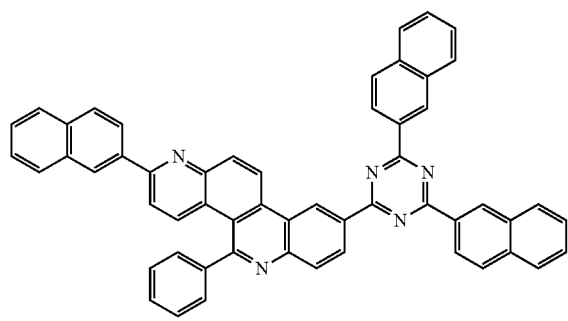
141
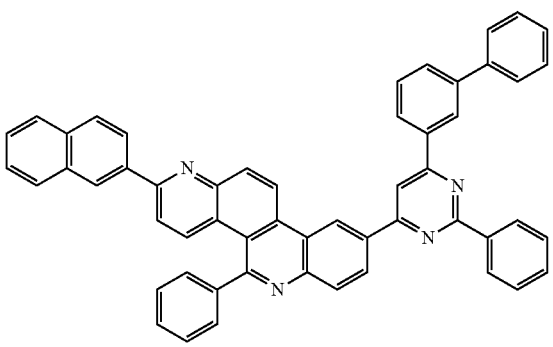
142
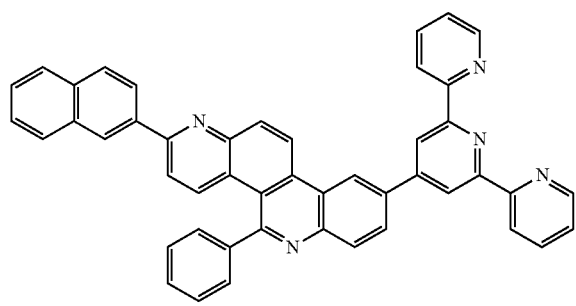
143
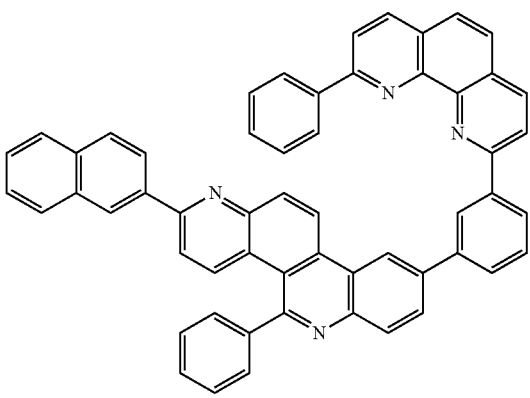

-continued
144
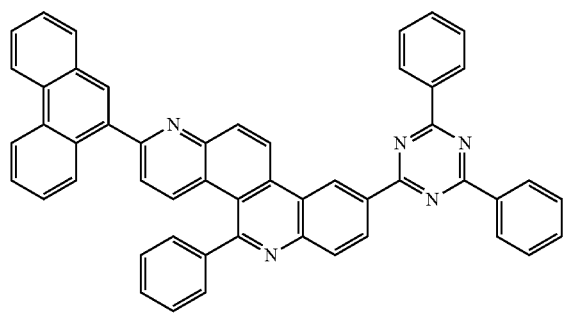
145
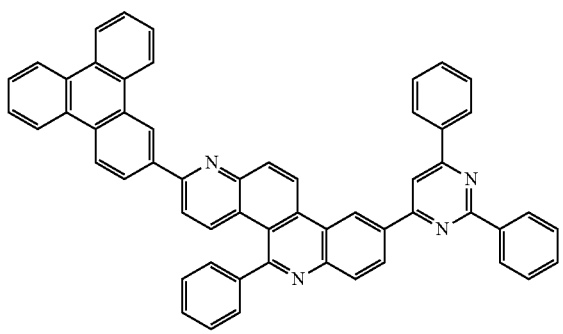
146
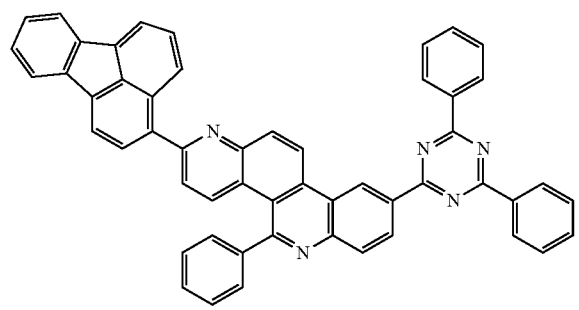
147
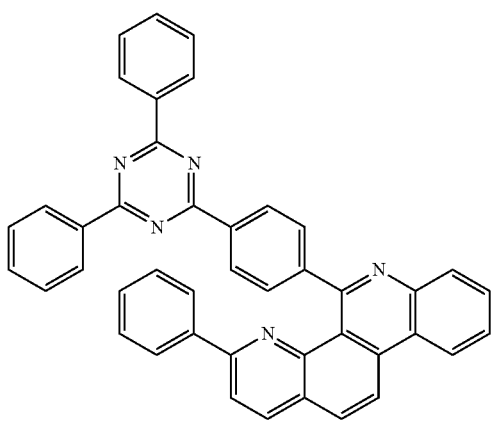
148
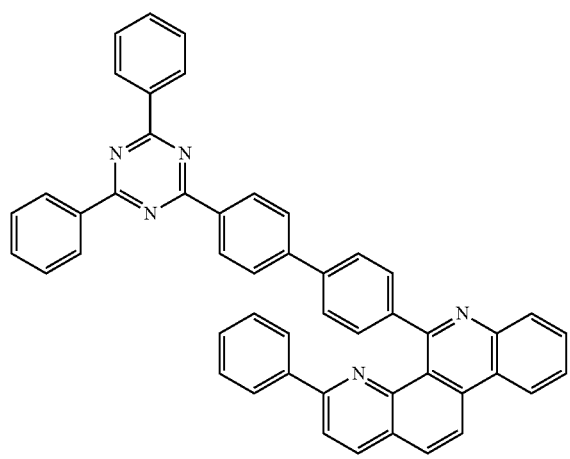
149
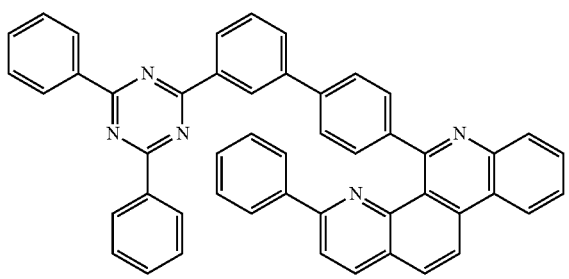

150
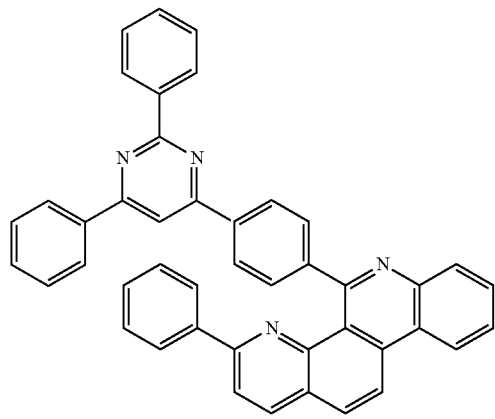
151
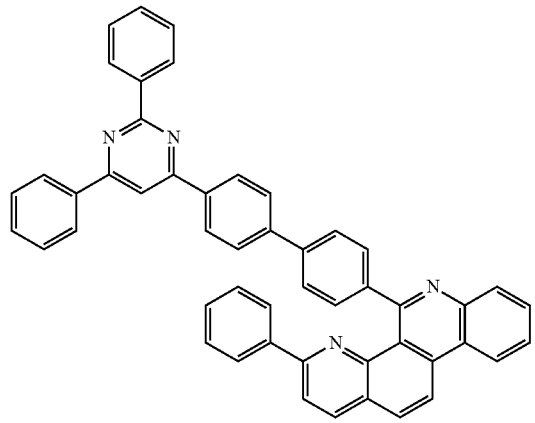
152
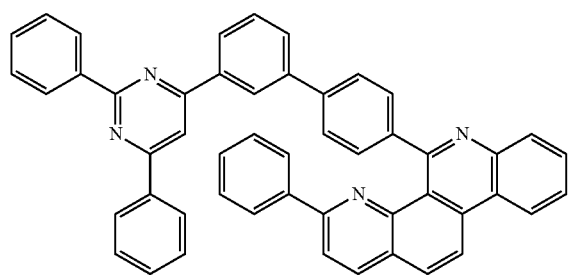
153
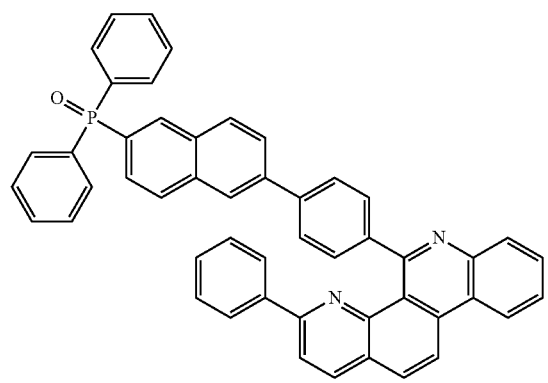
154
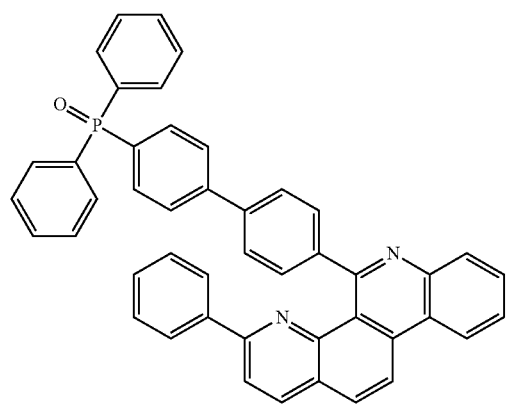
155
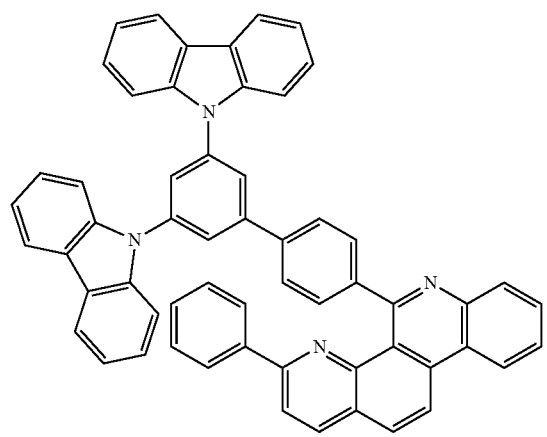

-continued
156
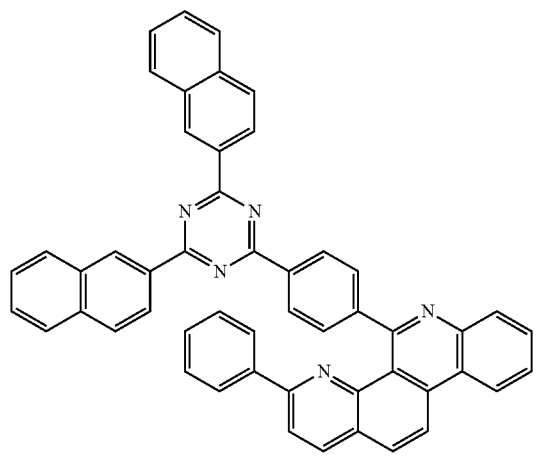
157
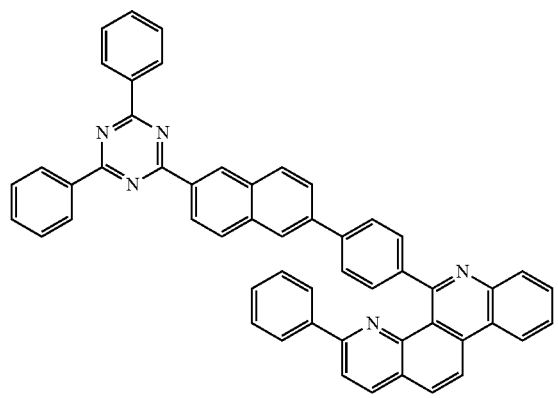
158
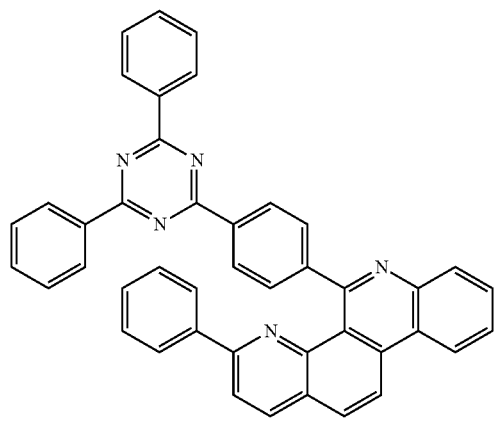
159
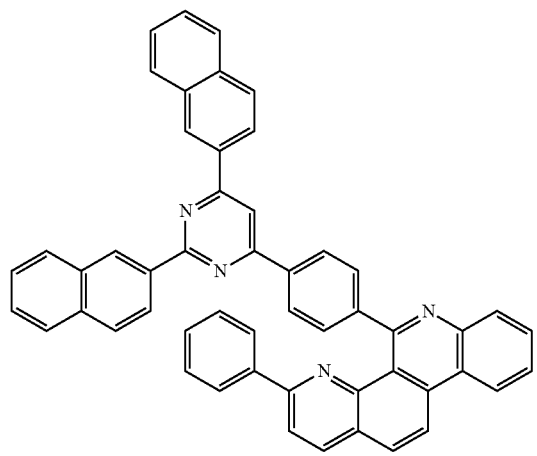
160
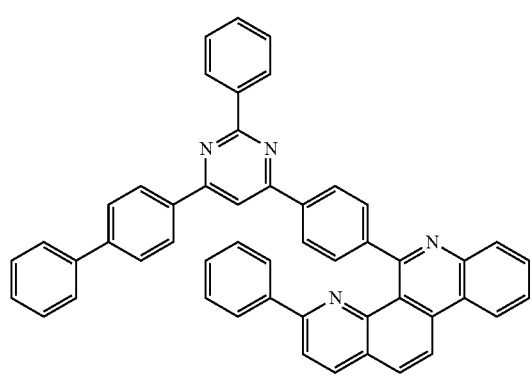
161
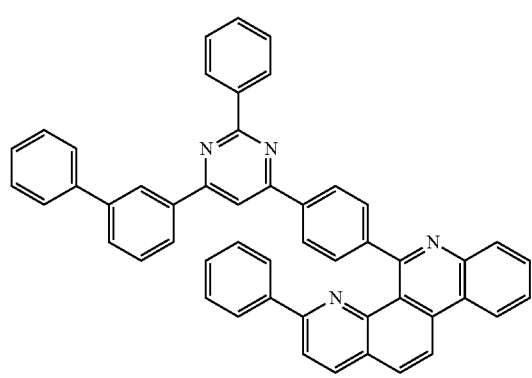

-continued
162 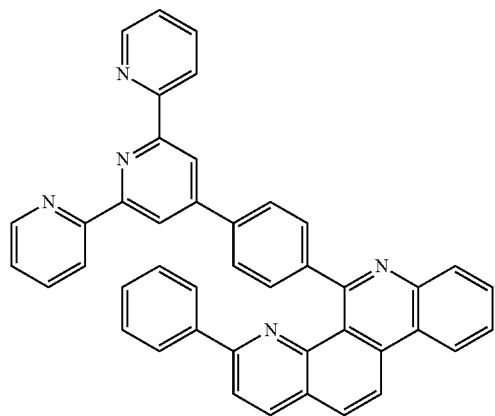
163 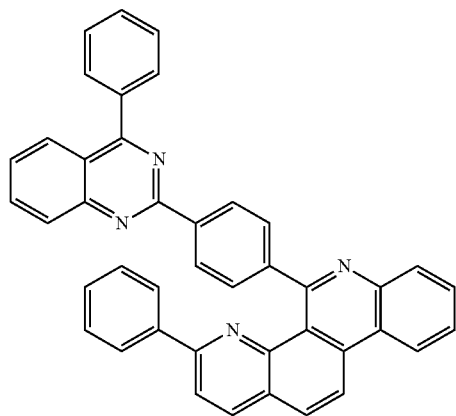
164 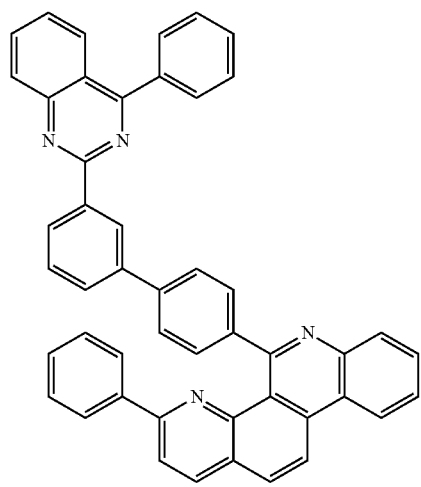
165 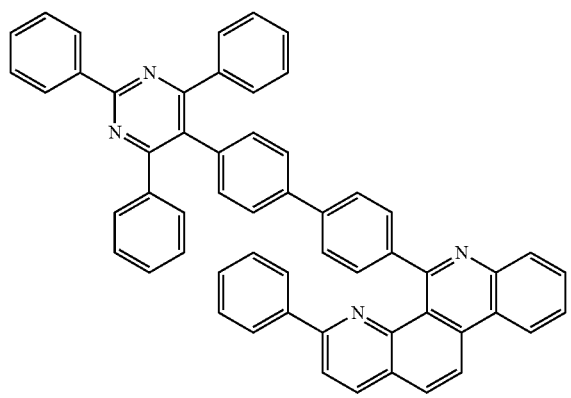
166 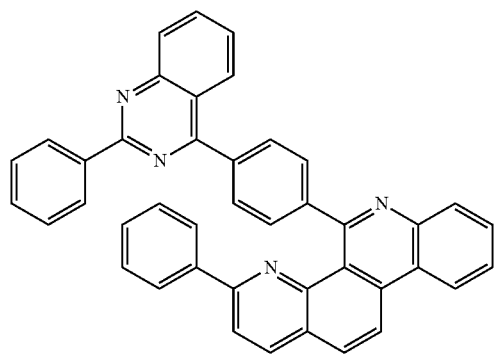
167 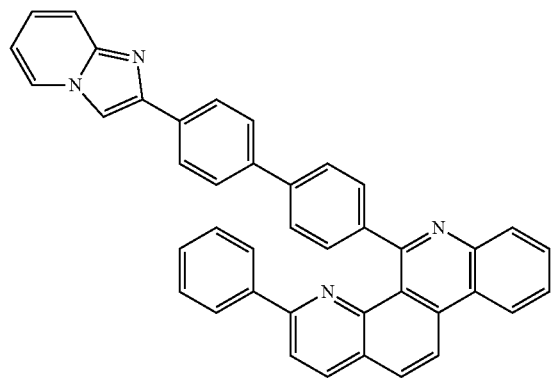

168 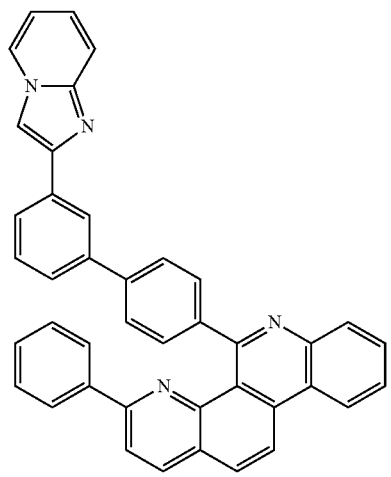
169 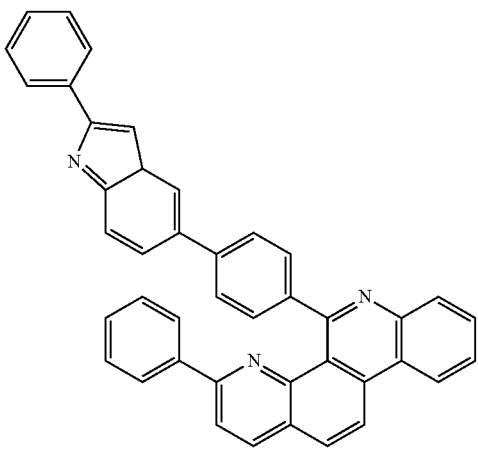
170 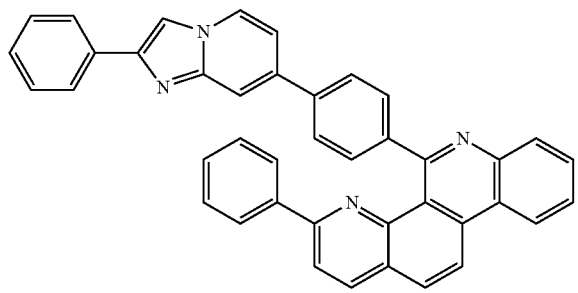
171 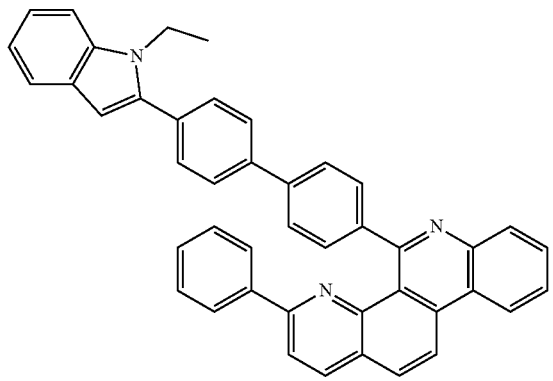
172 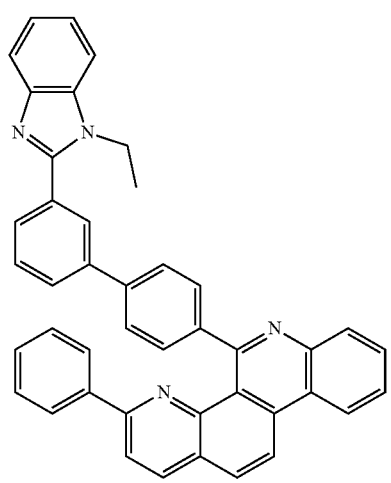
173 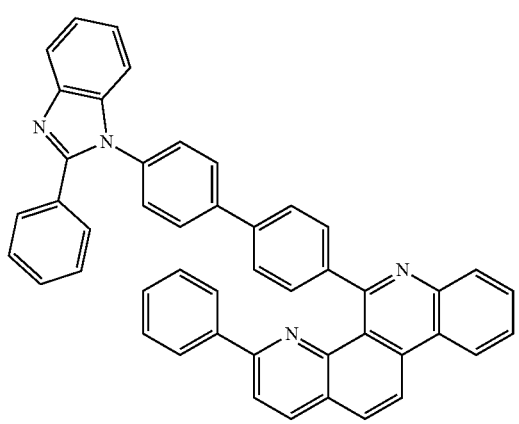

-continued
174
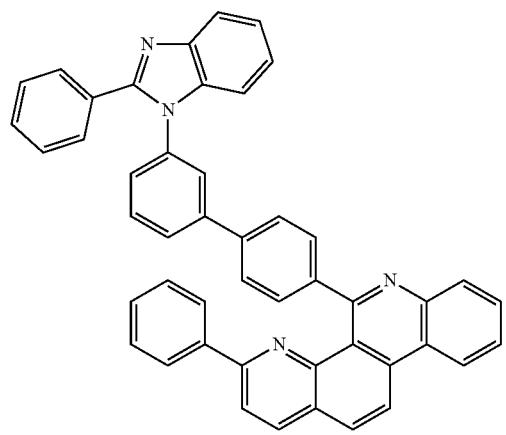
175
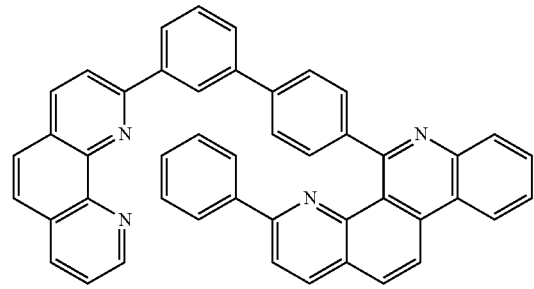
176
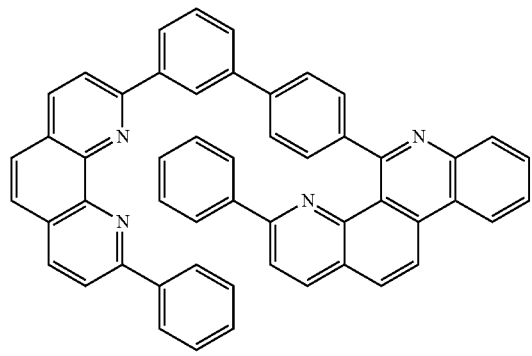
177
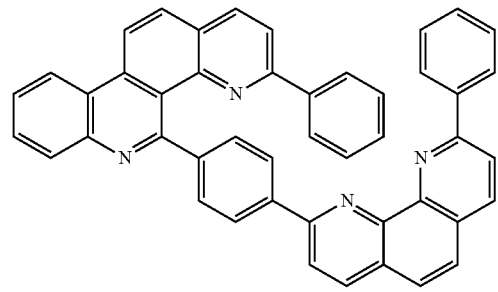
178
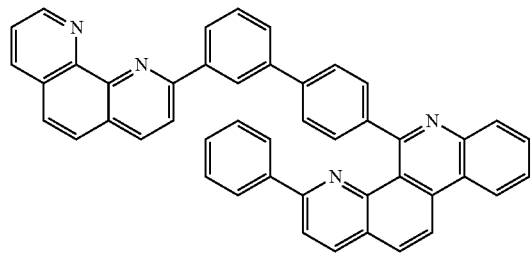
179
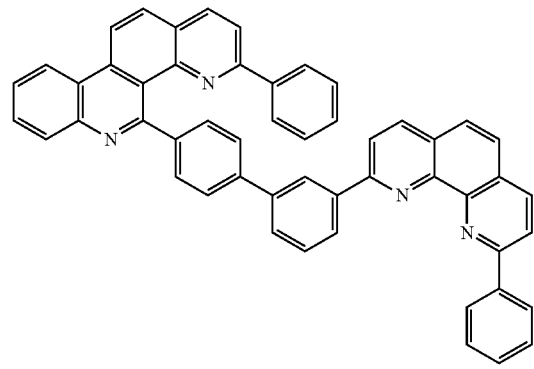
180
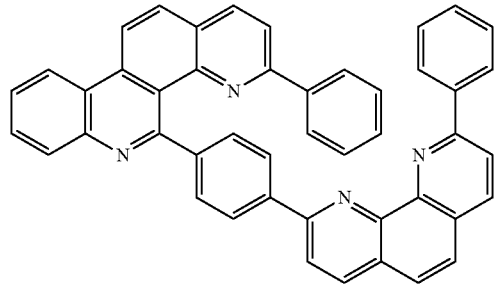
181
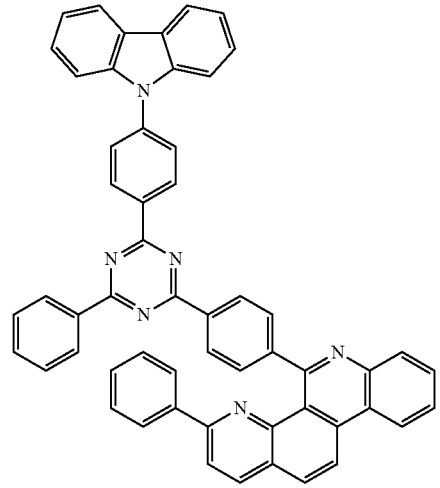

-continued
182 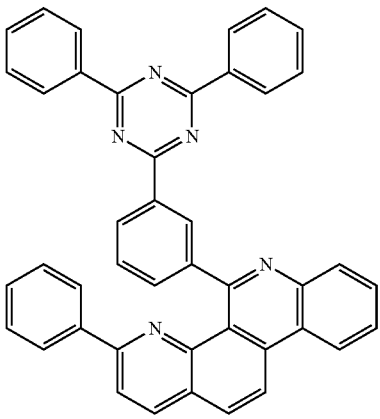
183 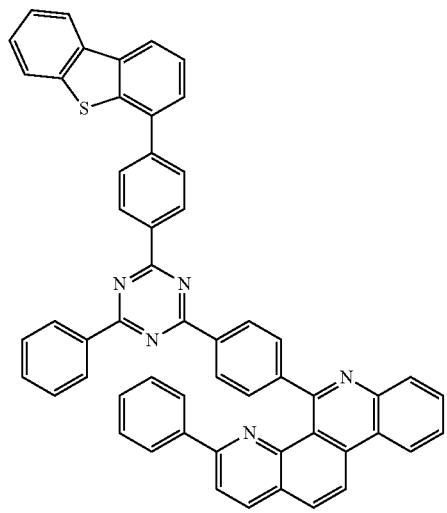
184 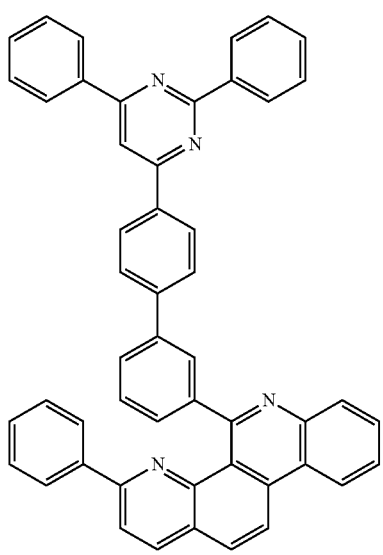
185 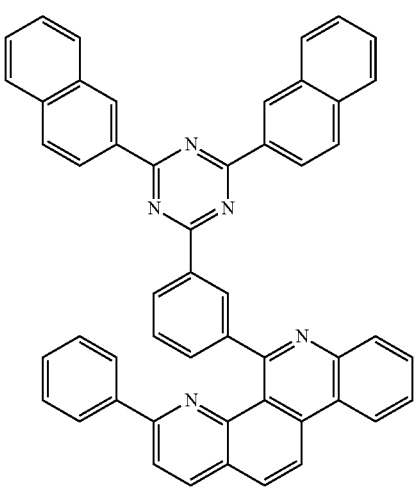
186 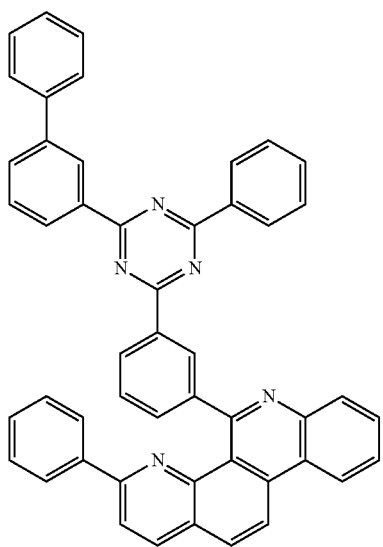
187 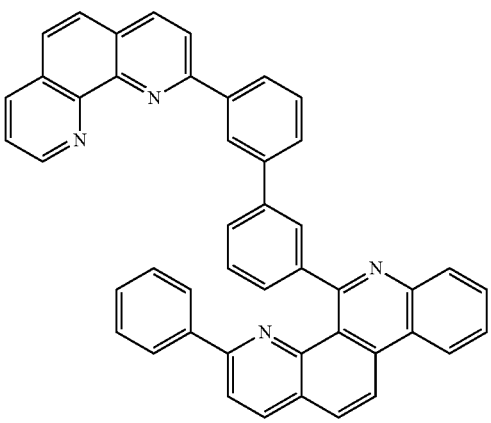

-continued
188
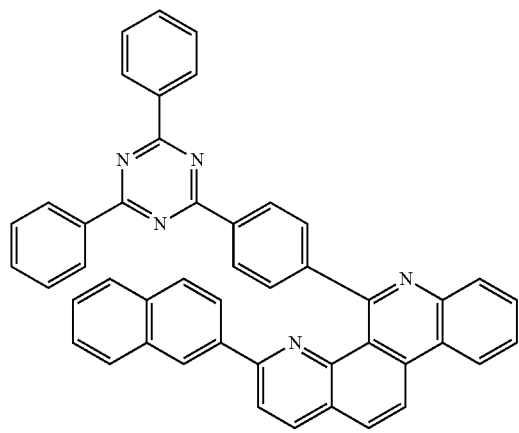
189
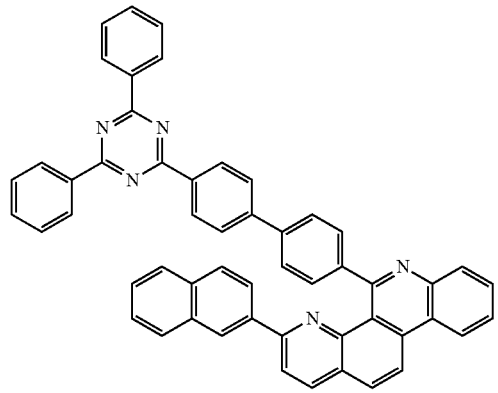
190
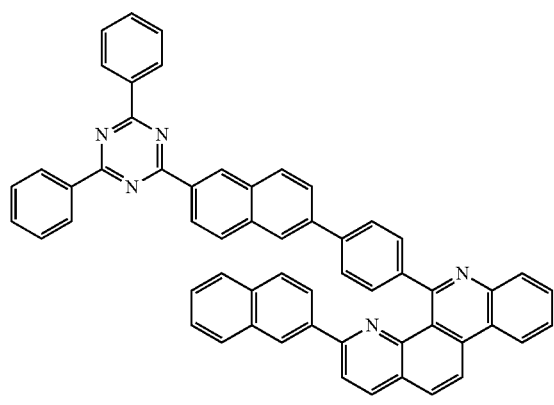
191
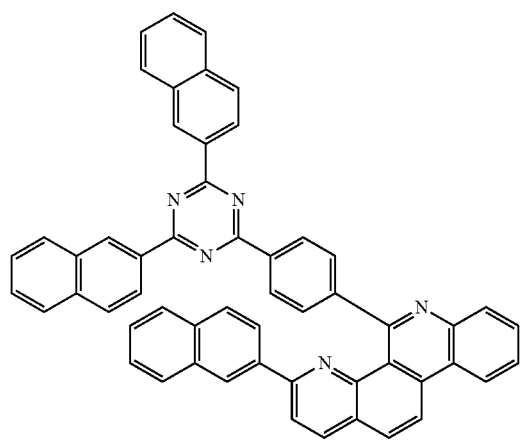
192
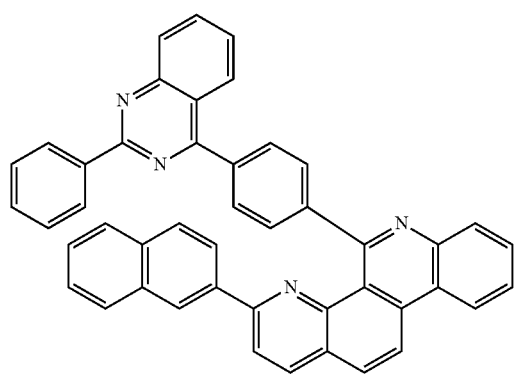
193
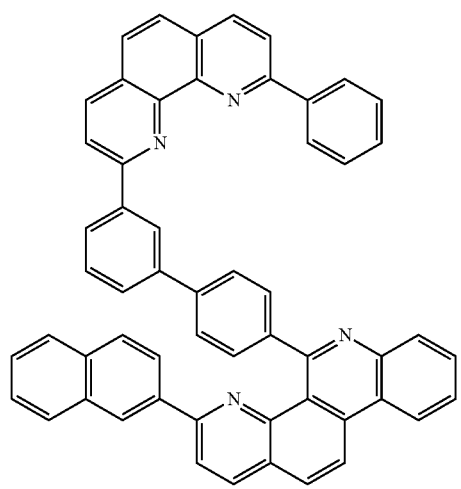

-continued
194
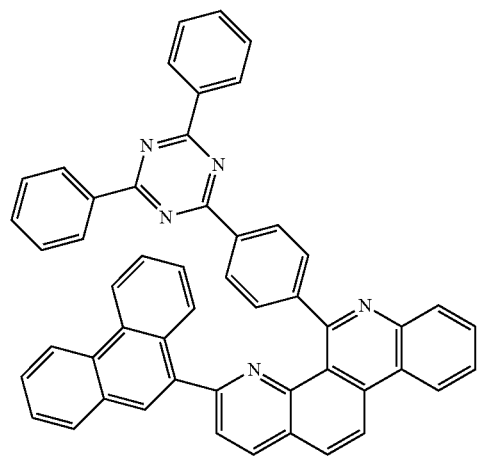
195
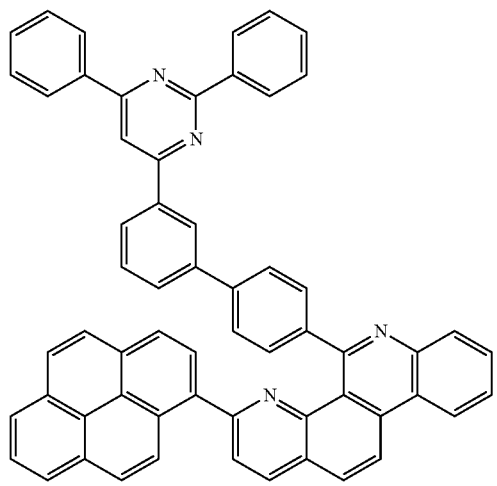
196
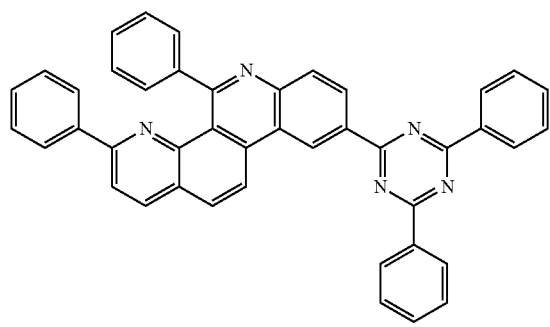
197
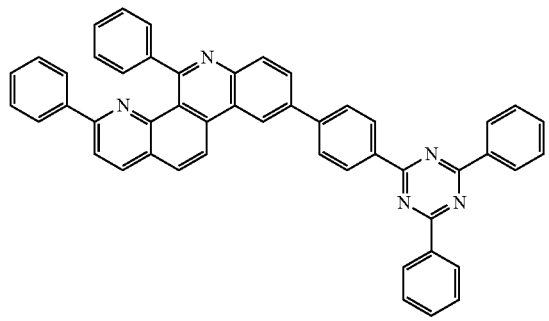
198
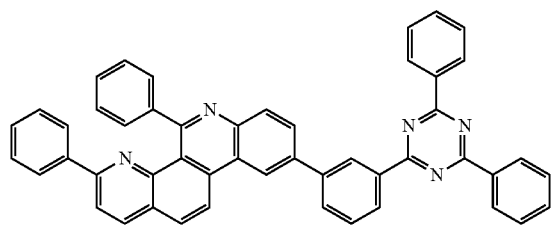
199
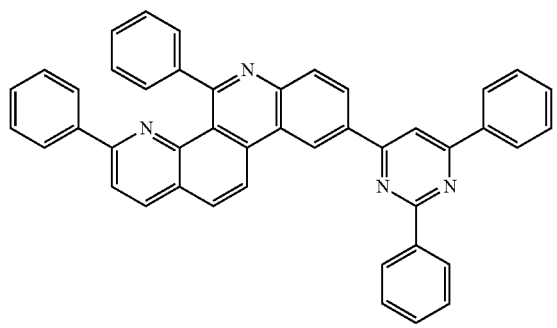
200
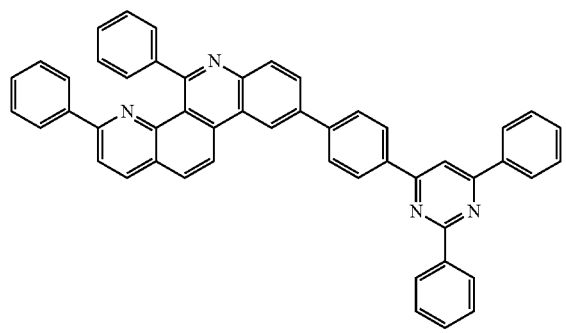
201
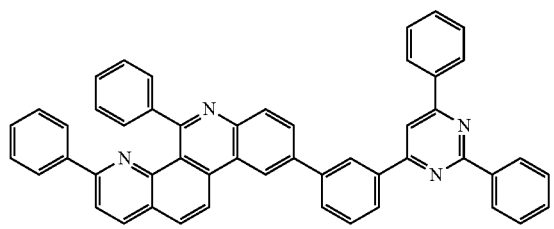

-continued
202
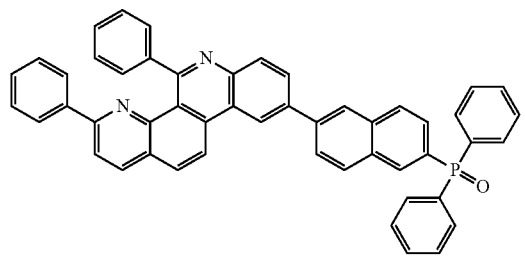
203
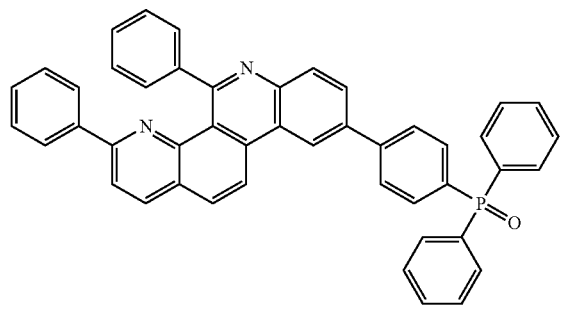
204
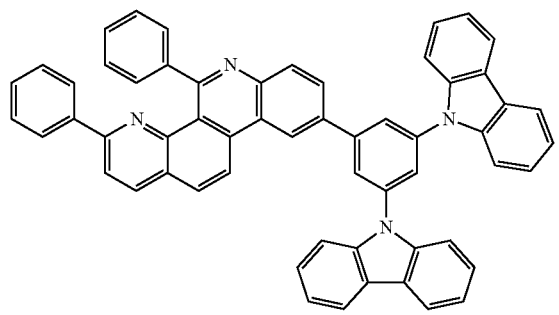
205
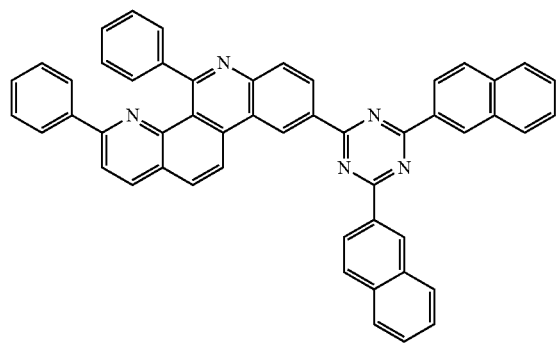
206
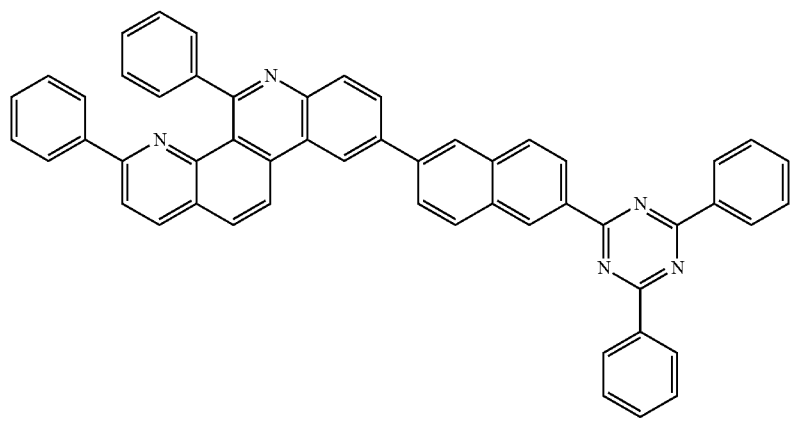
207
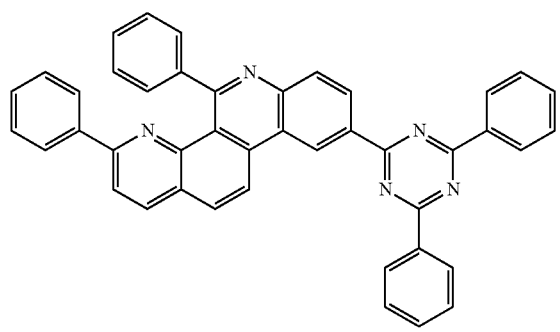
208
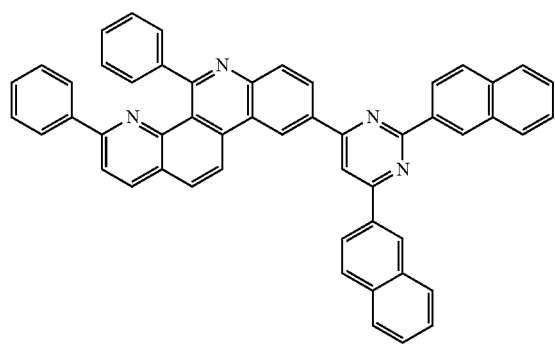

-continued
209
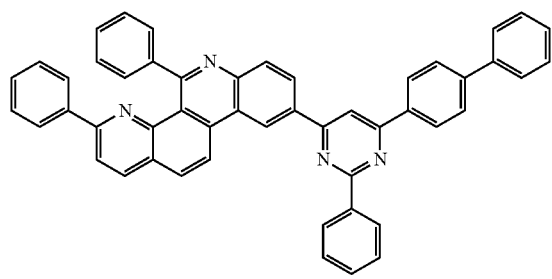
210
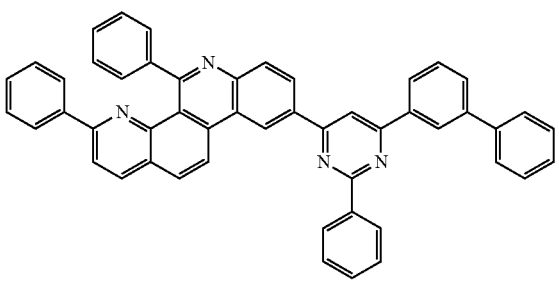
211
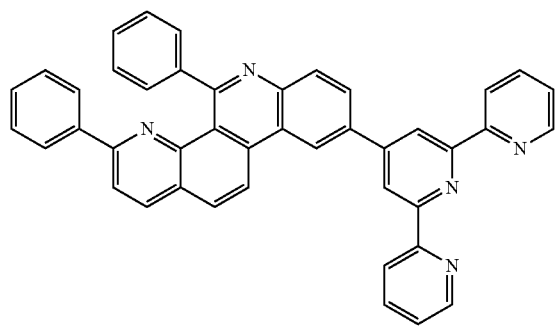
212
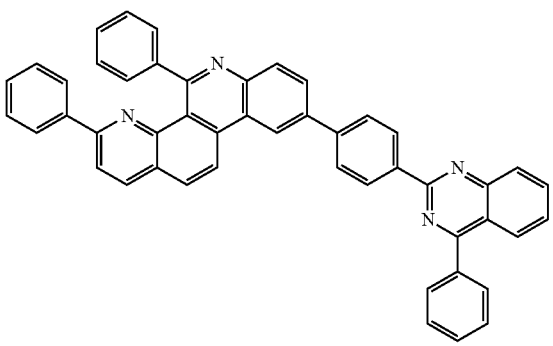
213
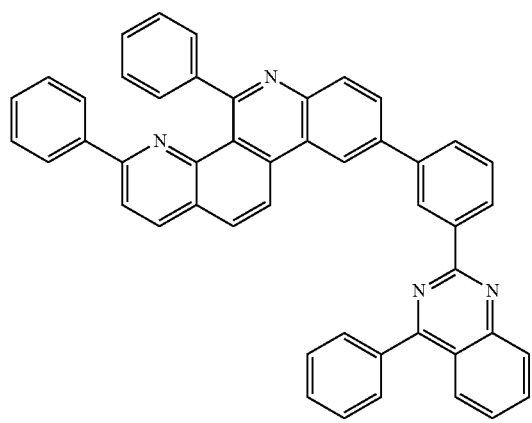
214
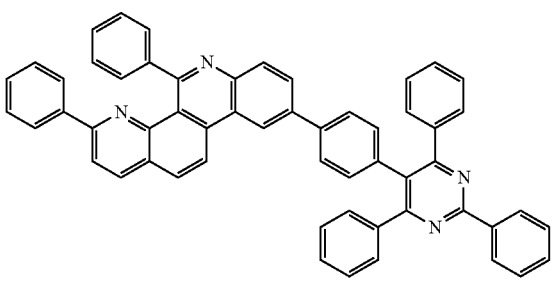
215
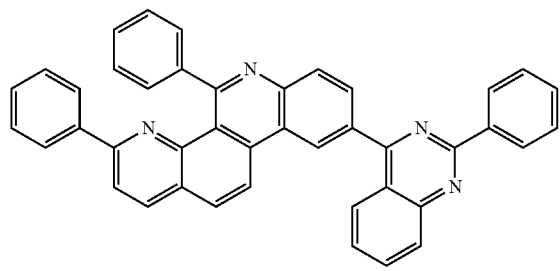
216
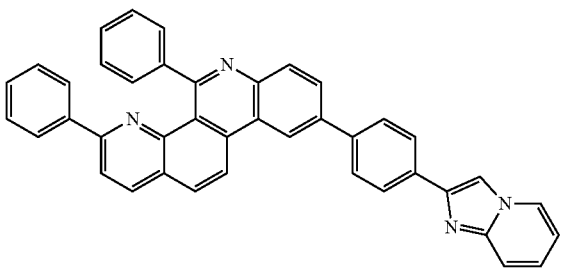

-continued
217
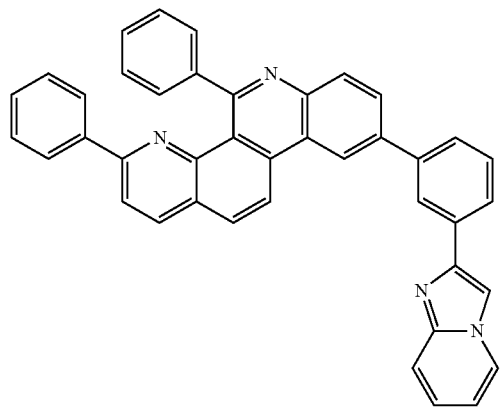
218
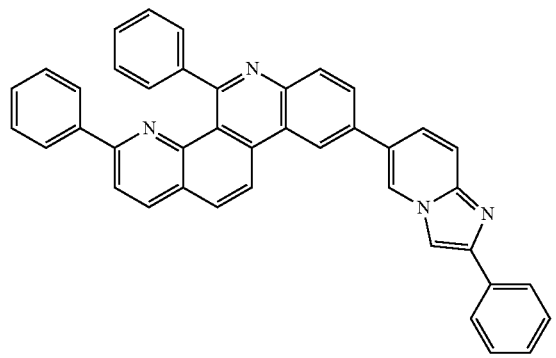
219
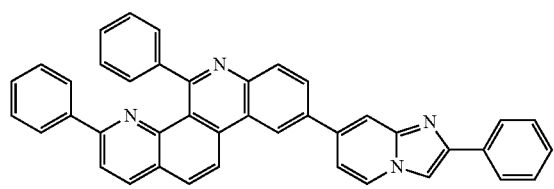
220
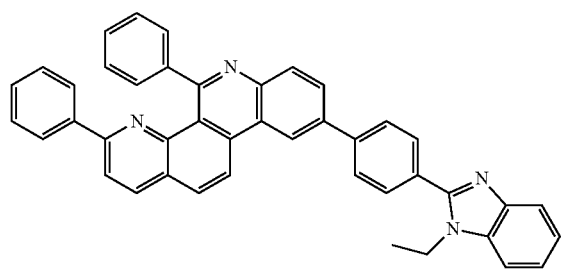
221
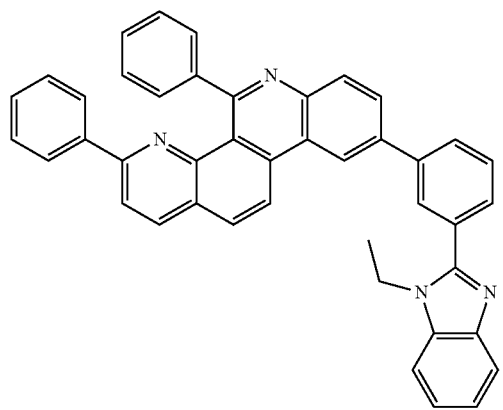
222
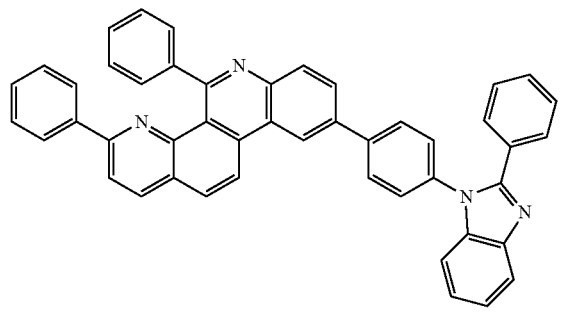
223
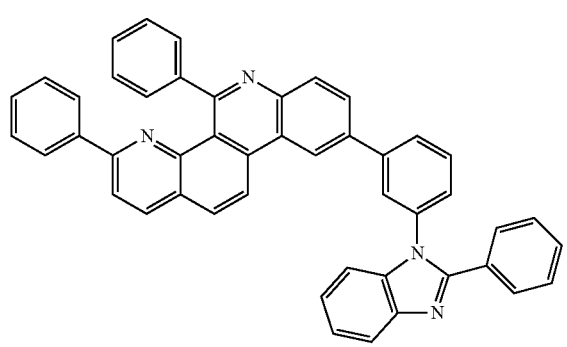
224
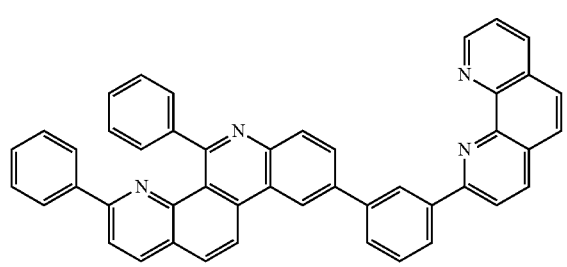

-continued
225
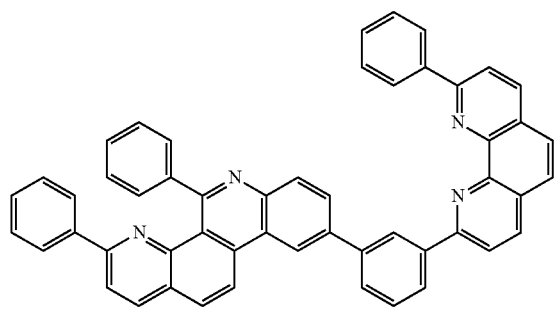
226
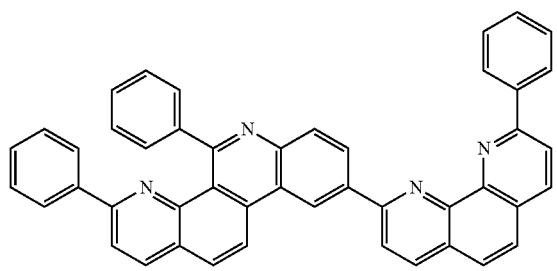
227
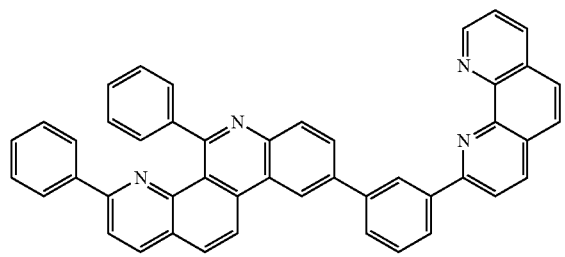
228
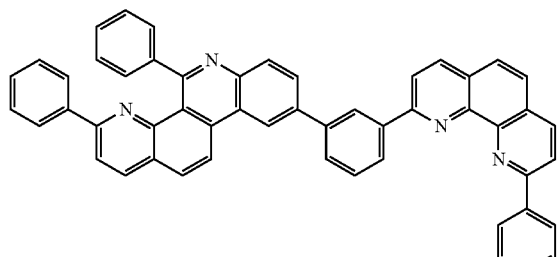
229
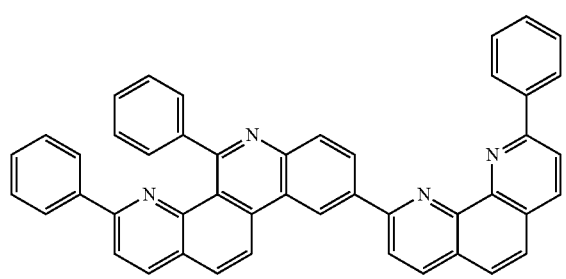
230
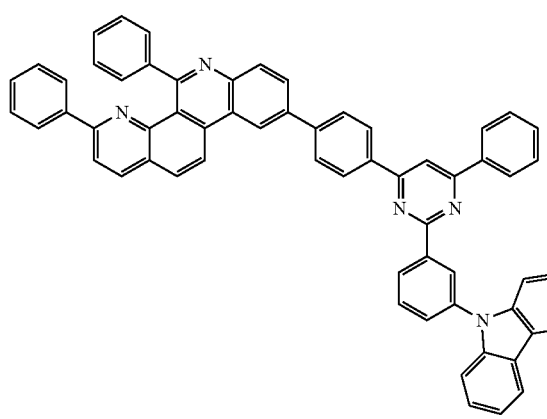
231
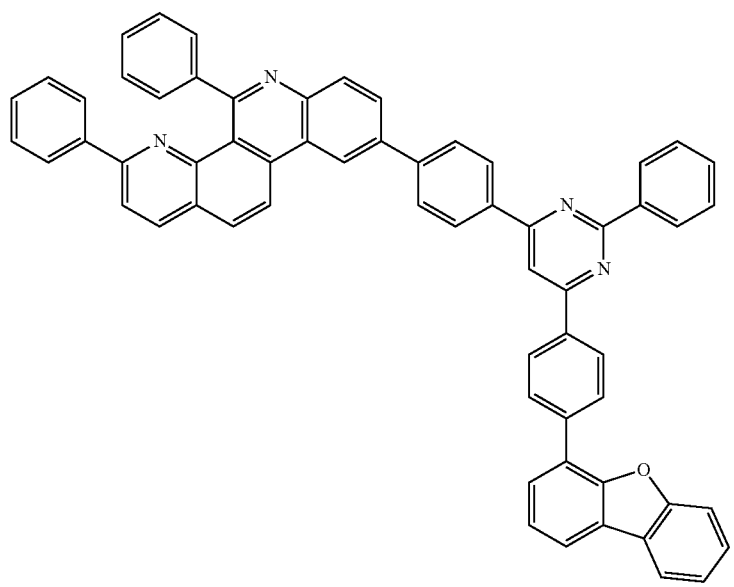

232
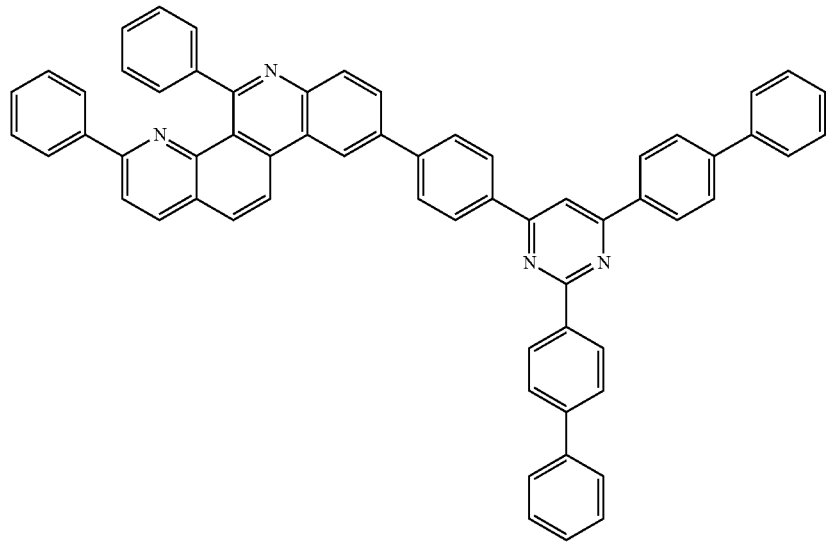
233
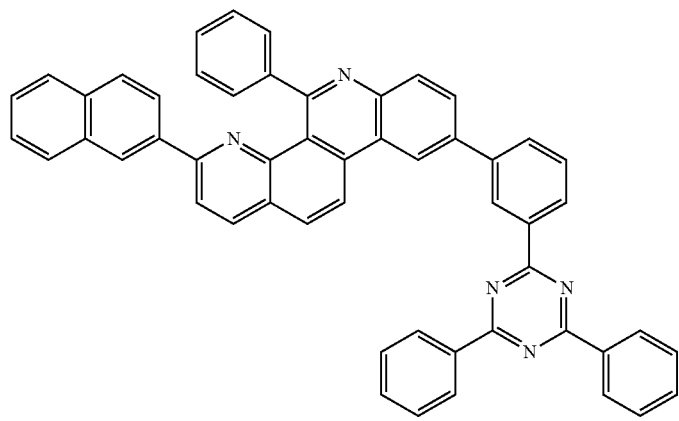
234
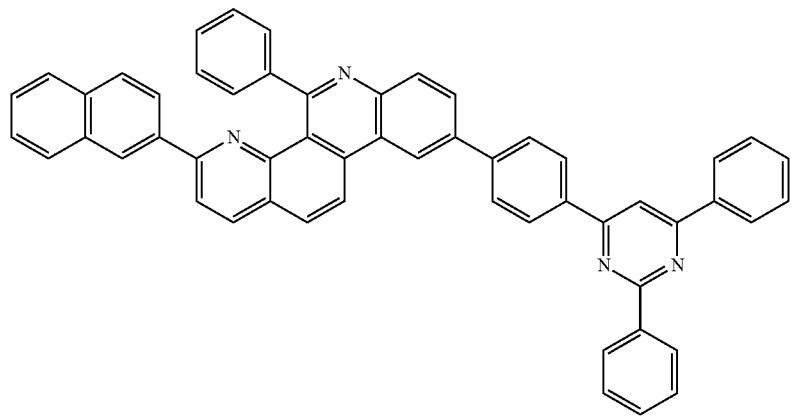

235
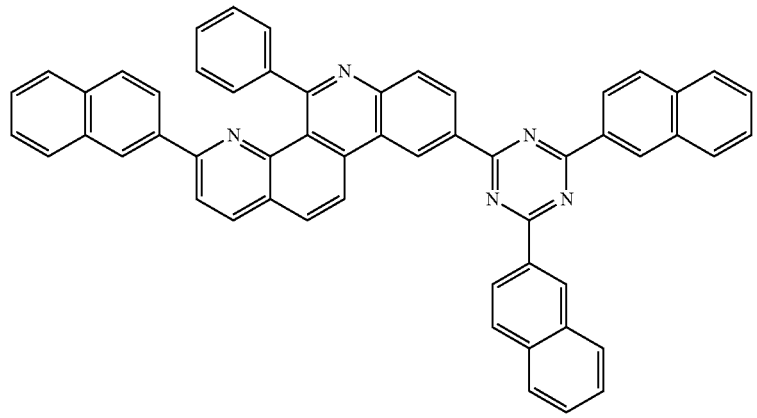
236
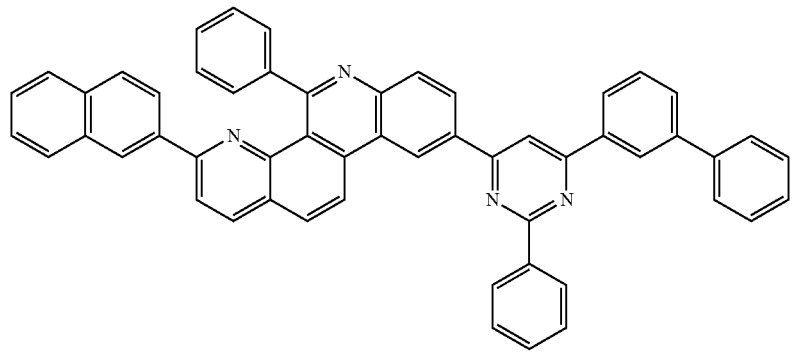
237 238
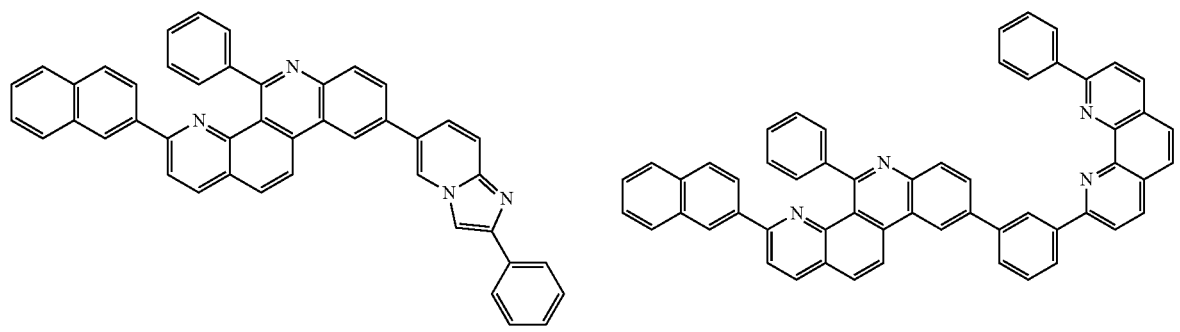
239 240
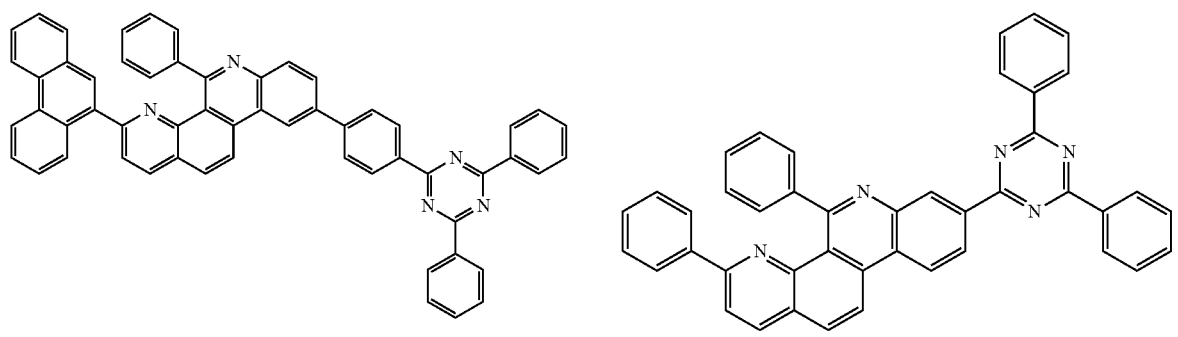

-continued
241
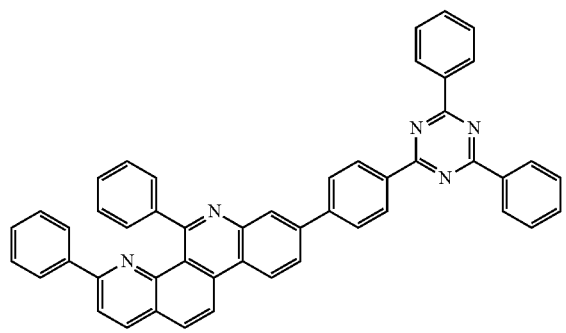
242
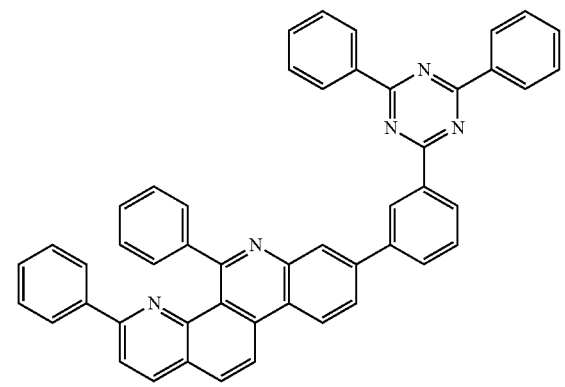
243
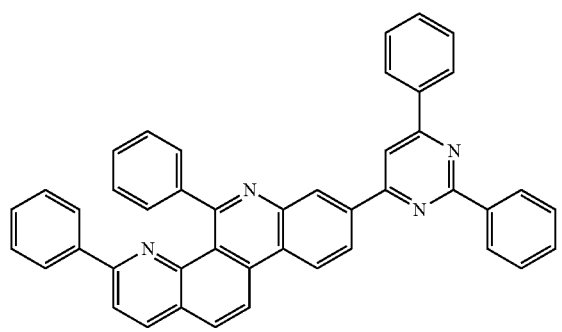
244
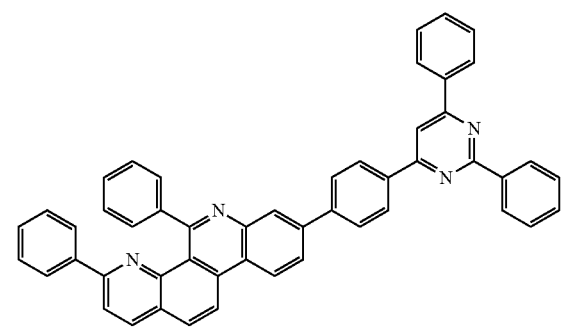
245
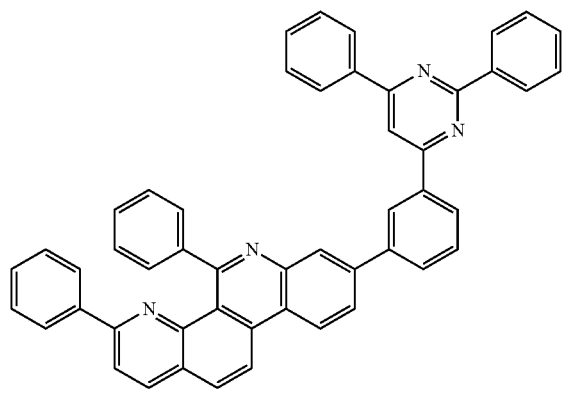
246
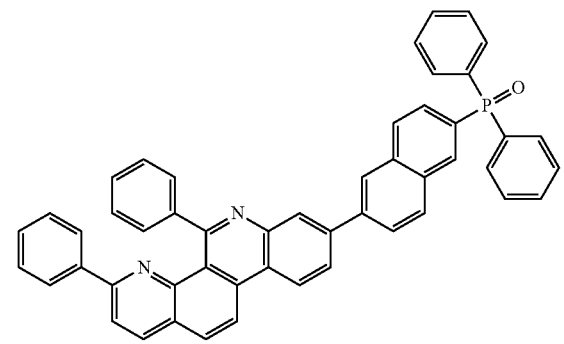
247
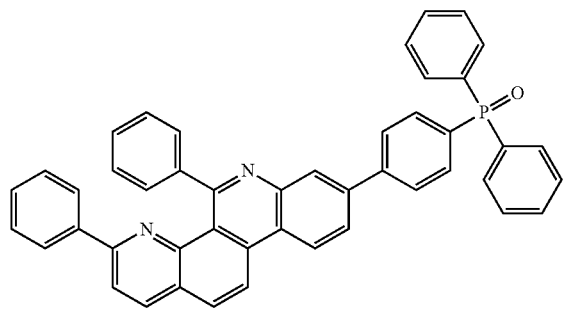
248
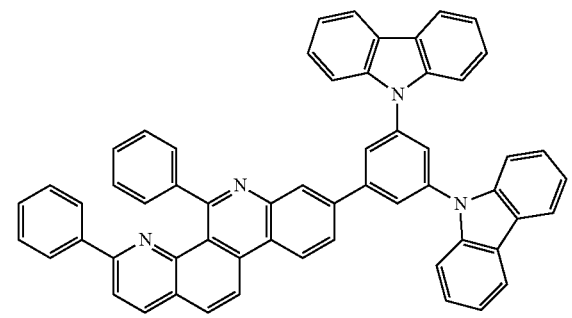

-continued
249
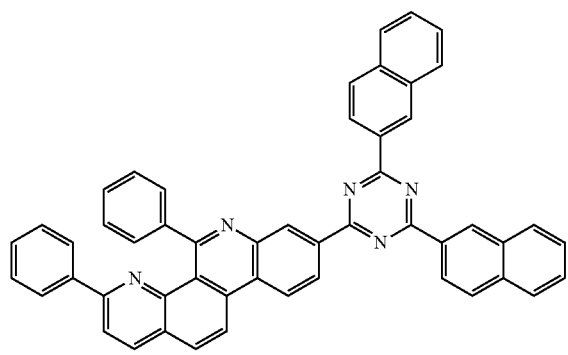
250
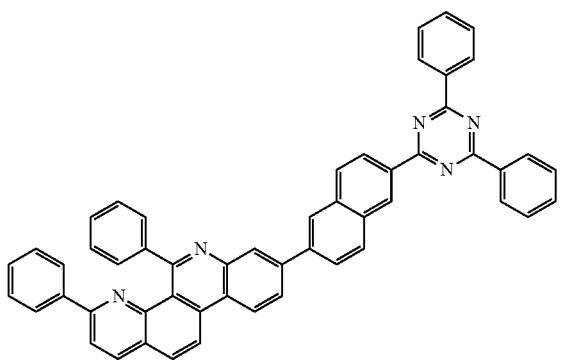
251
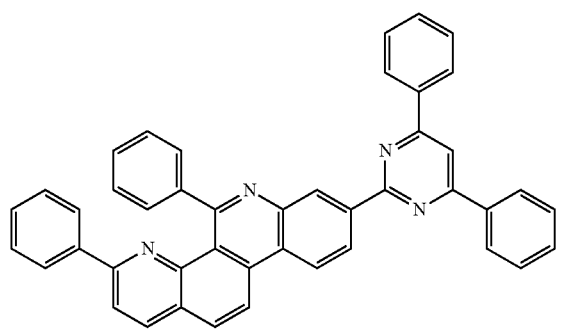
252
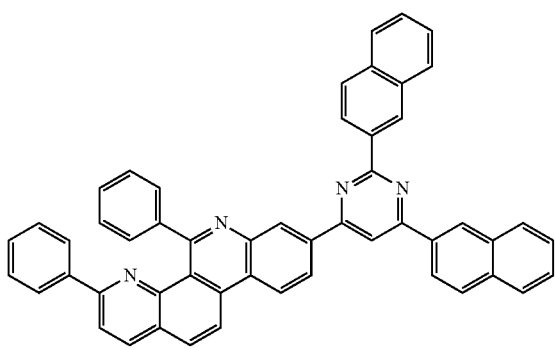
253
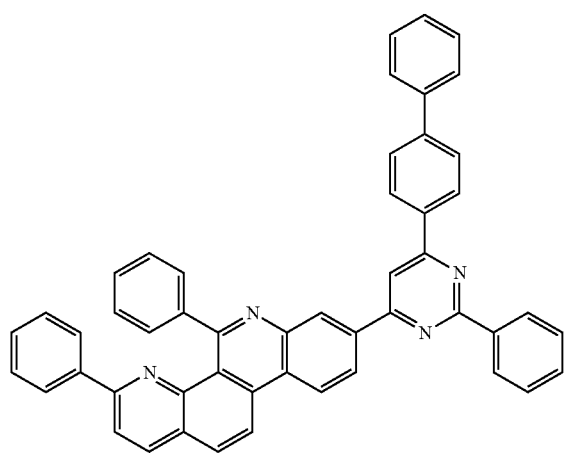
254
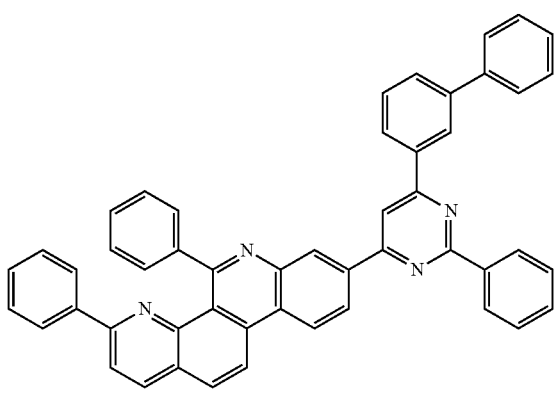
255
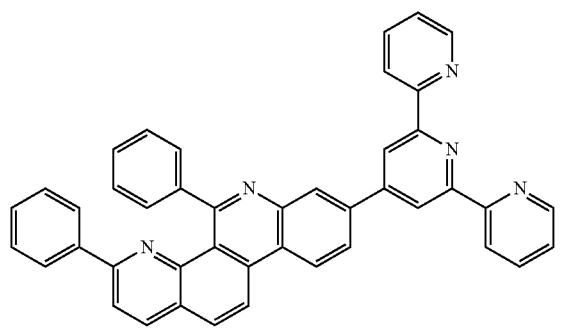
256
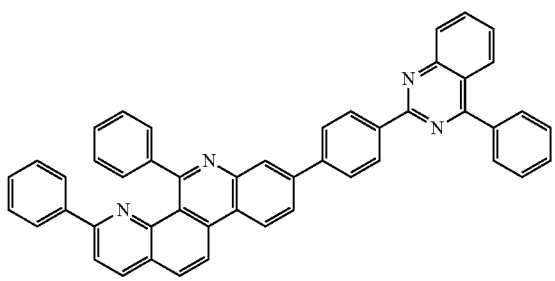

-continued
257
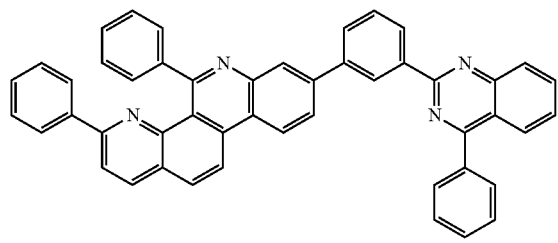
258
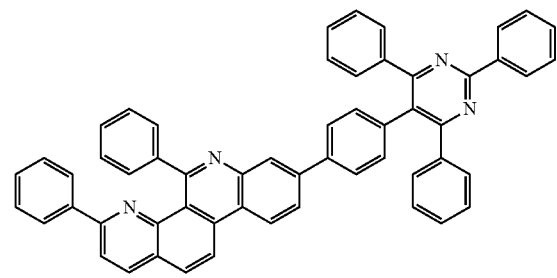
259
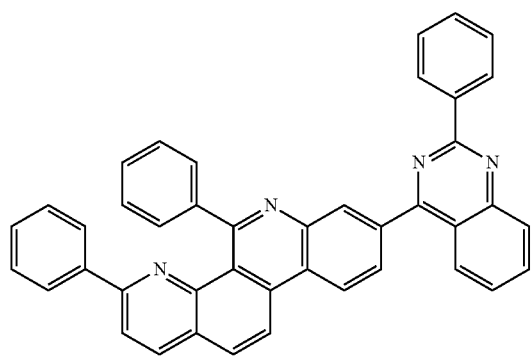
260
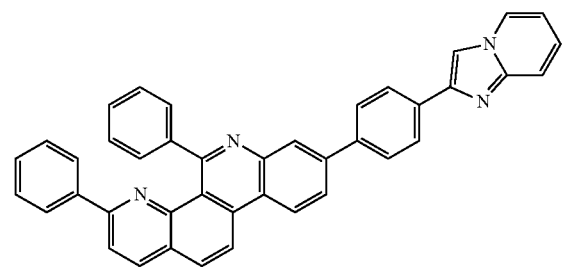
261
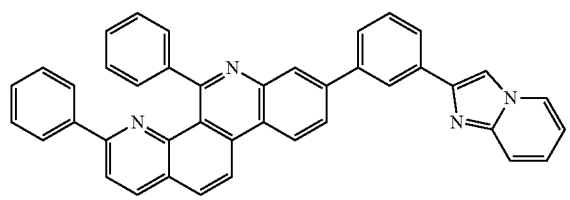
262
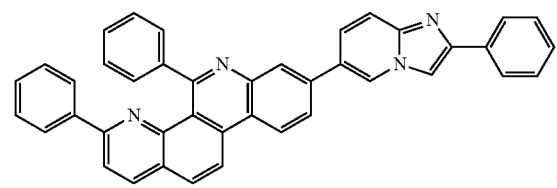
263
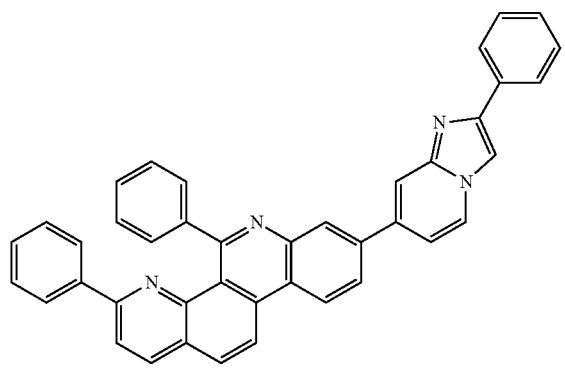
264
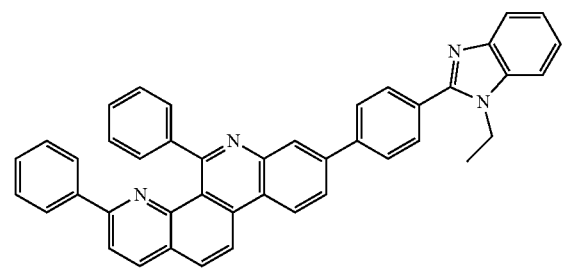
265
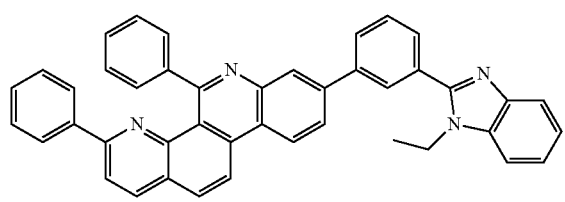
266
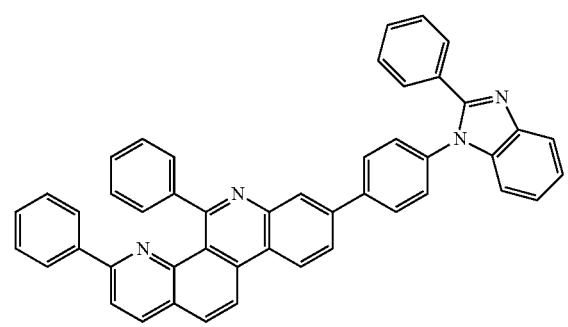

-continued
267
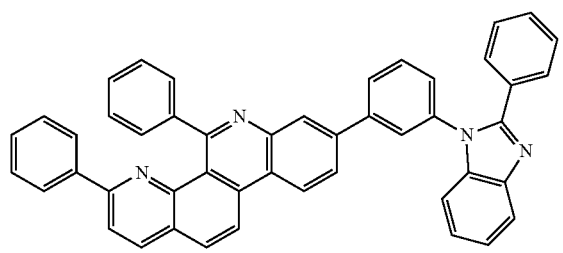
268
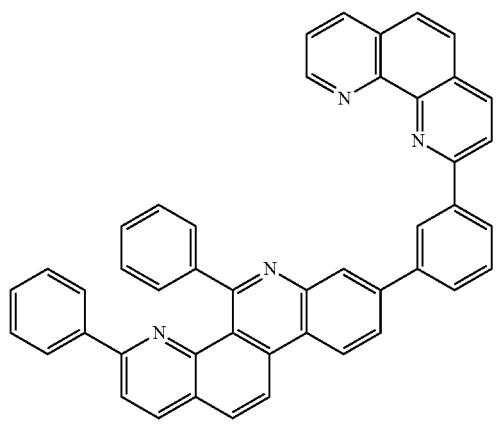
269
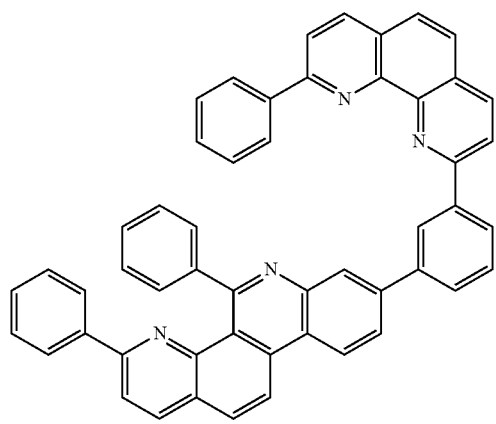
270
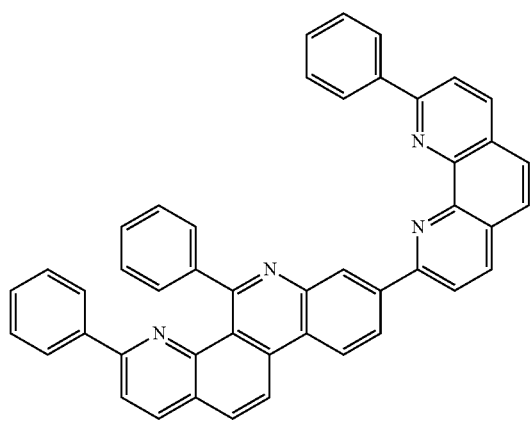
271
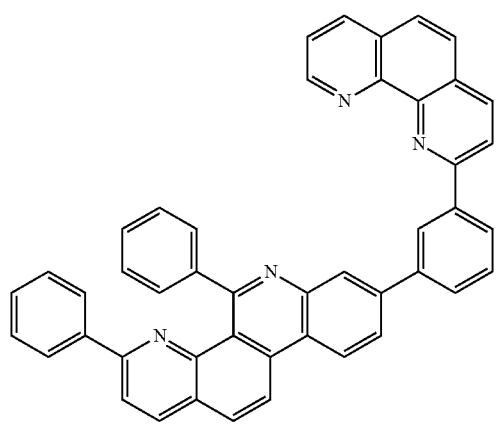
272
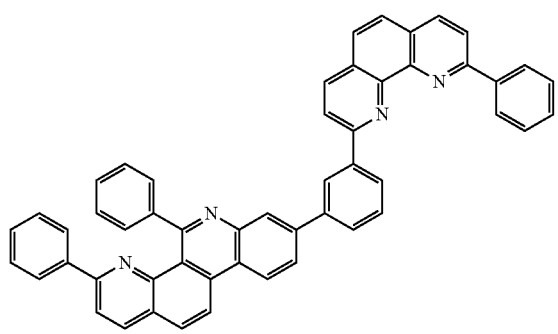

-continued
273
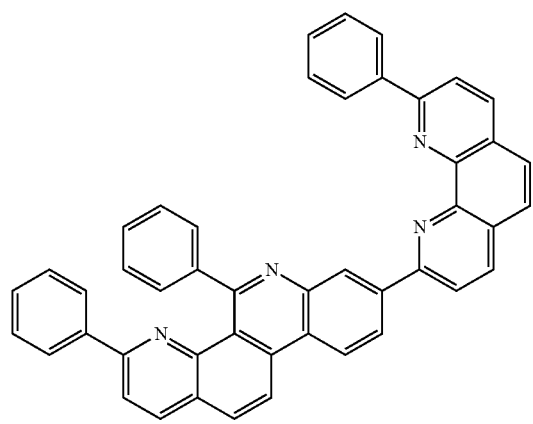
274
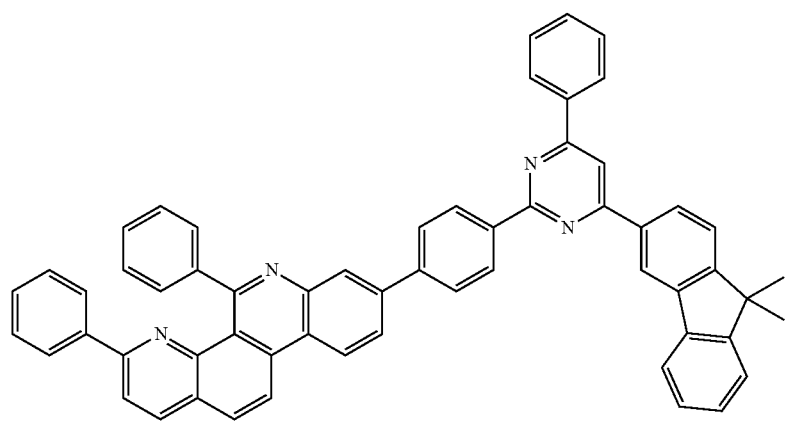
275
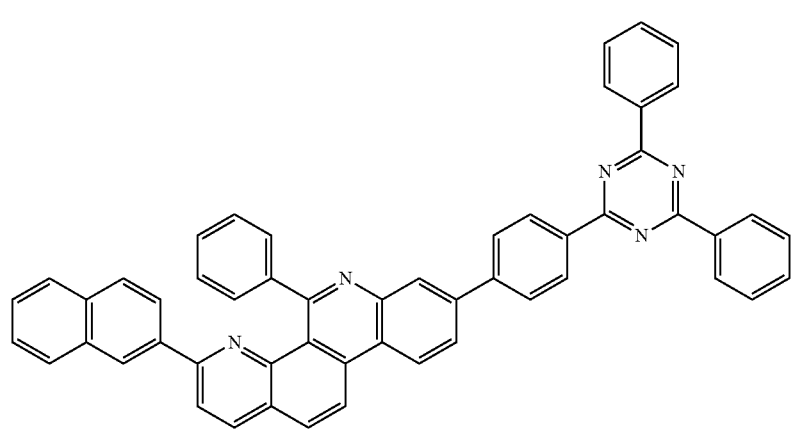
276
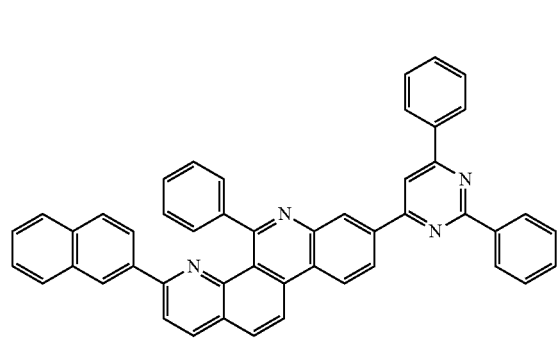
277
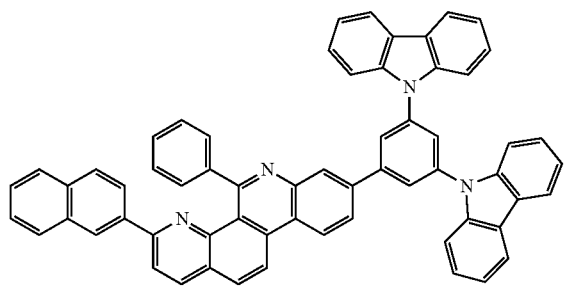

278
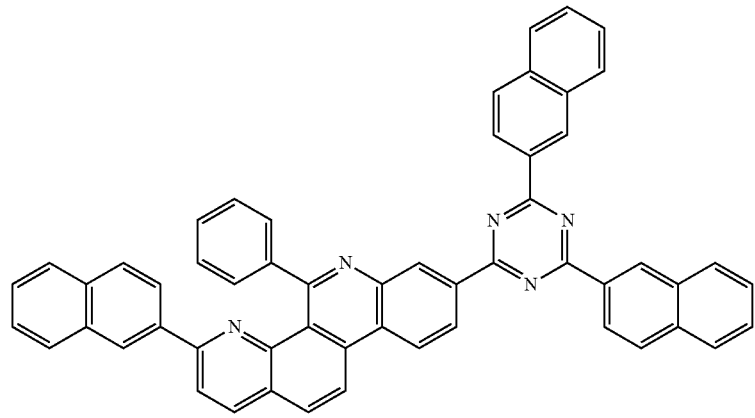
279
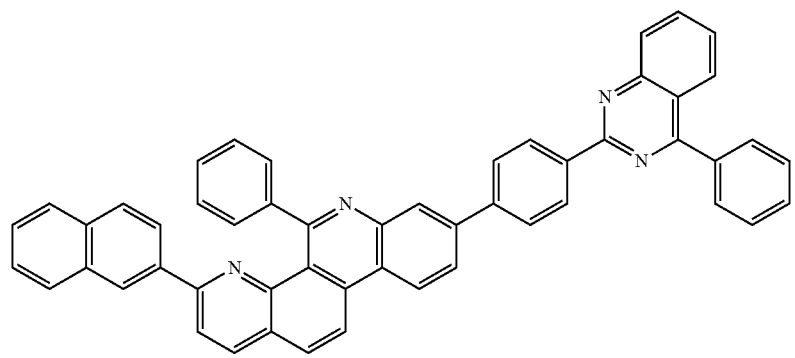
280
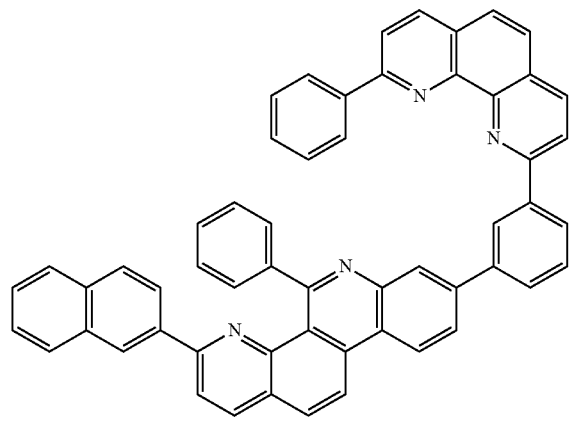
281
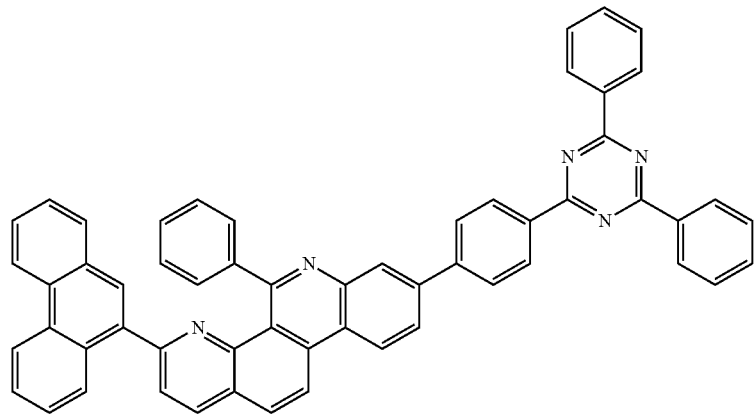

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises a light emitting layer, and the light emitting layer comprises the heterocyclic compound.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron blocking layer or a hole blocking layer, and the electron blocking layer or the hole blocking layer comprises the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100).

However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer comprising Chemical Formula 1 may further comprise other materials as necessary.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4''-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 1

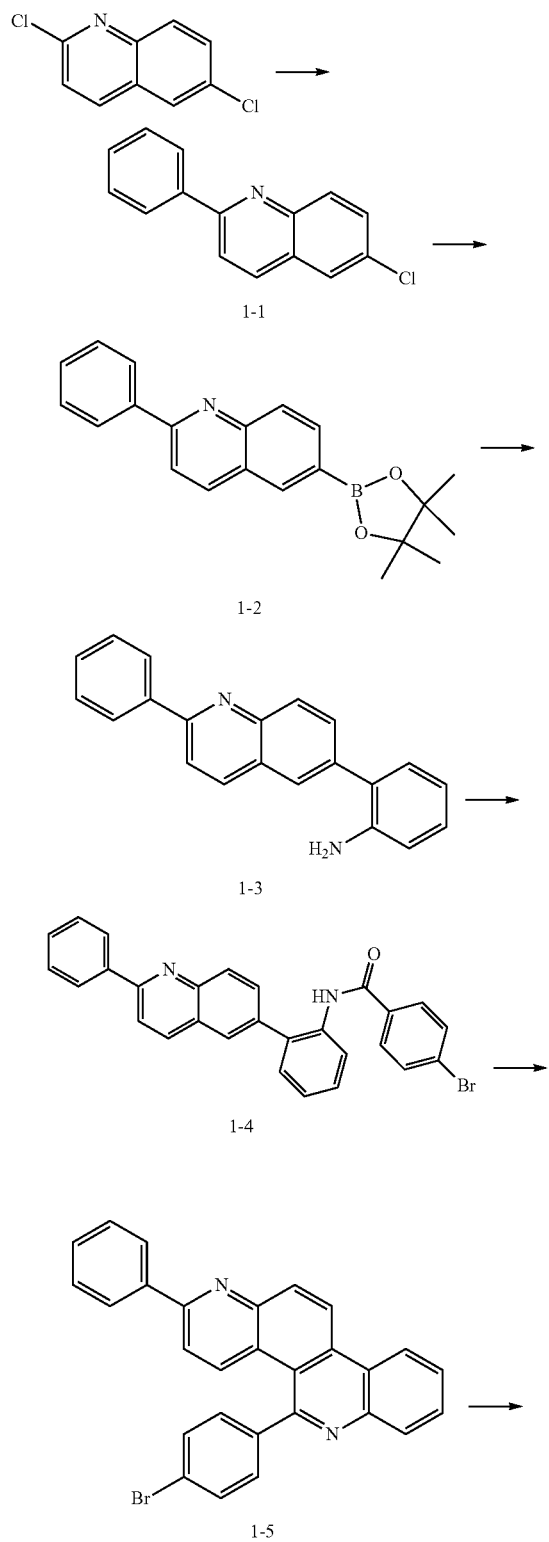

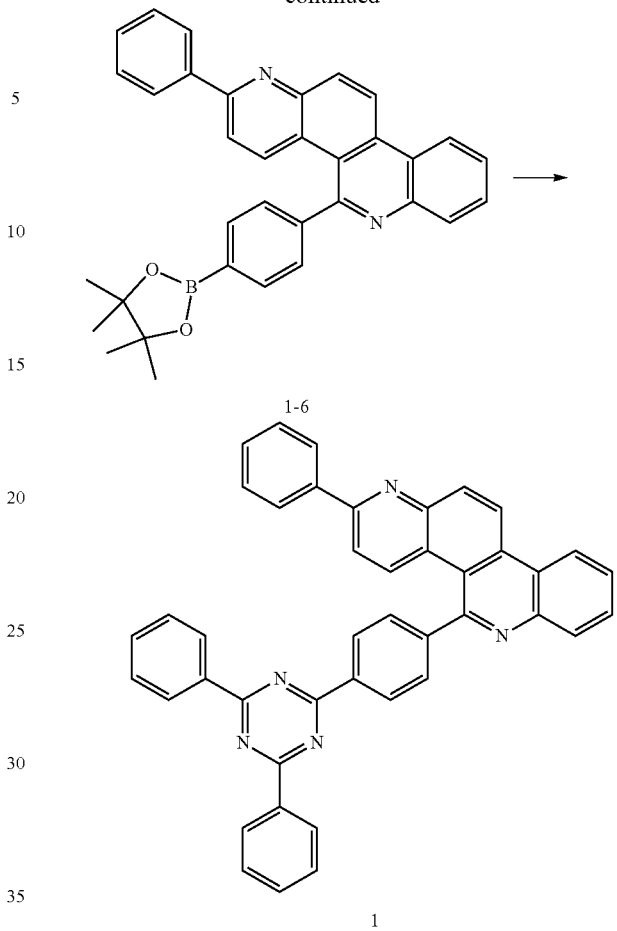

Preparation of Compound 1-1

2,6-Dichloroquinoline (20 g, 101 mmol, 1 eq.), Pd(PPh$_3$)$_4$ (5.8 g, 0.05 eq.), K$_2$CO$_3$ (41.9 g, 3.0 eq.) and toluene/EtOH/H$_2$O were added, and then stirred for 3 hours at 110° C. After the reaction was completed, the result was cooled to room temperature, and extracted with distilled water and ethyl acetate (EA). After drying the organic layer with anhydrous MgSO$_4$, the solvent was removed using a rotary evaporator, and the result was purified by column chromatography using dichloromethane and hexane as a developing solvent to obtain target Compound 1-1 (16.6 g, 69%).

Preparation of Compound 1-2

After dissolving Compound 1-1 (16.6 g, 69.3 mmol) in 1,4-dioxane, bis(pinacolato)diboron, Pd(dppf)Cl$_2$ and potassium acetate were added thereto, and the mixture was stirred for 2 hours at 110° C. After the reaction was completed, the result was extracted with distilled water and ethyl acetate (EA). After drying the organic layer with anhydrous MgSO$_4$, the solvent was removed using a rotary evaporator, and the result was purified by column chromatography using dichloromethane as a developing solvent to obtain target Compound 1-2 (18.8 g, 82%).

Preparation of Compound 1-3

After dissolving Compound 1-2 (18.8 g, 56.8 mmol) in 1,4-dioxane and H$_2$O, 2-bromoaniline (9.8 g, 1 eq.), Pd(PPh$_3$)$_4$ (3.3 g, 0.05 eq.) and K$_2$CO$_3$ (23.6 g, 3.0 eq.) were introduced thereto, and the mixture was stirred for 5 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 1-3 (12.3 g, 73%).

Preparation of Compound 1-4

After dissolving Compound 1-3 (12.3 g, 41.5 mmol) in dichloromethane (DCM), 4-bromobenzoyl chloride (10.0 g, 1.1 eq.) and triethanolamine (TEA) (8.7 ml, 1.5 eq.) were added thereto at 0° C., and the mixture was stirred for 2 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 1-4 (19.1 g, 96%).

Preparation of Compound 1-5

After dissolving Compound 1-4 (19.1 g, 39.8 mmol) in nitrobenzene, POCl$_3$ (3.7 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 1-5 (14 g, 76%).

Preparation of Compound 1-6

After dissolving Compound 1-5 (14 g, 30.3 mmol) in 1,4-dioxane, bis(pinacolato)diboron, Pd(dppf)Cl$_2$ and potassium acetate were added thereto, and the mixture was stirred for 2 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 1-6 (12.3 g, 80%).

Preparation of Compound 1

To Compound 1-6 (12.3 g, 24.2 mmol), 2-chloro-4,6-diphenyl-1,3,5-triazine (6.5 g, 1 eq.), Pd(PPh$_3$)$_4$ (1.4 g, 0.05 eq.), K$_2$CO$_3$ (10.0 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 1 (12.2 g, 82%).

[Preparation Example 2] Preparation of Compound 3

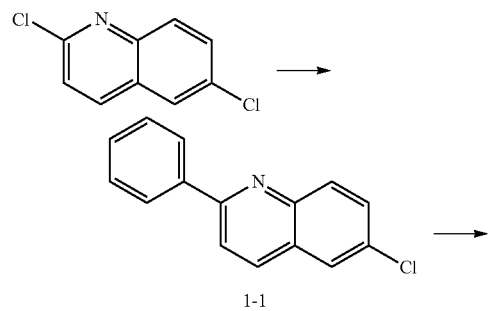

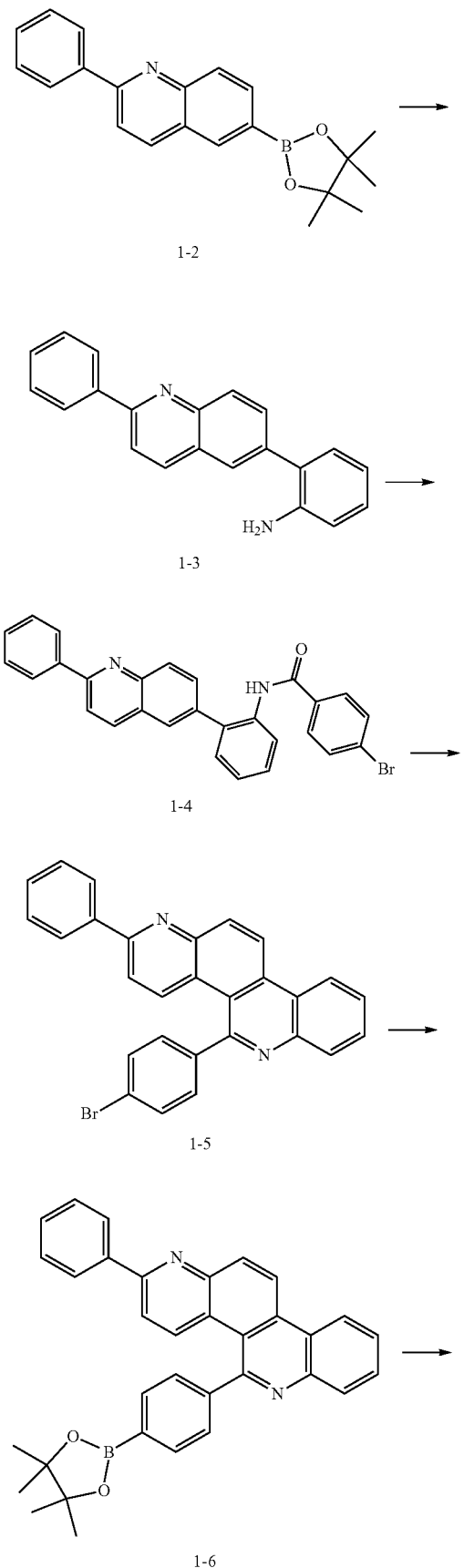

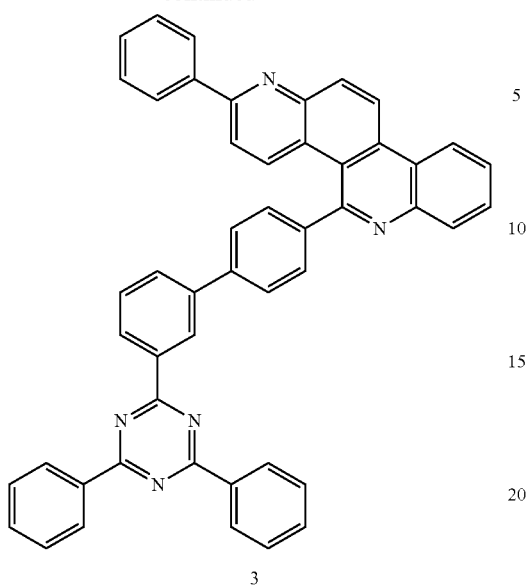
3
Preparation of Compound 3
Target Compound 3 was obtained in the same manner as in Preparation of Compound 1 in Preparation Example 1 except that 2-(3-bromophenyl)-4,6-diphenyl-1,3,5-triazine was used instead of 2-chloro-4,6-diphenyl-1,3,5-triazine.
[Preparation Example 3] Preparation of Compound 5
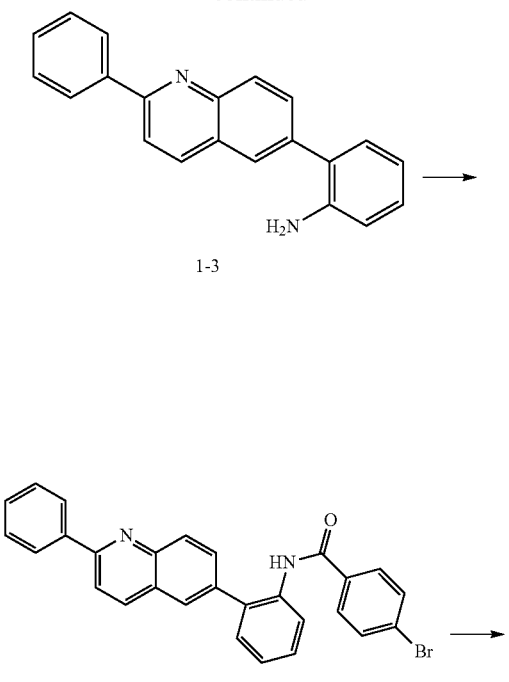
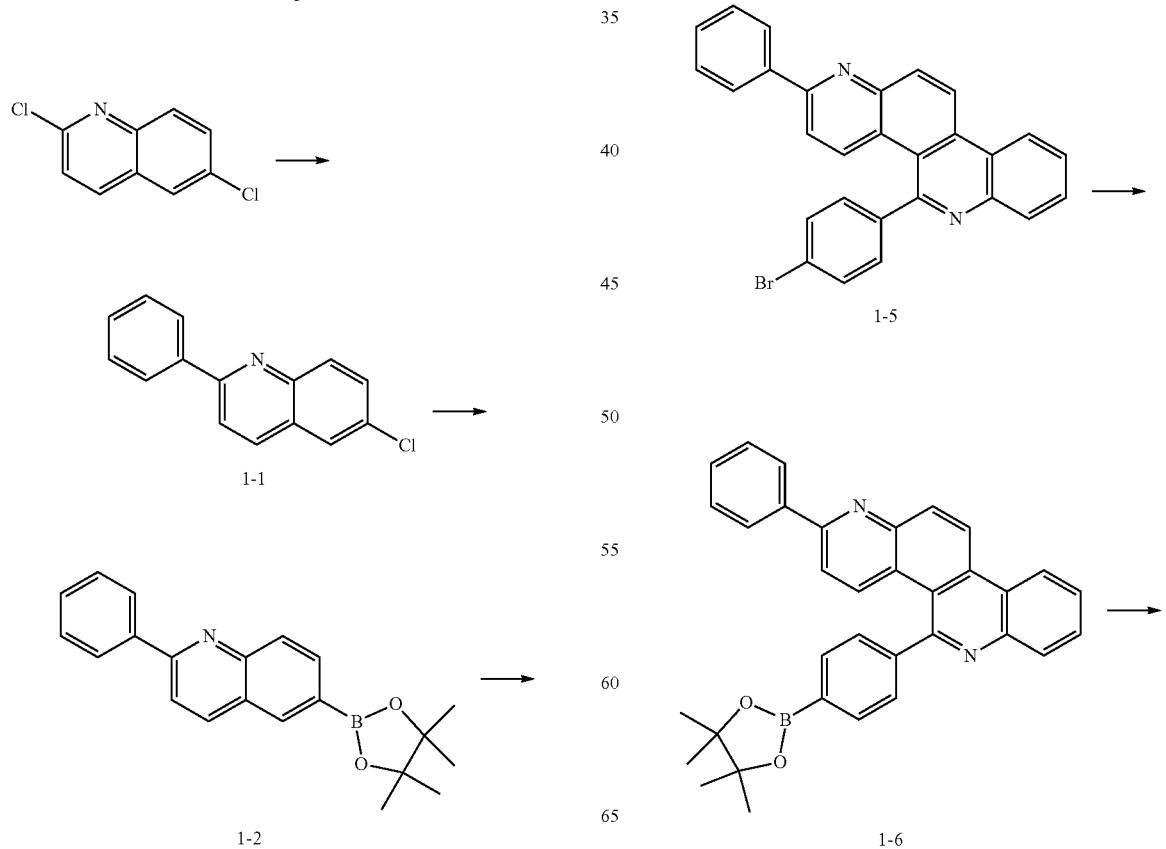

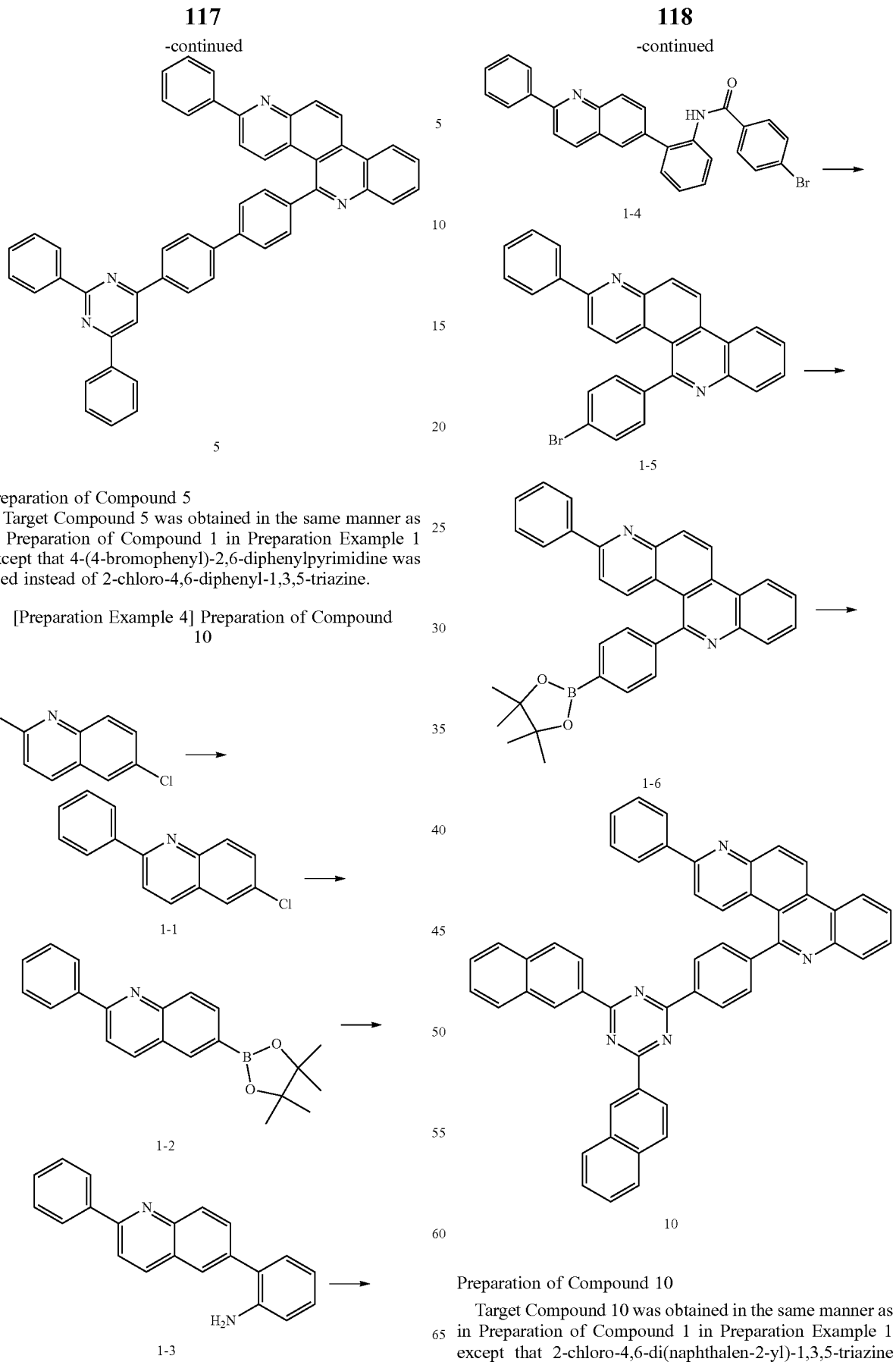

Preparation of Compound 5

Target Compound 5 was obtained in the same manner as in Preparation of Compound 1 in Preparation Example 1 except that 4-(4-bromophenyl)-2,6-diphenylpyrimidine was used instead of 2-chloro-4,6-diphenyl-1,3,5-triazine.

[Preparation Example 4] Preparation of Compound 10

Preparation of Compound 10

Target Compound 10 was obtained in the same manner as in Preparation of Compound 1 in Preparation Example 1 except that 2-chloro-4,6-di(naphthalen-2-yl)-1,3,5-triazine was used instead of 2-chloro-4,6-diphenyl-1,3,5-triazine.

[Preparation Example 5] Preparation of Compound 15
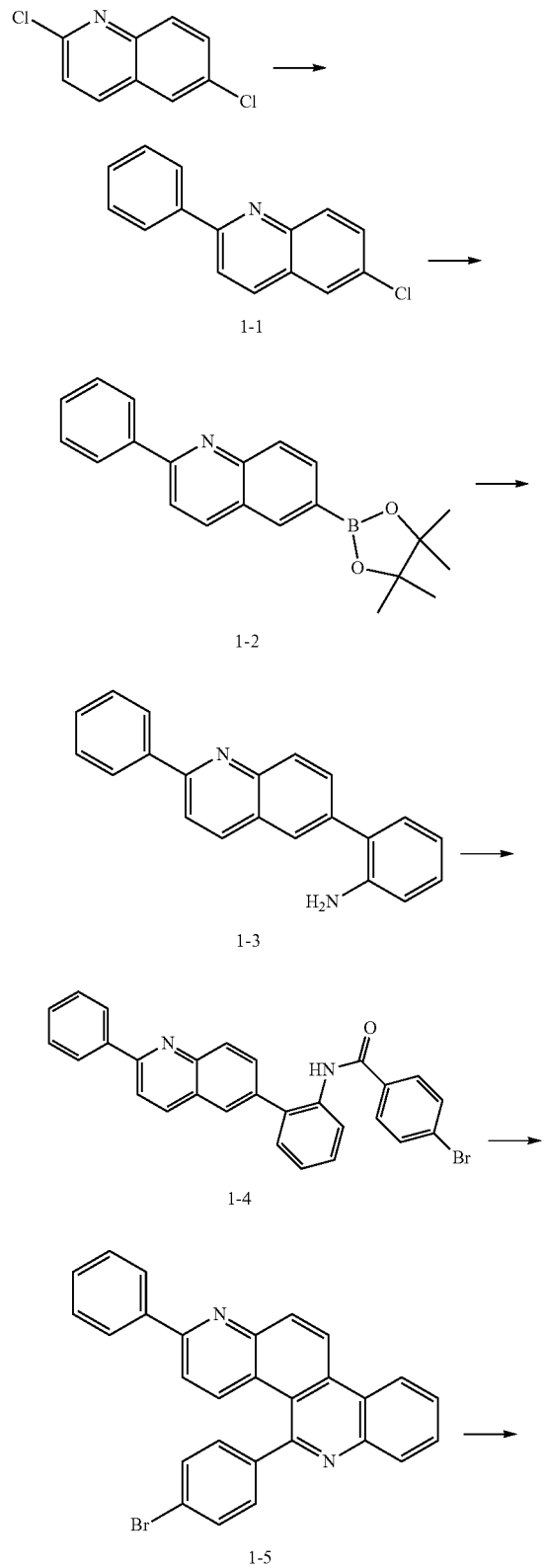
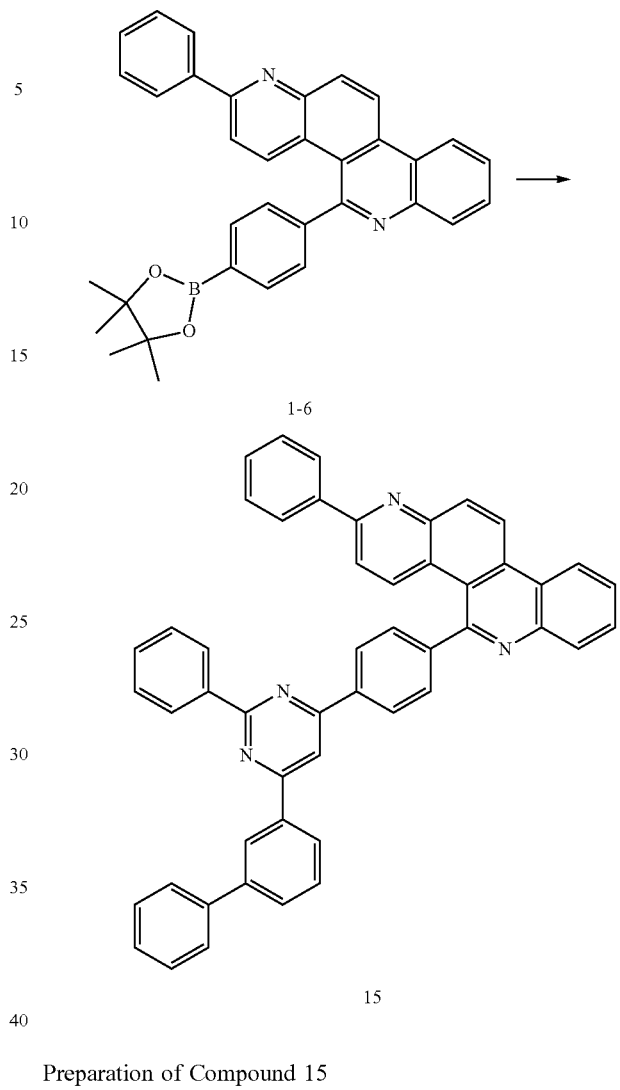
Preparation of Compound 15
Target Compound 15 was obtained in the same manner as in Preparation of Compound 1 in Preparation Example 1 except that 4-([1,1'-biphenyl]-3-yl)-6-chloro-2-phenylpyrimidine was used instead of 2-chloro-4,6-diphenyl-1,3,5-triazine.
[Preparation Example 6] Preparation of Compound 18
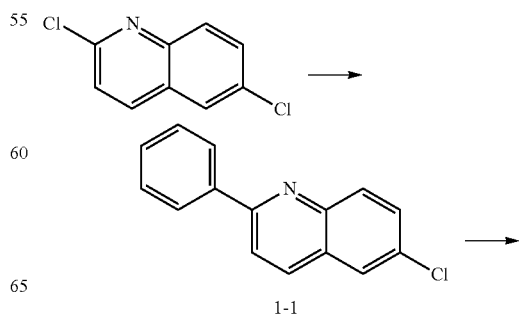

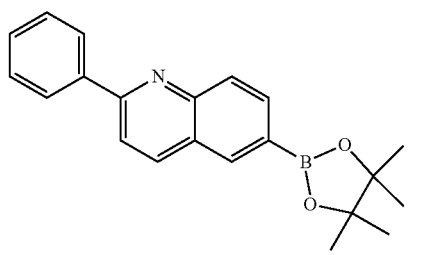
1-2
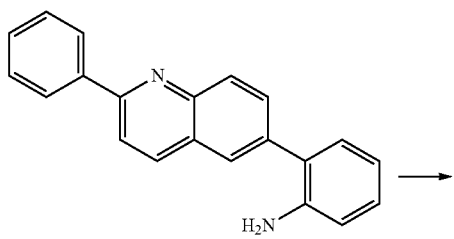
1-3
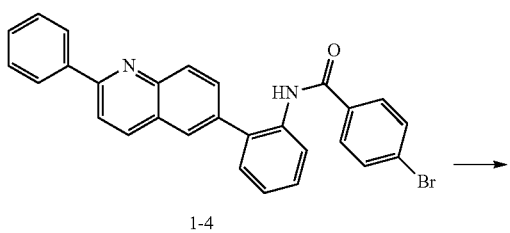
1-4
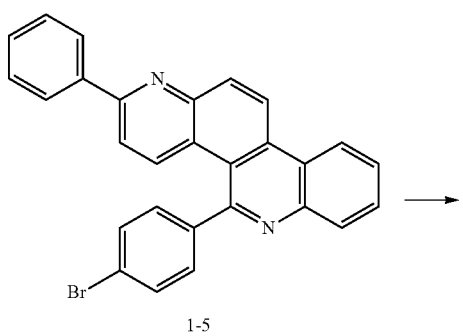
1-5
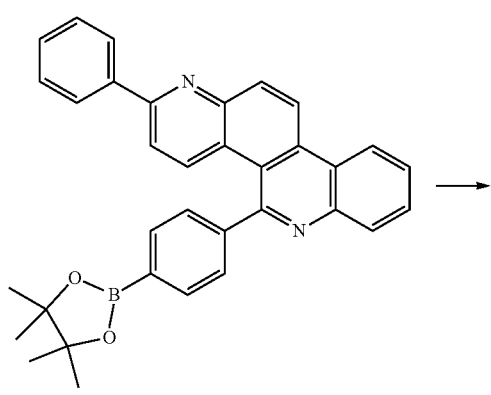
1-6
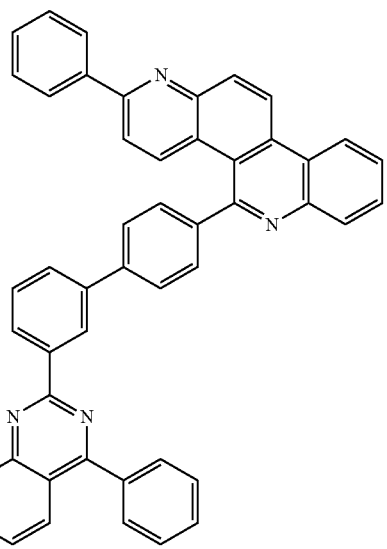
18
Preparation of Compound 18
Target Compound 18 was obtained in the same manner as in Preparation of Compound 1 in Preparation Example 1 except that 2-(3-bromophenyl)-4-phenylquinazoline was used instead of 2-chloro-4,6-diphenyl-1,3,5-triazine.
[Preparation Example 7] Preparation of Compound 22
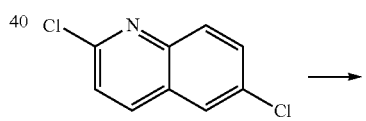
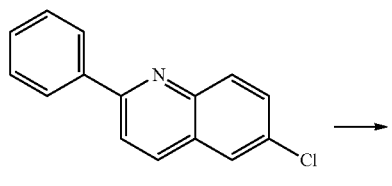
1-1
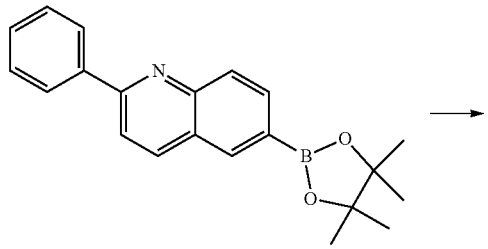
1-2

-continued
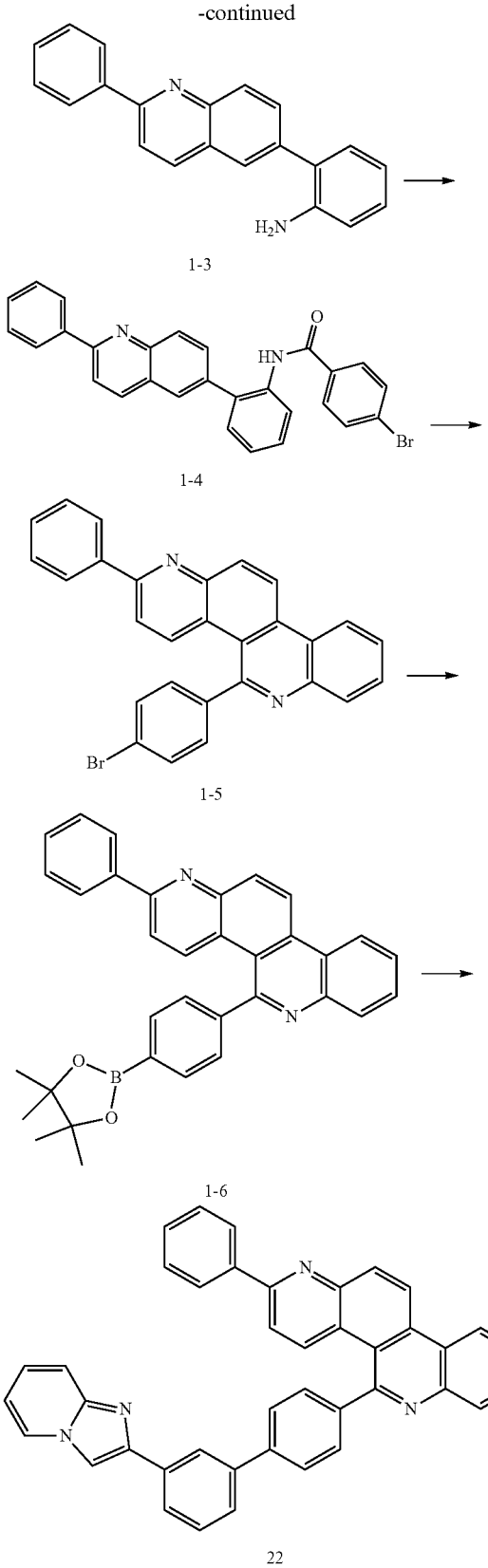
Preparation of Compound 22
Target Compound 22 was obtained in the same manner as in Preparation of Compound 1 in Preparation Example 1 except that 2-(3-bromophenyl)imidazo[1,2-a]pyridine was used instead of 2-chloro-4,6-diphenyl-1,3,5-triazine.
[Preparation Example 8] Preparation of Compound 27
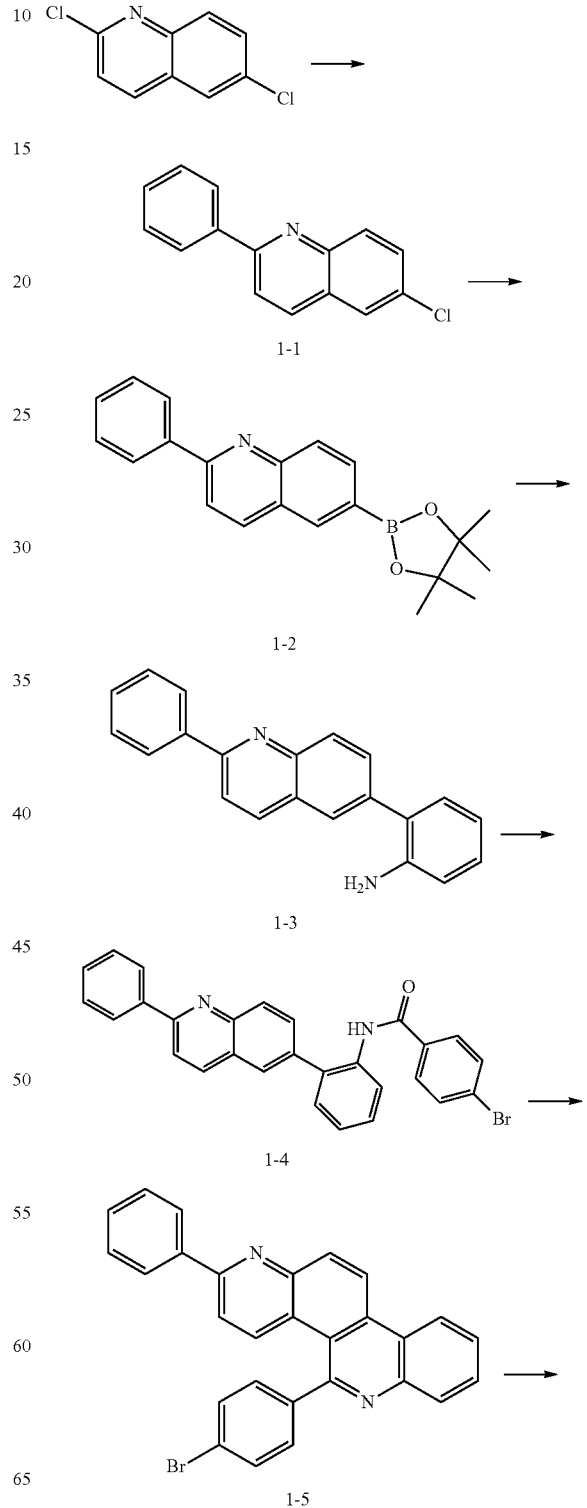

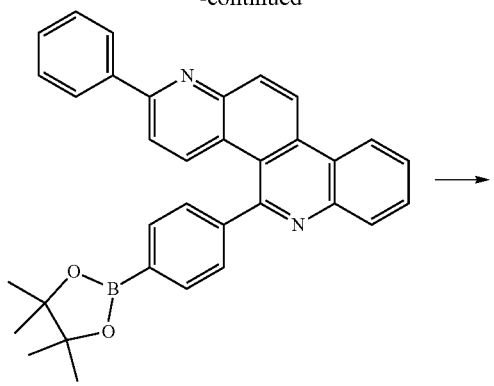
1-6
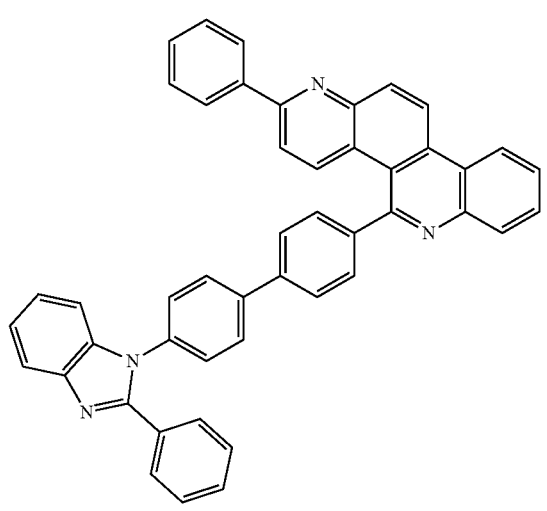
27
Preparation of Compound 27
Target Compound 27 was obtained in the same manner as in Preparation of Compound 1 in Preparation Example 1 except that 1-(4-bromophenyl)-2-phenyl-1H-benzo[d]imidazole was used instead of 2-chloro-4,6-diphenyl-1,3,5-triazine.
[Preparation Example 9] Preparation of Compound 30
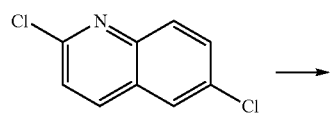
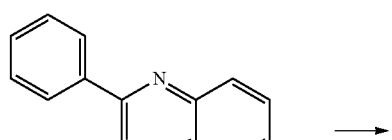
1-1
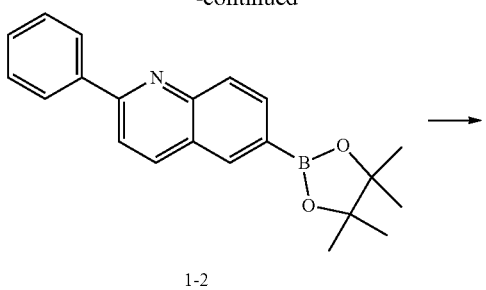
1-2
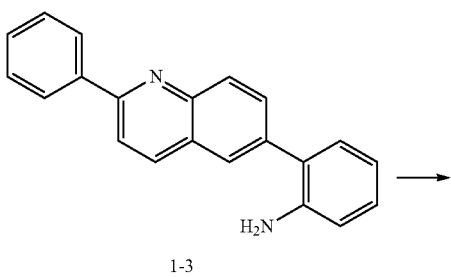
1-3
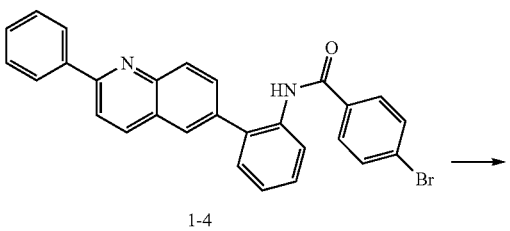
1-4
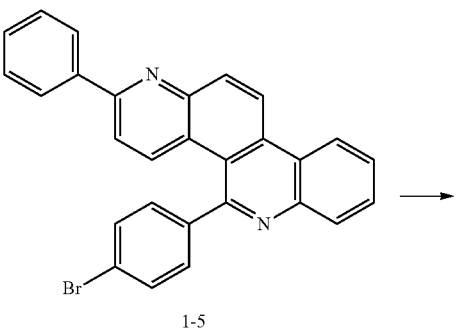
1-5
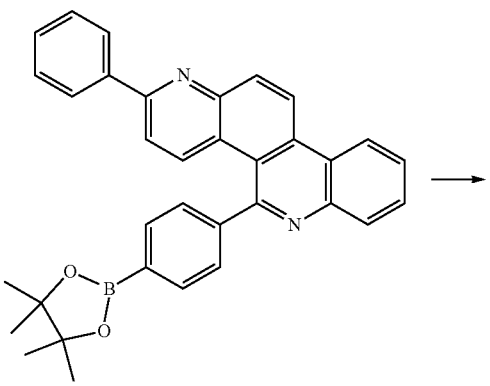
1-6

127
-continued
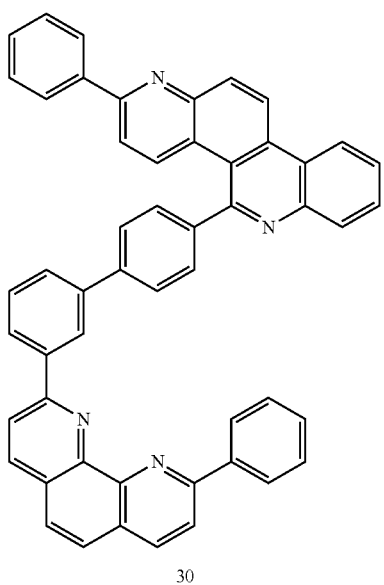
30
Preparation of Compound 30
Target Compound 30 was obtained in the same manner as in Preparation of Compound 1 in Preparation Example 1 except that 2-(3-bromophenyl)-9-phenyl-1,10-phenanthroline was used instead of 2-chloro-4,6-diphenyl-1,3,5-triazine.
[Preparation Example 10] Preparation of Compound 33
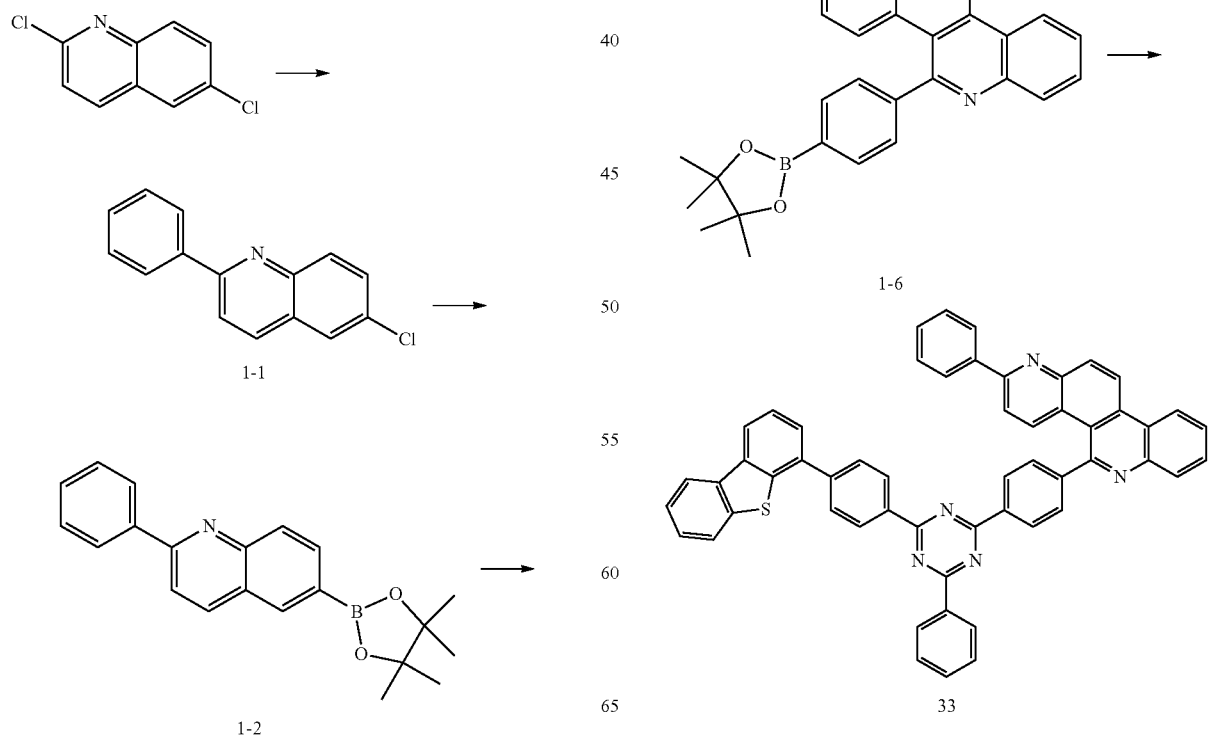
128
-continued
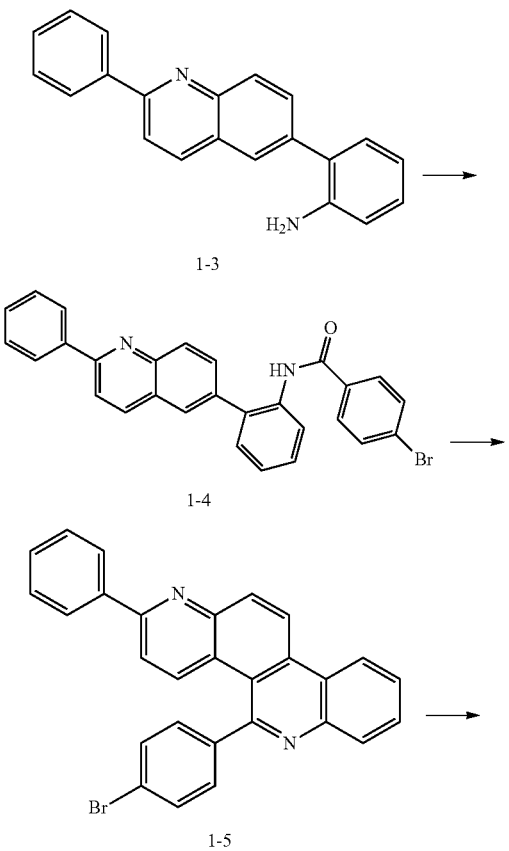

Preparation of Compound 33

Target Compound 33 was obtained in the same manner as in Preparation of Compound 1 in Preparation Example 1 except that 2-chloro-4-(4-(dibenzo[b,d]thiophen-4-yl)phenyl)-6-phenyl-1,3,5-triazine was used instead of 2-chloro-4,6-diphenyl-1,3,5-triazine.

[Preparation Example 11] Preparation of Compound 36

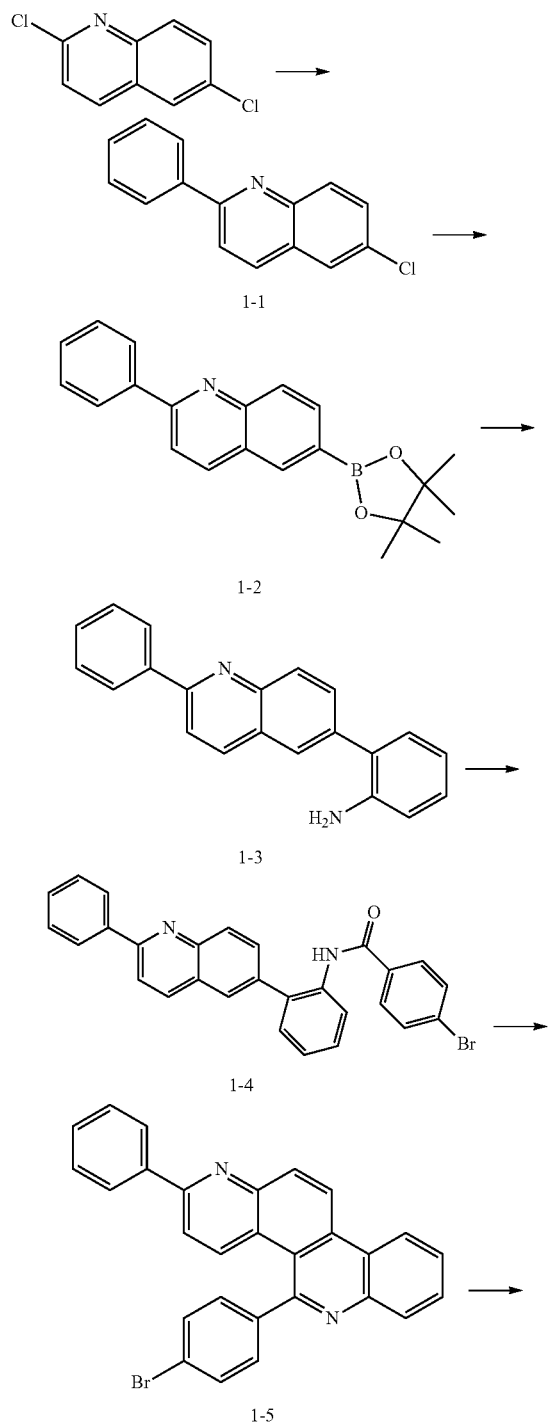

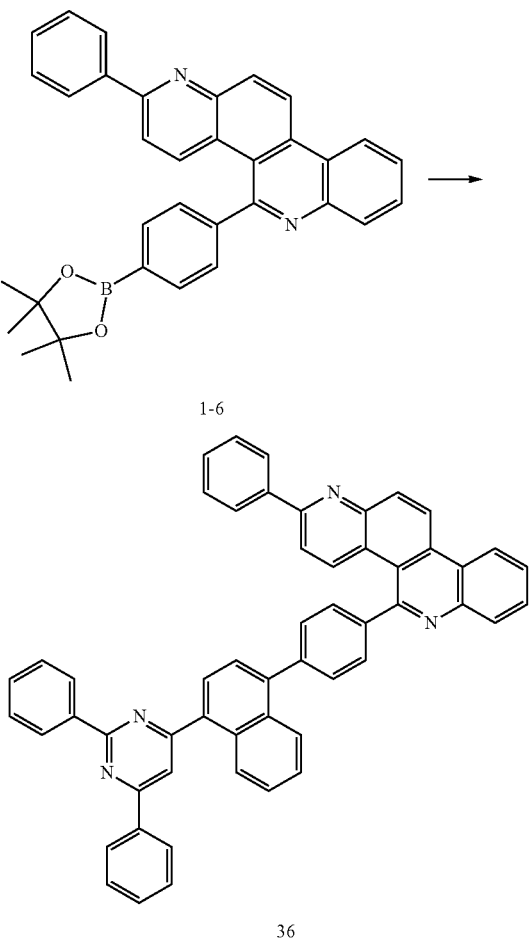

Preparation of Compound 36

Target Compound 36 was obtained in the same manner as in Preparation of Compound 1 in Preparation Example 1 except that 4-(4-bromonaphthalen-1-yl)-2,6-diphenylpyrimidine was used instead of 2-chloro-4,6-diphenyl-1,3,5-triazine.

[Preparation Example 12] Preparation of Compound 38

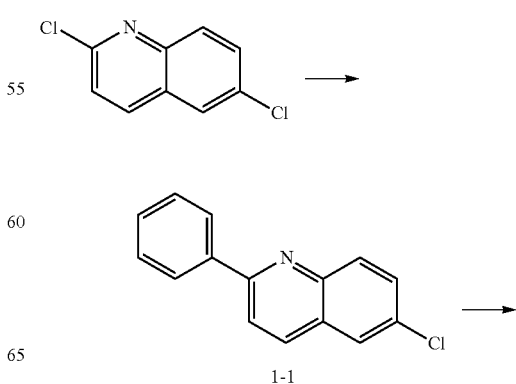

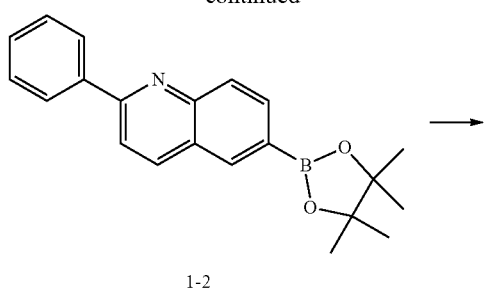
1-2
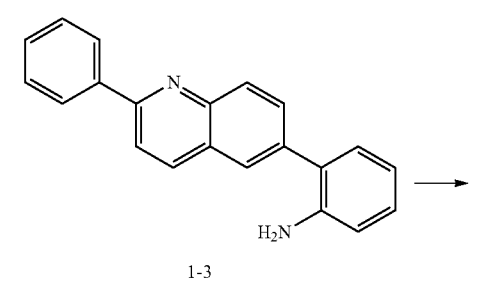
1-3
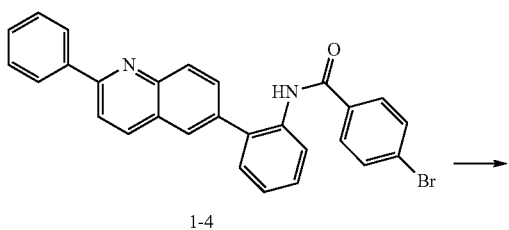
1-4
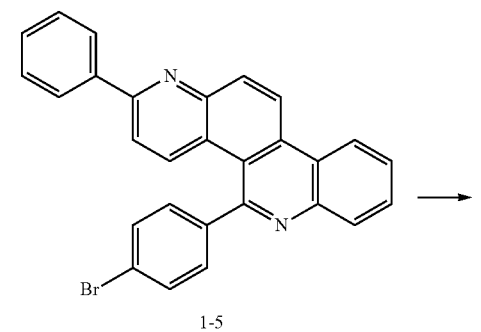
1-5
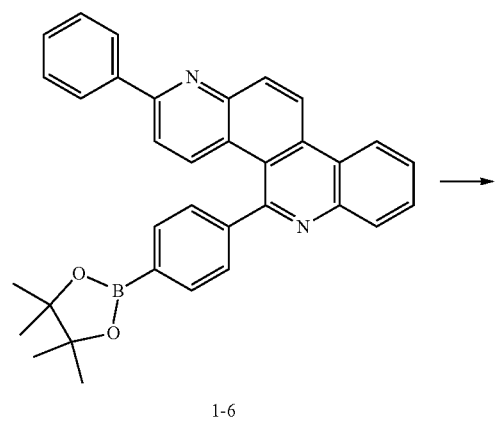
1-6
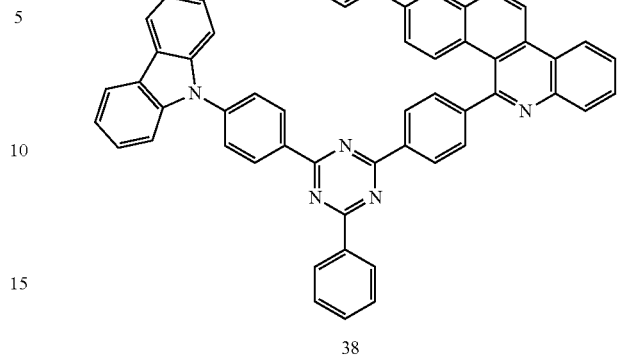
38
Preparation of Compound 38
Target Compound 38 was obtained in the same manner as in Preparation of Compound 1 in Preparation Example 1 except that 9-(4-(4-chloro-6-phenyl-1,3,5-triazin-2-yl)phenyl)-9H-carbazole was used instead of 2-chloro-4,6-diphenyl-1,3,5-triazine.
[Preparation Example 13] Preparation of Compound 41
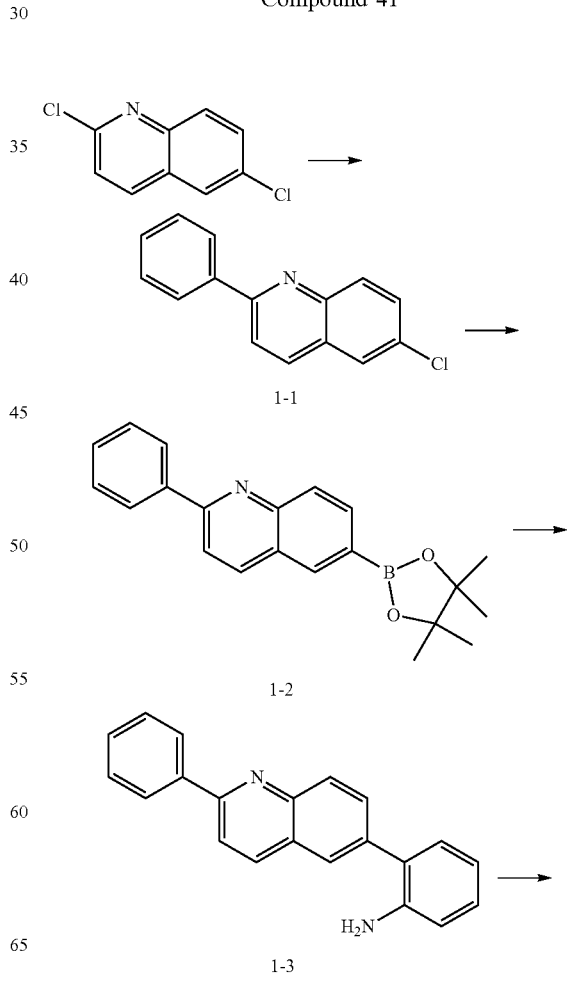

-continued

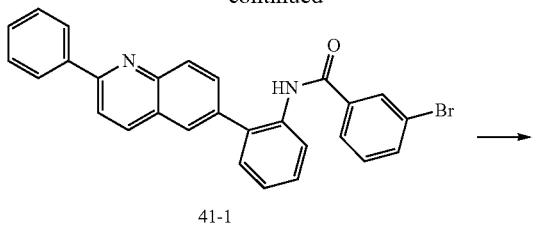

41-1

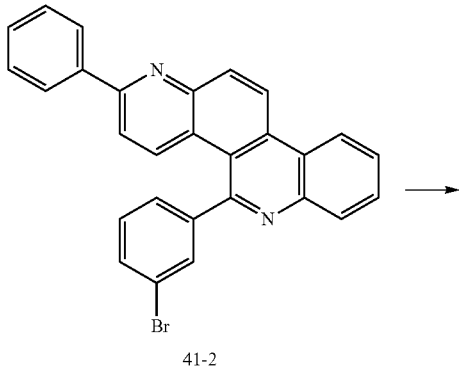

41-2

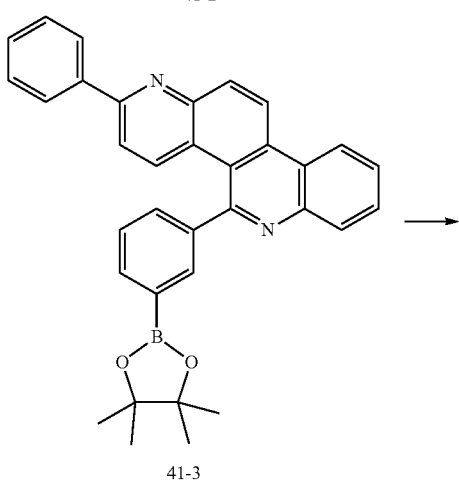

41-3

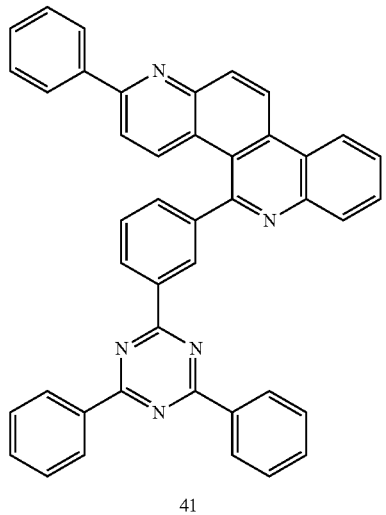

41

Preparation of Compound 41-1

After dissolving Compound 1-3 (12.3 g, 41.5 mmol) in dichloromethane (DCM), 3-bromobenzoyl chloride (10.0 g, 1.1 eq.) and triethanolamine (TEA) (8.7 ml, 1.5 eq.) were added thereto at 0° C., and the mixture was stirred for 2 hours at room temperature. After the reaction was completed, the result was cooled to room temperature, and then extracted with distilled water and dichloromethane. After drying the organic layer with anhydrous MgSO₄, the solvent was removed using a rotary evaporator, and the result was MeOH slurried to obtain target Compound 41-1 (19.5 g, 97%).

Preparation of Compound 41-2

After dissolving Compound 41-1 (19.5 g, 39.9 mmol) in nitrobenzene, POCl₃ (3.7 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 41-2 (13.8 g, 75%).

Preparation of Compound 41-3

After dissolving Compound 41-2 (13.8 g, 30.2 mmol) in 1,4-dioxane, bis(pinacolato)diboron, Pd(dppf)Cl₂ and potassium acetate were added thereto, and the mixture was stirred for 2 hours at 110° C. After the reaction was completed, the result was extracted with distilled water and EA. After drying the organic layer with anhydrous MgSO₄, the solvent was removed using a rotary evaporator, and the result was purified by column chromatography using dichloromethane as a developing solvent to obtain target Compound 41-3 (12.1 g, 79%).

Preparation of Compound 41

To Compound 41-3 (12.1 g, 24.1 mmol), 2-chloro-4,6-diphenyl-1,3,5-triazine (6.5 g, 1 eq.), Pd(PPh₃)₄ (1.4 g, 0.05 eq.), K₂CO₃ (10.0 g, 3.0 eq.) and 1,4-dioxane/H₂O were added, and the mixture was stirred for 3 hours at 110° C. After the reaction was completed, the result was cooled to room temperature, and produced solids were filtered to obtain target Compound 41 (12.1 g, 81%).

[Preparation Example 14] Preparation of Compound 44

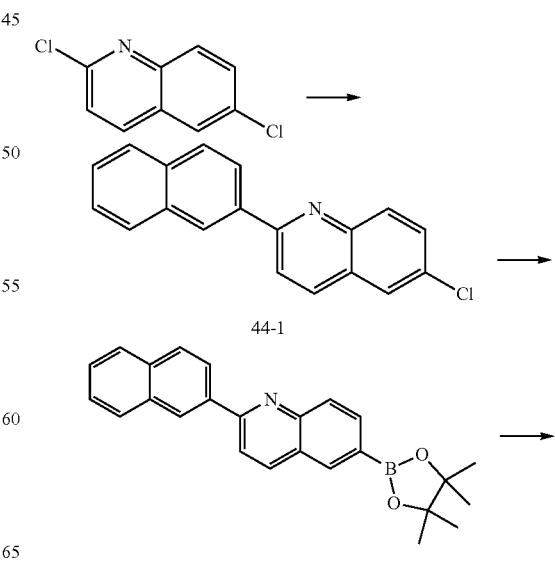

44-1

44-2

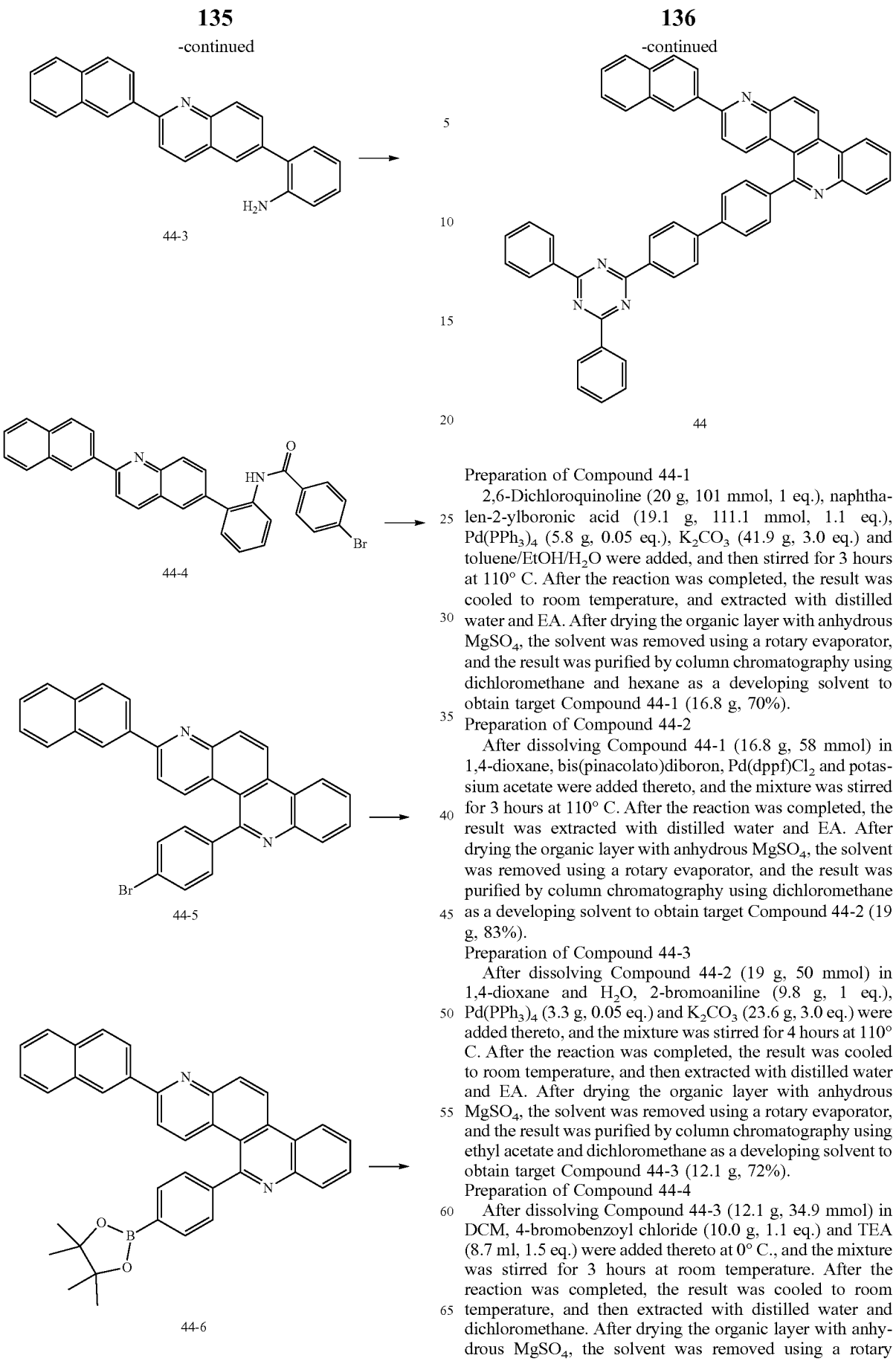

Preparation of Compound 44-1

2,6-Dichloroquinoline (20 g, 101 mmol, 1 eq.), naphthalen-2-ylboronic acid (19.1 g, 111.1 mmol, 1.1 eq.), Pd(PPh$_3$)$_4$ (5.8 g, 0.05 eq.), K$_2$CO$_3$ (41.9 g, 3.0 eq.) and toluene/EtOH/H$_2$O were added, and then stirred for 3 hours at 110° C. After the reaction was completed, the result was cooled to room temperature, and extracted with distilled water and EA. After drying the organic layer with anhydrous MgSO$_4$, the solvent was removed using a rotary evaporator, and the result was purified by column chromatography using dichloromethane and hexane as a developing solvent to obtain target Compound 44-1 (16.8 g, 70%).

Preparation of Compound 44-2

After dissolving Compound 44-1 (16.8 g, 58 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 44-2 (19 g, 83%).

Preparation of Compound 44-3

After dissolving Compound 44-2 (19 g, 50 mmol) in 1,4-dioxane and H$_2$O, 2-bromoaniline (9.8 g, 1 eq.), Pd(PPh$_3$)$_4$ (3.3 g, 0.05 eq.) and K$_2$CO$_3$ (23.6 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 44-3 (12.1 g, 72%).

Preparation of Compound 44-4

After dissolving Compound 44-3 (12.1 g, 34.9 mmol) in DCM, 4-bromobenzoyl chloride (10.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 44-4 (19.3 g, 97%).

Preparation of Compound 44-5

After dissolving Compound 44-4 (19.3 g, 36.5 mmol) in nitrobenzene, POCl₃ (3.7 ml, 1 eq.) was added thereto, and the mixture was stirred for 4 hours at 150° C. After the reaction was completed, the result was neutralized by adding an aqueous sodium bicarbonate solution thereto at room temperature, and produced solids were filtered to obtain target Compound 44-5 (13.8 g, 75%).

Preparation of Compound 44-6

After dissolving Compound 44-5 (13.8 g, 27 mmol) in 1,4-dioxane, bis(pinacolato)diboron, Pd(dppf)Cl₂ and potassium acetate were added thereto, and the mixture was stirred for 3 hours at 110° C. After the reaction was completed, the result was extracted with distilled water and EA. After drying the organic layer with anhydrous MgSO₄, the solvent was removed using a rotary evaporator, and the result was purified by column chromatography using dichloromethane as a developing solvent to obtain target Compound 44-6 (12.5 g, 81%).

Preparation of Compound 44

To Compound 44-6 (12.5 g, 22.4 mmol), 2-(4-chlorophenyl)-4,6-diphenyl-1,3,5-triazine (6.5 g, 1 eq.), Pd(PPh₃)₄ (1.4 g, 0.05 eq.), K₂CO₃ (10.0 g, 3.0 eq.) and 1,4-dioxane/H₂O were added, and the mixture was stirred for 3 hours at 110° C. After the reaction was completed, the result was cooled to room temperature, and produced solids were filtered to obtain target Compound 44 (11.2 g, 78%).

[Preparation Example 15] Preparation of Compound 45

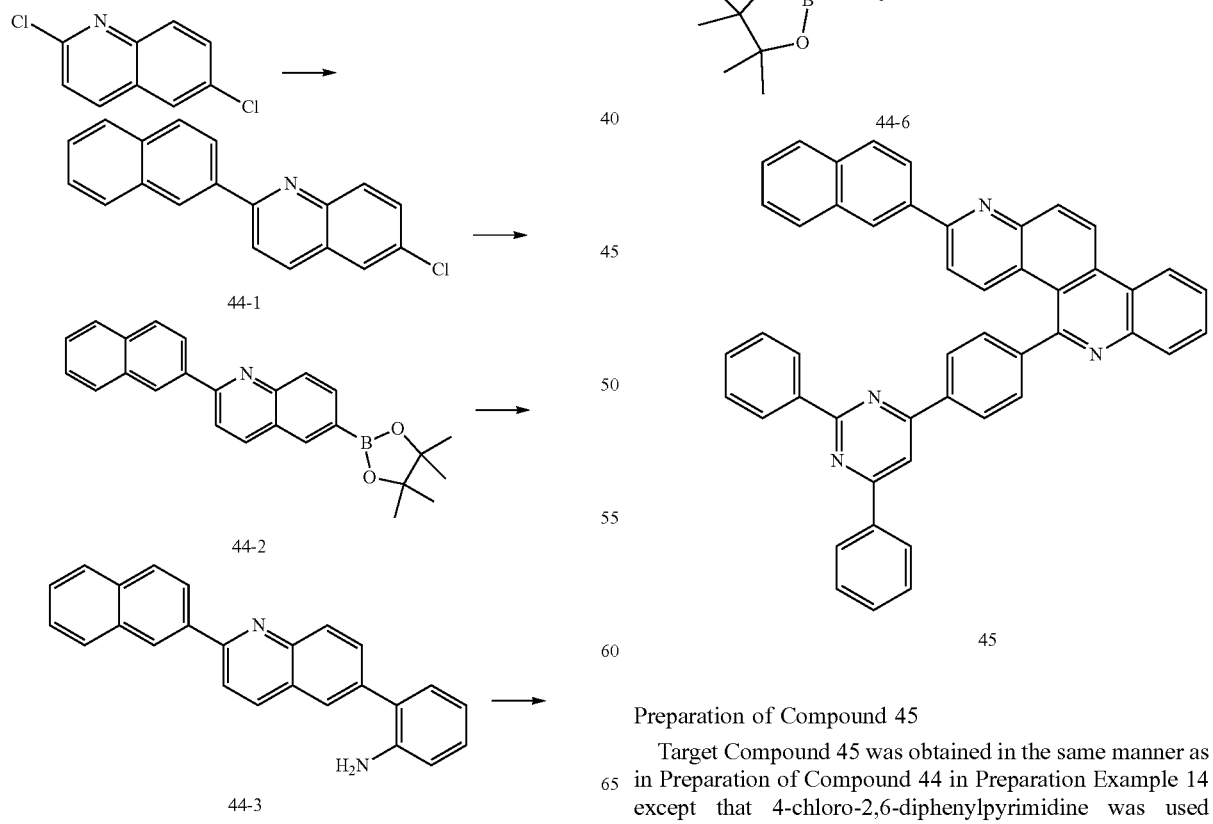

Preparation of Compound 45

Target Compound 45 was obtained in the same manner as in Preparation of Compound 44 in Preparation Example 14 except that 4-chloro-2,6-diphenylpyrimidine was used instead of 2-(4-chlorophenyl)-4,6-diphenyl-1,3,5-triazine.

[Preparation Example 16] Preparation of Compound 47
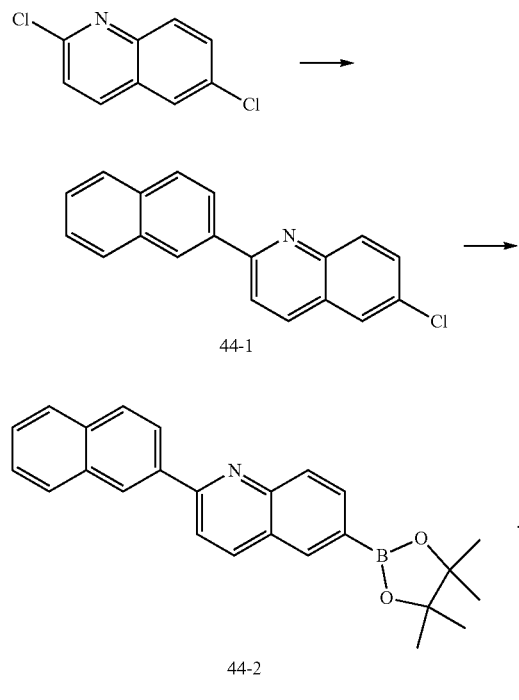
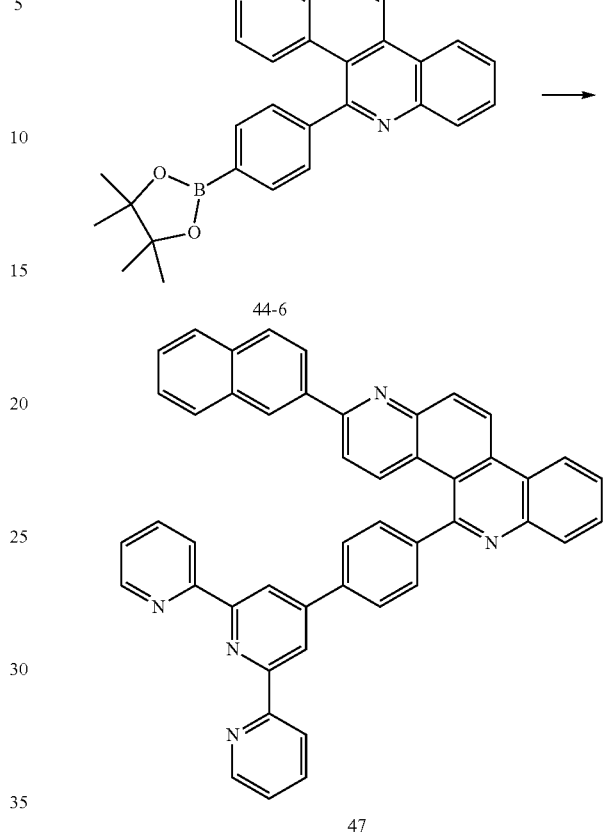
Preparation of Compound 47
Target Compound 47 was obtained in the same manner as in Preparation of Compound 45 in Preparation Example 15 except that 4'-bromo-2,2':6',2"-terpyridine was used instead of 2-(4-chlorophenyl)-4,6-diphenyl-1,3,5-triazine.
[Preparation Example 17] Preparation of Compound 51
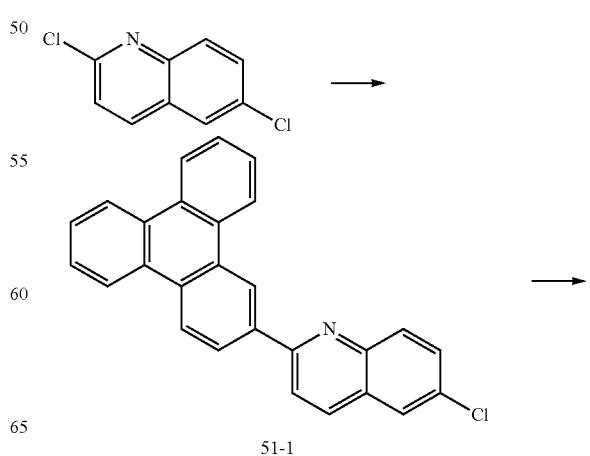

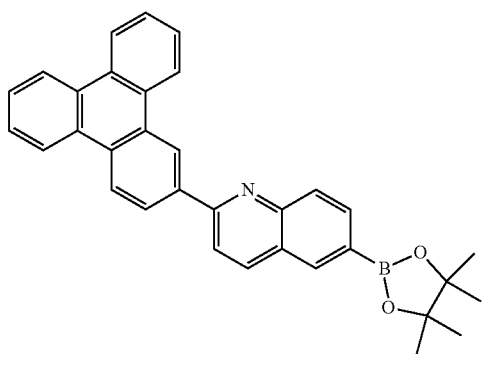

51-2

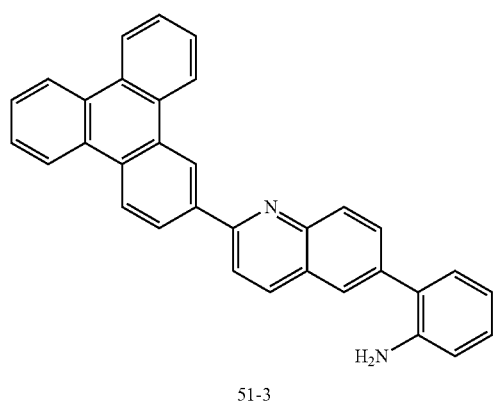

51-3

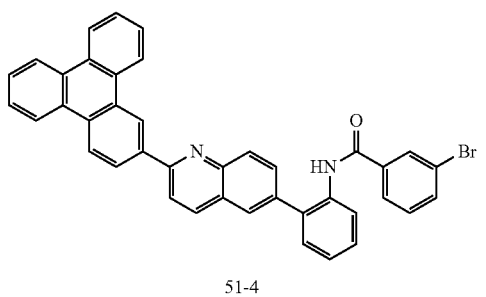

51-4

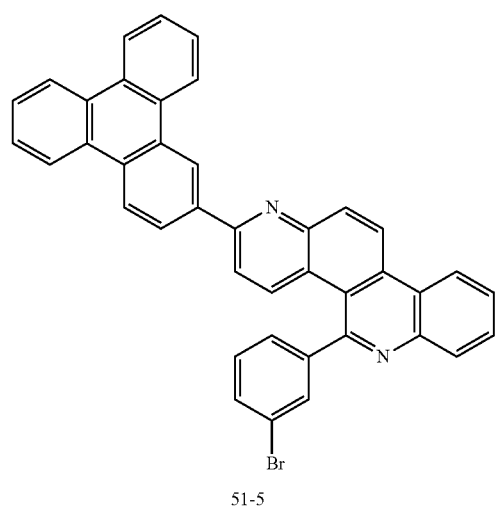

51-5

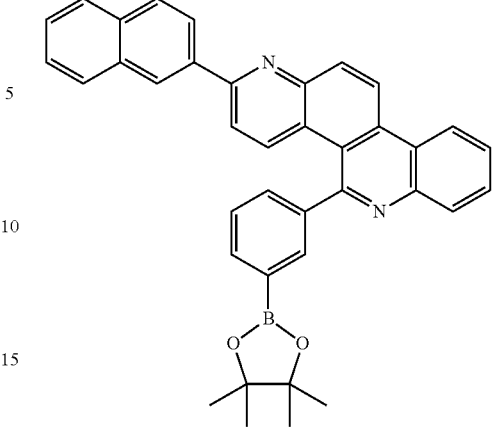

51-6

[structure]

51

Preparation of Compound 51-1

2,6-Dichloroquinoline (20 g, 101 mmol, 1 eq.), triphenylen-2-ylboronic acid (30.2 g, 111.1 mmol, 1.1 eq.), Pd(PPh$_3$)$_4$ (5.8 g, 0.05 eq.), K$_2$CO$_3$ (41.9 g, 3.0 eq.) and toluene/EtOH/H$_2$O were added, and then stirred for 3 hours at 110° C. After the reaction was completed, the result was cooled to room temperature, and extracted with distilled water and EA. After drying the organic layer with anhydrous MgSO$_4$, the solvent was removed using a rotary evaporator, and the result was purified by column chromatography using dichloromethane and hexane as a developing solvent to obtain target Compound 51-1 (17.8 g, 73%).

Preparation of Compound 51-2

After dissolving Compound 51-1 (17.8 g, 65.4 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 51-2 (19.5 g, 84%).

Preparation of Compound 51-3

After dissolving Compound 51-2 (19.5 g, 40.5 mmol) in 1,4-dioxane and H₂O, 2-bromoaniline (9.8 g, 1 eq.), Pd(PPh₃)₄ (3.3 g, 0.05 eq.) and K₂CO₃ (23.6 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO₄, the solvent was removed using a rotary evaporator, and the result was purified by column chromatography using ethyl acetate and dichloromethane as a developing solvent to obtain target Compound 51-3 (12.5 g, 73%).

Preparation of Compound 51-4

After dissolving Compound 51-3 (12.5 g, 28 mmol) in DCM, 3-bromobenzoyl chloride (10.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO₄, the solvent was removed using a rotary evaporator, and the result was MeOH slurried to obtain target Compound 51-4 (19.1 g, 96%).

Preparation of Compound 51-5

After dissolving Compound 51-4 (19.1 g, 30.3 mmol) in nitrobenzene, POCl₃ (3.7 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 51-5 (14.2 g, 76%).

Preparation of Compound 51-6

After dissolving Compound 51-5 (14.2 g, 23.2 mmol) in 1,4-dioxane, bis(pinacolato)diboron, Pd(dppf)Cl₂ and potassium acetate were added thereto, and the mixture was stirred for 3 hours at 110° C. After the reaction was completed, the result was extracted with distilled water and EA. After drying the organic layer with anhydrous MgSO₄, the solvent was removed using a rotary evaporator, and the result was purified by column chromatography using dichloromethane as a developing solvent to obtain target Compound 51-6 (12.8 g, 82%).

Preparation of Compound 51

To Compound 51-6 (12.5 g, 22.4 mmol), 2-chloro-4,6-diphenyl-1,3,5-triazine (6.5 g, 1 eq.), Pd(PPh₃)₄ (1.4 g, 0.05 eq.), K₂CO₃ (10.0 g, 3.0 eq.) and 1,4-dioxane/H₂O were added, and the mixture was stirred for 3 hours at 110° C. After the reaction was completed, the result was cooled to room temperature, and produced solids were filtered to obtain target Compound 51 (11.6 g, 79%).

[Preparation Example 18] Preparation of Compound 53

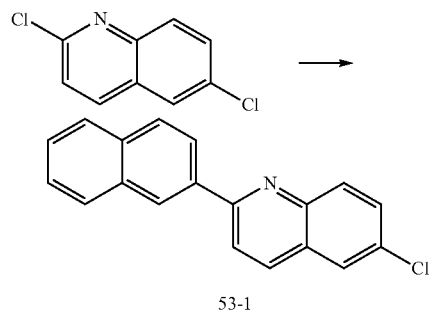

53-1

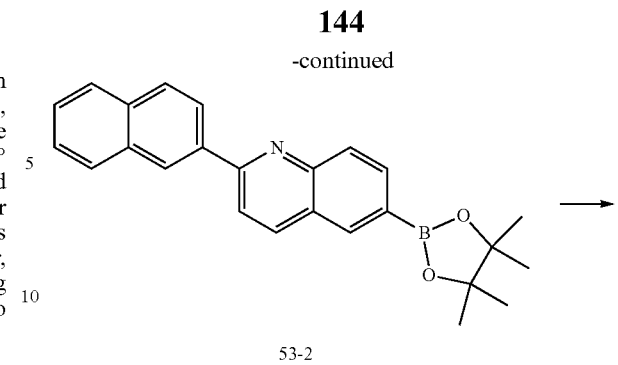

53-2

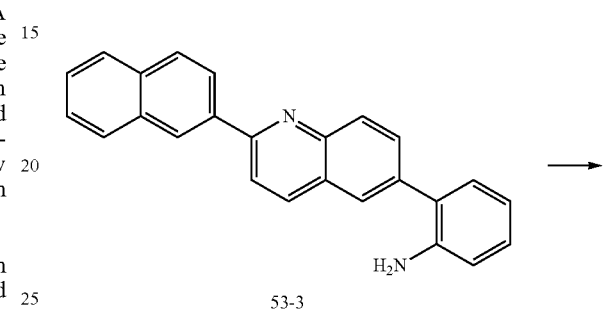

53-3

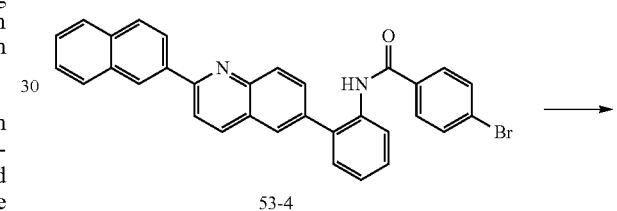

53-4

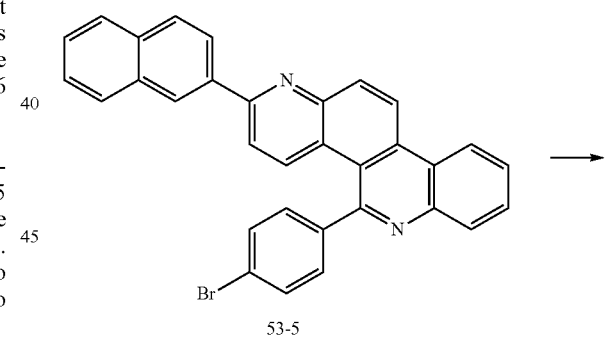

53-5

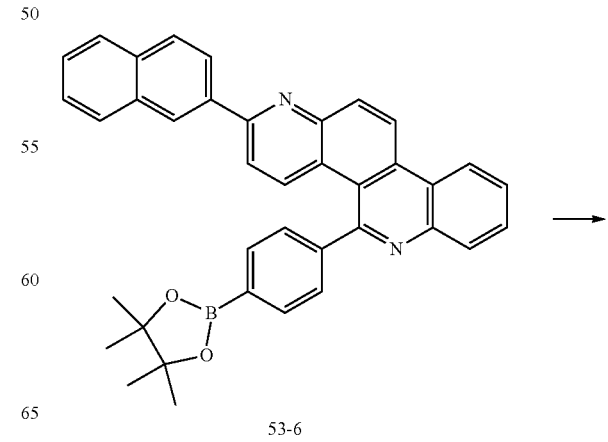

53-6

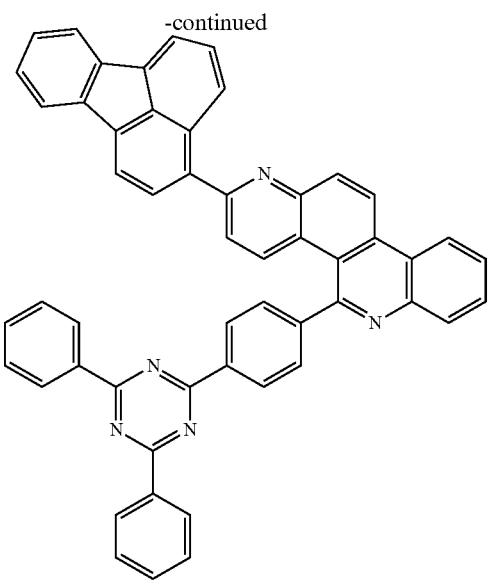

53

Preparation of Compound 53-1

2,6-Dichloroquinoline (20 g, 101 mmol, 1 eq.), fluoranthen-3-ylboronic acid (27.3 g, 111.1 mmol, 1.1 eq.), Pd(PPh$_3$)$_4$ (5.8 g, 0.05 eq.), K$_2$CO$_3$ (41.9 g, 3.0 eq.) and toluene/EtOH/H$_2$O were added, and the mixture was stirred for 4 hours at 110° C. After the reaction was completed, the result was cooled to room temperature, and extracted with distilled water and EA. After drying the organic layer with anhydrous MgSO$_4$, the solvent was removed using a rotary evaporator, and the result was purified by column chromatography using dichloromethane and hexane as a developing solvent to obtain target Compound 53-1 (16.5 g, 71%).

Preparation of Compound 53-2

After dissolving Compound 53-1 (16.5 g, 56.9 mmol) in 1,4-dioxane, bis(pinacolato)diboron, Pd(dppf)Cl$_2$ and potassium acetate were added thereto, and the mixture was stirred for 4 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 53-2 (18.5 g, 82%).

Preparation of Compound 53-3

After dissolving Compound 53-2 (18.5 g, 48.5 mmol) in 1,4-dioxane and H$_2$O, 2-bromoaniline (9.8 g, 1 eq.), Pd(PPh$_3$)$_4$ (3.3 g, 0.05 eq.) and K$_2$CO$_3$ (23.6 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 53-3 (12.3 g, 73%).

Preparation of Compound 53-4

After dissolving Compound 53-3 (12.3 g, 35.5 mmol) in DCM, 4-bromobenzoyl chloride (10.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 53-4 (19.1 g, 96%).

Preparation of Compound 53-5

After dissolving Compound 53-4 (19.1 g, 36.1 mmol) in nitrobenzene, POCl$_3$ (3.7 ml, 1 eq.) was added thereto, and the mixture was stirred for 3 hours at 150° C. After the reaction was completed, the result was neutralized by adding an aqueous sodium bicarbonate solution thereto at room temperature, and produced solids were filtered to obtain target Compound 53-5 (13.9 g, 75%).

Preparation of Compound 53-6

After dissolving Compound 53-5 (13.9 g, 27 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 53-6 (12.4 g, 81%).

Preparation of Compound 53

To Compound 53-6 (12.4 g, 22.2 mmol), 2-(4-chlorophenyl)-4,6-diphenyl-1,3,5-triazine (6.5 g, 1 eq.), Pd(PPh$_3$)$_4$ (1.4 g, 0.05 eq.), K$_2$CO$_3$ (10.0 g, 3.0 eq.) and 1,4-dioxane/H$_2$O were added, and the mixture was stirred for 4 hours at 110° C. After the reaction was completed, the result was cooled to room temperature, and produced solids were filtered to obtain target Compound 53 (11.5 g, 79%).

[Preparation Example 19] Preparation of Compound 56

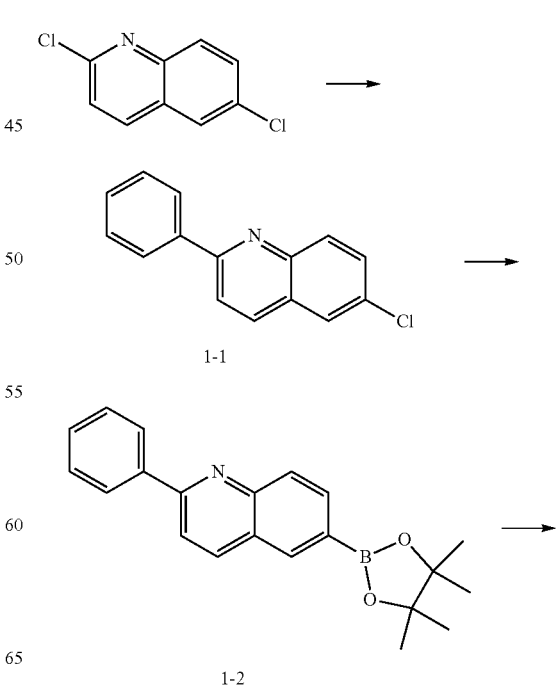

-continued

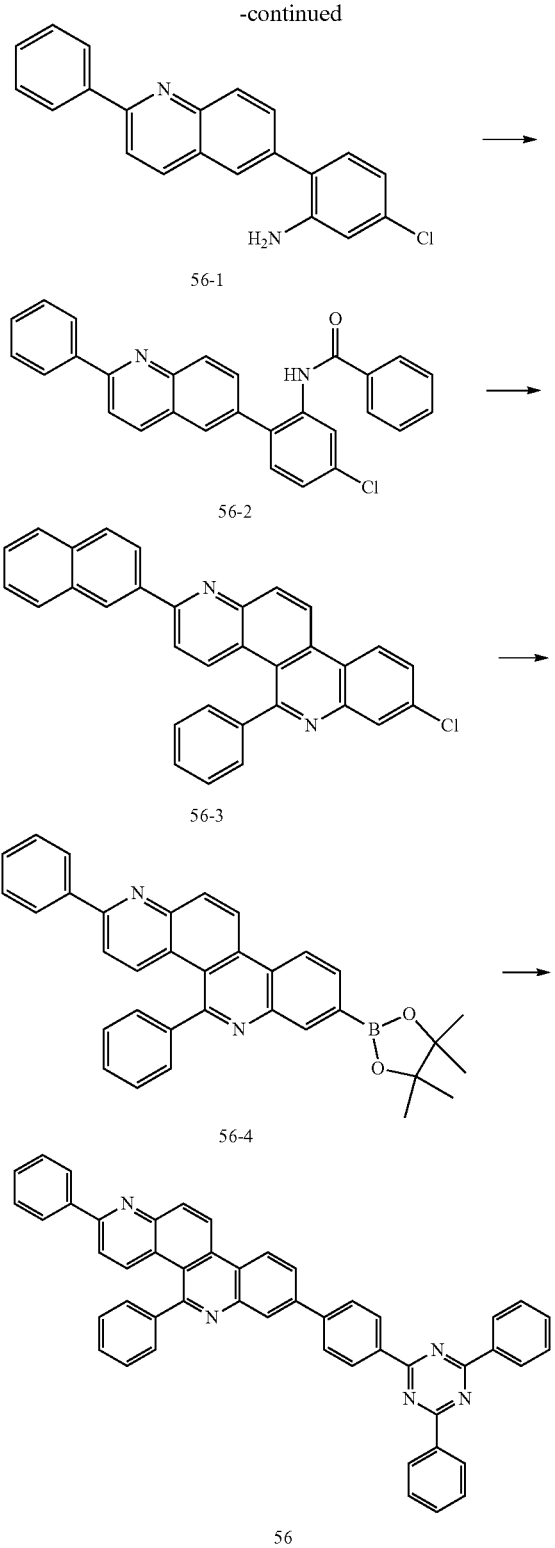

56-1

56-2

56-3

56-4

56

Preparation of Compound 56-1

After dissolving Compound 1-2 (18.4 g, 55.6 mmol) in 1,4-dioxane and H$_2$O, 2-bromo-5-chloroaniline (11.5 g, 1 eq.), Pd(PPh$_3$)$_4$ (3.3 g, 0.05 eq.) and K$_2$CO$_3$ (23.6 g, 3.0 eq.) were added thereto, and the mixture was stirred for 3 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 56-1 (12.9 g, 70%).

Preparation of Compound 56-2

After dissolving Compound 56-1 (12.9 g, 39 mmol) in DCM, benzoyl chloride (6.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 56-2 (15.3 g, 90%).

Preparation of Compound 56-3

After dissolving Compound 53-4 (15.3 g, 35.2 mmol) in nitrobenzene, POCl$_3$ (3.7 ml, 1 eq.) was added thereto, and the mixture was stirred for 3 hours at 150° C. After the reaction was completed, the result was neutralized by adding an aqueous sodium bicarbonate solution thereto at room temperature, and produced solids were filtered to obtain target Compound 56-3 (13.8 g, 94%).

Preparation of Compound 56-4

After dissolving Compound 56-3 (13.8 g, 33.1 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 56-4 (11.5 g, 68%).

Preparation of Compound 56

To Compound 56-4 (11.5 g, 22.6 mmol), 2-(4-bromophenyl)-4,6-diphenyl-1,3,5-triazine (6.5 g, 1 eq.), Pd(PPh$_3$)$_4$ (1.4 g, 0.05 eq.), K$_2$CO$_3$ (10.0 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 56 (10.1 g, 65%).

[Preparation Example 20] Preparation of Compound 58

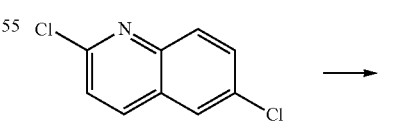

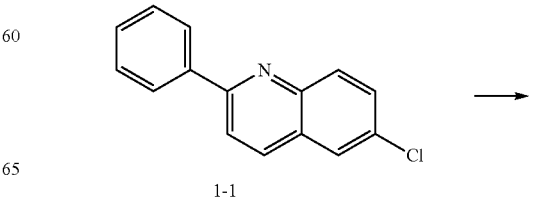

1-1

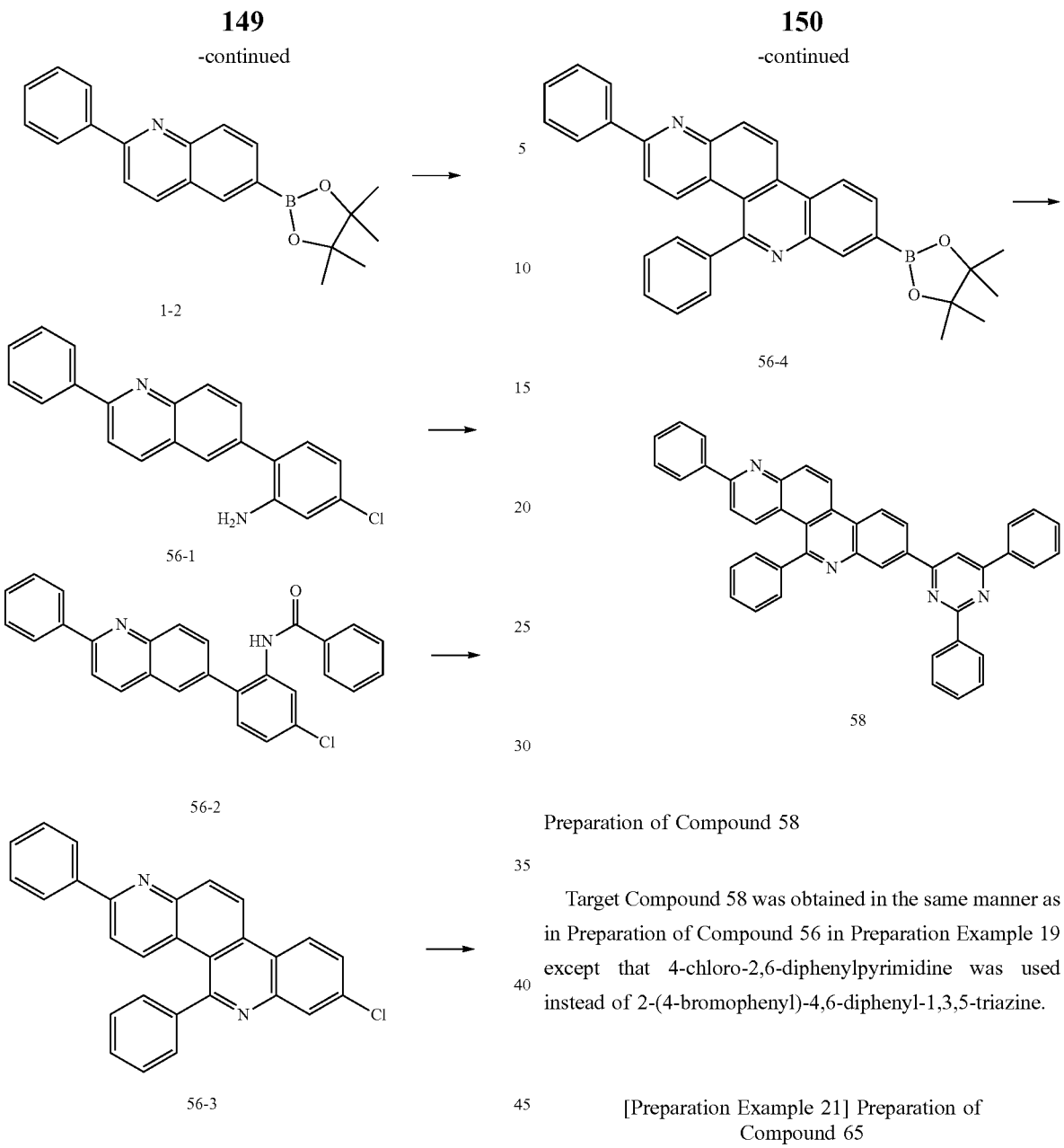
Preparation of Compound 58
Target Compound 58 was obtained in the same manner as in Preparation of Compound 56 in Preparation Example 19 except that 4-chloro-2,6-diphenylpyrimidine was used instead of 2-(4-bromophenyl)-4,6-diphenyl-1,3,5-triazine.
[Preparation Example 21] Preparation of Compound 65
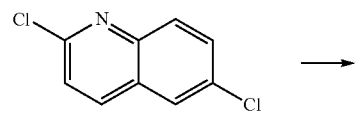
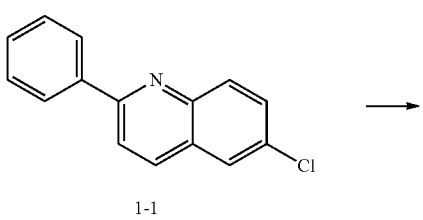

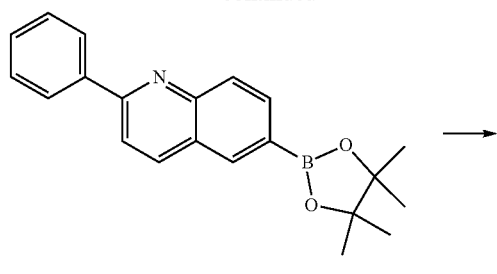
1-2
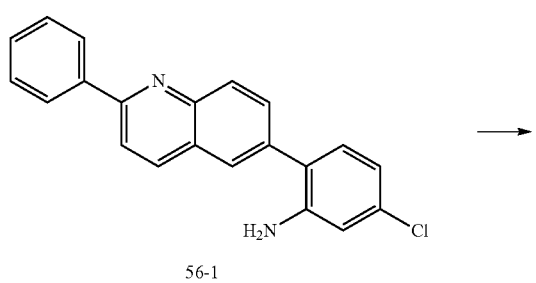
56-1
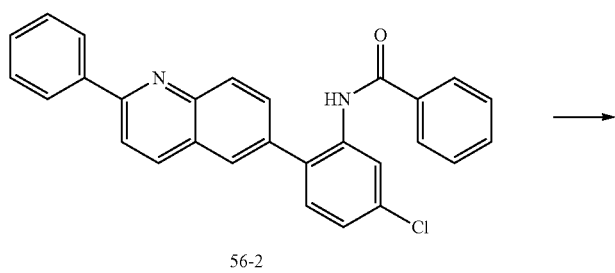
56-2
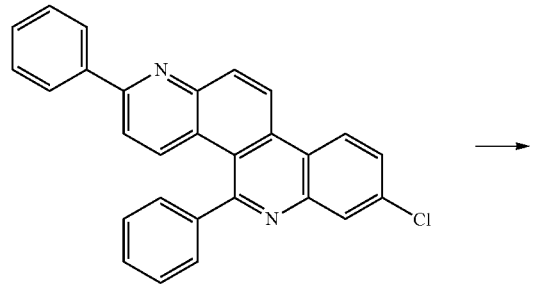
56-3
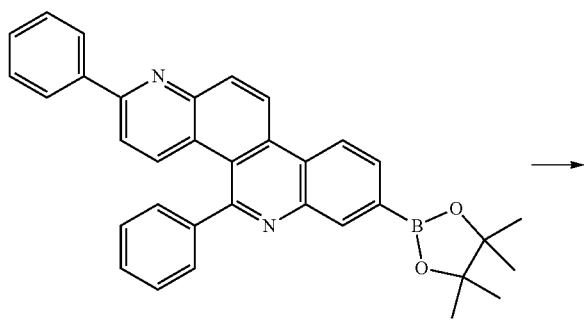
56-4

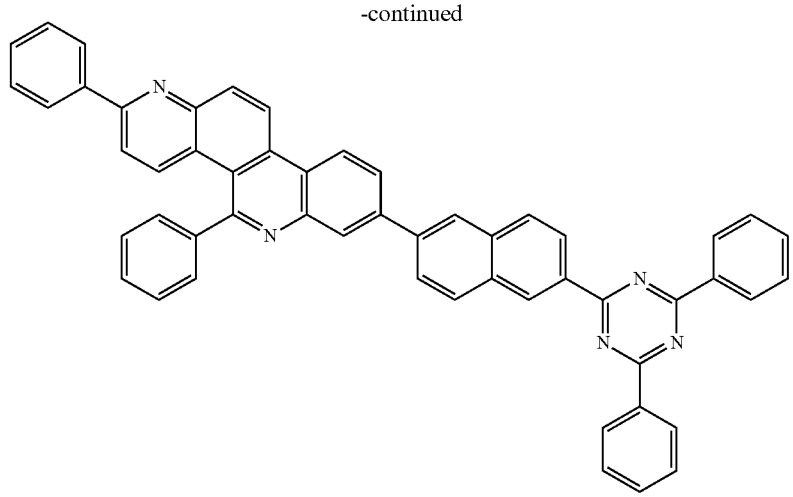
65
Preparation of Compound 65 Target Compound 65 was obtained in the same manner as in Preparation of Compound 58 in Preparation Example 20 except that 2-(6-bromonaphthalen-2-yl)-4,6-diphenyl-1,3,5-triazine was used instead of 4-chloro-2,6-diphenylpyrimidine.
[Preparation Example 22] Preparation of Compound 68
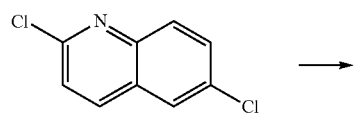
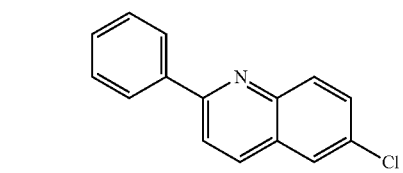
1-1
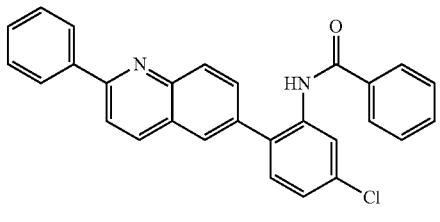
56-1
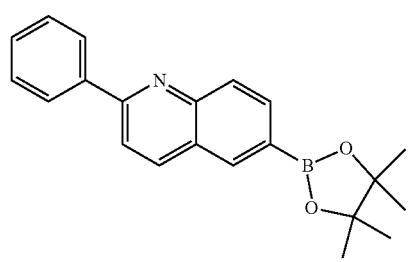
1-2
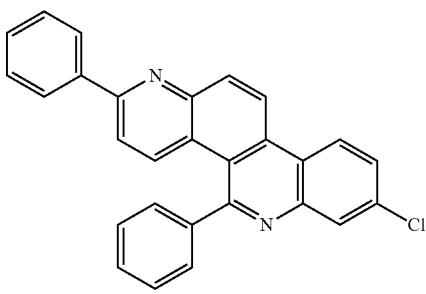
56-2
56-3

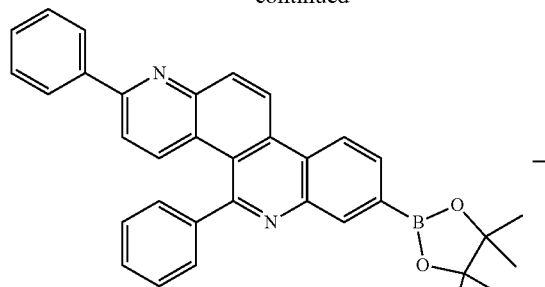

56-4

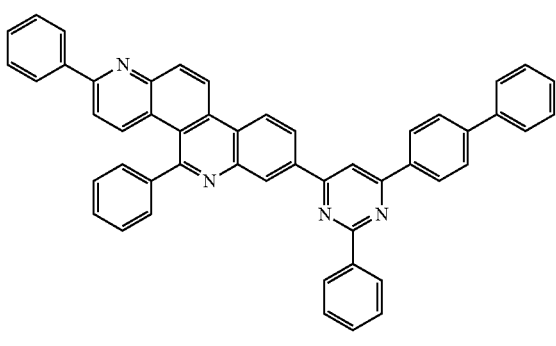

68

Preparation of Compound 68

Target Compound 68 was obtained in the same manner as in Preparation of Compound 58 in Preparation Example 20 except that 4-([1,1'-biphenyl]-4-yl)-6-chloro-2-phenylpyrimidine was used instead of 4-chloro-2,6-diphenylpyrimidine.

[Preparation Example 23] Preparation of Compound 71

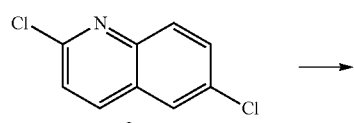

1-1

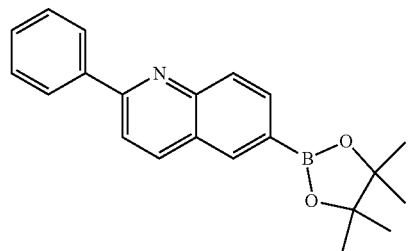

1-2

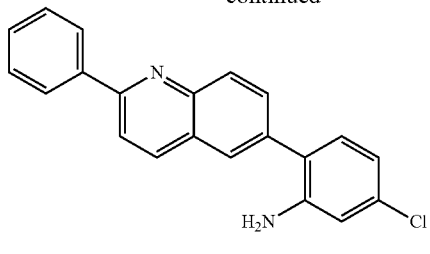

56-1

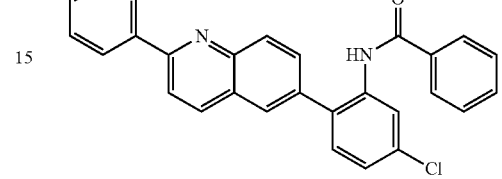

56-2

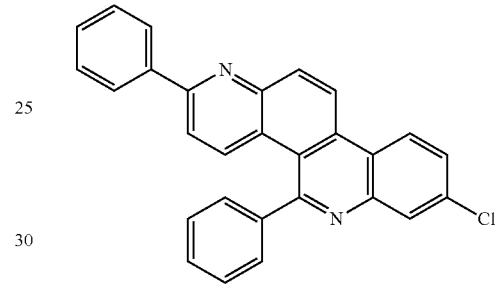

56-3

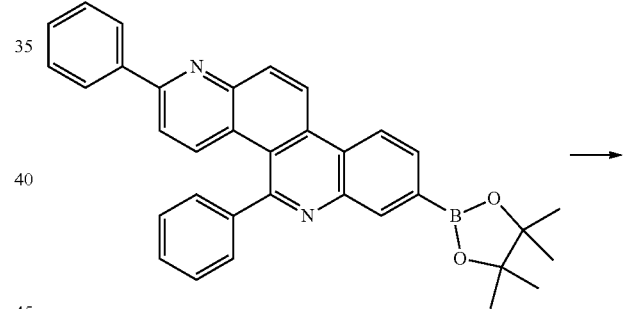

56-4

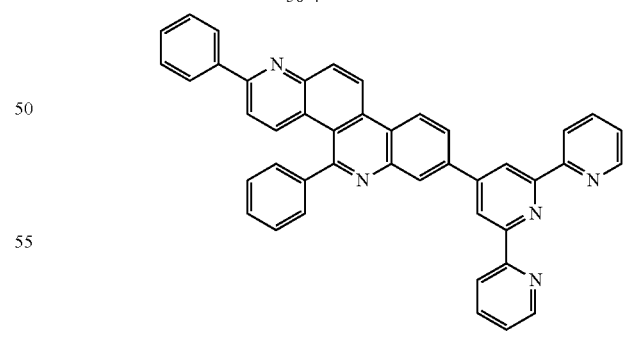

71

Preparation of Compound 71

Target Compound 71 was obtained in the same manner as in Preparation of Compound 58 in Preparation Example 20 except that 4'-bromo-2,2':6',2''-terpyridine was used instead of 4-chloro-2,6-diphenylpyrimidine.

[Preparation Example 24] Preparation of Compound 74
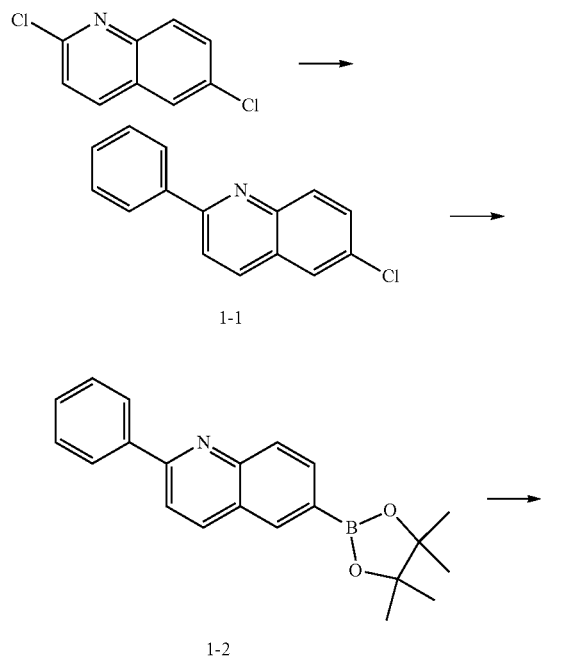
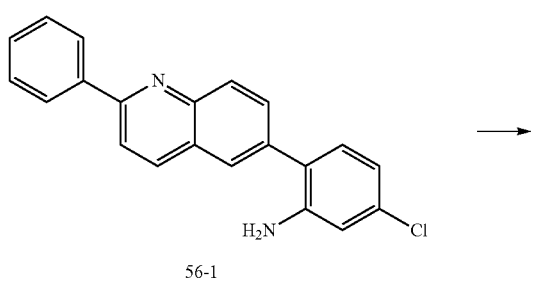
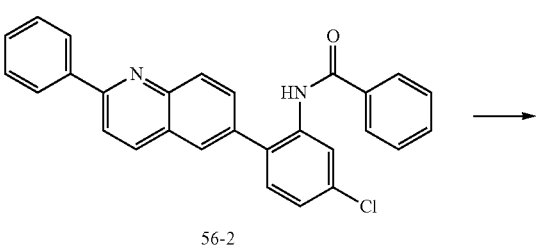
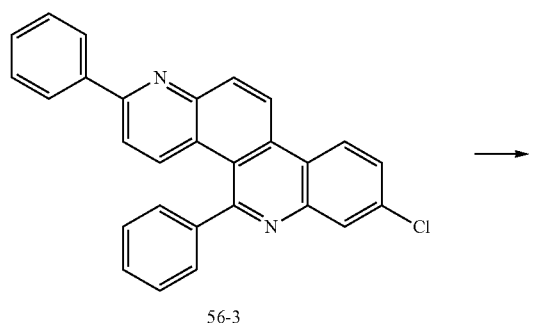
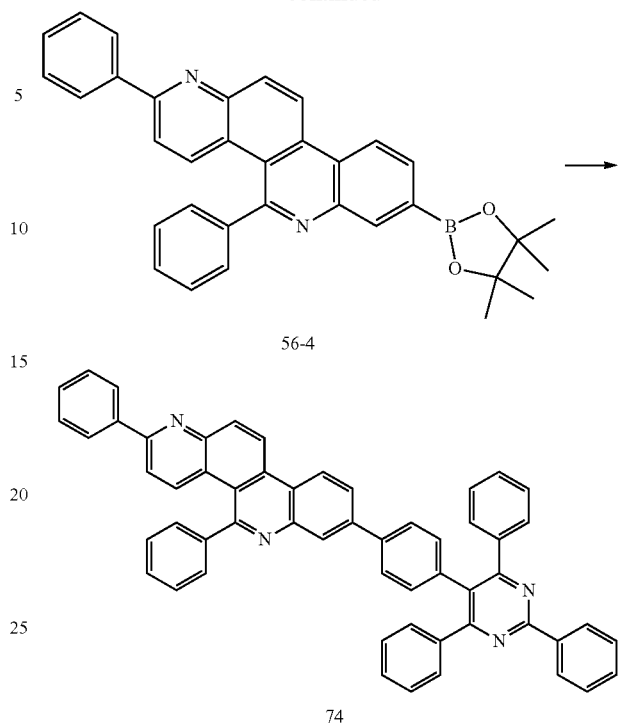
Preparation of Compound 74
Target Compound 74 was obtained in the same manner as in Preparation of Compound 58 in Preparation Example 20 except that 5-(4-bromophenyl)-2,4,6-triphenylpyrimidine was used instead of 4-chloro-2,6-diphenylpyrimidine.
[Preparation Example 25] Preparation of Compound 81
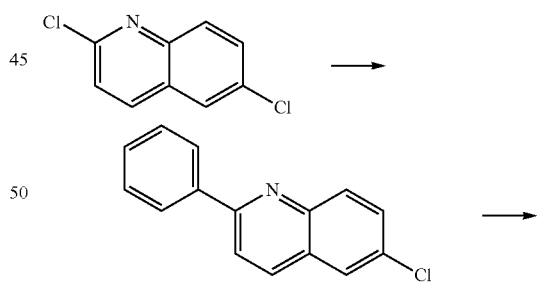
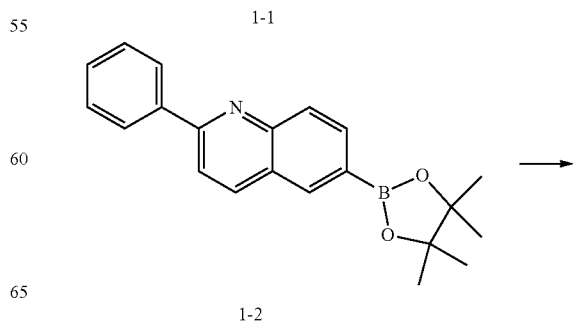

-continued
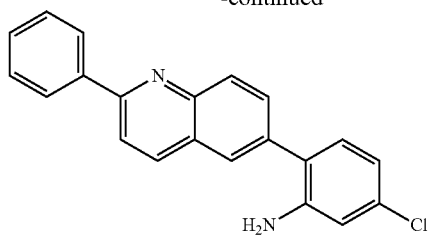
56-1
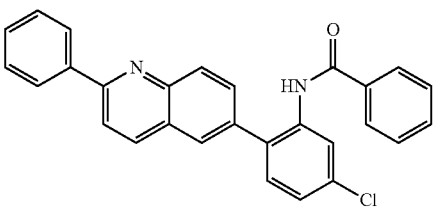
56-2
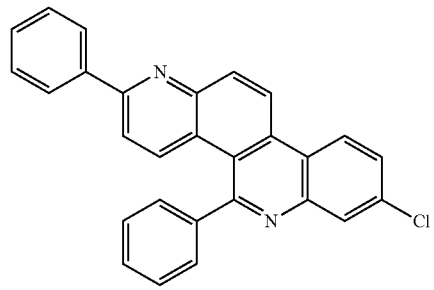
56-3
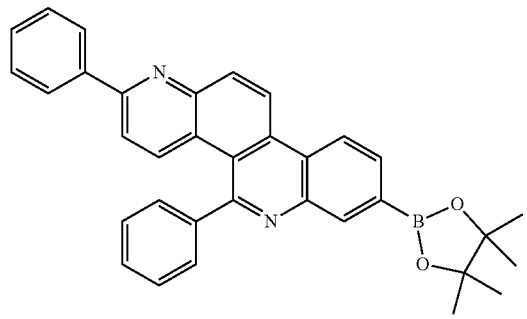
56-4
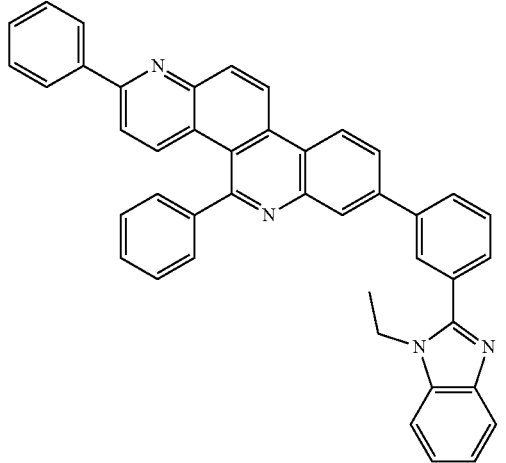
81
Preparation of Compound 81
Target Compound 81 was obtained in the same manner as in Preparation of Compound 58 in Preparation Example 20 except that 2-(3-bromophenyl)-1-ethyl-1H-benzo[d]imidazole was used instead of 4-chloro-2,6-diphenylpyrimidine.
[Preparation Example 26] Preparation of Compound 85
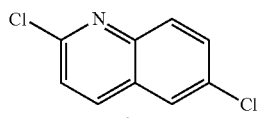
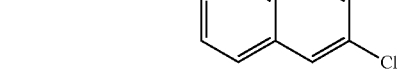
1-1
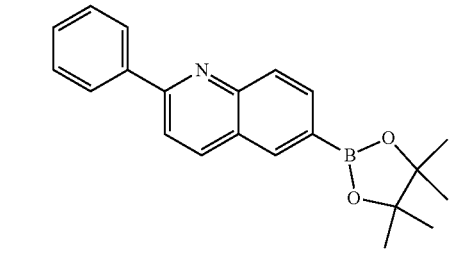
1-2
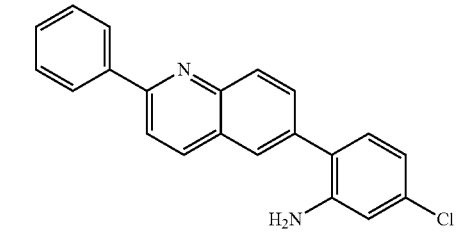
56-1
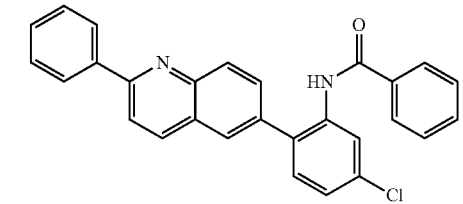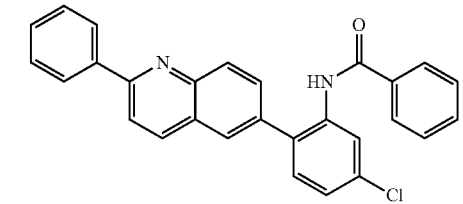
56-2
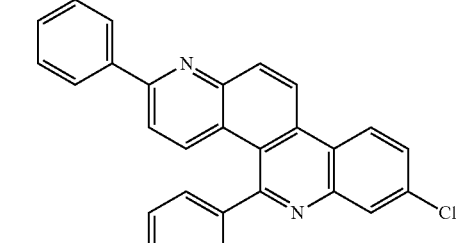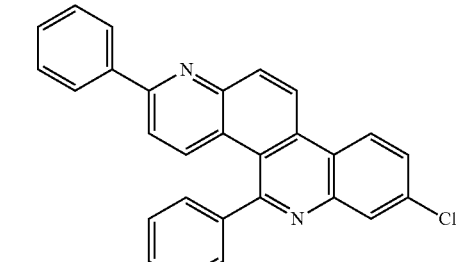
56-3
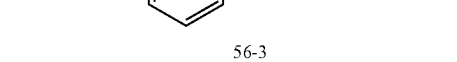

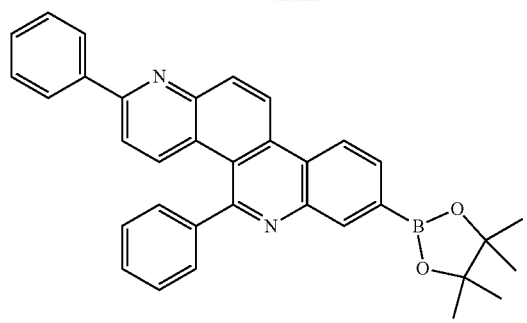
56-4
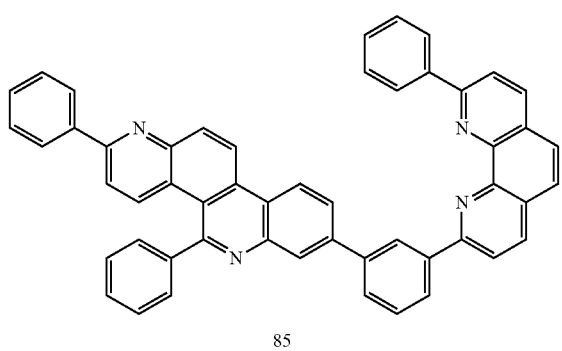
85
Preparation of Compound 85
Target Compound 85 was obtained in the same manner as in Preparation of Compound 58 in Preparation Example 20 except that 2-(3-bromophenyl)-9-phenyl-1,10-phenanthroline was used instead of 4-chloro-2,6-diphenylpyrimidine.
[Preparation Example 27] Preparation of Compound 91
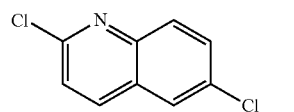
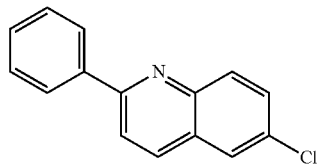
1-1
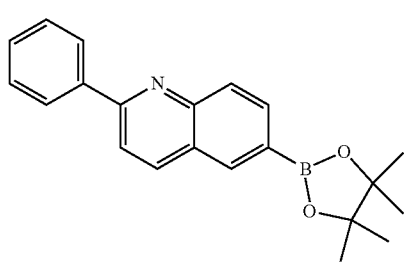
1-2
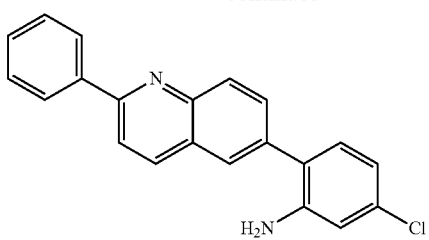
56-1
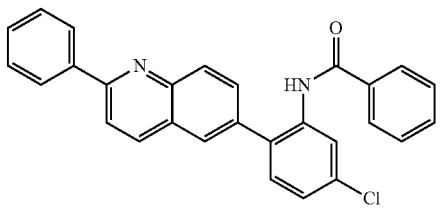
56-2
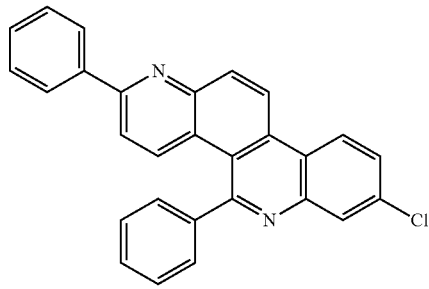
56-3
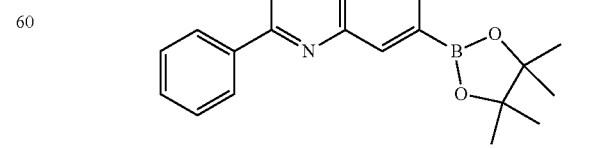
56-4

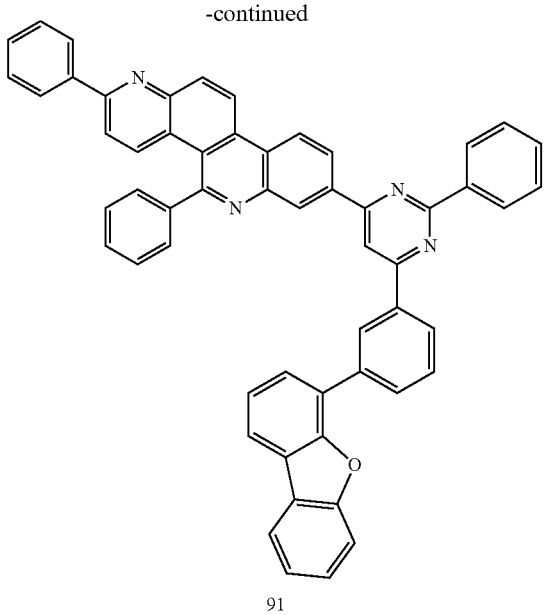

91

Preparation of Compound 91

Target Compound 91 was obtained in the same manner as in Preparation of Compound 58 in Preparation Example 20 except that 4-chloro-6-(3-(dibenzo[b,d]furan-4-yl)phenyl)-2-phenylpyrimidine was used instead of 4-chloro-2,6-diphenylpyrimidine.

[Preparation Example 28] Preparation of Compound 93

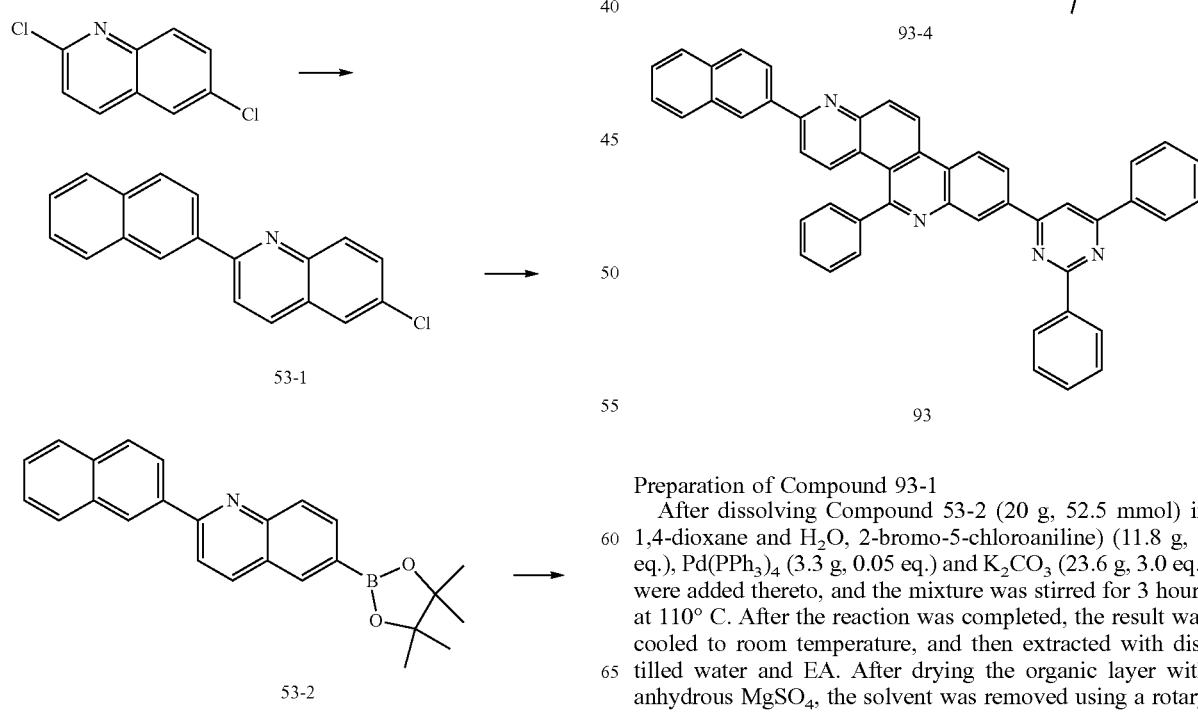

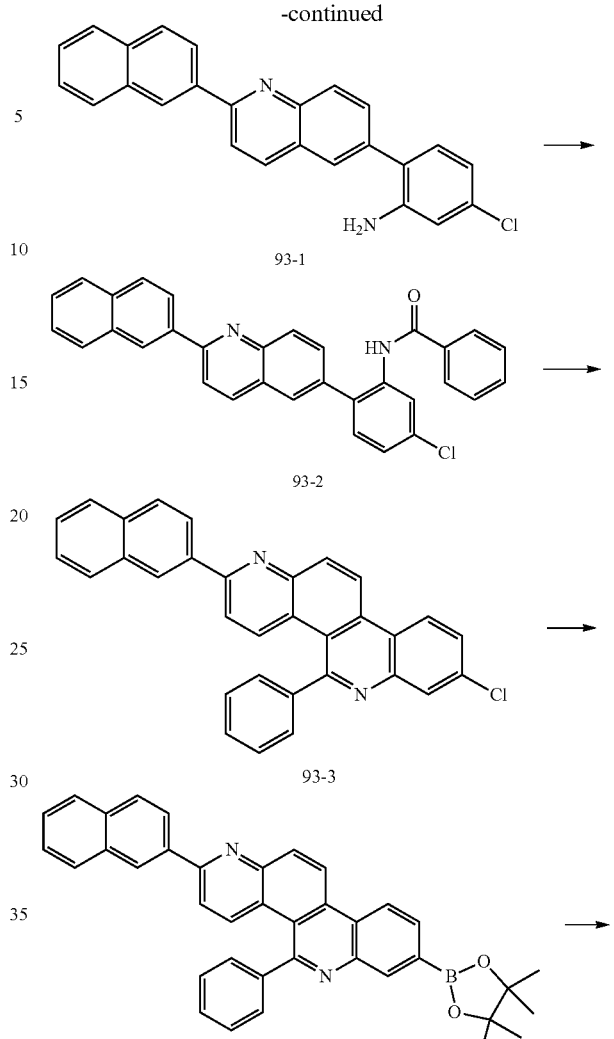

Preparation of Compound 93-1

After dissolving Compound 53-2 (20 g, 52.5 mmol) in 1,4-dioxane and H₂O, 2-bromo-5-chloroaniline) (11.8 g, 1 eq.), Pd(PPh₃)₄ (3.3 g, 0.05 eq.) and K₂CO₃ (23.6 g, 3.0 eq.) were added thereto, and the mixture was stirred for 3 hours at 110° C. After the reaction was completed, the result was cooled to room temperature, and then extracted with distilled water and EA. After drying the organic layer with anhydrous MgSO₄, the solvent was removed using a rotary evaporator, and the result was purified by column chromatography using ethyl acetate and dichloromethane as a developing solvent to obtain target Compound 93-1 (16.9 g, 85%).

Preparation of Compound 93-2

After dissolving Compound 93-1 (16.9 g, 44.4 mmol) in DCM, benzoyl chloride (6.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 93-2 (15.9 g, 74%).

Preparation of Compound 93-3

After dissolving Compound 93-2 (15.9 g, 32.8 mmol) in nitrobenzene, POCl$_3$ (3.7 ml, 1 eq.) was added thereto, and the mixture was stirred for 3 hours at 150° C. After the reaction was completed, the result was neutralized by adding an aqueous sodium bicarbonate solution thereto at room temperature, and produced solids were filtered to obtain target Compound 93-3 (13.5 g, 88%).

Preparation of Compound 93-4

After dissolving Compound 93-3 (13.5 g, 28.9 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 93-4 (11.9 g, 74%).

Preparation of Compound 93

To Compound 93-4 (11.9 g, 21.3 mmol), 4-chloro-2,6-diphenylpyrimidine (6.5 g, 1 eq.), Pd(PPh$_3$)$_4$ (1.4 g, 0.05 eq.), K$_2$CO$_3$ (10.0 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 93 (10.3 g, 73%).

[Preparation Example 29] Preparation of Compound 97

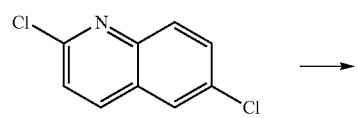

53-1

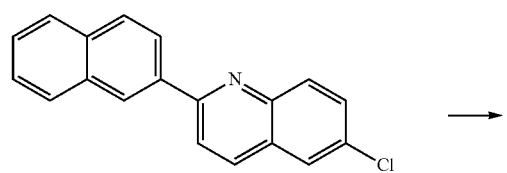

-continued

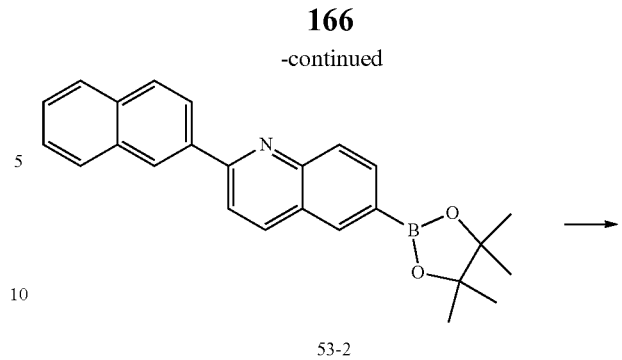

53-2

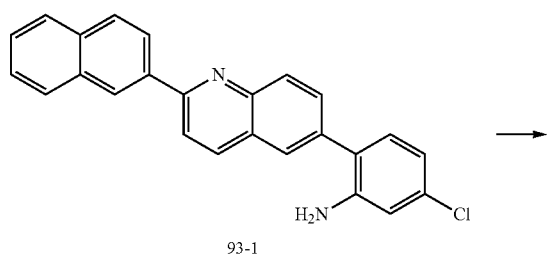

93-1

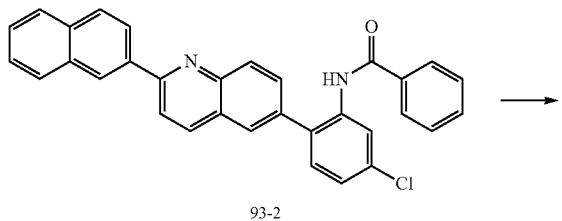

93-2

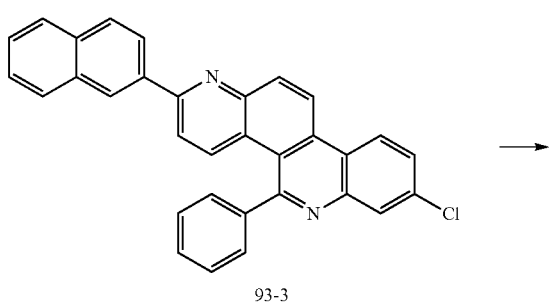

93-3

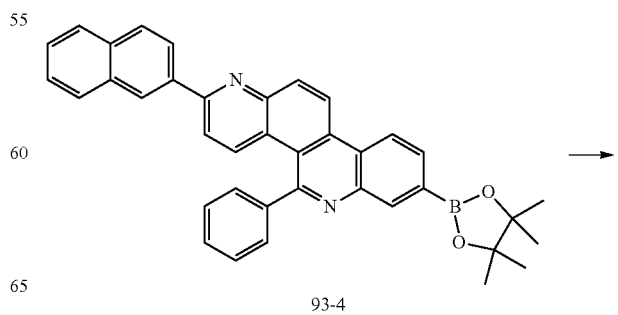

93-4

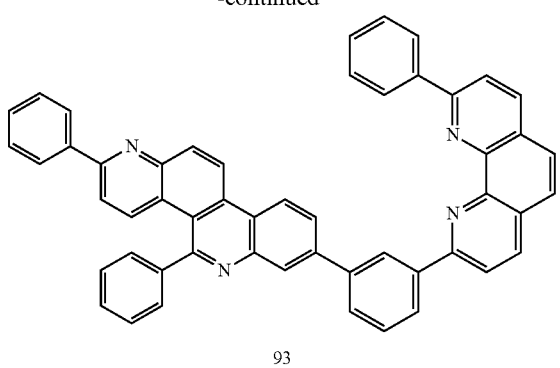

93

Preparation of Compound 97

Target Compound 97 was obtained in the same manner as in Preparation of Compound 93 in Preparation Example 28 except that 2-(3-bromophenyl)-9-phenyl-1,10-phenanthroline was used instead of 4-chloro-2,6-diphenylpyrimidine.

[Preparation Example 30] Preparation of Compound 98

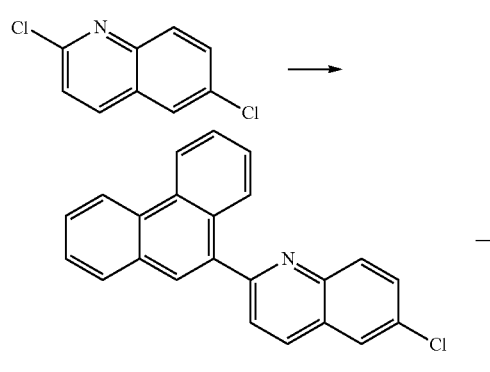

98-1

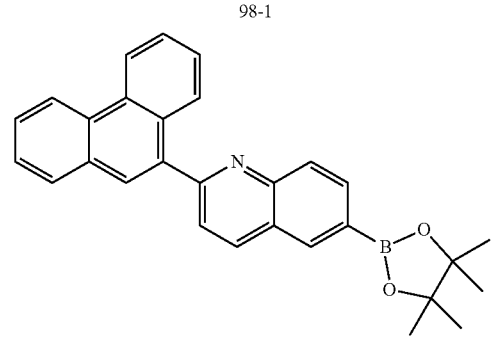

98-2

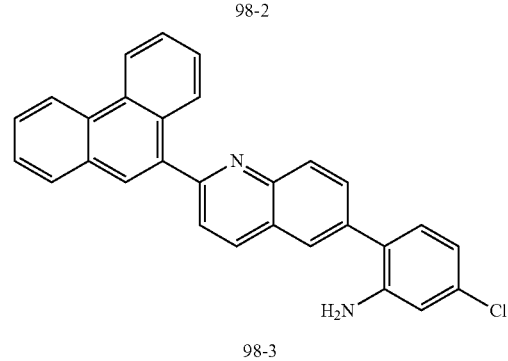

98-3

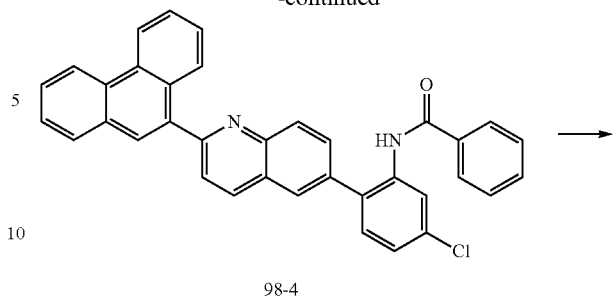

98-4

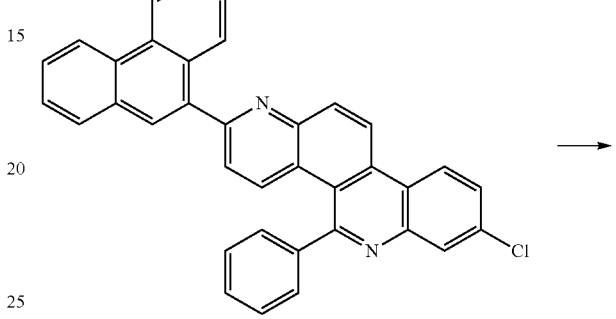

98-5

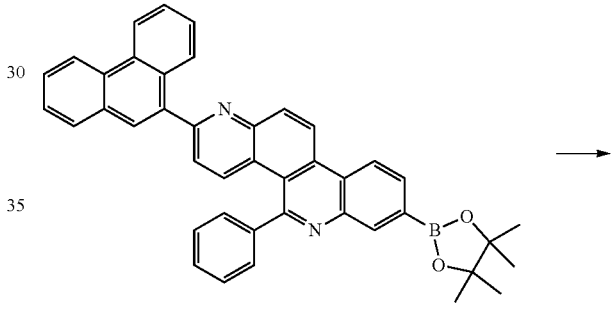

98-6

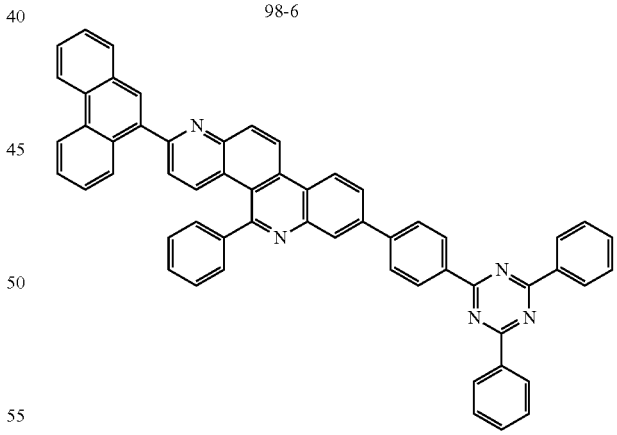

98

Preparation of Compound 98-1

2,6-Dichloroquinoline (20 g, 101 mmol, 1 eq.), phenanthren-9-ylboronic acid (24.7 g, 111.1 mmol, 1.1 eq.), $Pd(PPh_3)_4$ (5.8 g, 0.05 eq.), $K_2CO_3$ (41.9 g, 3.0 eq.) and toluene/EtOH/$H_2O$ were added, and stirred for 3 hours at 110° C. After the reaction was completed, the result was cooled to room temperature, and extracted with distilled water and EA. After drying the organic layer with anhydrous $MgSO_4$, the solvent was removed using a rotary evaporator, and the result was purified by column chromatography using dichloromethane and hexane as a developing solvent to obtain target Compound 98-1 (25.1 g, 75%).

Preparation of Compound 98-2

After dissolving Compound 98-1 (25.1 g, 74.8 mmol) in 1,4-dioxane, bis(pinacolato)diboron, Pd(dppf)Cl$_2$ and potassium acetate were added thereto, and the mixture was stirred for 4 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 98-2 (24.3 g, 75%).

Preparation of Compound 98-3

After dissolving Compound 98-2 (24.3 g, 56.3 mmol) in 1,4-dioxane and H$_2$O, 2-bromo-5-chloroaniline (11.8 g, 1 eq.), Pd(PPh$_3$)$_4$ (3.3 g, 0.05 eq.) and K$_2$CO$_3$ (23.6 g, 3.0 eq.) were added thereto, and the mixture was stirred for 3 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 98-3 (22.9 g, 94%).

Preparation of Compound 98-4

After dissolving Compound 98-3 (22.9 g, 53.1 mmol) in DCM, benzoyl chloride (6.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 98-4 (20.9 g, 74%).

Preparation of Compound 98-5

After dissolving Compound 98-4 (20.9 g, 39.1 mmol) in nitrobenzene, POCl$_3$ (3.7 ml, 1 eq.) was added thereto, and the mixture was stirred for 3 hours at 150° C. After the reaction was completed, the result was neutralized by adding an aqueous sodium bicarbonate solution thereto at room temperature, and produced solids were filtered to obtain target Compound 98-5 (19.3 g, 95%).

Preparation of Compound 98-6

After dissolving Compound 98-5 (13.5 g, 37.3 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 98-6 (14 g, 62%).

Preparation of Compound 98

To Compound 98-6 (14 g, 23 mmol), 2-(4-bromophenyl)-4,6-diphenyl-1,3,5-triazine (6.5 g, 1 eq.), Pd(PPh$_3$)$_4$ (1.4 g, 0.05 eq.), K$_2$CO$_3$ (10.0 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 98 (12.5 g, 69%).

[Preparation Example 31] Preparation of Compound 101

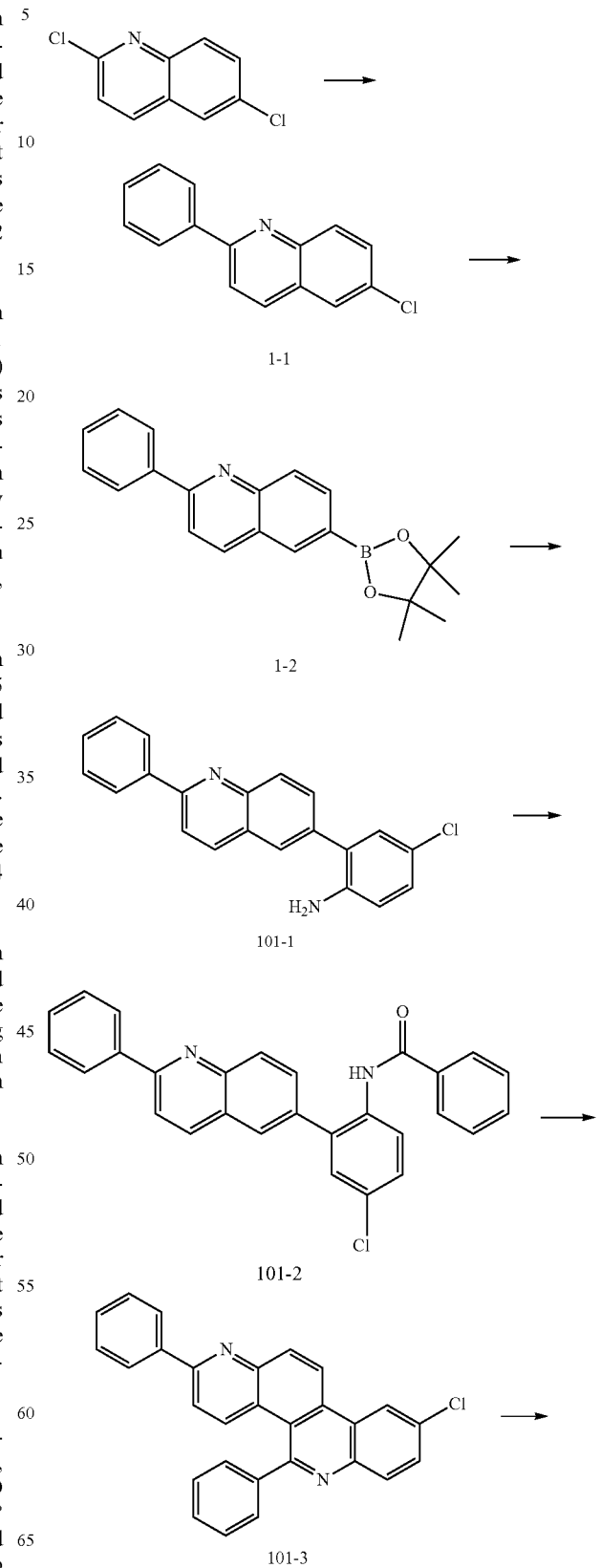

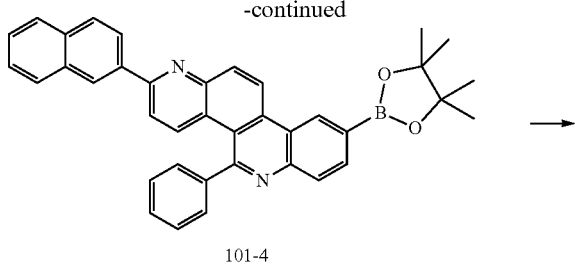

101-4

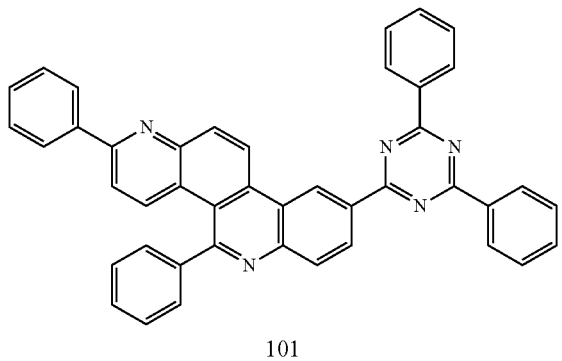

101

Preparation of Compound 101-1

After dissolving Compound 1-2 (18.4 g, 55.6 mmol) in 1,4-dioxane and H$_2$O, 2-bromo-4-chloroaniline (11.5 g, 1 eq.), Pd(PPh$_3$)$_4$ (3.3 g, 0.05 eq.) and K$_2$CO$_3$ (23.6 g, 3.0 eq.) were added thereto, and the mixture was stirred for 3 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 101-1 (12.2 g, 66%).

Preparation of Compound 101-2

After dissolving Compound 101-1 (12.2 g, 36.9 mmol) in DCM, benzoyl chloride (6.0 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 101-2 (14.9 g, 93%).

Preparation of Compound 101-3

After dissolving Compound 101-2 (14.9 g, 34.2 mmol) in nitrobenzene, POCl$_2$ (3.7 ml, 1 eq.) was added thereto, and the mixture was stirred for 3 hours at 150° C. After the reaction was completed, the result was neutralized by adding an aqueous sodium bicarbonate solution thereto at room temperature, and produced solids were filtered to obtain target Compound 101-3 (13.1 g, 92%).

Preparation of Compound 101-4

After dissolving Compound 101-3 (13.1 g, 31.4 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 101-4 (11.2 g, 70%).

Preparation of Compound 101

To Compound 101-4 (11.2 g, 21.9 mmol), 2-chloro-4,6-diphenyl-1,3,5-triazine (6.3 g, 1 eq.), Pd(PPh$_3$)$_4$ (1.3 g, 0.05 eq.), K$_2$CO$_3$ (10.0 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 101 (9.81 g, 73%).

Preparation of Compound 105

Target Compound 105 was obtained in the same manner as in Preparation of Compound 101 in Preparation Example 31 except that 4-(4-bromophenyl)-2,6-diphenylpyrimidine was used instead of 2-chloro-4,6-diphenyl-1,3,5-triazine.

Preparation of Compound 108

Target Compound 108 was obtained in the same manner as in Preparation of Compound 101 in Preparation Example 31 except that (4-bromophenyl)diphenylphosphine oxide was used instead of 2-chloro-4,6-diphenyl-1,3,5-triazine.

Preparation of Compound 112

Target Compound 112 was obtained in the same manner as in Preparation of Compound 101 in Preparation Example 31 except that 2-chloro-4,6-diphenylpyrimidine was used instead of 2-chloro-4,6-diphenyl-1,3,5-triazine.

Preparation of Compound 114

Target Compound 114 was obtained in the same manner as in Preparation of Compound 101 in Preparation Example 31 except that 4-([1,1'-biphenyl]-4-yl)-6-chloro-2-phenylpyrimidine was used instead of 2-chloro-4,6-diphenyl-1,3,5-triazine.

Preparation of Compound 118

Target Compound 118 was obtained in the same manner as in Preparation of Compound 101 in Preparation Example 31 except that 2-(3-bromophenyl)-4-phenylquinazoline was used instead of 2-chloro-4,6-diphenyl-1,3,5-triazine.

Preparation of Compound 122

Target Compound 122 was obtained in the same manner as in Preparation of Compound 101 in Preparation Example 31 except that 2-(3-bromophenyl)imidazo[1,2-a]pyridine was used instead of 2-chloro-4,6-diphenyl-1,3,5-triazine.

Preparation of Compound 130

Target Compound 130 was obtained in the same manner as in Preparation of Compound 101 in Preparation Example 31 except that 2-bromo-9-phenyl-1,10-phenanthroline was used instead of 2-chloro-4,6-diphenyl-1,3,5-triazine.

Preparation of Compound 134

Target Compound 134 was obtained in the same manner as in Preparation of Compound 101 in Preparation Example 31 except that 9-(3-(6-chloro-2-phenylpyrimidin-4-yl)phenyl)-9H-carbazole was used instead of 2-chloro-4,6-diphenyl-1,3,5-triazine.

Preparation of Compound 136

Target Compound 136 was obtained in the same manner as in Preparation of Compound 101 in Preparation Example 31 except that 2-chloro-4-(9,9-dimethyl-9H-fluoren-3-yl)-6-phenyl-1,3,5-triazine was used instead of 2-chloro-4,6-diphenyl-1,3,5-triazine.

[Preparation Example 32] Preparation of Compound 140

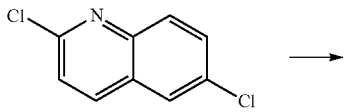

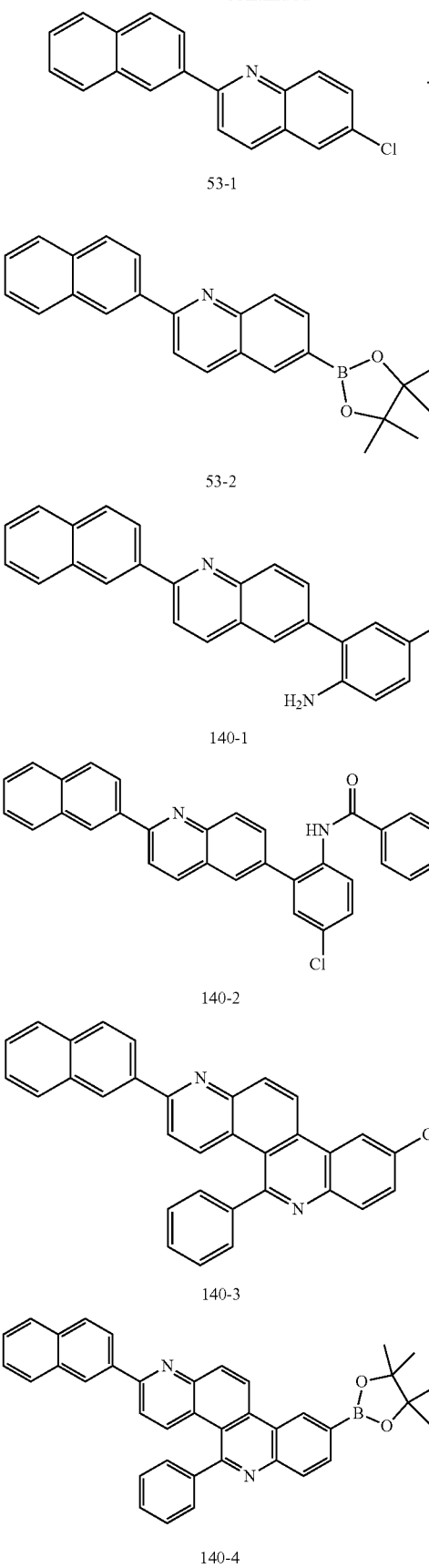

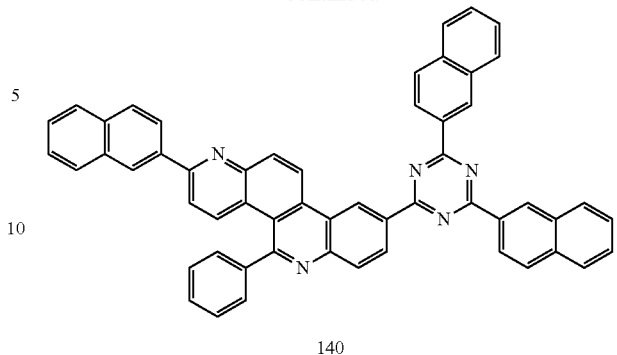

140

Preparation of Compound 140-1

After dissolving Compound 53-2 (20 g, 52.5 mmol) in 1,4-dioxane and H$_2$O, 2-bromo-4-chloroaniline (13.5 g, 1 eq.), Pd(PPh$_3$)$_4$ (3.3 g, 0.05 eq.) and K$_2$CO$_3$ (23.6 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 140-1 (14.2 g, 71%).

Preparation of Compound 140-2

After dissolving Compound 140-1 (14.2 g, 37.3 mmol) in DCM, benzoyl chloride (6.5 g, 1.1 eq.) and TEA (8.7 ml, 1.5 eq.) were added thereto at 0° C., and the mixture was stirred for 2 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 140-2 (16.1 g, 89%).

Preparation of Compound 140-3

After dissolving Compound 140-2 (16.1 g, 33.2 mmol) in nitrobenzene, POCl$_3$ (3.8 ml, 1 eq.) was added thereto, and the mixture was stirred for 4 hours at 150° C. After the reaction was completed, the result was neutralized by adding an aqueous sodium bicarbonate solution thereto at room temperature, and produced solids were filtered to obtain target Compound 140-3 (14.1 g, 91%).

Preparation of Compound 140-4

After dissolving Compound 140-3 (14.1 g, 30.2 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 140-4 (13.2 g, 78%).

Preparation of Compound 140

To Compound 140-4 (13.2 g, 23.6 mmol), 2-chloro-4,6-di(naphthalen-2-yl)-1,3,5-triazine (6.3 g, 1 eq.), Pd(PPh$_3$)$_4$ (1.3 g, 0.05 eq.), K$_2$CO$_3$ (10.0 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 140 (13.5 g, 75%).

[Preparation Example 33] Preparation of Compound 144

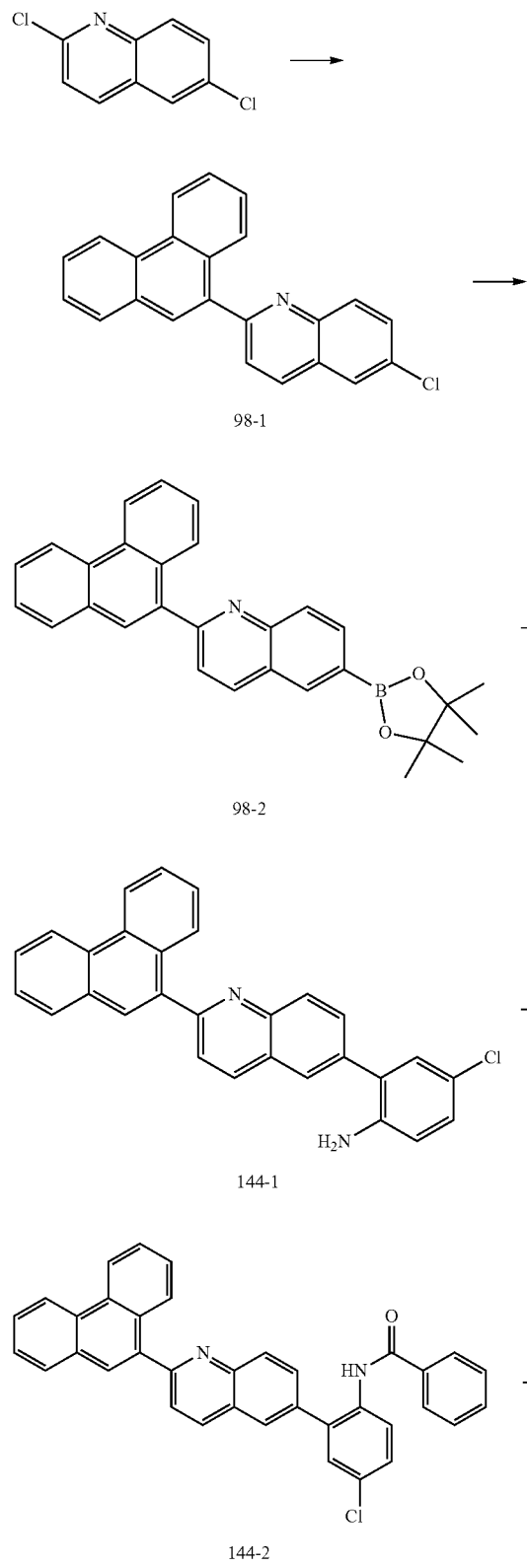

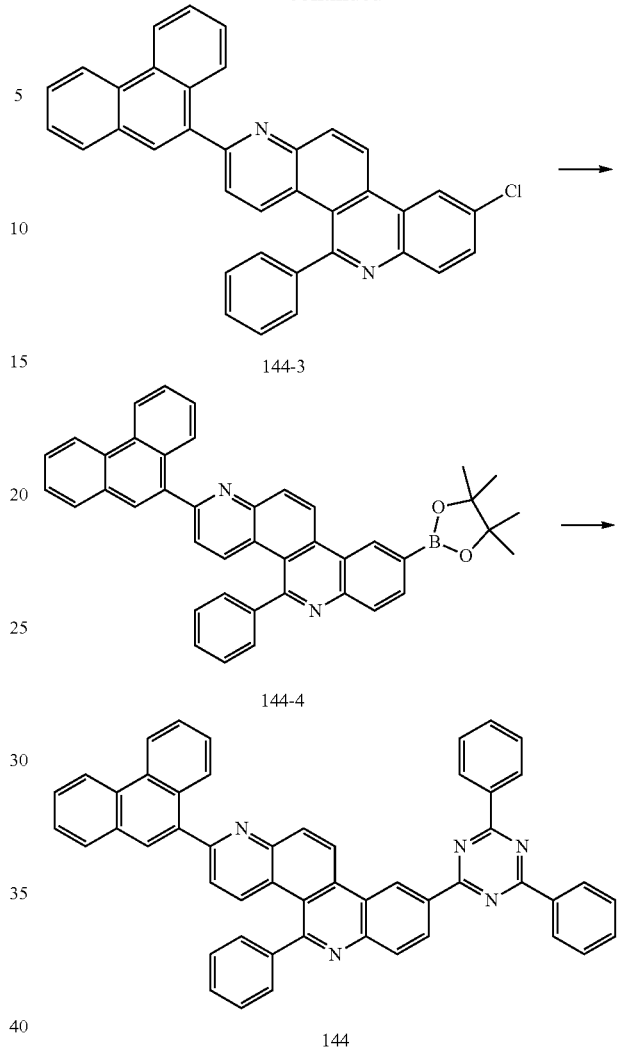

Preparation of Compound 144-1

After dissolving Compound 98-2 (20 g, 46.4 mmol) in 1,4-dioxane and $H_2O$, 2-bromo-4-chloroaniline (13.5 g, 1 eq.), $Pd(PPh_3)_4$ (3.3 g, 0.05 eq.) and $K_2CO_3$ (23.6 g, 3.0 eq.) were added thereto, and the mixture was stirred for 3 hours at 110° C. After the reaction was completed, the result was cooled to room temperature, and then extracted with distilled water and EA. After drying the organic layer with anhydrous $MgSO_4$, the solvent was removed using a rotary evaporator, and the result was purified by column chromatography using ethyl acetate and dichloromethane as a developing solvent to obtain target Compound 144-1 (15.6 g, 78%).

Preparation of Compound 144-2

After dissolving Compound 144-1 (15.6 g, 36.2 mmol) in DCM, benzoyl chloride (6.5 g, 1.1 eq.) and TEA (8.7 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous $MgSO_4$, the solvent was removed using a rotary evaporator, and the result was MeOH slurried to obtain target Compound 144-2 (16.5 g, 85%).

Preparation of Compound 144-3

After dissolving Compound 144-2 (16.5 g, 30.8 mmol) in nitrobenzene, $POCl_2$ (3.8 ml, 1 eq.) was added thereto, and the mixture was stirred for 4 hours at 150° C. After the reaction was completed, the result was neutralized by adding an aqueous sodium bicarbonate solution thereto at room temperature, and produced solids were filtered to obtain target Compound 144-3 (14.3 g, 90%).

Preparation of Compound 144-4

After dissolving Compound 144-3 (14.3 g, 27.7 mmol) in 1,4-dioxane, bis(pinacolato)diboron, $Pd(dppf)Cl_2$ and potassium acetate were added thereto, and the mixture was stirred for 3 hours at 110° C. After the reaction was completed, the result was extracted with distilled water and EA. After drying the organic layer with anhydrous $MgSO_4$, the solvent was removed using a rotary evaporator, and the result was purified by column chromatography using dichloromethane as a developing solvent to obtain target Compound 144-4 (13.7 g, 81%).

Preparation of Compound 144

To Compound 144-4 (13.7 g, 22.4 mmol), 2-chloro-4,6-diphenyl-1,3,5-triazine (6.3 g, 1 eq.), $Pd(PPh_3)_4$ (1.3 g, 0.05 eq.), $K_2CO_3$ (10.0 g, 3.0 eq.) and 1,4-dioxane/$H_2O$ were added, and the mixture was stirred for 3 hours at 110° C. After the reaction was completed, the result was cooled to room temperature, and produced solids were filtered to obtain target Compound 144 (13.3 g, 83%).

[Preparation Example 34] Preparation of Compound 148

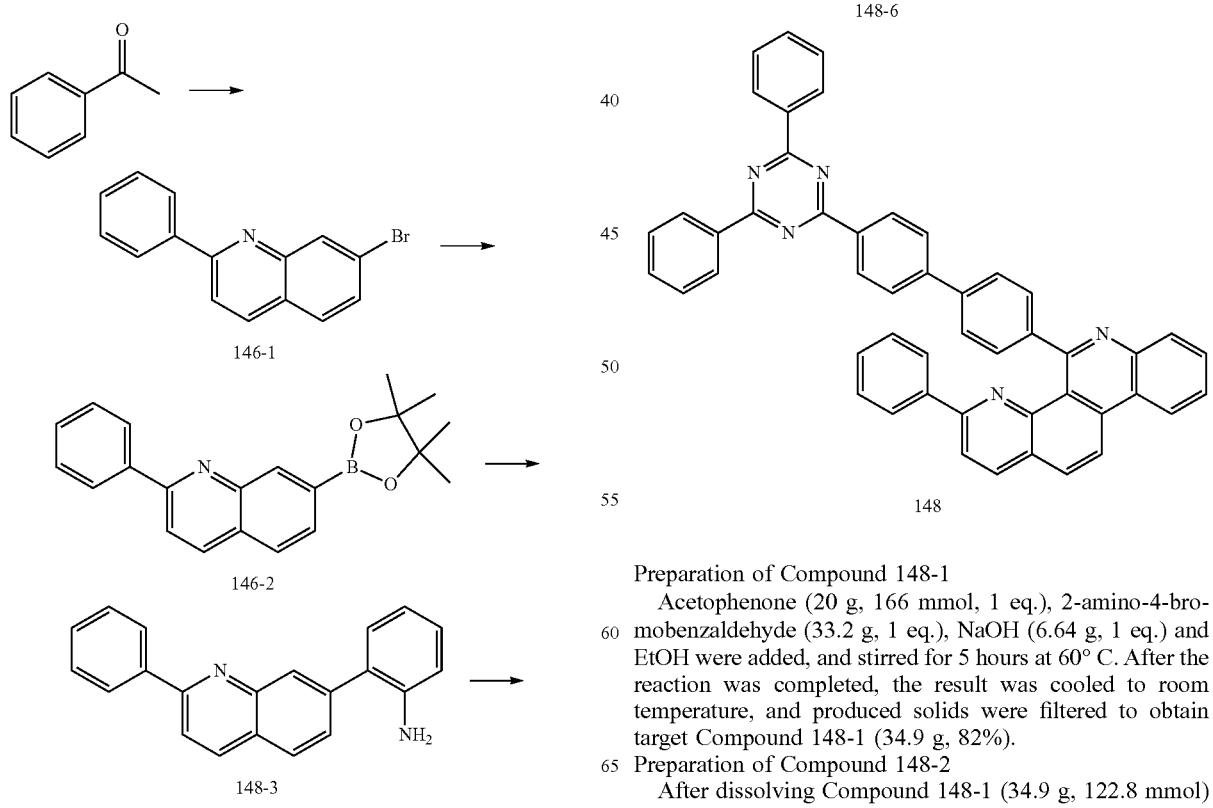

Preparation of Compound 148-1

Acetophenone (20 g, 166 mmol, 1 eq.), 2-amino-4-bromobenzaldehyde (33.2 g, 1 eq.), NaOH (6.64 g, 1 eq.) and EtOH were added, and stirred for 5 hours at 60° C. After the reaction was completed, the result was cooled to room temperature, and produced solids were filtered to obtain target Compound 148-1 (34.9 g, 82%).

Preparation of Compound 148-2

After dissolving Compound 148-1 (34.9 g, 122.8 mmol) in 1,4-dioxane, bis(pinacolato)diboron, $Pd(dppf)Cl_2$ and potassium acetate were added thereto, and the mixture was stirred for 3 hours at 110° C. After the reaction was completed, the result was extracted with distilled water and EA. After drying the organic layer with anhydrous $MgSO_4$, the solvent was removed using a rotary evaporator, and the result was purified by column chromatography using dichloromethane as a developing solvent to obtain target Compound 148-2 (24.8 g, 61%).

Preparation of Compound 148-3

After dissolving Compound 148-2 (24.8 g, 74.9 mmol) in 1,4-dioxane and $H_2O$, 2-bromoaniline (12.8 g, 1 eq.), $Pd(PPh_3)_4$ (4.3 g, 0.05 eq.) and $K_2CO_3$ (31.1 g, 3.0 eq.) were added thereto, and the mixture was stirred for 4 hours at 110° C. After the reaction was completed, the result was cooled to room temperature, and then extracted with distilled water and EA. After drying the organic layer with anhydrous $MgSO_4$, the solvent was removed using a rotary evaporator, and the result was purified by column chromatography using ethyl acetate and dichloromethane as a developing solvent to obtain target Compound 148-3 (17.5 g, 79%).

Preparation of Compound 148-4

After dissolving Compound 148-3 (17.5 g, 59.2 mmol) in DCM, 4-bromobenzoyl chloride (14.3 g, 1.1 eq.) and TEA (12.4 ml, 1.5 eq.) were added thereto at 0° C., and the mixture was stirred for 2 hours at room temperature. After the reaction was completed, the result was cooled to room temperature, and then extracted with distilled water and dichloromethane. After drying the organic layer with anhydrous $MgSO_4$, the solvent was removed using a rotary evaporator, and the result was MeOH slurried to obtain target Compound 148-4 (17 g, 60%).

Preparation of Compound 148-5

After dissolving Compound 148-4 (17 g, 35.5 mmol) in nitrobenzene, $POCl_3$ (3.3 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 148-5 (12.3 g, 75%).

Preparation of Compound 148-6

After dissolving Compound 148-5 (12.3 g, 26.6 mmol) in 1,4-dioxane, bis(pinacolato)diboron, $Pd(dppf)Cl_2$ and potassium acetate were added thereto, and the mixture was stirred for 3 hours at 110° C. After the reaction was completed, the result was extracted with distilled water and EA. After drying the organic layer with anhydrous $MgSO_4$, the solvent was removed using a rotary evaporator, and the result was purified by column chromatography using dichloromethane as a developing solvent to obtain target Compound 148-6 (11.1 g, 82%).

Preparation of Compound 148

To Compound 148-6 (11.1 g, 21.8 mmol), 2-chloro-4,6-diphenyl-1,3,5-triazine (7.1 g, 1 eq.), $Pd(PPh_3)_4$ (1.5 g, 0.05 eq.), $K_2CO_3$ (10.5 g, 3.0 eq.) and 1,4-dioxane/$H_2O$ were added, and the mixture was stirred for 3 hours at 110° C. After the reaction was completed, the result was cooled to room temperature, and produced solids were filtered to obtain target Compound 148 (12.3 g, 82%).

Preparation of Compound 149

Target Compound 149 was obtained in the same manner as in Preparation of Compound 148 in Preparation Example 34 except that 2-(3-bromophenyl)-4,6-diphenyl-1,3,5-triazine was used instead of 2-chloro-4,6-diphenyl-1,3,5-triazine.

Preparation of Compound 153

Target Compound 153 was obtained in the same manner as in Preparation of Compound 148 in Preparation Example 34 except that (6-bromonaphthalen-2-yl)diphenylphosphine oxide was used instead of 2-chloro-4,6-diphenyl-1,3,5-triazine.

Preparation of Compound 155

Target Compound 155 was obtained in the same manner as in Preparation of Compound 148 in Preparation Example 34 except that 9,9'-(5-bromo-1,3-phenylene)bis(9H-carbazole) was used instead of 2-chloro-4,6-diphenyl-1,3,5-triazine.

Preparation of Compound 158

Target Compound 158 was obtained in the same manner as in Preparation of Compound 148 in Preparation Example 34 except that 2-chloro-4,6-diphenylpyrimidine was used instead of 2-chloro-4,6-diphenyl-1,3,5-triazine.

Preparation of Compound 161

Target Compound 161 was obtained in the same manner as in Preparation of Compound 148 in Preparation Example 34 except that 4-([1,1'-biphenyl]-3-yl)-6-chloro-2-phenylpyrimidine was used instead of 2-chloro-4,6-diphenyl-1,3,5-triazine.

Preparation of Compound 166

Target Compound 166 was obtained in the same manner as in Preparation of Compound 148 in Preparation Example 34 except that 4-chloro-2-phenylquinazoline was used instead of 2-chloro-4,6-diphenyl-1,3,5-triazine.

Preparation of Compound 173

Target Compound 173 was obtained in the same manner as in Preparation of Compound 148 in Preparation Example 34 except that 1-(4-bromophenyl)-2-phenyl-1H-benzo[d]imidazole was used instead of 2-chloro-4,6-diphenyl-1,3,5-triazine.

Preparation of Compound 176

Target Compound 176 was obtained in the same manner as in Preparation of Compound 148 in Preparation Example 34 except that 2-(3-bromophenyl)-9-phenyl-1,10-phenanthroline was used instead of 2-chloro-4,6-diphenyl-1,3,5-triazine.

Preparation of Compound 180

Target Compound 180 was obtained in the same manner as in Preparation of Compound 148 in Preparation Example 34 except that 2-bromo-9-phenyl-1,10-phenanthroline was used instead of 2-chloro-4,6-diphenyl-1,3,5-triazine.

Preparation of Compound 181

Target Compound 181 was obtained in the same manner as in Preparation of Compound 148 in Preparation Example 34 except that 9-(4-(4-chloro-6-phenyl-1,3,5-triazin-2-yl)phenyl)-9H-carbazole was used instead of 2-chloro-4,6-diphenyl-1,3,5-triazine.

[Preparation Example 35] Preparation of Compound 188

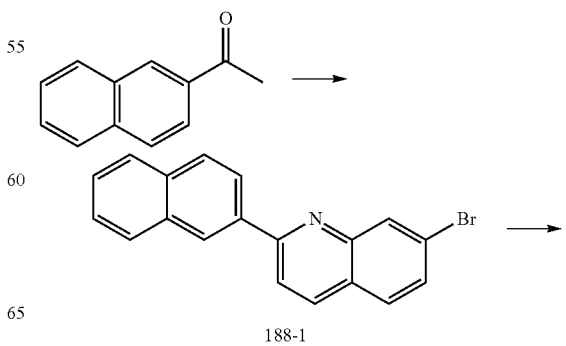

188-1

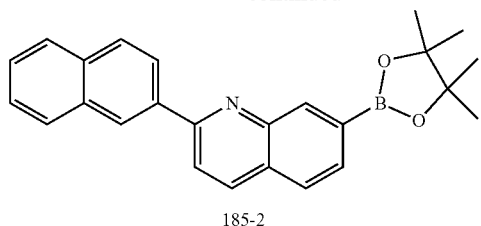

185-2

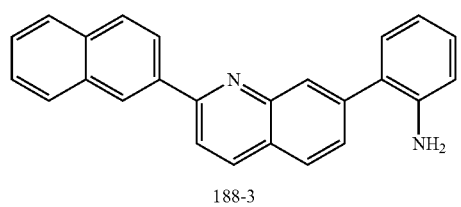

188-3

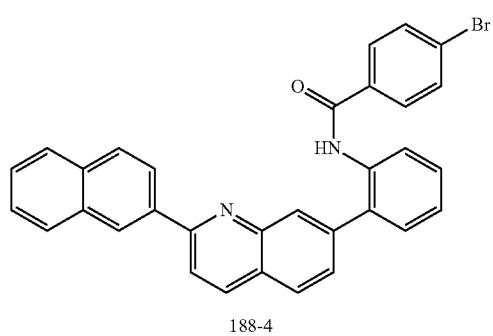

188-4

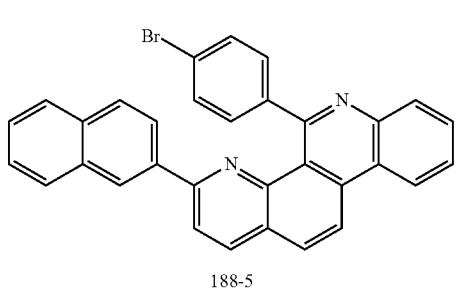

188-5

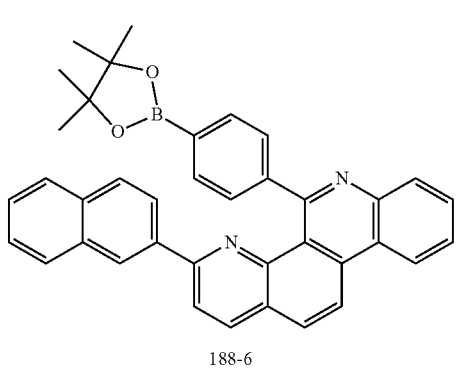

188-6

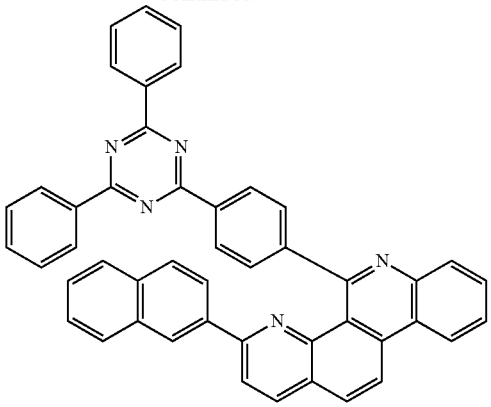

168

Preparation of Compound 188-1

1-(Naphthalen-2-yl)ethanone (20 g, 118 mmol, 1 eq.), 2-amino-4-bromobenzaldehyde (32.2 g, 1 eq.), NaOH (6.59 g, 1 eq.) and EtOH were added, and stirred for 4 hours at 60° C. After the reaction was completed, the result was cooled to room temperature, and produced solids were filtered to obtain target Compound 188-1 (31.5 g, 80%).

Preparation of Compound 188-2

After dissolving Compound 188-1 (31.5 g, 94.4 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 188-2 (25.2 g, 70%).

Preparation of Compound 188-3

After dissolving Compound 188-2 (25.2 g, 66.1 mmol) in 1,4-dioxane and H$_2$O, 2-bromoaniline (12.8 g, 1 eq.), Pd(PPh$_3$)$_4$ (4.3 g, 0.05 eq.) and K$_2$CO$_3$ (31.1 g, 3.0 eq.) were added thereto, and the mixture was stirred for 4 hours at 110° C.

After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 188-3 (17.2 g, 75%).

Preparation of Compound 188-4

After dissolving Compound 188-3 (17.2 g, 49.6 mmol) in DCM, 4-bromobenzoyl chloride (14.3 g, 1.1 eq.) and TEA (12.4 ml, 1.5 eq.) were added thereto at 0° C., and the mixture was stirred for 2 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 188-4 (17.8 g, 68%).

Preparation of Compound 188-5

After dissolving Compound 188-4 (17.8 g, 33.7 mmol) in nitrobenzene, POCl$_3$ (3.3 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 188-5 (13.6 g, 79%).

Preparation of Compound 188-6

After dissolving Compound 188-5 (13.6 g, 26.6 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 188-6 (11.8 g, 80%).

Preparation of Compound 188

To Compound 188-6 (11.8 g, 21.3 mmol), 2-chloro-4,6-diphenyl-1,3,5-triazine (7 g, 1 eq.), Pd(PPh$_3$)$_4$ (1.5 g, 0.05 eq.), K$_2$CO$_3$ (10.5 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 188 (11 g, 78%).

Preparation of Compound 189

Target Compound 189 was obtained in the same manner as in Preparation of Compound 188 in Preparation Example 35 except that 4-(4-bromophenyl)-2,6-diphenylpyrimidine was used instead of 2-chloro-4,6-diphenyl-1,3,5-triazine.

Preparation of Compound 193

Target Compound 193 was obtained in the same manner as in Preparation of Compound 188 in Preparation Example 35 except that 2-(3-bromophenyl)-9-phenyl-1,10-phenanthroline was used instead of 2-chloro-4,6-diphenyl-1,3,5-triazine.

[Preparation Example 36] Preparation of Compound 197

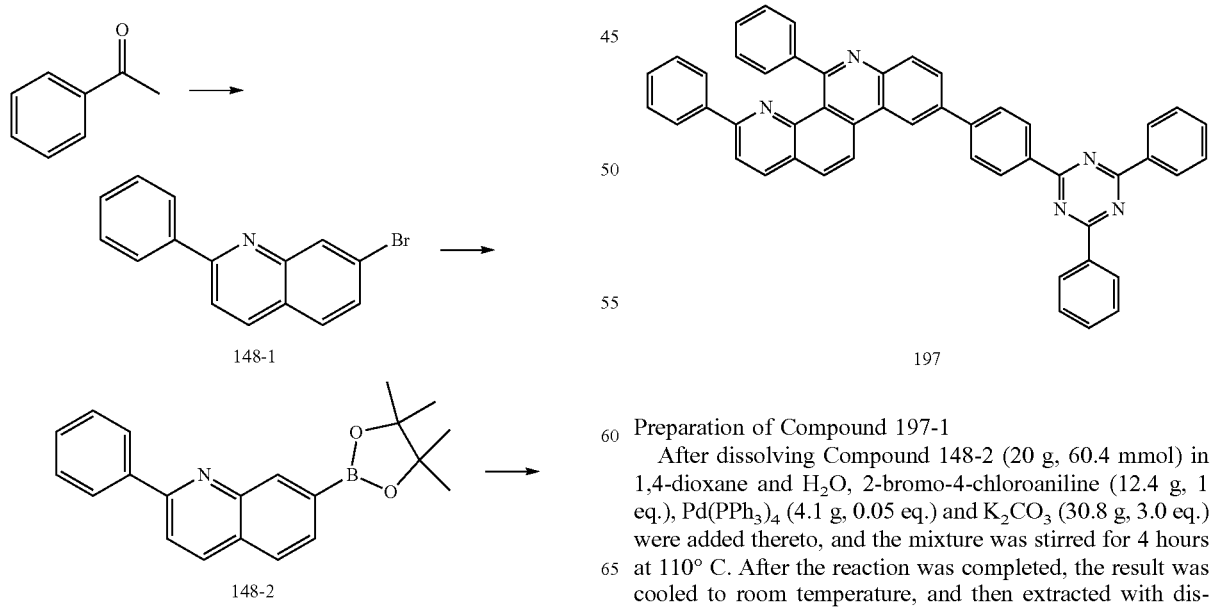

Preparation of Compound 197-1

After dissolving Compound 148-2 (20 g, 60.4 mmol) in 1,4-dioxane and H$_2$O, 2-bromo-4-chloroaniline (12.4 g, 1 eq.), Pd(PPh$_3$)$_4$ (4.1 g, 0.05 eq.) and K$_2$CO$_3$ (30.8 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO₄, the solvent was removed using a rotary evaporator, and the result was purified by column chromatography using ethyl acetate and dichloromethane as a developing solvent to obtain target Compound 197-1 (14.9 g, 75%).

Preparation of Compound 197-2

After dissolving Compound 148-3 (14.9 g, 45.3 mmol) in DCM, benzoyl chloride (7 g, 1.1 eq.) and TEA (12.4 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO₄, the solvent was removed using a rotary evaporator, and the result was MeOH slurried to obtain target Compound 197-2 (14 g, 71%).

Preparation of Compound 197-3

After dissolving Compound 197-2 (14 g, 32.2 mmol) in nitrobenzene, POCl₃ (3.3 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 197-3 (10.6 g, 79%).

Preparation of Compound 197-4

After dissolving Compound 197-3 (10.6 g, 25.4 mmol) in 1,4-dioxane, bis(pinacolato)diboron, Pd(dppf)Cl₂ and potassium acetate were added thereto, and the mixture was stirred for 3 hours at 110° C. After the reaction was completed, the result was extracted with distilled water and EA. After drying the organic layer with anhydrous MgSO₄, the solvent was removed using a rotary evaporator, and the result was purified by column chromatography using dichloromethane as a developing solvent to obtain target Compound 197-4 (11 g, 85%).

Preparation of Compound 197

To Compound 197-4 (11 g, 21.6 mmol), 2-(4-bromophenyl)-4,6-diphenyl-1,3,5-triazine (8.3 g, 1 eq.), Pd(PPh₃)₄ (1.5 g, 0.05 eq.), K₂CO₃ (10.5 g, 3.0 eq.) and 1,4-dioxane/H₂O were added, and the mixture was stirred for 3 hours at 110° C. After the reaction was completed, the result was cooled to room temperature, and produced solids were filtered to obtain target Compound 197 (11.9 g, 82%).

Preparation of Compound 201

Target Compound 201 was obtained in the same manner as in Preparation of Compound 197 in Preparation Example 36 except that 4-(3-bromophenyl)-2,6-diphenylpyrimidine was used instead of 2-(4-bromophenyl)-4,6-diphenyl-1,3,5-triazine.

Preparation of Compound 207

Target Compound 207 was obtained in the same manner as in Preparation of Compound 197 in Preparation Example 36 except that 2-chloro-4,6-diphenylpyrimidine was used instead of 2-(4-bromophenyl)-4,6-diphenyl-1,3,5-triazine.

Preparation of Compound 208

Target Compound 208 was obtained in the same manner as in Preparation of Compound 197 in Preparation Example 36 except that 4-chloro-2,6-di(naphthalen-2-yl)pyrimidine was used instead of 2-(4-bromophenyl)-4,6-diphenyl-1,3,5-triazine.

Preparation of Compound 214

Target Compound 214 was obtained in the same manner as in Preparation of Compound 197 in Preparation Example 36 except that 5-(4-bromophenyl)-2,4,6-triphenylpyrimidine was used instead of 2-(4-bromophenyl)-4,6-diphenyl-1,3,5-triazine.

Preparation of Compound 220

Target Compound 220 was obtained in the same manner as in Preparation of Compound 197 in Preparation Example 36 except that 2-(4-bromophenyl)-1-ethyl-1H-benzo[d]imidazole was used instead of 2-(4-bromophenyl)-4,6-diphenyl-1,3,5-triazine.

Preparation of Compound 225

Target Compound 225 was obtained in the same manner as in Preparation of Compound 197 in Preparation Example 36 except that 2-(3-bromophenyl)-9-phenyl-1,10-phenanthroline was used instead of 2-(4-bromophenyl)-4,6-diphenyl-1,3,5-triazine.

Preparation of Compound 230

Target Compound 230 was obtained in the same manner as in Preparation of Compound 197 in Preparation Example 36 except that 9-(3-(4-(4-bromophenyl)-6-phenylpyrimidin-2-yl)phenyl)-9H-carbazole was used instead of 2-(4-bromophenyl)-4,6-diphenyl-1,3,5-triazine.

[Preparation Example 37] Preparation of Compound 233

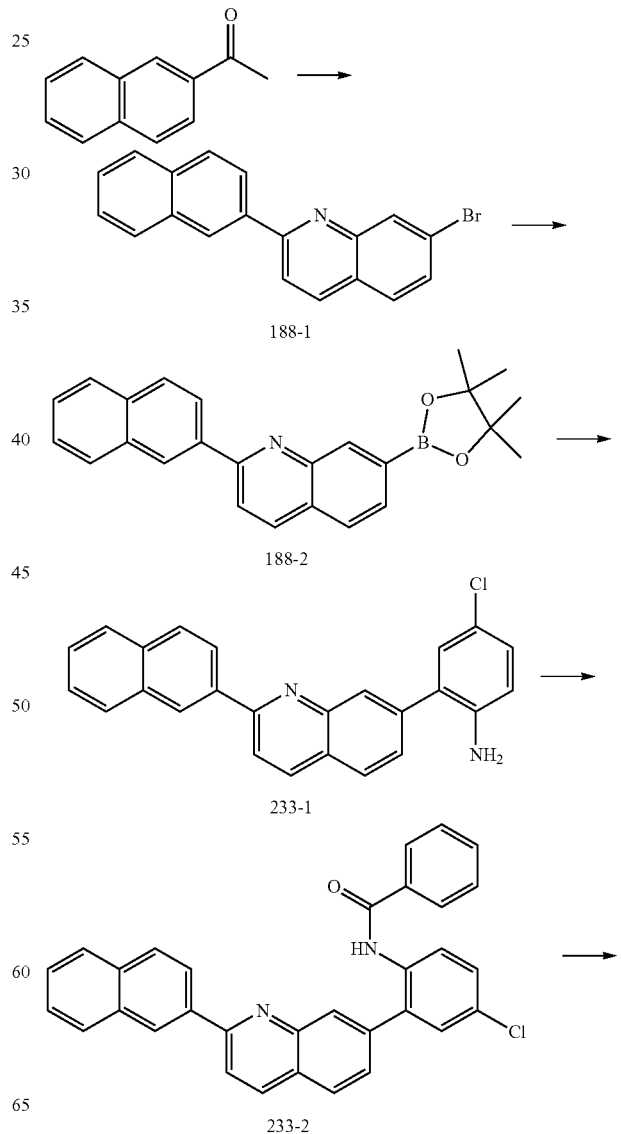

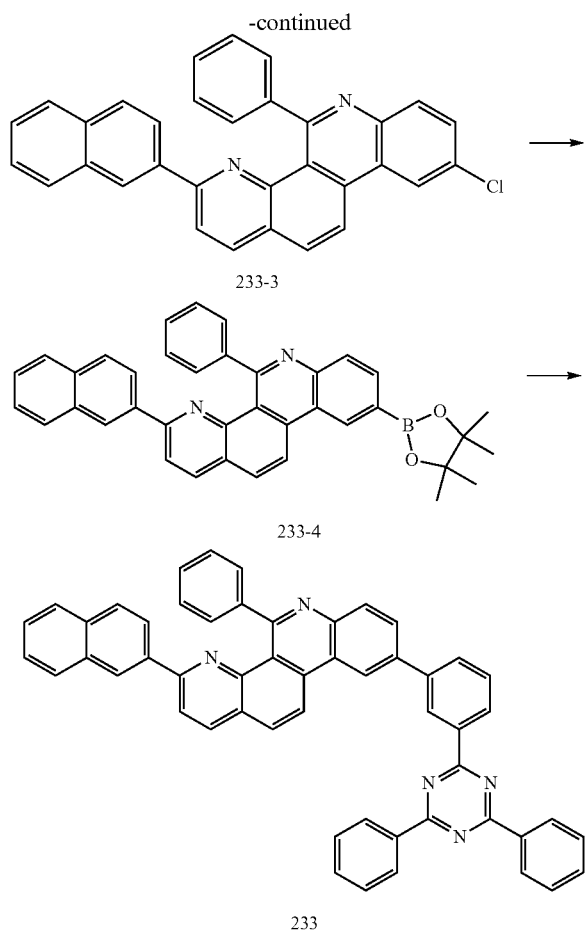

Preparation of Compound 233-1

After dissolving Compound 188-2 (25.2 g, 66.1 mmol) in 1,4-dioxane and H₂O, 2-bromo-4-chloroaniline (12.8 g, 1 eq.), Pd(PPh₃)₄ (4.3 g, 0.05 eq.) and K₂CO₃ (31.1 g, 3.0 eq.) were added thereto, and the mixture was stirred for 3 hours at 110° C. After the reaction was completed, the result was cooled to room temperature, and then extracted with distilled water and EA. After drying the organic layer with anhydrous MgSO₄, the solvent was removed using a rotary evaporator, and the result was purified by column chromatography using ethyl acetate and dichloromethane as a developing solvent to obtain target Compound 233-1 (19.1 g, 76%).

Preparation of Compound 233-2

After dissolving Compound 233-1 (19.1 g, 50.2 mmol) in DCM, benzoyl chloride (13.3 g, 1.1 eq.) and TEA (12.4 ml, 1.5 eq.) were added thereto at 0° C., and the mixture was stirred for 2 hours at room temperature. After the reaction was completed, the result was cooled to room temperature, and then extracted with distilled water and dichloromethane. After drying the organic layer with anhydrous MgSO₄, the solvent was removed using a rotary evaporator, and the result was MeOH slurried to obtain target Compound 233-2 (17.8 g, 73%).

Preparation of Compound 233-3

After dissolving Compound 233-2 (17.8 g, 36.6 mmol) in nitrobenzene, POCl₃ (3.3 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 233-3 (12.8 g, 75%).

Preparation of Compound 233-4

After dissolving Compound 233-3 (12.8 g, 27.5 mmol) in 1,4-dioxane, bis(pinacolato)diboron, Pd(dppf)Cl₂ and potassium acetate were added thereto, and the mixture was stirred for 3 hours at 110° C. After the reaction was completed, the result was extracted with distilled water and EA. After drying the organic layer with anhydrous MgSO₄, the solvent was removed using a rotary evaporator, and the result was purified by column chromatography using dichloromethane as a developing solvent to obtain target Compound 233-4 (12.1 g, 79%).

Preparation of Compound 233

To Compound 233-4 (12.1 g, 21.7 mmol), 2-(3-bromophenyl)-4,6-diphenyl-1,3,5-triazine (7.1 g, 1 eq.), Pd(PPh₃)₄ (1.5 g, 0.05 eq.), K₂CO₃ (10.5 g, 3.0 eq.) and 1,4-dioxane/H₂O were added, and the mixture was stirred for 3 hours at 110° C. After the reaction was completed, the result was cooled to room temperature, and produced solids were filtered to obtain target Compound 233 (13 g, 81%).

Preparation of Compound 236

Target Compound 236 was obtained in the same manner as in Preparation of Compound 233 in Preparation Example 37 except that 4-([1,1'-biphenyl]-3-yl)-6-chloro-2-phenylpyrimidine was used instead of 2-(3-bromophenyl)-4,6-diphenyl-1,3,5-triazine.

Preparation of Compound 238

Target Compound 238 was obtained in the same manner as in Preparation of Compound 233 in Preparation Example 37 except that 2-(3-bromophenyl)-9-phenyl-1,10-phenanthroline was used instead of 2-(3-bromophenyl)-4,6-diphenyl-1,3,5-triazine.

[Preparation Example 38] Preparation of Compound 240

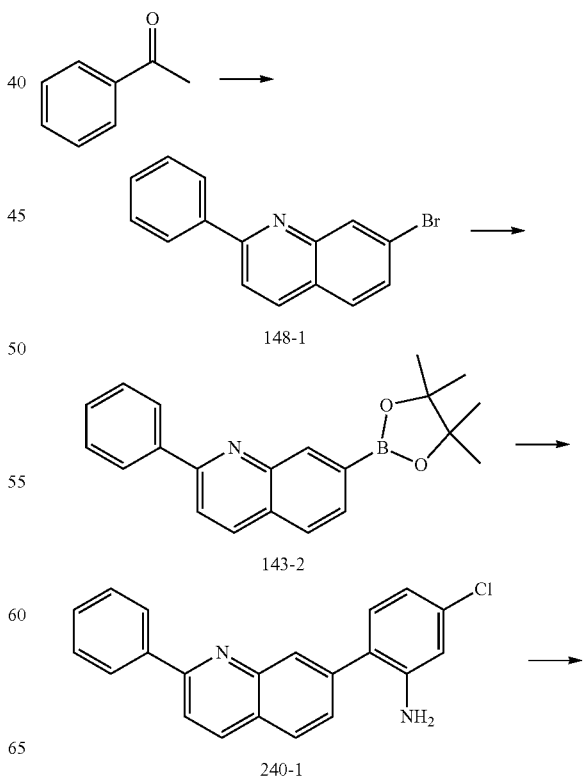

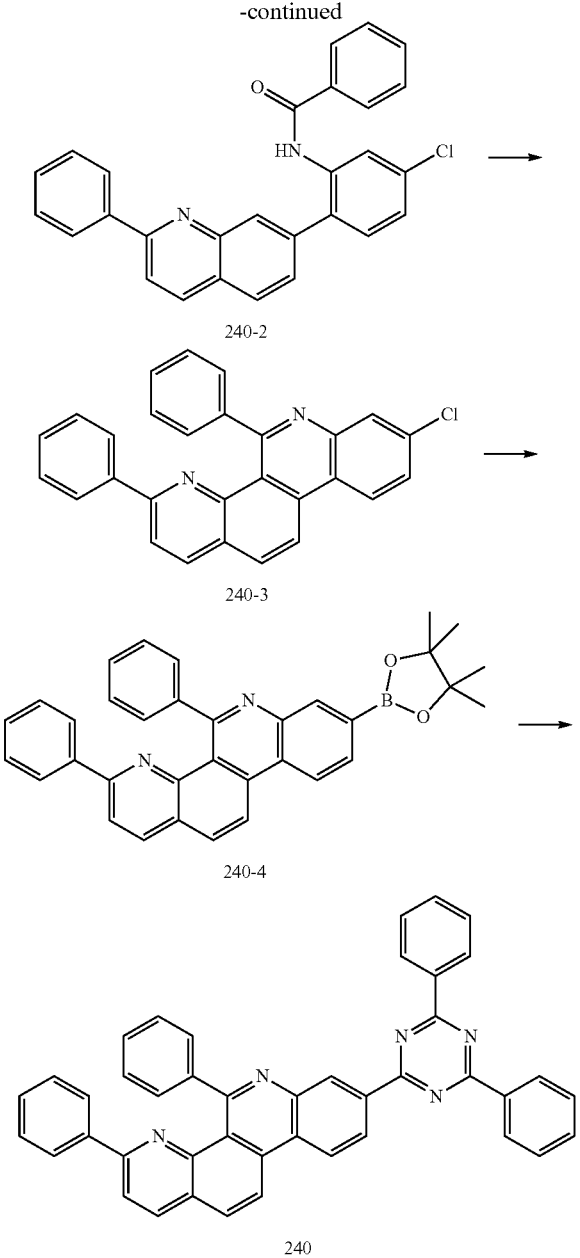

Preparation of Compound 240-1

After dissolving Compound 148-2 (20 g, 60.4 mmol) in 1,4-dioxane and H₂O, 2-bromo-5-chloroaniline (12.4 g, 1 eq.), Pd(PPh₃)₄ (4.1 g, 0.05 eq.) and K₂CO₃ (30.8 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO₄, the solvent was removed using a rotary evaporator, and the result was purified by column chromatography using ethyl acetate and dichloromethane as a developing solvent to obtain target Compound 240-1 (15.8 g, 79%).

Preparation of Compound 240-2

After dissolving Compound 240-1 (15.8 g, 47.7 mmol) in DCM, benzoyl chloride (7.1 g, 1.1 eq.) and TEA (12.4 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO₄, the solvent was removed using a rotary evaporator, and the result was MeOH slurried to obtain target Compound 240-2 (15.8 g, 76%).

Preparation of Compound 240-3

After dissolving Compound 240-2 (15.8 g, 36.3 mmol) in nitrobenzene, POCl₃ (3.3 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 240-3 (10.6 g, 76%).

Preparation of Compound 240-4

After dissolving Compound 240-3 (10.6 g, 27.6 mmol) in 1,4-dioxane, bis(pinacolato)diboron, Pd(dppf)Cl₂ and potassium acetate were added thereto, and the mixture was stirred for 3 hours at 110° C. After the reaction was completed, the result was extracted with distilled water and EA. After drying the organic layer with anhydrous MgSO₄, the solvent was removed using a rotary evaporator, and the result was purified by column chromatography using dichloromethane as a developing solvent to obtain target Compound 240-4 (11.5 g, 81%).

Preparation of Compound 240

To Compound 240-4 (11.5 g, 22.3 mmol), 2-chloro-4,6-diphenyl-1,3,5-triazine (8.1 g, 1 eq.), Pd(PPh₃)₄ (1.5 g, 0.05 eq.), K₂CO₃ (10.5 g, 3.0 eq.) and 1,4-dioxane/H₂O were added, and the mixture was stirred for 3 hours at 110° C. After the reaction was completed, the result was cooled to room temperature, and produced solids were filtered to obtain target Compound 240 (11.8 g, 86%).

Preparation of Compound 245

Target Compound 245 was obtained in the same manner as in Preparation of Compound 240 in Preparation Example 38 except that 4-(3-bromophenyl)-2,6-diphenylpyrimidine was used instead of 2-chloro-4,6-diphenyl-1,3,5-triazine.

Preparation of Compound 247

Target Compound 247 was obtained in the same manner as in Preparation of Compound 240 in Preparation Example 38 except that (4-bromophenyl)diphenylphosphine oxide was used instead of 2-chloro-4,6-diphenyl-1,3,5-triazine.

Preparation of Compound 252

Target Compound 252 was obtained in the same manner as in Preparation of Compound 240 in Preparation Example 38 except that 4-chloro-2,6-di(naphthalen-2-yl)pyrimidine was used instead of 2-chloro-4,6-diphenyl-1,3,5-triazine.

Preparation of Compound 255

Target Compound 255 was obtained in the same manner as in Preparation of Compound 240 in Preparation Example 38 except that 4'-chloro-2,2':6',2"-terpyridine was used instead of 2-chloro-4,6-diphenyl-1,3,5-triazine.

Preparation of Compound 258

Target Compound 258 was obtained in the same manner as in Preparation of Compound 240 in Preparation Example 38 except that 5-(4-bromophenyl)-2,4,6-triphenylpyrimidine was used instead of 2-chloro-4,6-diphenyl-1,3,5-triazine.

Preparation of Compound 263

Target Compound 263 was obtained in the same manner as in Preparation of Compound 240 in Preparation Example 38 except that 7-bromo-2-phenylimidazo[1,2-a]pyridine was used instead of 2-chloro-4,6-diphenyl-1,3,5-triazine.

Preparation of Compound 267

Target Compound 267 was obtained in the same manner as in Preparation of Compound 240 in Preparation Example 38 except that 1-(3-bromophenyl)-2-phenyl-1H-benzo[d]imidazole was used instead of 2-chloro-4,6-diphenyl-1,3,5-triazine.

Preparation of Compound 269

Target Compound 269 was obtained in the same manner as in Preparation of Compound 240 in Preparation Example 38 except that 2-(3-bromophenyl)-9-phenyl-1,10-phenanthroline was used instead of 2-chloro-4,6-diphenyl-1,3,5-triazine.

Preparation of Compound 274

Target Compound 274 was obtained in the same manner as in Preparation of Compound 240 in Preparation Example 38 except that 2-(4-bromophenyl)-4-(9,9-dimethyl-9H-fluoren-3-yl)-6-phenylpyrimidine was used instead of 2-chloro-4,6-diphenyl-1,3,5-triazine.

[Preparation Example 39] Preparation of Compound 276

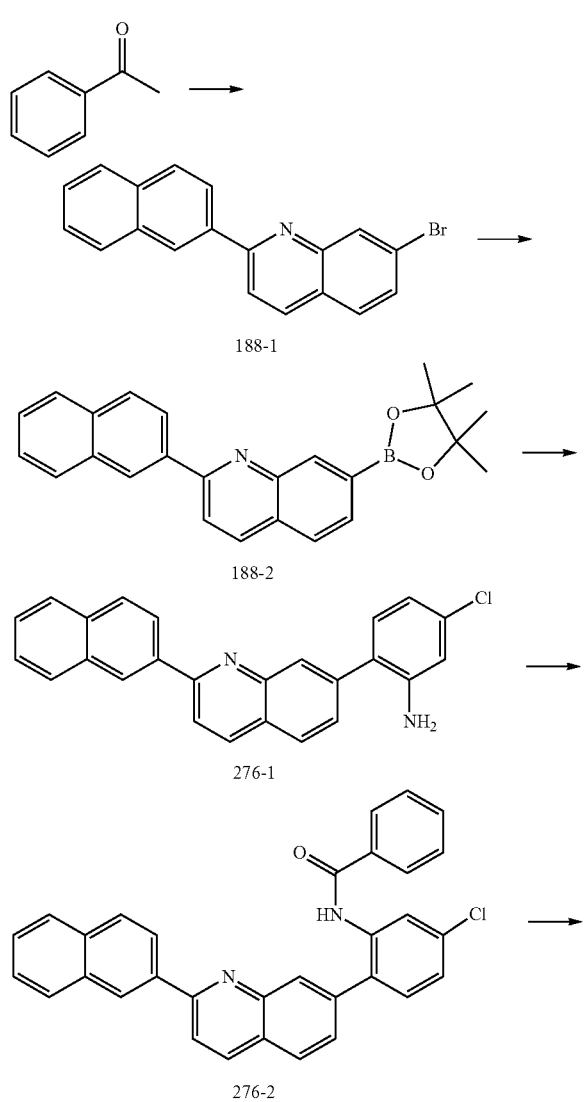

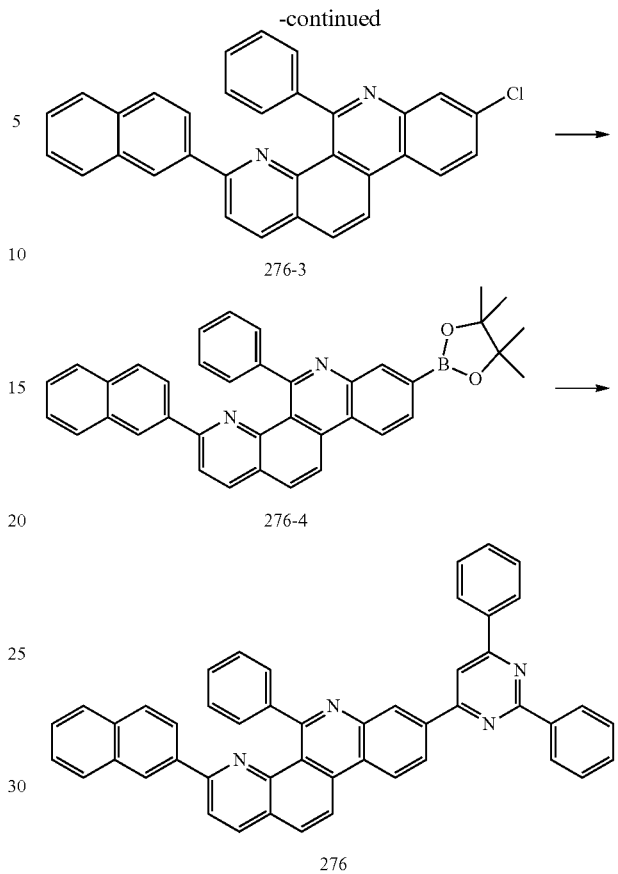

Preparation of Compound 276-1

After dissolving Compound 188-2 (20 g, 52.5 mmol) in 1,4-dioxane and H$_2$O, 2-bromo-5-chloroaniline (12.1 g, 1 eq.), Pd(PPh$_3$)$_4$ (4.1 g, 0.05 eq.) and K$_2$CO$_3$ (30.8 g, 3.0 eq.) were added thereto, and the mixture was stirred for 4 hours at 110° C. After the reaction was completed, the result was cooled to room temperature, and then extracted with distilled water and EA. After drying the organic layer with anhydrous MgSO$_4$, the solvent was removed using a rotary evaporator, and the result was purified by column chromatography using ethyl acetate and dichloromethane as a developing solvent to obtain target Compound 276-1 (16.4 g, 79%).

Preparation of Compound 276-2

After dissolving Compound 276-1 (16.4 g, 43.1 mmol) in DCM, benzoyl chloride (7.1 g, 1.1 eq.) and TEA (12.4 ml, 1.5 eq.) were added thereto at 0° C., and the mixture was stirred for 3 hours at room temperature. After the reaction was completed, the result was cooled to room temperature, and then extracted with distilled water and dichloromethane. After drying the organic layer with anhydrous MgSO$_4$, the solvent was removed using a rotary evaporator, and the result was MeOH slurried to obtain target Compound 276-2 (15.7 g, 75%).

Preparation of Compound 276-3

After dissolving Compound 276-2 (15.7 g, 32.3 mmol) in nitrobenzene, POCl$_3$ (3.3 ml, 1 eq.) was added thereto, and the mixture was stirred for 5 hours at 150° C. After the reaction was completed, the result was neutralized by adding an aqueous sodium bicarbonate solution thereto at room temperature, and produced solids were filtered to obtain target Compound 276-3 (12.1 g, 80%).

Preparation of Compound 276-4

After dissolving Compound 276-3 (12.1 g, 25.8 mmol) in 1,4-dioxane, bis(pinacolato)diboron, Pd(dppf)Cl$_2$ and potassium acetate were added thereto, and the mixture was stirred for 3 hours at 110° C. After the reaction was completed, the result was extracted with distilled water and EA. After drying the organic layer with anhydrous MgSO$_4$, the solvent was removed using a rotary evaporator, and the result was purified by column chromatography using dichloromethane as a developing solvent to obtain target Compound 276-4 (12 g, 83%).

Preparation of Compound 276

To Compound 276-4 (12 g, 21.4 mmol), 4-chloro-2,6-diphenylpyrimidine (8 g, 1 eq.), Pd(PPh$_3$)$_4$ (1.5 g, 0.05 eq.), K$_2$CO$_3$ (10.5 g, 3.0 eq.) and 1,4-dioxane/H$_2$O were added, and the mixture was stirred for 3 hours at 110° C. After the reaction was completed, the result was cooled to room temperature, and produced solids were filtered to obtain target Compound 276 (11.8 g, 83%).

Preparation of Compound 280

Target Compound 280 was obtained in the same manner as in Preparation of Compound 276 in Preparation Example 39 except that 2-(3-bromophenyl)-9-phenyl-1,10-phenanthroline was used instead of 4-chloro-2,6-diphenylpyrimidine.

Compounds 1 to 281 other than the compounds described in the preparation examples were also prepared in the same manner as in the preparation examples, and the synthesis identification results are described in the following Table 1 and Table 2.

| NO | $^1$H NMR (CDCl$_3$, 300 Mz) |
|---|---|
| 1 | δ=8.81(2H, d), 8.28~8.30(6H, m), 7.98~8.10(5H, m), 7.88(2H, d), 7.78(1H, t), 7.41~7.60(11H, m) |
| 3 | δ=8.81(1H, d), 8.24~8.30(7H, m), 7.98~8.10(5H, m), 7.88(2H, d), 7.78(1H, t), 7.70(1H, s), 7.41~7.60(13H, m) |
| 5 | δ=8.81(1H, d), 8.23~8.30(7H, m), 7.98~8.06(5H, m), 7.78~7.85(7H, m), 7.35~7.60(11H, m) |
| 10 | δ=9.09(2H, s), 8.81(2H, d), 8.49(2H, d), 8.30(2H, d), 7.88~8.06(13H, m), 7.78(1H, t), 7.47~7.60(8H, m), 7.35(1H, d) |
| 15 | δ=8.81(1H, d), 8.28~8.33(7H, m), 7.98~8.10(5H, m), 7.70~7.78(3H, m), 7.35~7.60(15H, m) |
| 18 | δ=8.81(2H, d), 7.98~8.30(9H, m), 7.70~7.88(8H, m), 7.35~7.60(11H, m) |
| 22 | δ=8.81(2H, d), 8.48(1H, d), 8.37(1H, s), 8.30(2H, d), 7.98~8.06(5H, m), 7.88(2H, d), 7.70~7.78(3H, m), 7.47~7.60(7H, m), 7.35(1H, d), 7.21(1H, t), 6.86(1H, t) |
| 27 | δ=8.81(2H, d), 8.56(1H, m), 8.28~8.30(4H, m), 7.98~8.06(5H, m), 7.35~7.88(16H, m), 7.22(2H, m) |
| 30 | δ=8.81(2H, d), 8.21~8.30(6H, m), 7.98~8.10(8H, m), 7.78~7.88(4H, m), 7.47~7.60(9H, m), 7.35(3H, d) |
| 33 | δ=8.81(2H, d), 8.28~8.30(4H, m), 7.78~8.06(13H, m), 7.25~7.66(14H, m) |
| 36 | δ=8.81(2H, d), 8.55(2H, m), 8.28~8.30(5H, m), 7.98~8.06(7H, m), 7.78~7.79(3H, m), 7.28~7.60(15H, m) |
| 38 | δ=8.81(2H, d), 8.55(1H, d), 8.28~8.30(4H, m), 7.88~8.12(9H, m), 7.78(1H, t), 7.25~7.60(13H, m) |
| 41 | δ=8.21~8.30(9H, m), 7.98~8.06(5H, m), 7.78(1H, t), 7.41~7.60(12H, m) |
| 44 | δ=8.81~8.85(3H, m), 8.38(1H, d), 8.28(4H, d), 7.78~8.06(13H, m), 7.35~7.60(10H, m), 7.25(2H, d) |
| 45 | δ=8.81~8.85(3H, m), 8.23~8.38(6H, m), 7.95~8.10(8H, m), 7.78~7.79(3H, m), 7.35~7.60(10H, m) |
| 47 | δ=9.30 (2H, m), 9.15 (2H, s), 8.81~8.85 (3H, m), 8.53 (2H, d), 8.38(1H, d), 7.88~8.06 (10H, m), 7.59~7.78(6H, m), 7.35(1H, d), 7.14(2H, t) |
| 51 | δ=9.66(1H, s), 8.93(2H, d), 8.55(2H, d), 8.21~8.28(8H, m), 7.98~8.12(7H, m), 7.78~7.88(5H, m), 7.35~7.60 (9H, m) |
| 53 | δ=8.81 (2H, d), 8.42(2H, d), 8.28~8.31(5H, m), 7.88~8.10 (11H, m), 7.70~7.78 (2H, m), 7.35~7.60 (9H, m) |

-continued

| NO | $^1$H NMR (CDCl$_3$, 300 Mz) |
|---|---|
| 56 | δ=8.28~8.30(8H, m), 8.10~8.12(2H, t), 7.98~8.03(3H, m), 7.85(2H, d), 7.35~7.54(13H, m), 7.25(2H, d) |
| 58 | δ=8.23~8.30(8H, m), 7.98~8.03(5H, m), 7.79(2H, m), 7.41~7.54(13H, m) |
| 65 | δ=9.09(1H, s), 8.49(1H, m), 8.27~8.30(9H, m), 7.92~8.12(7H, m), 7.73(1H, d), 7.35~7.58(14H, m) |
| 68 | δ=8.23~8.30(10H, m), 8.10~8.12(2H, t), 7.98~8.03(3H, t), 7.85(2H, m), 7.35~7.54(15H, m) |
| 71 | δ=9.30(2H, d), 9.15(1H, s), 8.53 (2H, d), 8.27~8.30(5H, m), 7.98~8.12(5H, m), 7.70(2H, m), 7.47~7.54(6H, m), 7.35(1H, d), 7.14(2H, t) |
| 74 | δ=8.27~8.30(7H, m), 8.10~8.12(2H, t), 7.98~8.03(3H, m), 7.79(4H, d), 7.41~7.54(16H, m), 7.25(4H, d) |
| 81 | δ=8.24~8.30(6H, m), 7.98~8.12(5H, m), 7.70(1H, s), 7.47~7.59(10H, m), 7.35(1H, d), 7.22(2H, m), 4.12(2H, m), 1.29(3H, m) |
| 85 | δ=8.21~8.30(9H, m), 7.98~8.12(8H, m), 7.81(1H, m), 7.47~7.60(11H, m), 7.35(3H, d) |
| 91 | δ=8.23~8.30(8H, m), 7.98~8.12(5H, m), 7.66~7.89(6H, m), 7.38~7.57(15H, m) |
| 93 | δ=8.85(1H, s), 8.23~8.38(7H, m), 7.95~8.03(8H, m), 7.79(2H, m), 7.35~7.59(12H, m) |
| 97 | δ=8.85(1H, s), 8.21~8.38(8H, m), 7.95~8.12(11H, m), 7.81(1H, d), 7.47~7.60(5H, m), 7.35(3H, d) |
| 98 | δ=8.93(2H, m), 8.44(1H, s), 8.27~8.30(7H, m), 7.98~8.12(7H, m), 7.82~7.88(6H, m), 7.25~7.54 (10H, m), 7.25(2H, d) |
| 101 | δ=8.28~8.30 (9H, m), 7.98~8.10 (4H, m), 7.90(1H, d), 7.35~7.54(13H, m) |
| 105 | δ=8.21~8.30 (10H, m), 7.98~8.10 (4H, m), 7.79~7.90 (5H, m), 7.41~7.54(13H, m) |
| 108 | δ=8.30(4H, m), 8.21(1H, d), 7.98~8.10 (4H, m), 7.90(1H, d), 7.77~7.83(8H, m), 7.45~7.54(12H, m), 7.35(1H, d) |
| 112 | δ=8.21~8.30 (6H, m), 7.98~8.10 (4H, m), 7.90(1H, d), 7.79(4H, m), 7.35~7.54(13H, m) |
| 114 | δ=8.23~8.30 (10H, m), 7.98~8.10 (4H, m), 7.85~7.90 (3H, m), 7.41~7.54(15H, m) |
| 118 | δ=7.98~8.30 (11H, m), 7.79~7.90 (5H, m), 7.70(1H, s), 7.41~7.58(13H, m) |
| 122 | δ=8.48(1H, m), 8.30~8.37(5H, m), 8.21(1H, m), 7.98~8.10 (4H, m), 7.90(1H, s), 7.70~7.75(2H, m), 7.47~7.57(9H, m), 7.35(1H, d), 7.21(1H, m), 6.86(1H, t) |
| 130 | δ=8.21~8.30 (9H, m), 7.98~8.10 (7H, m), 7.90(1H, s), 7.81(1H, m), 7.47~7.60 (11H, m), 7.35(3H, d) |
| 134 | δ=8.55(1H, d), 8.21~8.30 (8H, m), 7.90~8.12(8H, m), 7.79(1H, m), 7.25~7.54(17H, m) |
| 136 | δ=8.28~8.30(7P1, m), 7.98~8.06 (5H, m), 7.87~7.90 (2H, m), 7.35~7.61(15H, m), 1.72(6H, s) |
| 140 | δ=9.09(2H, s), 8.85(1H, s), 8.49(2H, d), 8.38(1H, d), 8.30(2H, m), 8.21(1H, d), 7.92~8.00 (14H, m), 7.47~7.59(9H, m) |
| 144 | δ=8.93 (2H, d), 8.44(1H, s), 8.44(1H, s), 8.21~8.30 (7H, m), 7.98~8.12(6H, m), 7.82~7.90 (5H, m), 7.41~7.54 (10H, m) |
| 148 | δ=8.81(2H, d), 8.28~8.30 (6H, m), 8.06~8.10 (3H, m), 7.98(1H, d), 7.78~7.85(6H, m), 7.35~7.60 (11H, m) |
| 149 | δ=8.81(2P1, d), 8.28~8.30 (7H, m), 8.06~8.10 (3H, m), 7.98(1H, d), 7.78~7.88(4H, m), 7.70(1H, s), 7.35~7.60(13H, m) |
| 153 | δ=8.81(2H, d), 7.88~8.30(2H, d), 7.73~8.06(16H, m), 7.45~7.60(12H, m) |
| 155 | δ=8.81(2H, d), 8.55(2H, d), 8.30(2H, d), 7.78~8.12(14H, m), 7.25~7.60(16H, m) |
| 158 | δ=8.81(2H, d), 7.88~8.30(2H, d), 8.23(1H, s), 8.06~8.10(3H, m), 7.98(1H, d), 7.78~7.88(8H, m), 7.35~7.60(11H, m) |
| 161 | δ=8.81(2H, d), 8.28~8.33(7H, m), 8.06~8.10(3H, m), 7.98(1H, s), 7.70~7.81(4H, m), 7.35~7.60(15H, m) |
| 166 | δ=8.81(2H, d), 8.28~8.33(6H, m), 7.98~8.16(5H, m), 7.78~7.84(4H, m), 7.35~7.60(9H, m) |
| 173 | δ=8.81(2H, d), 8.56(1H, m), 8.28~8.30(4H, m), 7.98~8.10(4H, m), 7.35~7.88(17H, m), 7.22(2H, d) |
| 176 | δ=8.81(2H, d), 8.21~8.30(6H, m), 7.98~8.10(7H, m), 7.78~7.88(5H, m), 7.35~7.60(9H, m), 7.35(3H, d) |
| 180 | δ=8.84(4H, s), 8.30(4H, d), 7.98~8.10(7H, m), 7.81(2H, m), 7.47~7.60(7H, m), 7.35(3H, d) |
| 181 | δ=8.81(2H, d), 8.55(1H, d), 8.28~8.30(4H, m), 7.25~8.10(27H, m) |

| NO | ¹H NMR (CDCl₃, 300 Mz) |
|---|---|
| 188 | δ=8.81~8.85(3H, t), 8.38(1H, d), 8.28(4H, d), 7.78~8.10(11H, m), 7.35~7.60(10H, m) |
| 189 | δ=8.81~8.85(3H, t), 8.23~8.30(6H, m), 7.78~8.10(15H, m), 7.35~7.60(10H, m) |
| 193 | δ=8.81~8.85(3H, m), 8.21~8.30(5H, m), 7.60~8.10(15H, m), 7.47~7.60(8H, m), 7.35(3H, d) |
| 197 | δ=8.21~8.30(9H, m), 8.04~8.10(3H, m), 7.81~7.90(4H, m), 7.35~7.54(13H, m), 7.25(2H, d) |
| 201 | δ=8.21~8.30(8H, m), 8.04~8.10(3H, m), 7.90(1H, s), 7.70~7.81(5H, m), 7.35~7.54(15H, m) |
| 207 | δ=8.21~8.30(6H, m), 8.04~8.10(3H, m), 7.90(1H, d), 7.79~7.81(5H, m), 7.35~7.54(13H, m) |
| 208 | δ=9.09(1H, s), 8.49(1H, d), 8.21 8.34(7H, m), 7.81~8.10 (12H, m), 7.47~7.59 (10H, m) |
| 214 | δ=8.21~8.30 (7H, m), 8.04~8.10 (3H, m), 7.90(1H, d), 7.79 7.81(5H, m), 7.41 7.54(16H, m), 7.25(4H, d) |
| 220 | δ=8.30(4H, m), 8.21(1H, d), 8.04~8.10 (3H, m), 7.81~7.90 (4H, m), 7.47~7.59(8H, m), 7.35(1H, d), 7.22~7.25(4H, m), 4.12(2H, m), 1.29(3H, m) |
| 225 | δ=8.21~8.30 (9H, m), 8.04~8.10 (6H, m), 7.90(1H, s), 7.81(2H, d), 7.47~7.60 (11H, m), 7.35 (3H, d) |
| 230 | δ=8.55(1H, d), 8.21~8.30 (9H, m), 8.04~8.12(5H, m), 7.79 7.94(7H, m), 7.63(1H, d), 7.25 7.54(16H, m) |
| 233 | δ=8.85(1H, s), 8.21~8.30 (9H, m), 7.90~8.10 (7H, m), 7.81(1H, d), 7.70(1H, s), 7.35~7.59(14H, m) |
| 236 | δ=8.85(1H, s), 8.38(1H, d), 8.21~8.30 (6H, m), 7.90~8.10 (7H, m), 7.70~7.81 (3H, m), 7.35 7.59(16H, m) |
| 238 | δ=8.85(1H, s), 8.21~8.30 (8H, m), 7.90~8.10 (10H, m), 7.81 (2H, d), 7.47~7.60 (10H, m), 7.35(2H, d) |
| 240 | δ=8.27~8.30 (9H, m), 8.03~8.12(4H, m), 7.81(1H, d), 7.35~7.54(13H, m) |
| 245 | δ=8.23~8.30 (8H, m), 8.03~8.12 (4H, m), 7.75 7.81(5H, m), 7.35 7.57(15H, m) |
| 247 | δ=8.30(4H, m), 8.03~8.12(4H, m), 7.77~7.81(9H, m), 7.45~7.54(12H, m), 7.35 (1H, d) |
| 252 | δ=9.09(1H, s), 8.49(1H, d), 8.23 8.34(7H, m), 7.92~8.10 (12H, m), 7.47~7.59 (10H, m), 7.35 (1H, d) |
| 255 | δ=9.30(2H, d), 9.15(2H, s), 8.53 (2H, d), 8.27~8.30 (5H, m), 8.03~8.12 (4H, m), 7.81(1H, d), 7.70(2H, m), 7.47~7.54(6H, m), 7.35 (1H, d), 7.14(2H, m) |
| 258 | δ=8.27~8.30 (7H, m), 8.03~8.12 (4H, m), 7.79 7.81(5H, m), 7.35~7.54(16H, m), 7.25 (4H, d) |
| 263 | δ=8.54(1H, d), 8.27~8.37(6H, m), 8.03~8.13(6H, m), 7.81(1H, d), 7.35~7.54 (10H, m), 6.87(1H, d) |
| 267 | δ=8.56(1H, m), 8.27~8.30 (7H, m), 8.03~8.12(5H, m), 7.81(1H, d), 7.35~7.59(14H, m), 7.22(2h, m) |
| 269 | δ=8.21~8.30 (9H, m), 8.03~8.12(7H, m), 7.81(2H, d), 7.47~7.60 (11H, m), 7.35(2H, d) |
| 274 | δ=8.21~8.30 (9H, m), 8.03~8.12(7H, m), 7.81(2H, d), 7.47~7.60 (11H, m), 7.35(2H, d) |
| 276 | δ=8.85(1H, s), 8.23~8.30 (7H, m), 7.95~8.12(7H, m), 7.79 7.81(3H, m), 7.35 7.59(12H, m) |
| 280 | δ=8.85(1H, s), 8.21~8.30 (8H, m), 7.95~8.12 (10H, m), 7.81(2H, d), 7.47~7.60 (10H, m), 7.35 (3H, d) |

| Compound | FD~MS | Compound | FD~MS |
|---|---|---|---|
| 1 | m/z=613.71 (C43H27Nδ=613.23) | 2 | m/z=689.80 (C49H31Nδ=689.26) |
| 3 | m/z=689.80 (C49H31Nδ=689.26) | 4 | m/z=612.72 (C44H28N4=612.23) |
| 5 | m/z=688.82 (C50H32N4=688.26) | 6 | m/z=688.82 (C50H32N4=688.26) |
| 7 | m/z=708.78 (C50H33N2OP=708.23) | 8 | m/z=658.72 (C46H31N2OP=658.22) |
| 9 | m/z=788.93 (C58H36N4=788.29) | 10 | m/z=713.83 (C51H31Nδ=713.26) |
| 11 | m/z=739.86 (C53H33Nδ=739.27) | 12 | m/z=612.72 (C44H28N4=612.23) |
| 13 | m/z=712.84 (C52H32N4=712.26) | 14 | m/z=688.82 (C50H32N4=688.26) |
| 15 | m/z=688.82 (C50H32N4=688.26) | 16 | m/z=613.71 (C43H27Nδ=613.23) |
| 17 | m/z=662.78 (C48H30N4=662.25) | 18 | m/z=662.78 (C48H30N4=662.25) |
| 19 | m/z=764.91 (C56H36N4=764.29) | 20 | m/z=586.68 (C42H26N4=586.22) |
| 21 | m/z=574.67 (C41H26N4=574.22) | 22 | m/z=574.67 (C41H26N4=574.22) |
| 23 | m/z=574.67 (C41H26N4=574.22) | 24 | m/z=574.67 (C41H26N4=574.22) |
| 25 | m/z=602.73 (C43H30N4=602.25) | 26 | m/z=602.73 (C43H30N4=602.25) |
| 27 | m/z=650.77 (C47H30N4=650.25) | 28 | m/z=650.77 (C47H30N4=650.25) |
| 29 | m/z=636.74 (C46H28N4=636.23) | 30 | m/z=712.84 (C52H32N4=712.26) |
| 31 | m/z=712.84 (C52H32N4=712.26) | 32 | m/z=712.84 (C52H32N4=712.26) |
| 33 | m/z=794.96 (C56H34N4S=794.25) | 34 | m/z=712.84 (C52H32N4=712.26) |
| 35 | m/z=841.01 (C62H40N4=840.33) | 36 | m/z=814.97 (C60H38N4=814.31) |
| 37 | m/z=854.99 (C62H38N4O=854.30) | 38 | m/z=854.99 (C61H38N6=854.32) |
| 39 | m/z=764.91 (C56H36N4=764.29) | 40 | m/z=712.84 (C52H32N4=712.26) |
| 41 | m/z=689.80 (C49H31Nδ=689.26) | 42 | m/z=764.91 (C56H36N4=764.29) |
| 43 | m/z=788.93 (C58H36N4=788.29) | 44 | m/z=814.97 (C60H38Nδ=814.31) |
| 45 | m/z=738.87 (C54H34N4=738.28) | 46 | m/z=738.87 (C54H34N4=738.28) |
| 47 | m/z=663.77 (C47H29Nδ=663.24) | 48 | m/z=636.74 (C46H28N4=636.23) |
| 49 | m/z=762.90 (C56H34N4=762.28) | 50 | m/z=713.83 (C51H31Nδ=713.26) |
| 51 | m/z=763.89 (C55H33Nδ=763.27) | 52 | m/z=813.94 (C59H35Nδ=813.29) |
| 53 | m/z=737.85 (C53H31Nδ=737.26) | 54 | m/z=851.00 (C63H38N4=850.31) |
| 55 | m/z=613.71 (C43H27Nδ=613.23) | 56 | m/z=689.80 (C49H31Nδ=689.26) |
| 57 | m/z=689.80 (C49H31Nδ=689.26) | 58 | m/z=612.72 (C44H28N4=612.23) |
| 59 | m/z=688.82 (C50H32N4=688.26) | 60 | m/z=688.82 (C50H32N4=688.26) |
| 61 | m/z=708.78 (C50H33N2OP=708.23) | 62 | m/z=658.72 (C46H31N2OP=658.22) |
| 63 | m/z=788.93 (C58H36N4=788.29) | 64 | m/z=713.83 (C51H31Nδ=713.26) |
| 65 | m/z=739.86 (C53H33Nδ=739.27) | 66 | m/z=612.72 (C44H28N4=612.23) |
| 67 | m/z=712.84 (C52H32N4=712.26) | 68 | m/z=688.82 (C50H32N4=688.26) |
| 69 | m/z=688.82 (C50H32N4=688.26) | 70 | m/z=764.91 (C56H36N4=764.29) |
| 71 | m/z=613.71 (C43H27Nδ=613.23) | 72 | m/z=662.78 (C48H30N4=662.25) |
| 73 | m/z=662.78 (C48H30N4=662.25) | 74 | m/z=764.91 (C56H36N4=764.29) |
| 75 | m/z=586.68 (C42H26N4=586.22) | 76 | m/z=574.67 (C41H26N4=574.22) |
| 77 | m/z=574.67 (C41H26N4=574.22) | 78 | m/z=574.67 (C41H26N4=574.22) |
| 79 | m/z=574.67 (C41H26N4=574.22) | 80 | m/z=602.73 (C43H30N4=602.25) |
| 81 | m/z=602.73 (C43H30N4=602.25) | 82 | m/z=650.77 (C47H30N4=650.25) |
| 83 | m/z=650.77 (C47H30N4=650.25) | 84 | m/z=636.74 (C46H28N4=636.23) |
| 85 | m/z=712.84 (C52H32N4=712.26) | 86 | m/z=636.74 (C46H28N4=636.23) |
| 87 | m/z=636.74 (C46H28N4=636.23) | 88 | m/z=712.84 (C52H32N4=712.26) |
| 89 | m/z=636.74 (C46H28N4=636.23) | 90 | m/z=778.90 (C55H34N6=778.28) |
| 91 | m/z=778.90 (C56H34N4O=778.27) | 92 | m/z=739.86 (C53H33Nδ=739.27) |

-continued

| Compound | FD-MS | Compound | FD-MS |
|---|---|---|---|
| 93 | m/z=662.78 (C48H30N4=662.25) | 94 | m/z=738.87 (C54H34N4=738.28) |
| 95 | m/z=663.77 (C47H29N5=663.24) | 96 | m/z=636.74 (C46H28N4=636.23) |
| 97 | m/z=762.90 (C56H34N4=762.28) | 98 | m/z=789.92 (C57H35N5=789.29) |
| 99 | m/z=710.82 (C52H30N4=710.25) | 100 | m/z=838.99 (C62H38N4=838.31) |
| 101 | m/z=613.71 (C43H27N5=613.23) | 102 | m/z=689.80 (C49H31N5=689.26) |
| 103 | m/z=689.80 (C49H31N5=689.26) | 104 | m/z=612.72 (C44H28N4=612.23) |
| 105 | m/z=688.82 (C50H32N4=688.26) | 106 | m/z=688.82 (C50H32N4=688.26) |
| 107 | m/z=708.78 (C50H33N2OP=708.23) | 108 | m/z=739.86 (C53H33N5=739.27) |
| 109 | m/z=788.93 (C58H36N4=788.29) | 110 | m/z=713.83 (C51H31N5=713.26) |
| 111 | m/z=739.86 (C53H33N5=739.27) | 112 | m/z=612.72 (C44H28N4=612.23) |
| 113 | m/z=712.84 (C52H32N4=712.26) | 114 | m/z=688.82 (C50H32N4=688.26) |
| 115 | m/z=688.82 (C50H32N4=688.26) | 116 | m/z=636.74 (C43H27N5=613.23) |
| 117 | m/z=662.78 (C48H30N4=662.25) | 118 | m/z=662.78 (C48H30N4=662.25) |
| 119 | m/z=764.91 (C56H36N4=764.29) | 120 | m/z=586.68 (C42H26N4=586.22) |
| 121 | m/z=574.67 (C41H26N4=574.22) | 122 | m/z=574.67 (C41H26N4=574.22) |
| 123 | m/z=574.67 (C41H26N4=574.22) | 124 | m/z=650.77 (C47H30N4=650.25) |
| 125 | m/z=602.73 (C43H30N4=602.25) | 126 | m/z=602.73 (C43H30N4=602.25) |
| 127 | m/z=650.77 (C47H30N4=650.25) | 128 | m/z=650.77 (C47H30N4=650.25) |
| 129 | m/z=636.74 (C46H28N4=636.23) | 130 | m/z=712.84 (C52H32N4=712.26) |
| 131 | m/z=636.74 (C46H28N4=636.23) | 132 | m/z=636.74 (C46H28N4=636.23) |
| 133 | m/z=712.84 (C52H32N4=712.26) | 134 | m/z=777.91 (C56H35N5=777.29) |
| 135 | m/z=794.96 (C56H34N4S=794.25) | 136 | m/z=729.87 (C52H35N5=729.29) |
| 137 | m/z=636.74 (C46H28N4=636.23) | 138 | m/z=739.86 (C53H33N5=739.27) |
| 139 | m/z=662.78 (C48H30N4=662.25) | 140 | m/z=763.88 (C55H33N5=763.27) |
| 141 | m/z=738.87 (C54H34N4=738.28) | 142 | m/z=663.77 (C47H29N5=663.24) |
| 143 | m/z=762.90 (C56H34N4=762.28) | 144 | m/z=713.83 (C51H31N5=713.26) |
| 145 | m/z=762.90 (C56H34N4=762.28) | 146 | m/z=737.85 (C53H31N5=737.26) |
| 147 | m/z=613.71 (C43H27N5=613.23) | 148 | m/z=689.80 (C49H31N5=689.26) |
| 149 | m/z=689.80 (C49H31N5=689.26) | 150 | m/z=612.72 (C44H28N4=612.23) |
| 151 | m/z=688.82 (C50H32N4=688.26) | 152 | m/z=688.82 (C50H32N4=688.26) |
| 153 | m/z=708.78 (C50H33N2OP=708.23) | 154 | m/z=658.72 (C46H31N2OP=658.22) |
| 155 | m/z=788.93 (C58H36N4=788.29) | 156 | m/z=713.83 (C51H31N5=713.26) |
| 157 | m/z=739.86 (C53H33N5=739.27) | 158 | m/z=612.72 (C44H28N4=612.23) |
| 159 | m/z=712.84 (C52H32N4=712.26) | 160 | m/z=688.82 (C50H32N4=688.26) |
| 161 | m/z=688.82 (C50H32N4=688.26) | 162 | m/z=613.71 (C43H27N5=613.23) |
| 163 | m/z=662.78 (C48H30N4=662.25) | 164 | m/z=662.78 (C48H30N4=662.25) |
| 165 | m/z=574.67 (C41H26N4=574.22) | 166 | m/z=586.68 (C42H26N4=586.22) |
| 167 | m/z=574.67 (C41H26N4=574.22) | 168 | m/z=574.67 (C41H26N4=574.22) |
| 169 | m/z=574.67 (C41H26N4=574.22) | 170 | m/z=574.67 (C41H26N4=574.22) |
| 171 | m/z=602.73 (C43H30N4=602.25) | 172 | m/z=602.73 (C43H30N4=602.25) |
| 173 | m/z=650.77 (C47H30N4=650.25) | 174 | m/z=650.77 (C47H30N4=650.25) |
| 175 | m/z=636.74 (C46H28N4=636.23) | 176 | m/z=712.84 (C52H32N4=712.26) |
| 177 | m/z=636.74 (C46H28N4=636.23) | 178 | m/z=636.74 (C46H28N4=636.23) |
| 179 | m/z=712.84 (C52H32N4=712.26) | 180 | m/z=636.74 (C46H28N4=636.23) |
| 181 | m/z=778.90 (C55H34N6=778.28) | 182 | m/z=795.95 (C55H33N5S=795.25) |
| 183 | m/z=613.71 (C43H27N5=613.23) | 184 | m/z=688.82 (C50H32N4=688.26) |
| 185 | m/z=713.83 (C51H31N5=713.26) | 186 | m/z=688.82 (C50H32N4=688.26) |
| 187 | m/z=636.74 (C46H28N4=636.23) | 188 | m/z=663.77 (C54H34N4=738.28) |
| 189 | m/z=738.87 (C54H34N4=738.28) | 190 | m/z=789.92 (C57H35N5=789.29) |
| 191 | m/z=762.90 (C56H34N4=762.28) | 192 | m/z=636.74 (C46H28N4=636.23) |
| 193 | m/z=762.90 (C56H34N4=762.28) | 194 | m/z=713.83 (C51H31N5=713.26) |
| 195 | m/z=812.95 (C60H36N4=812.29) | 196 | m/z=613.71 (C43H27N5=613.23) |
| 197 | m/z=689.80 (C49H31N5=689.26) | 198 | m/z=689.80 (C49H31N5=689.26) |
| 199 | m/z=612.72 (C44H28N4=612.23) | 200 | m/z=688.82 (C50H32N4=688.26) |
| 201 | m/z=688.82 (C50H32N4=688.26) | 202 | m/z=708.78 (C50H33N2OP=708.23) |
| 203 | m/z=658.72 (C46H31N2OP=658.22) | 204 | m/z=788.93 (C58H36N4=788.29) |
| 205 | m/z=713.83 (C51H31N5=713.26) | 206 | m/z=739.86 (C53H33N5=739.27) |
| 207 | m/z=612.72 (C44H28N4=612.23) | 208 | m/z=712.84 (C52H32N4=712.26) |
| 209 | m/z=688.82 (C50H32N4=688.26) | 210 | m/z=688.82 (C50H32N4=688.26) |
| 211 | m/z=613.71 (C43H27N5=613.23) | 212 | m/z=662.78 (C48H30N4=662.25) |
| 213 | m/z=662.78 (C48H30N4=662.25) | 214 | m/z=764.91 (C56H36N4=764.29) |
| 215 | m/z=586.68 (C42H26N4=586.22) | 216 | m/z=574.67 (C41H26N4=574.22) |
| 217 | m/z=574.67 (C41H26N4=574.22) | 218 | m/z=574.67 (C41H26N4=574.22) |
| 219 | m/z=574.67 (C41H26N4=574.22) | 220 | m/z=602.73 (C43H30N4=602.25) |
| 221 | m/z=602.73 (C43H30N4=602.25) | 222 | m/z=650.77 (C47H30N4=650.25) |
| 223 | m/z=650.77 (C47H30N4=650.25) | 224 | m/z=636.74 (C46H28N4=636.23) |
| 225 | m/z=712.84 (C52H32N4=712.26) | 226 | m/z=636.74 (C46H28N4=636.23) |
| 227 | m/z=636.74 (C46H28N4=636.23) | 228 | m/z=712.84 (C52H32N4=712.26) |
| 229 | m/z=636.74 (C46H28N4=636.23) | 230 | m/z=854.01 (C62H39N5=853.32) |
| 231 | m/z=854.99 (C62H38N4O=854.30) | 232 | m/z=841.01 (C62H40N4=840.33) |
| 233 | m/z=738.87 (C54H34N4=738.28) | 234 | m/z=738.87 (C54H34N4=738.28) |
| 235 | m/z=704.86 (C51H36N4=704.29) | 236 | m/z=738.87 (C54H34N4=738.28) |
| 237 | m/z=624.73 (C45H28N4=624.23) | 238 | m/z=762.90 (C56H34N4=762.28) |
| 239 | m/z=789.92 (C57H35N5=789.29) | 240 | m/z=613.71 (C43H27N5=613.23) |
| 241 | m/z=689.80 (C49H31N5=689.26) | 242 | m/z=689.80 (C49H31N5=689.26) |
| 243 | m/z=612.72 (C44H28N4=612.23) | 244 | m/z=688.82 (C50H32N4=688.26) |

-continued

| Compound | FD~MS | Compound | FD~MS |
|---|---|---|---|
| 245 | m/z=688.82 (C50H32N4=688.26) | 246 | m/z=708.78 (C50H33N2OP=708.23) |
| 247 | m/z=658.72 (C46H31N2OP=658.22) | 248 | m/z=788.93 (C58H36N4=788.29) |
| 249 | m/z=713.83 (C51H31Nδ=713.26) | 250 | m/z=739.86 (C53H33Nδ=739.27) |
| 251 | m/z=612.72 (C44H28N4=612.23) | 252 | m/z=712.84 (C52H32N4=712.26) |
| 253 | m/z=688.82 (C50H32N4=688.26) | 254 | m/z=688.82 (C50H32N4=688.26) |
| 255 | m/z=613.71 (C43H27Nδ=613.23) | 256 | m/z=662.78 (C48H30N4=662.25) |
| 257 | m/z=662.78 (C48H30N4=662.25) | 258 | m/z=764.91 (C56H36N4=764.29) |
| 259 | m/z=586.68 (C42H26N4=586.22) | 260 | m/z=574.67 (C41H26N4=574.22) |
| 261 | m/z=574.67 (C41H26N4=574.22) | 262 | m/z=574.67 (C41H26N4=574.22) |
| 263 | m/z=574.67 (C41H26N4=574.22) | 264 | m/z=602.73 (C43H30N4=602.25) |
| 265 | m/z=602.73 (C43H30N4=602.25) | 266 | m/z=650.77 (C47H30N4=650.25) |
| 267 | m/z=650.77 (C47H30N4=650.25) | 268 | m/z=636.74 (C46H28N4=636.23) |
| 269 | m/z=712.84 (C52H32N4=712.26) | 270 | m/z=636.74 (C46H28N4=636.23) |
| 271 | m/z=636.74 (C46H28N4=636.23) | 272 | m/z=712.84 (C52H32N4=712.26) |
| 273 | m/z=636.74 (C46H28N4=636.23) | 274 | m/z=804.98 (C59H40N4=804.33) |
| 275 | m/z=739.86 (C53H33Nδ=739.27) | 276 | m/z=662.78 (C48H3ON4=662.25) |
| 277 | m/z=838.99 (C62H38N4=838.31) | 278 | m/z=763.88 (C55H33Nδ=763.27) |
| 279 | m/z=712.84 (C52H32N4=712.26) | 280 | m/z=762.90 (C56H34N4=762.28) |
| 281 | m/z=789.92 (C57H35Nδ=789.29) | | |

EXPERIMENTAL EXAMPLE

Experimental Example 1

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

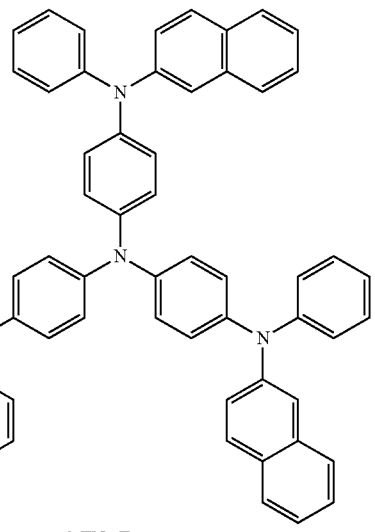

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

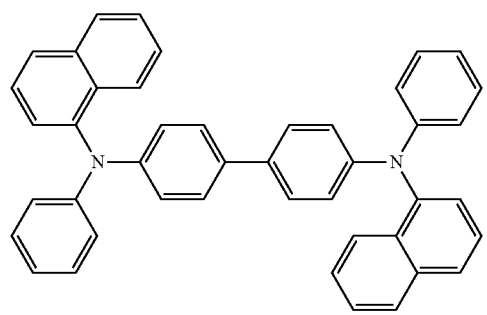

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

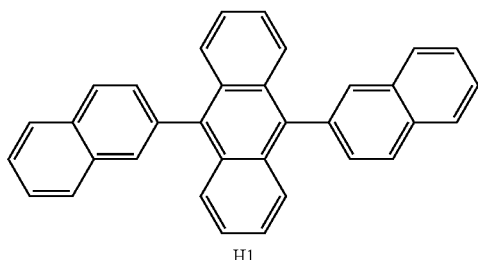

H1

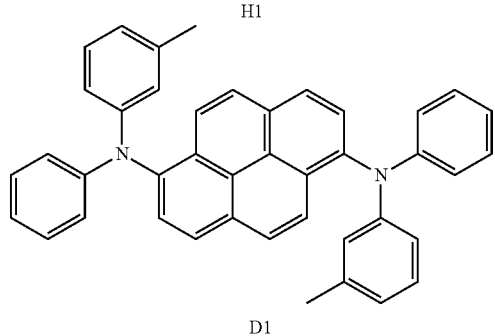

D1

Subsequently, a compound of the following Structural Formula E1 was deposited to a thickness of 300 Å as an electron transfer layer.

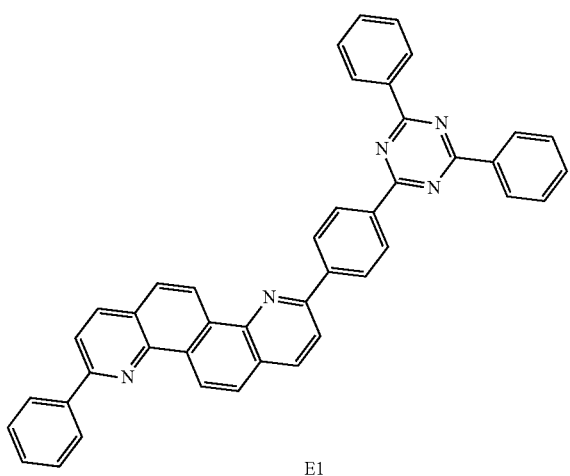 [SMILES: c1ccc(-c2ccc3ccc4c(ccc5ccc(-c6ccc(-c7nc(-c8ccccc8)nc(-c8ccccc8)n7)cc6)nc54)c3n2)cc1]

E1

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

Organic electroluminescent devices were manufactured in the same manner as in Experimental Example 1 except that compounds shown in the following Table 3 were used instead of the compounds of E1, E2 and E3 used when forming the electron transfer layer.

Results of measuring driving voltage, light emission efficiency, color coordinate (CIE) and lifetime of the blue organic light emitting devices manufactured according to the present disclosure are as shown in the following Table 3.

TABLE 3

| | Compound | Driving Voltage (V) | Light Emission Efficiency (cd/A) | CIE (x, y) | Lifetime (T95) |
|---|---|---|---|---|---|
| Comparative Example 1 | E1 | 4.91 | 6.49 | (0.141, 0.092) | 35 |
| Comparative Example 2 | E2 | 4.83 | 6.29 | (0.138, 0.093) | 34 |
| Comparative Example 3 | E3 | 4.95 | 6.50 | (0.138, 0.088) | 36 |
| Example 1 | 1 | 4.81 | 6.59 | (0.133, 0.101) | 39 |
| Example 2 | 3 | 4.45 | 6.62 | (0.134, 0.101) | 38 |
| Example 3 | 5 | 4.62 | 6.91 | (0.135, 0.103) | 41 |
| Example 4 | 10 | 4.80 | 6.56 | (0.135, 0.101) | 40 |
| Example 5 | 15 | 4.62 | 6.59 | (0.133, 0.102) | 39 |
| Example 6 | 18 | 4.75 | 6.62 | (0.134, 0.102) | 44 |
| Example 7 | 22 | 4.48 | 6.53 | (0.133, 0.101) | 39 |
| Example 8 | 27 | 4.44 | 6.51 | (0.134, 0.102) | 44 |
| Example 9 | 30 | 4.62 | 6.61 | (0.135, 0.102) | 41 |
| Example 10 | 33 | 4.41 | 6.50 | (0.134, 0.103) | 45 |
| Example 11 | 36 | 4.60 | 6.57 | (0.134, 0.101) | 44 |
| Example 12 | 38 | 4.44 | 6.72 | (0.135, 0.101) | 38 |
| Example 13 | 41 | 4.75 | 6.61 | (0.132, 0.100) | 42 |
| Example 14 | 44 | 4.63 | 6.58 | (0.133, 0.102) | 39 |
| Example 15 | 45 | 4.71 | 6.73 | (0.134, 0.100) | 42 |
| Example 16 | 47 | 4.81 | 6.60 | (0.135, 0.102) | 41 |
| Example 17 | 51 | 4.78 | 6.61 | (0.133, 0.103) | 38 |
| Example 18 | 53 | 4.62 | 6.75 | (0.134, 0.102) | 39 |
| Example 19 | 56 | 4.40 | 6.51 | (0.135, 0.102) | 39 |
| Example 20 | 58 | 4.37 | 6.63 | (0.133, 0.101) | 41 |
| Example 21 | 65 | 4.35 | 6.62 | (0.133, 0.101) | 39 |
| Example 22 | 68 | 4.41 | 6.55 | (0.134, 0.102) | 42 |
| Example 23 | 71 | 4.71 | 6.52 | (0.133, 0.101) | 39 |
| Example 24 | 74 | 4.81 | 6.55 | (0.133, 0.103) | 38 |
| Example 25 | 81 | 4.78 | 6.63 | (0.135, 0.101) | 42 |
| Example 26 | 85 | 4.67 | 6.52 | (0.134, 0.102) | 39 |
| Example 27 | 91 | 4.62 | 6.62 | (0.134, 0.100) | 42 |
| Example 28 | 93 | 4.41 | 6.51 | (0.133, 0.100) | 38 |
| Example 29 | 97 | 4.38 | 6.55 | (0.134, 0.103) | 40 |
| Example 30 | 98 | 4.39 | 6.56 | (0.135, 0.101) | 40 |
| Example 31 | 101 | 4.38 | 6.60 | (0.132, 0.102) | 40 |
| Example 32 | 105 | 4.39 | 6.52 | (0.133, 0.102) | 43 |
| Example 33 | 108 | 4.72 | 6.60 | (0.134, 0.103) | 39 |
| Example 34 | 112 | 4.37 | 6.64 | (0.135, 0.101) | 40 |
| Example 35 | 114 | 4.36 | 6.62 | (0.133, 0.102) | 41 |
| Example 36 | 118 | 4.39 | 6.52 | (0.133, 0.101) | 42 |
| Example 37 | 122 | 4.71 | 6.51 | (0.134, 0.101) | 38 |
| Example 38 | 130 | 4.79 | 6.56 | (0.135, 0.103) | 37 |
| Example 39 | 134 | 4.80 | 6.62 | (0.131, 0.100) | 43 |
| Example 40 | 136 | 4.66 | 6.52 | (0.134, 0.102) | 40 |
| Example 41 | 140 | 4.62 | 6.61 | (0.134, 0.100) | 41 |
| Example 42 | 144 | 4.40 | 6.55 | (0.135, 0.100) | 39 |
| Example 43 | 148 | 4.38 | 6.53 | (0.134, 0.103) | 39 |
| Example 44 | 149 | 4.39 | 6.54 | (0.133, 0.101) | 40 |
| Example 45 | 153 | 4.36 | 6.60 | (0.132, 0.102) | 40 |
| Example 46 | 155 | 4.39 | 6.51 | (0.134, 0.101) | 43 |
| Example 47 | 158 | 4.39 | 6.61 | (0.133, 0.102) | 41 |
| Example 48 | 161 | 4.79 | 6.61 | (0.135, 0.100) | 39 |
| Example 49 | 166 | 4.64 | 6.74 | (0.134, 0.102) | 39 |
| Example 50 | 173 | 4.41 | 6.53 | (0.134, 0.103) | 39 |
| Example 51 | 176 | 4.80 | 6.61 | (0.133, 0.102) | 41 |
| Example 52 | 180 | 4.37 | 6.64 | (0.133, 0.101) | 42 |
| Example 53 | 181 | 4.36 | 6.62 | (0.133, 0.102) | 41 |
| Example 54 | 188 | 4.39 | 6.52 | (0.133, 0.101) | 41 |
| Example 55 | 189 | 4.71 | 6.51 | (0.135, 0.101) | 38 |
| Example 56 | 193 | 4.79 | 6.55 | (0.133, 0.103) | 37 |
| Example 57 | 197 | 4.80 | 6.61 | (0.131, 0.100) | 42 |
| Example 58 | 201 | 4.76 | 6.60 | (0.134, 0.101) | 39 |
| Example 59 | 207 | 4.36 | 6.62 | (0.133, 0.101) | 40 |
| Example 60 | 208 | 4.35 | 6.62 | (0.135, 0.102) | 41 |
| Example 61 | 214 | 4.38 | 6.51 | (0.133, 0.103) | 42 |
| Example 62 | 220 | 4.62 | 6.58 | (0.133, 0.102) | 38 |
| Example 63 | 225 | 4.72 | 6.63 | (0.134, 0.102) | 44 |
| Example 64 | 230 | 4.48 | 6.50 | (0.133, 0.101) | 39 |
| Example 65 | 233 | 4.36 | 6.61 | (0.135, 0.102) | 41 |
| Example 66 | 236 | 4.39 | 6.50 | (0.133, 0.101) | 42 |
| Example 67 | 238 | 4.71 | 6.55 | (0.134, 0.103) | 38 |
| Example 68 | 240 | 4.79 | 6.55 | (0.133, 0.101) | 37 |
| Example 69 | 245 | 4.62 | 6.60 | (0.134, 0.100) | 41 |

TABLE 3-continued

| | Com-pound | Driving Voltage (V) | Light Emission Efficiency (cd/A) | CIE (x, y) | Lifetime (T95) |
|---|---|---|---|---|---|
| Example 70 | 247 | 4.40 | 6.54 | (0.133, 0.100) | 39 |
| Example 71 | 252 | 4.37 | 6.54 | (0.135, 0.101) | 41 |
| Example 72 | 255 | 4.63 | 6.55 | (0.133, 0.103) | 39 |
| Example 73 | 258 | 4.71 | 6.74 | (0.134, 0.100) | 42 |
| Example 74 | 263 | 4.81 | 6.61 | (0.133, 0.102) | 42 |
| Example 75 | 267 | 4.36 | 6.54 | (0.135, 0.101) | 39 |
| Example 76 | 269 | 4.39 | 6.54 | (0.133, 0.101) | 41 |
| Example 77 | 274 | 4.80 | 6.62 | (0.132, 0.101) | 43 |
| Example 78 | 276 | 4.67 | 6.50 | (0.134, 0.103) | 39 |
| Example 79 | 280 | 4.64 | 6.61 | (0.134, 0.100) | 43 |

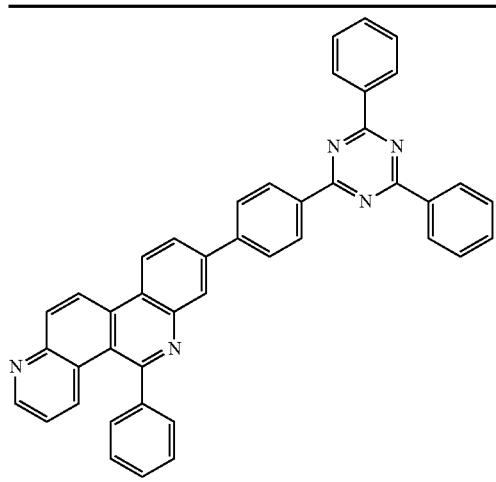

E2

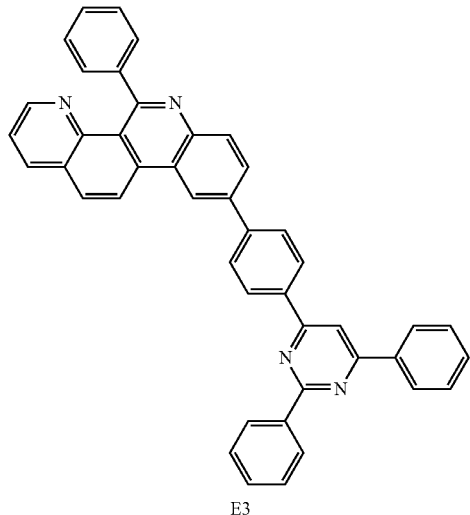 [SMILES: c1ccc(-c2cc(-c3ccc(-c4ccc5nc(-c6ccccc6)c6c(ccc7cccnc76)c5c4)cc3)nc(-c3ccccc3)n2)cc1]

E3

As seen from the results of Table 3, it was identified that the organic light emitting device using the electron transfer layer material of the blue organic light emitting device of the present disclosure had lower driving voltage, and significantly improved light emission efficiency and lifetime compared to Comparative Examples 1, 2 and 3.

<Experimental Example 2>—Manufacture of Organic Light Emitting Device

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

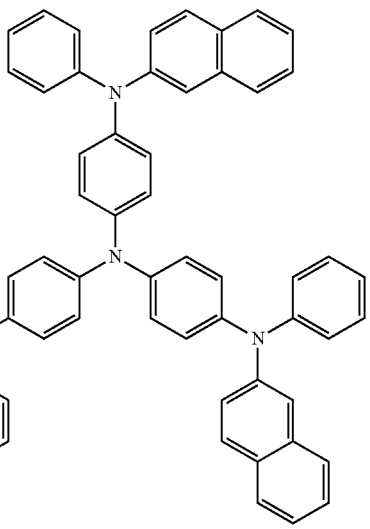

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

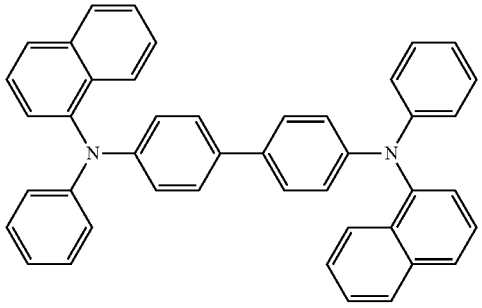

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

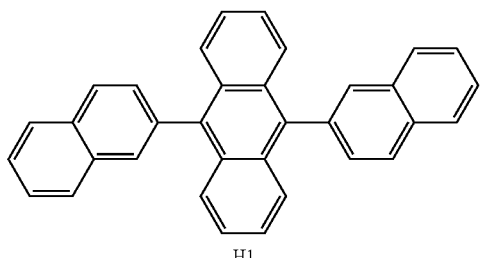

H1

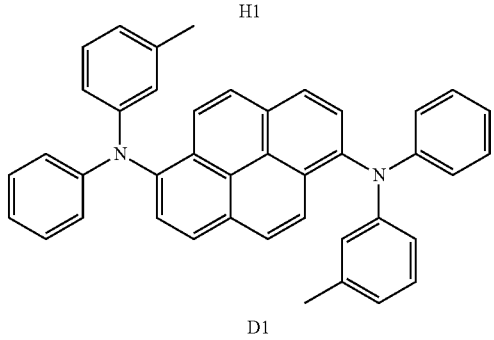

D1

Subsequently, a compound of the following Structural Formula ET was deposited to a thickness of 300 Å as an electron transfer layer.

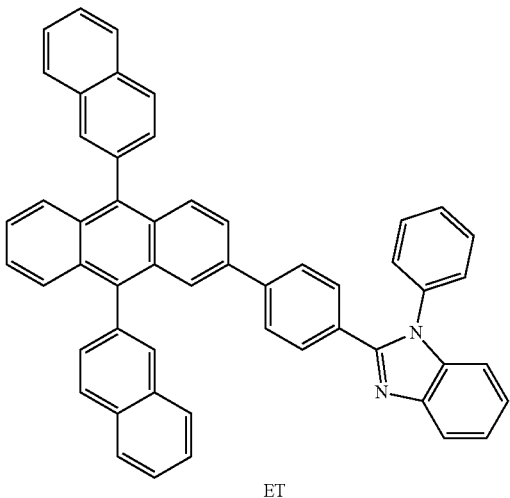 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

ET

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

Organic light emitting devices were manufactured in the same manner as in Experimental Example 2 except that the electron transfer layer ET was formed to a thickness of 250 Å, and then a hole blocking layer was formed on the electron transfer layer to a thickness of 50 Å using a compound shown in the following Table 4.

Results of measuring driving voltage, light emission efficiency, color coordinate (CIE) and lifetime of the blue organic light emitting devices manufactured according to the present disclosure are as shown in Table 4.

TABLE 4

| | Compound | Driving Voltage (V) | Light Emission Efficiency (cd/A) | CIE (x, y) | Lifetime (T95) |
|---|---|---|---|---|---|
| Comparative Example 4 | E1 | 4.91 | 6.49 | (0.141, 0.092) | 35 |
| Comparative Example 5 | E2 | 4.83 | 6.29 | (0.138, 0.093) | 34 |
| Comparative Example 6 | E3 | 4.95 | 6.50 | (0.138, 0.088) | 36 |
| Example 80 | 1 | 4.81 | 6.56 | (0.134, 0.101) | 40 |
| Example 81 | 3 | 4.45 | 6.61 | (0.134, 0.102) | 38 |
| Example 82 | 5 | 4.61 | 6.95 | (0.135, 0.102) | 41 |
| Example 83 | 10 | 4.81 | 6.59 | (0.134, 0.100) | 40 |
| Example 84 | 15 | 4.61 | 6.59 | (0.133, 0.102) | 40 |
| Example 85 | 18 | 4.72 | 6.61 | (0.134, 0.101) | 43 |
| Example 86 | 22 | 4.50 | 6.50 | (0.133, 0.101) | 38 |
| Example 87 | 27 | 4.45 | 6.53 | (0.134, 0.102) | 42 |
| Example 88 | 30 | 4.65 | 6.66 | (0.135, 0.102) | 40 |
| Example 89 | 33 | 4.45 | 6.50 | (0.133, 0.102) | 43 |
| Example 90 | 36 | 4.60 | 6.56 | (0.134, 0.101) | 42 |
| Example 91 | 38 | 4.44 | 6.72 | (0.134, 0.101) | 39 |
| Example 92 | 41 | 4.77 | 6.67 | (0.133, 0.100) | 41 |
| Example 93 | 44 | 4.64 | 6.55 | (0.134, 0.103) | 39 |
| Example 94 | 45 | 4.70 | 6.74 | (0.133, 0.100) | 41 |
| Example 95 | 47 | 4.82 | 6.61 | (0.134, 0.102) | 41 |
| Example 96 | 51 | 4.78 | 6.62 | (0.133, 0.100) | 39 |
| Example 97 | 53 | 4.63 | 6.74 | (0.134, 0.101) | 40 |
| Example 98 | 56 | 4.41 | 6.52 | (0.135, 0.102) | 38 |
| Example 99 | 58 | 4.39 | 6.59 | (0.134, 0.101) | 41 |
| Example 100 | 65 | 4.35 | 6.63 | (0.133, 0.102) | 39 |
| Example 101 | 68 | 4.42 | 6.51 | (0.134, 0.101) | 42 |
| Example 102 | 71 | 4.71 | 6.53 | (0.134, 0.102) | 39 |
| Example 103 | 74 | 4.81 | 6.55 | (0.133, 0.101) | 39 |
| Example 104 | 81 | 4.80 | 6.66 | (0.134, 0.100) | 43 |
| Example 105 | 85 | 4.66 | 6.50 | (0.134, 0.102) | 38 |
| Example 106 | 91 | 4.63 | 6.64 | (0.135, 0.101) | 42 |
| Example 107 | 93 | 4.40 | 6.54 | (0.132, 0.100) | 38 |
| Example 108 | 97 | 4.39 | 6.54 | (0.134, 0.101) | 40 |
| Example 109 | 98 | 4.39 | 6.55 | (0.133, 0.102) | 42 |
| Example 110 | 101 | 4.36 | 6.65 | (0.132, 0.102) | 40 |
| Example 111 | 105 | 4.38 | 6.52 | (0.134, 0.102) | 42 |
| Example 112 | 108 | 4.76 | 6.63 | (0.134, 0.101) | 38 |
| Example 113 | 112 | 4.81 | 6.61 | (0.134, 0.101) | 41 |
| Example 114 | 114 | 4.77 | 6.61 | (0.135, 0.100) | 40 |
| Example 115 | 118 | 4.80 | 6.66 | (0.131, 0.100) | 43 |
| Example 116 | 122 | 4.67 | 6.53 | (0.134, 0.102) | 38 |
| Example 117 | 130 | 4.77 | 6.67 | (0.132, 0.100) | 41 |
| Example 118 | 134 | 4.63 | 6.54 | (0.134, 0.103) | 39 |
| Example 119 | 136 | 4.81 | 6.58 | (0.134, 0.100) | 40 |
| Example 120 | 140 | 4.63 | 6.59 | (0.133, 0.101) | 40 |
| Example 121 | 144 | 4.66 | 6.50 | (0.134, 0.102) | 38 |
| Example 122 | 148 | 4.62 | 6.65 | (0.134, 0.101) | 42 |
| Example 123 | 149 | 4.70 | 6.72 | (0.135, 0.100) | 42 |
| Example 124 | 153 | 4.81 | 6.65 | (0.133, 0.102) | 41 |
| Example 125 | 155 | 4.72 | 6.62 | (0.134, 0.102) | 44 |
| Example 126 | 158 | 4.45 | 6.50 | (0.133, 0.102) | 43 |
| Example 127 | 161 | 4.59 | 6.56 | (0.134, 0.101) | 42 |
| Example 128 | 166 | 4.44 | 6.72 | (0.134, 0.101) | 39 |
| Example 129 | 173 | 4.39 | 6.54 | (0.134, 0.101) | 40 |
| Example 130 | 176 | 4.39 | 6.56 | (0.135, 0.102) | 42 |
| Example 131 | 180 | 4.76 | 6.63 | (0.134, 0.101) | 38 |
| Example 132 | 181 | 4.81 | 6.61 | (0.134, 0.101) | 41 |
| Example 133 | 188 | 4.78 | 6.61 | (0.133, 0.100) | 40 |
| Example 134 | 189 | 4.59 | 6.56 | (0.134, 0.101) | 42 |
| Example 135 | 193 | 4.44 | 6.72 | (0.134, 0.101) | 39 |
| Example 136 | 197 | 4.76 | 6.67 | (0.133, 0.100) | 41 |
| Example 137 | 201 | 4.35 | 6.63 | (0.133, 0.102) | 39 |
| Example 138 | 207 | 4.42 | 6.51 | (0.134, 0.101) | 42 |
| Example 139 | 208 | 4.71 | 6.53 | (0.134, 0.102) | 39 |
| Example 140 | 214 | 4.66 | 6.55 | (0.134, 0.102) | 38 |
| Example 141 | 220 | 4.61 | 6.64 | (0.134, 0.101) | 42 |
| Example 142 | 225 | 4.64 | 6.55 | (0.134, 0.103) | 39 |
| Example 143 | 230 | 4.69 | 6.74 | (0.135, 0.100) | 41 |
| Example 144 | 233 | 4.82 | 6.61 | (0.134, 0.102) | 41 |
| Example 145 | 236 | 4.45 | 6.62 | (0.134, 0.102) | 38 |
| Example 146 | 238 | 4.62 | 6.95 | (0.135, 0.102) | 41 |
| Example 147 | 240 | 4.81 | 6.58 | (0.134, 0.100) | 40 |
| Example 148 | 245 | 4.35 | 6.63 | (0.133, 0.102) | 39 |

TABLE 4-continued

| Compound | Driving Voltage (V) | Light Emission Efficiency (cd/A) | CIE (x, y) | Lifetime (T95) |
|---|---|---|---|---|
| Example 149 | 247 | 4.42 | 6.51 | (0.134, 0.101) | 42 |
| Example 150 | 252 | 4.70 | 6.62 | (0.135, 0.102) | 44 |
| Example 151 | 255 | 4.45 | 6.50 | (0.133, 0.102) | 43 |
| Example 152 | 258 | 4.60 | 6.56 | (0.134, 0.101) | 42 |
| Example 153 | 263 | 4.66 | 6.50 | (0.134, 0.102) | 38 |
| Example 154 | 267 | 4.61 | 6.64 | (0.134, 0.101) | 42 |
| Example 155 | 269 | 4.41 | 6.54 | (0.132, 0.100) | 38 |
| Example 156 | 274 | 4.80 | 6.65 | (0.131, 0.100) | 43 |
| Example 157 | 276 | 4.67 | 6.52 | (0.135, 0.102) | 38 |
| Example 158 | 280 | 4.76 | 6.63 | (0.134, 0.101) | 38 |

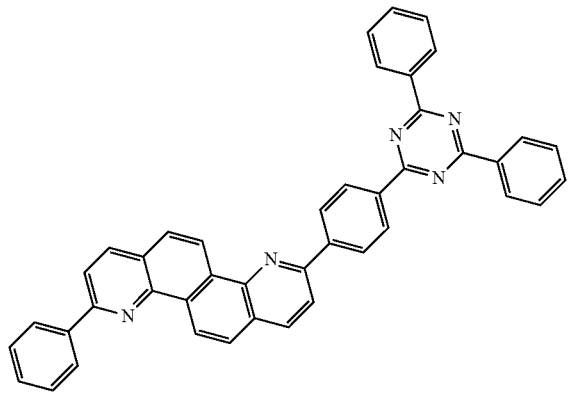

E1

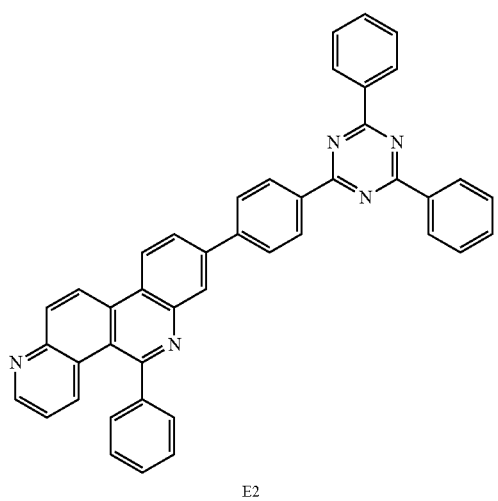 [SMILES: c1ccc(-c2nc(-c3ccccc3)nc(-c3ccc(-c4ccc5c(c4)nc(-c4ccccc4)c4c6cccnc6ccc54)cc3)n2)cc1]

E2

E3

<Experimental Example 3>—Manufacture of Organic Light Emitting Device

1) Manufacture of Organic Light Emitting Device

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO (ultraviolet ozone) treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. The light emitting layer was deposited to 300 Å by doping TCz1, a host, with FIrpic, a blue phosphorescent dopant, by 8%. After forming an electron transfer layer to 400 Å using TmPyPB, a compound described in the following Table 5 was doped with $Cs_2CO_3$ by 20% to form an n-type charge generation layer to 100 Å.

As for the second stack, $MoO_3$ was thermal vacuum deposited first to a thickness of 50 Å to form a hole injection layer. A hole transfer layer that is a common layer was formed to 100 Å by doping $MoO_3$ to TAPC by 20%, and then depositing TAPC to 300 Å. A light emitting layer was deposited to 300 Å thereon by doping TCz1, a host, with $Ir(ppy)_3$, a green phosphorescent dopant, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

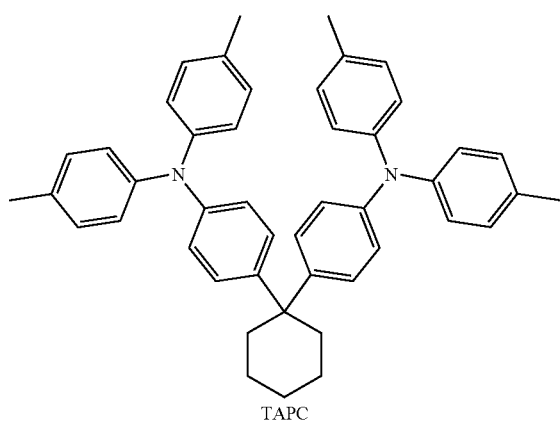

TAPC

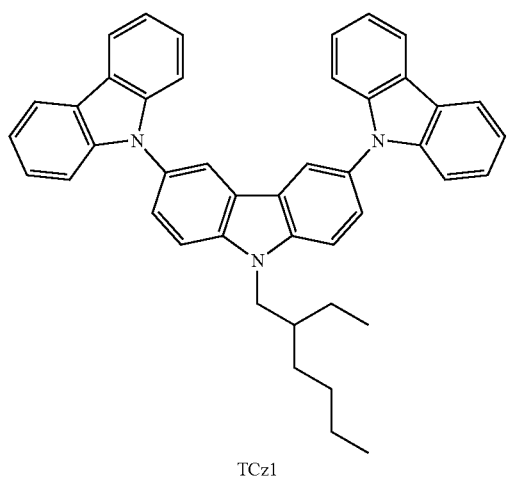

TCz1

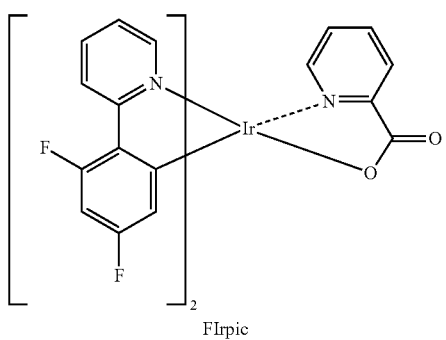

FIrpic

-continued

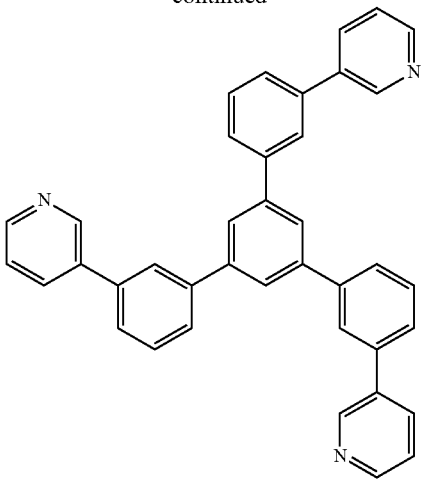

TmPyPB

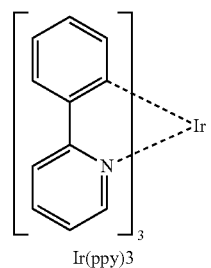

Ir(ppy)3

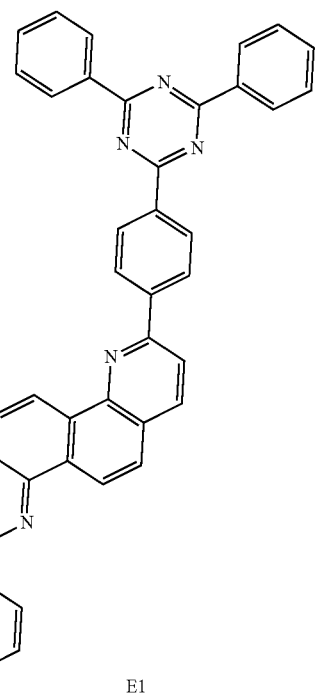

E1

-continued

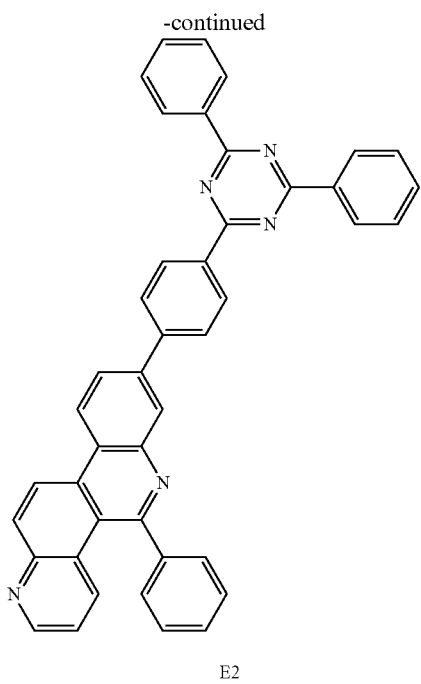

E2

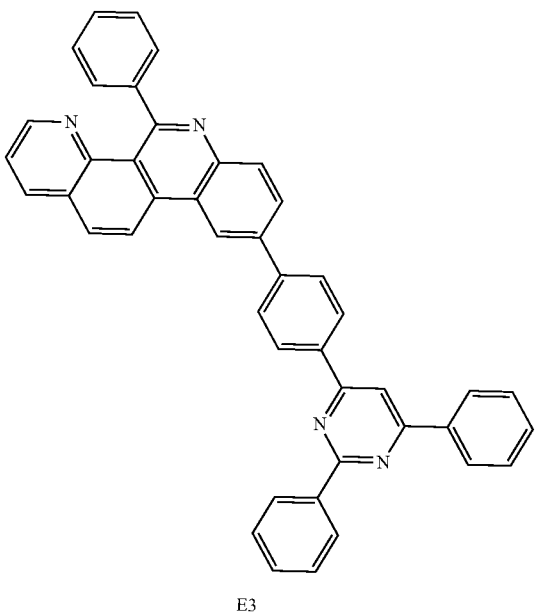 [SMILES: c1ccc(-c2cc(-c3ccc(-c4ccc5nc(-c6ccccc6)c6c(ccc7cccnc76)c5c4)cc3)nc(-c3ccccc3)n2)cc1]

E3

TABLE 5

|  | Compound | Driving Voltage (V) | Light Emission Efficiency (cd/A) | CIE (x,y) | Lifetime (T95) |
| --- | --- | --- | --- | --- | --- |
| Comparative Example 7 | E1 | 4.90 | 6.50 | (0.141, 0.092) | 35 |
| Comparative Example 8 | E2 | 4.83 | 6.30 | (0.139, 0.094) | 34 |
| Comparative Example 9 | E3 | 4.96 | 6.50 | (0.139, 0.088) | 36 |
| Example 159 | 30 | 4.78 | 6.61 | (0.133, 0.100) | 39 |
| Example 160 | 85 | 4.63 | 6.76 | (0.133, 0.101) | 40 |
| Example 161 | 88 | 4.41 | 6.53 | (0.134, 0.102) | 38 |
| Example 162 | 130 | 4.39 | 6.52 | (0.134, 0.101) | 41 |

As seen from the results of Table 5, it was seen that the organic light emitting device using the charge generation layer material of the 2-stack white organic light emitting device of the present disclosure had lower driving voltage and improved light emission efficiency compared to the comparative examples.

The invention claimed is:
1. A heterocyclic compound represented by the following Chemical Formula 1:

[Chemical Formula 1]

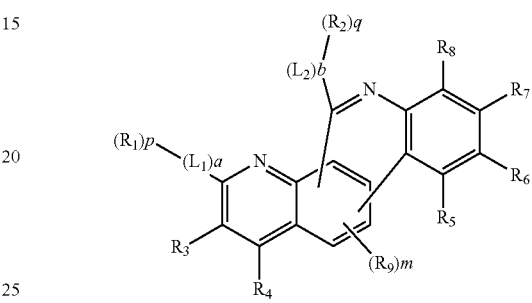

wherein, in Chemical Formula 1,
$L_1$ and $L_2$ are the same as or different from each other, and each independently a direct bond; a substituted or unsubstituted C6 to C60 arylene group; or a substituted or unsubstituted C2 to C60 heteroarylene group, and a and b are an integer of 0 to 4;
$R_1$ is selected from the group consisting of a substituted or unsubstituted C1 to C60 alkyl group; a substituted or unsubstituted C6 to C60 aryl group; a substituted or unsubstituted $C_2$ to C60 heteroaryl group; —SiRR'R''; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group;
$R_2$ is selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R''; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group;
p and q are an integer of 1 to 5;
$R_3$ to $R_9$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R''; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring;

R, R' and R" are a substituted or unsubstituted C1 to C60 alkyl group; a substituted or unsubstituted C6 to C60 aryl group; or a substituted or unsubstituted C2 to C60 heteroaryl group; and m is an integer of 0 or 1.

2. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and R, R' and R" have the same definitions as in Chemical Formula 1.

3. The heterocyclic compound of claim 1, wherein Chemical Formula 1 is represented by any one of the following Chemical Formula 2 to Chemical Formula 5:

[Chemical Formula 2]

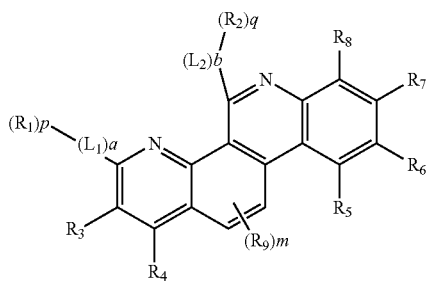

[Chemical Formula 3]

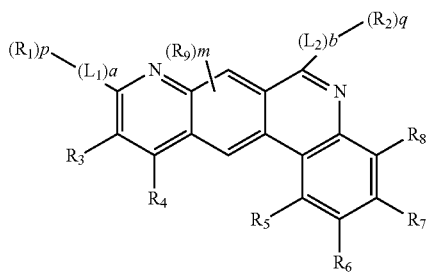

[Chemical Formula 4]

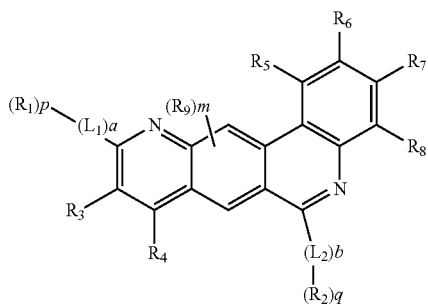

[Chemical Formula 5]

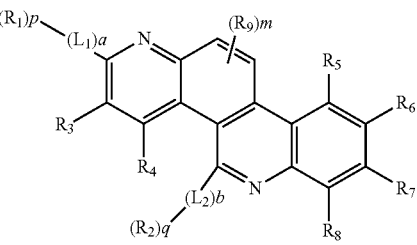

in Chemical Formulae 2 to 5,
$R_1$ to $R_9$, $L_1$, $L_2$, m, a, b, p and q have the same definitions as in Chemical Formula 1.

4. The heterocyclic compound of claim 1, wherein Chemical Formula 1 is represented by any one of the following Chemical Formulae 6 to 8:

[Chemical Formula 6]

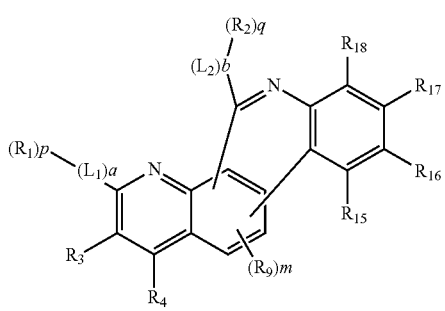

[Chemical Formula 7]

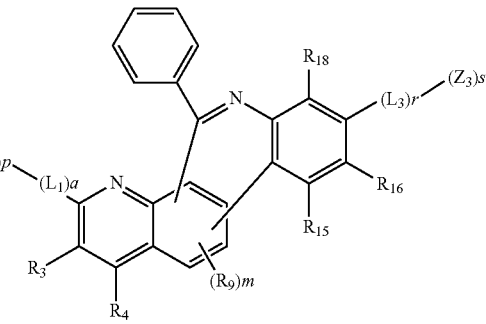

[Chemical Formula 8]

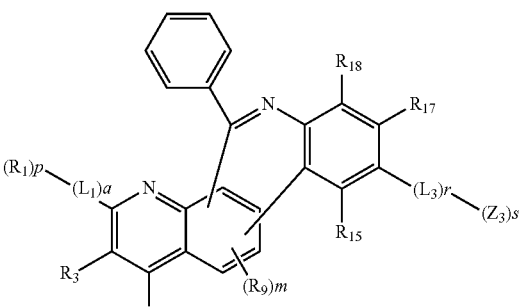

in Chemical Formulae 6 to 8,
$R_1$, $R_2$, $L_1$, $L_2$, a, b, p, q, $R_3$, $R_4$, $R_9$ and m have the same definitions as in Chemical Formula 1;
$R_{15}$ to $R_{18}$ are hydrogen;
$L_3$ is a direct bond; a substituted or unsubstituted C6 to C60 arylene group; or a substituted or unsubstituted C2 to C60 heteroarylene group;

$Z_3$ is selected from the group consisting of a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group;
r is an integer of 0 to 4;
s is an integer of 1 to 5; and R, R' and R" have the same definitions as in Chemical Formula 1.

5. The heterocyclic compound of claim 1, wherein $R_1$ is a substituted or unsubstituted C6 to C60 aryl group.

6. The heterocyclic compound of claim 1, wherein $R_3$, $R_4$ and $R_9$ are hydrogen.

7. The heterocyclic compound of claim 1, wherein Chemical Formula 1 is represented by any one of the following compounds:

1

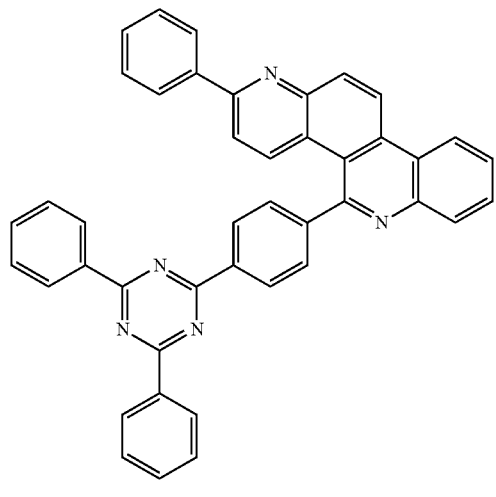

2

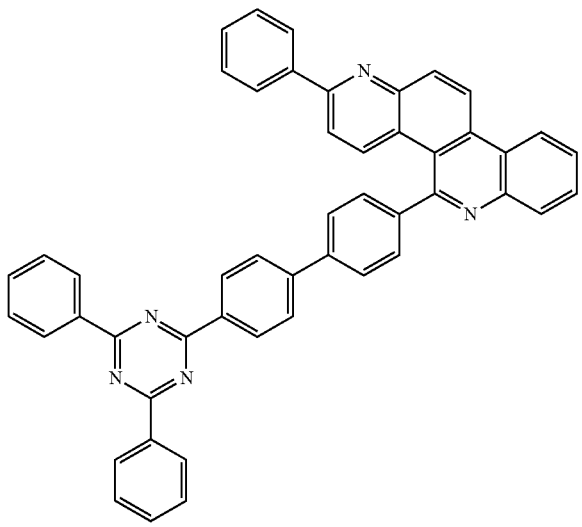

3

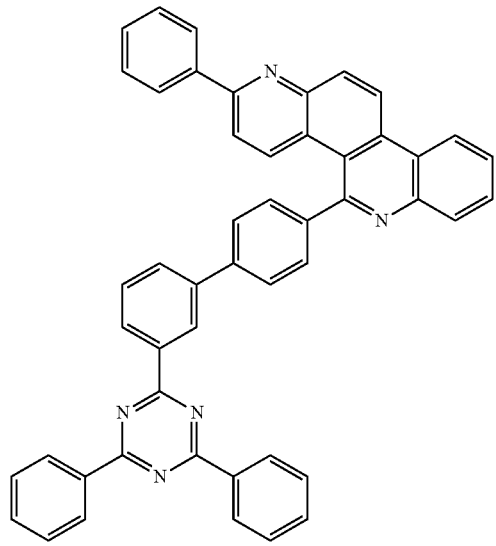

4

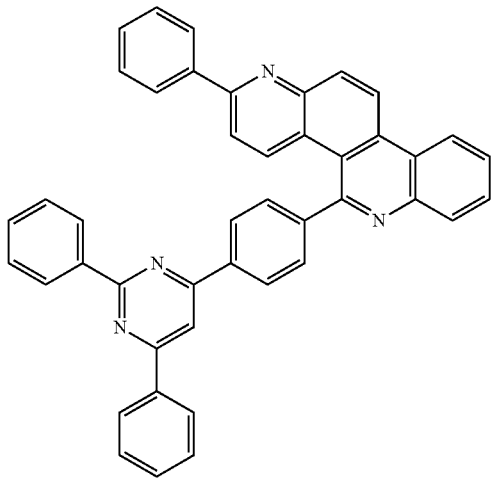

-continued
5
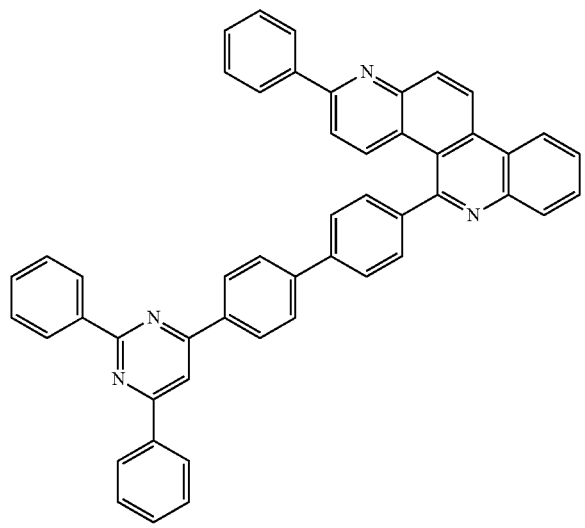
6
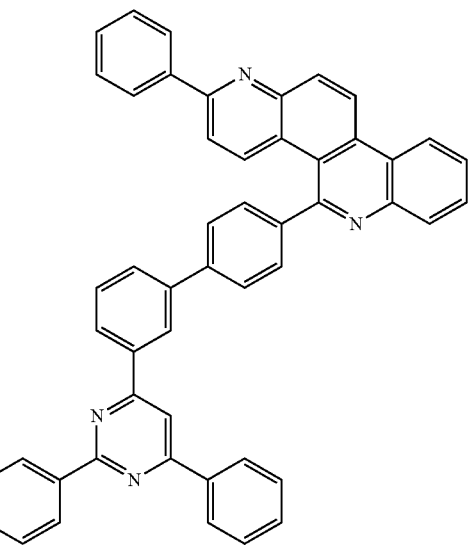
7
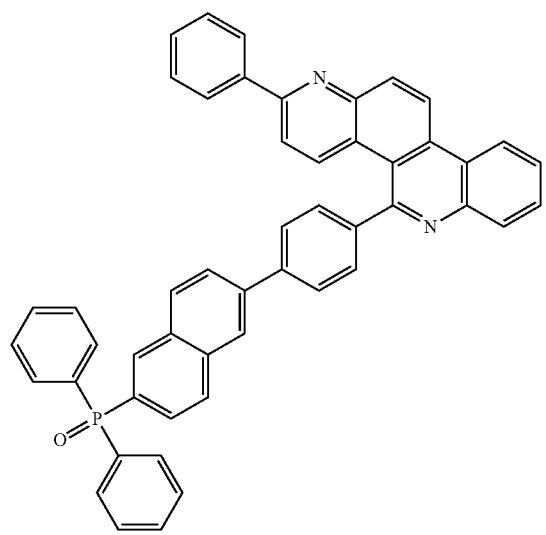
8
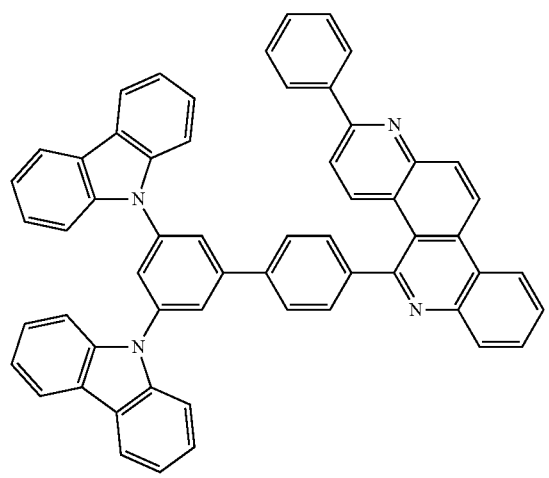
9
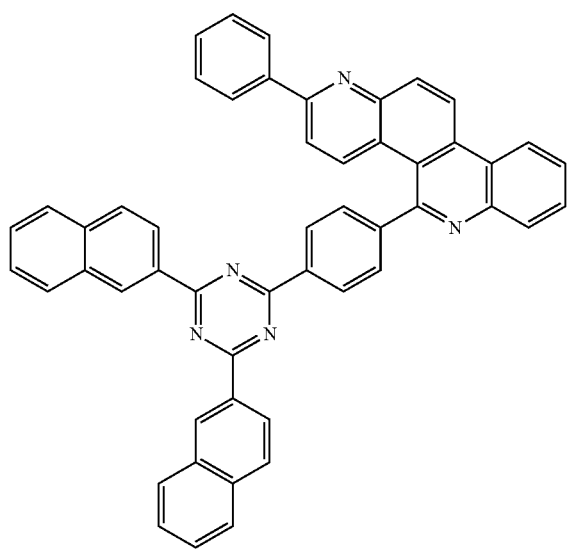
10

219
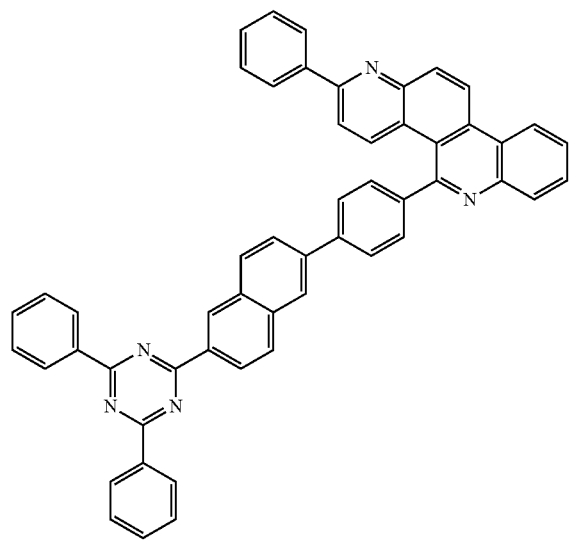
11
220
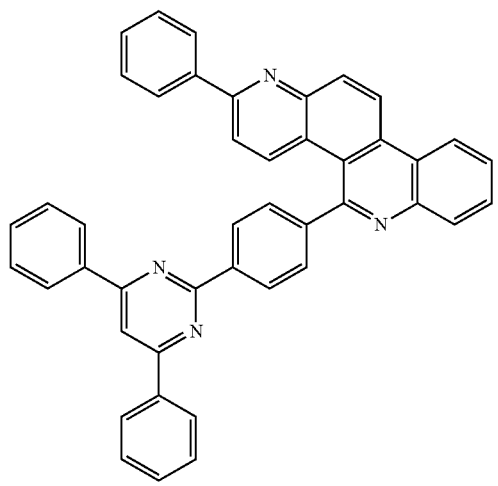
12
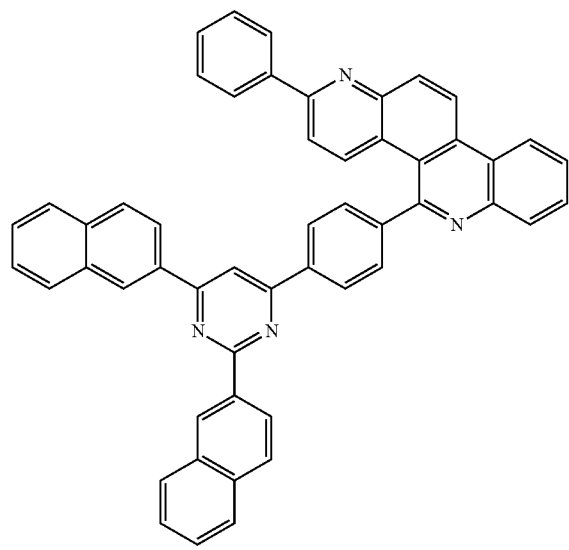
13
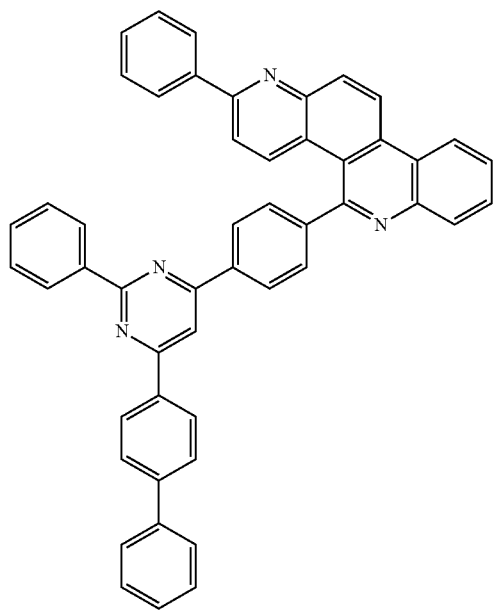
14

-continued
15
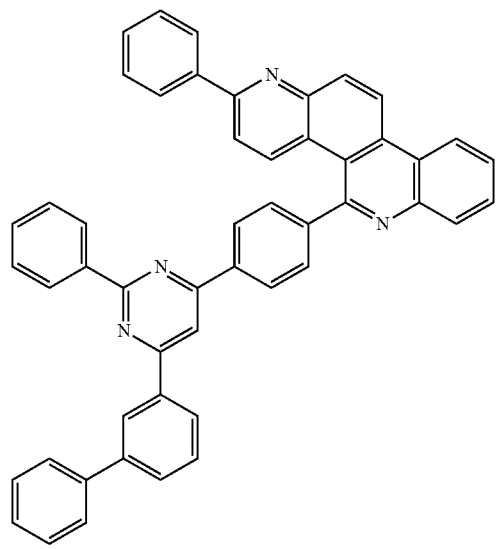
16
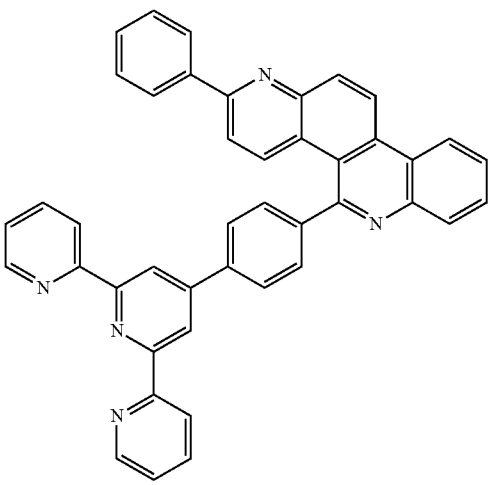
17
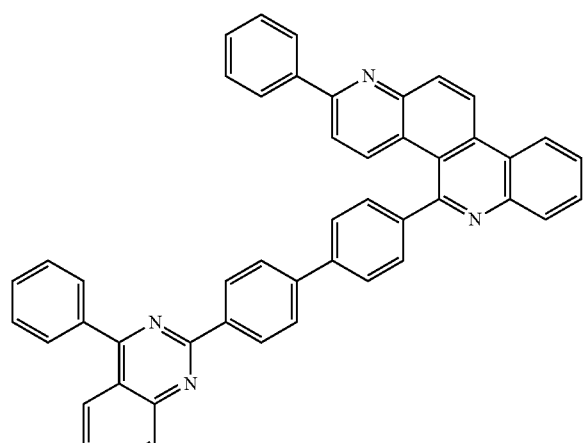
18
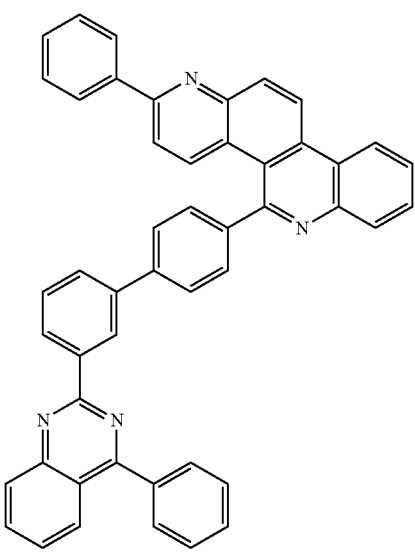
19
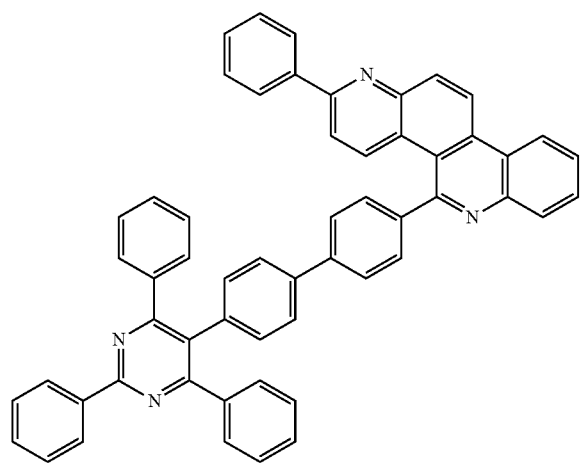
20
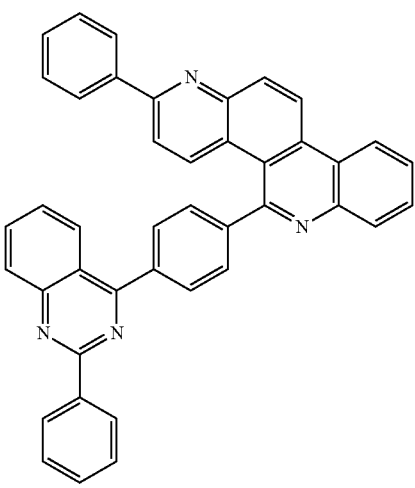

-continued
21
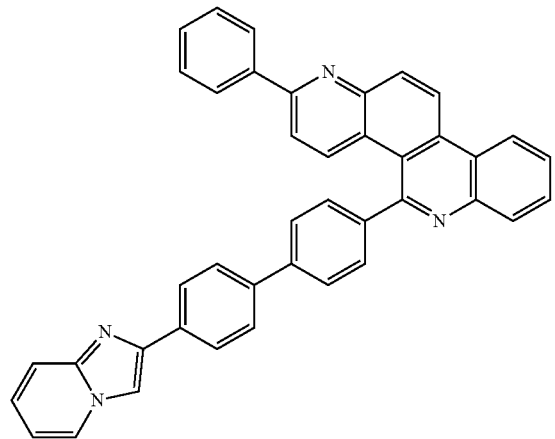
22
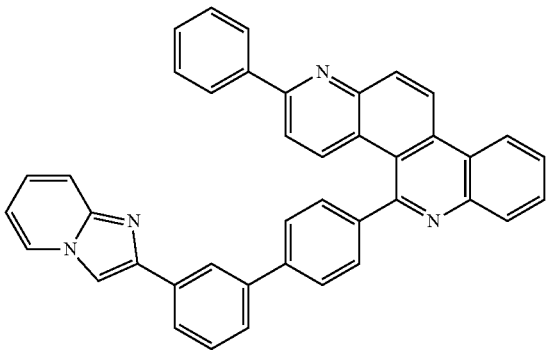
23
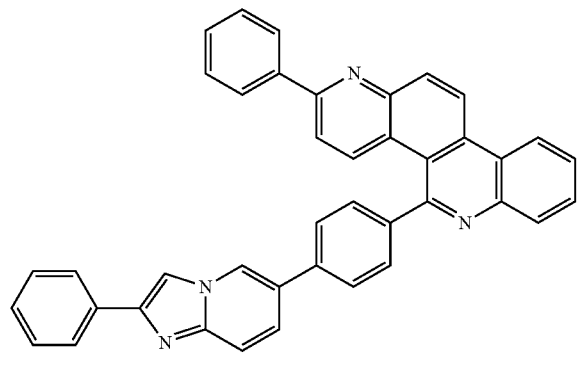
24
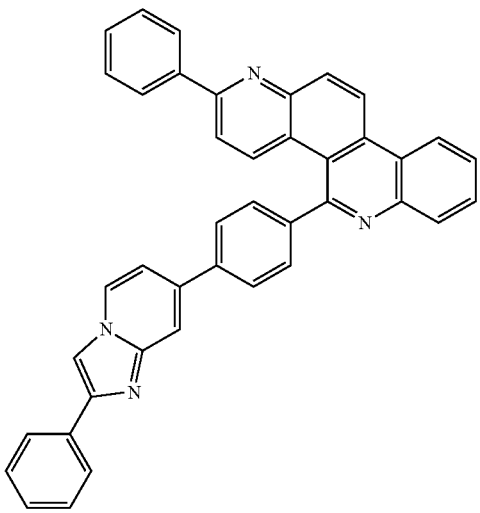
25
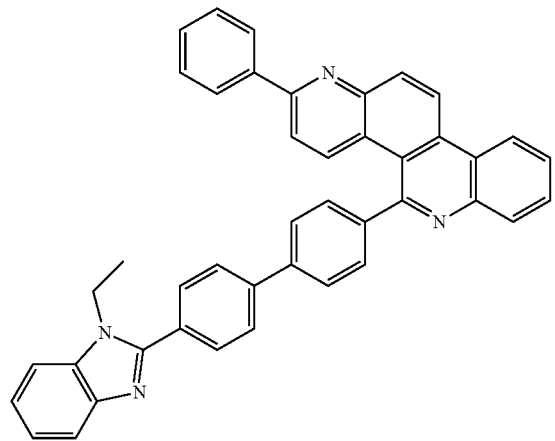
26
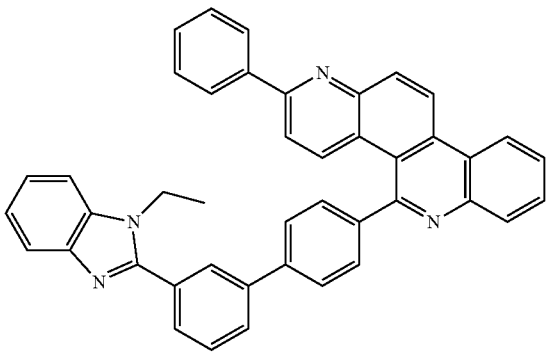

-continued
27
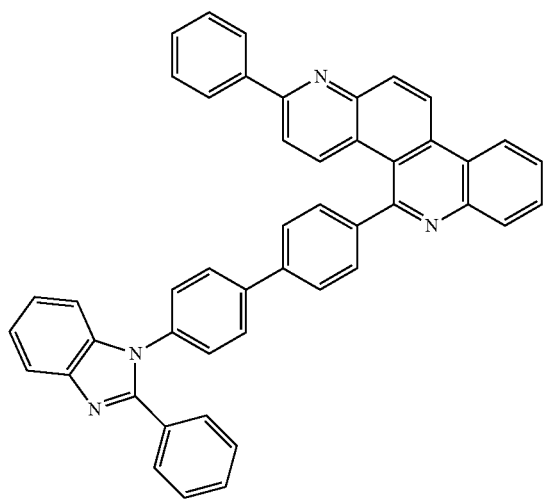
28
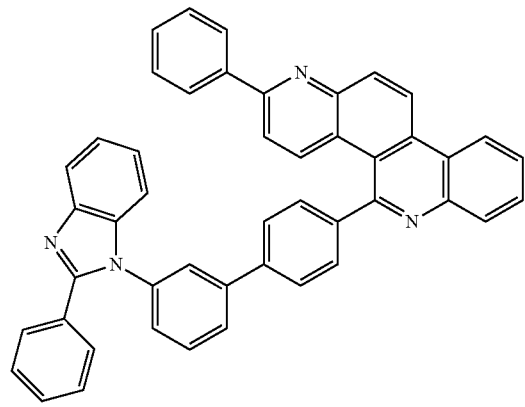
29
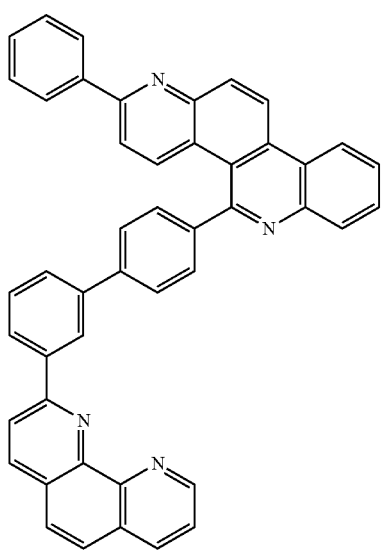
30
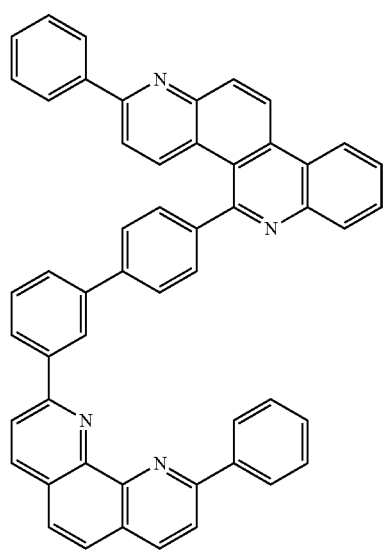
31
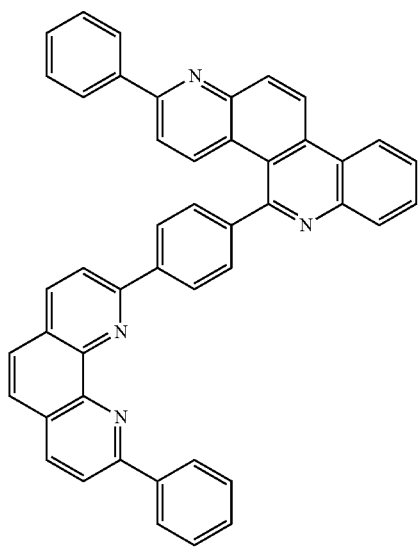
32
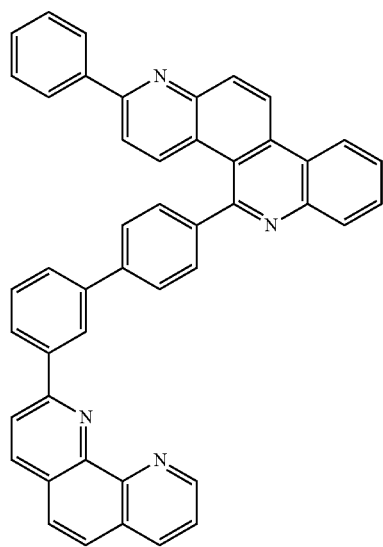

-continued
33
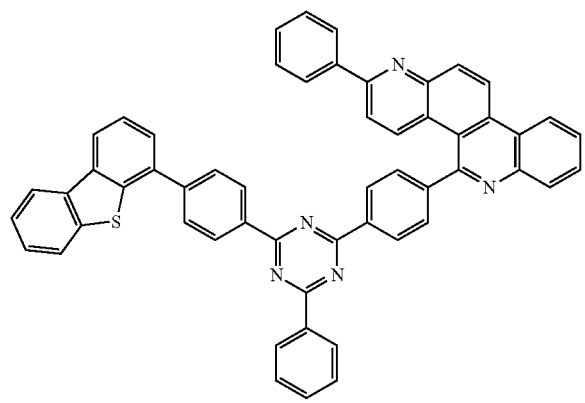
34
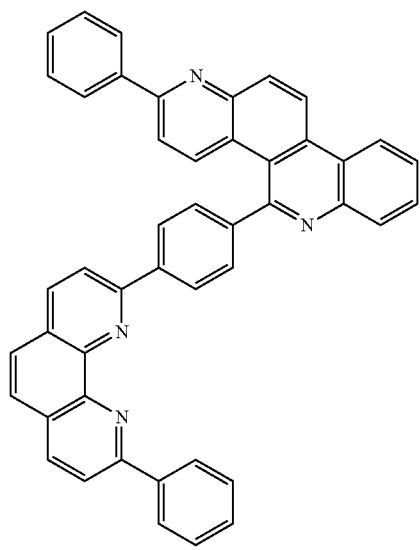
35
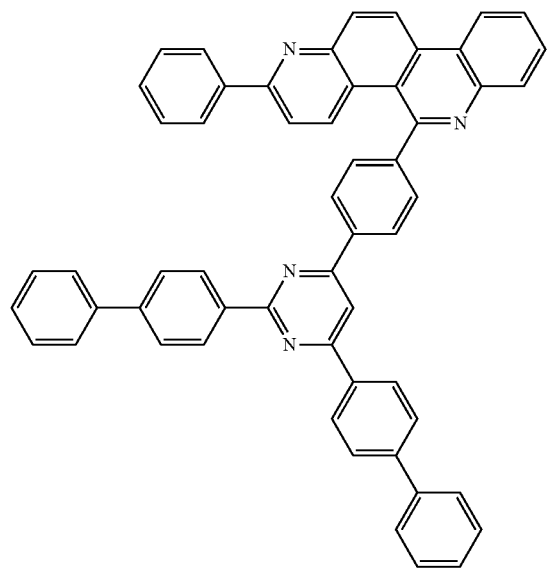
36
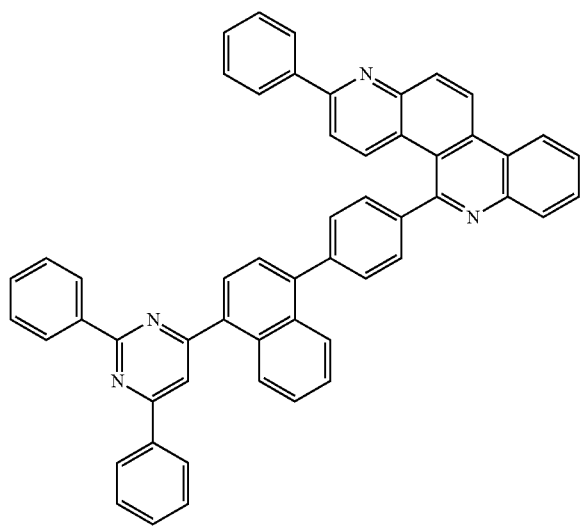

37
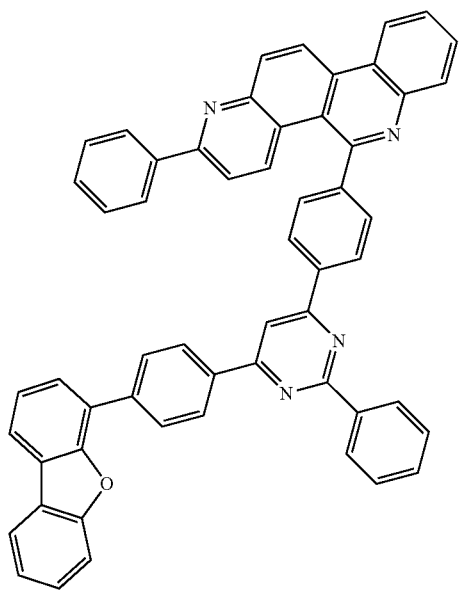
38
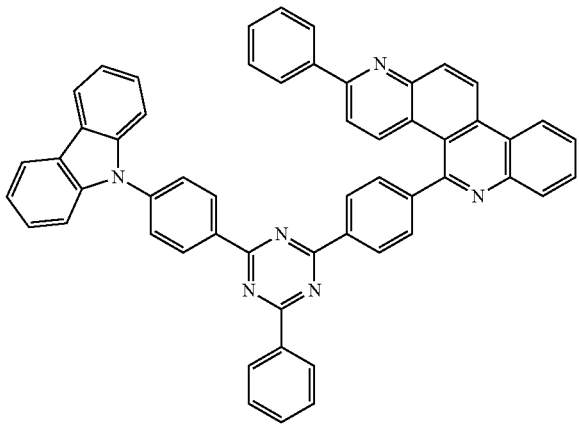
39
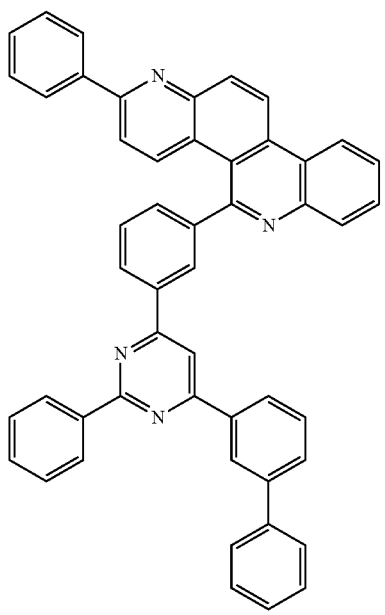
40
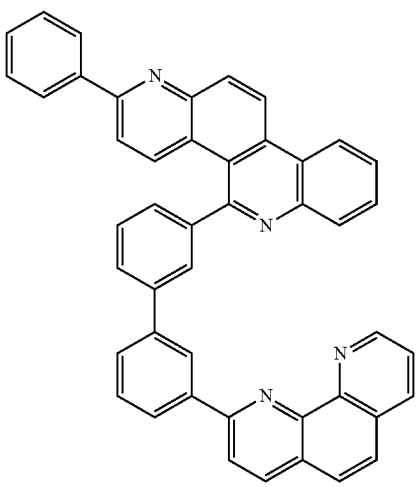

-continued
41
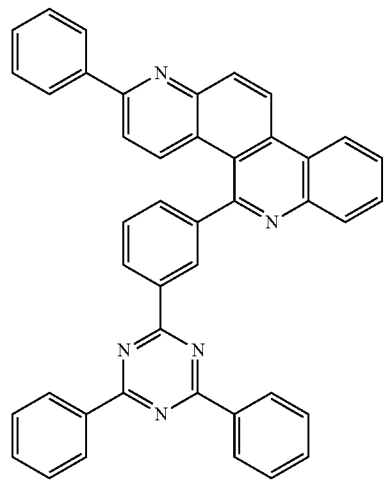
42
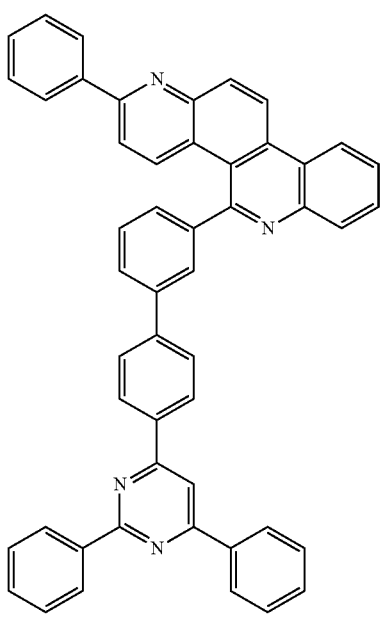
43
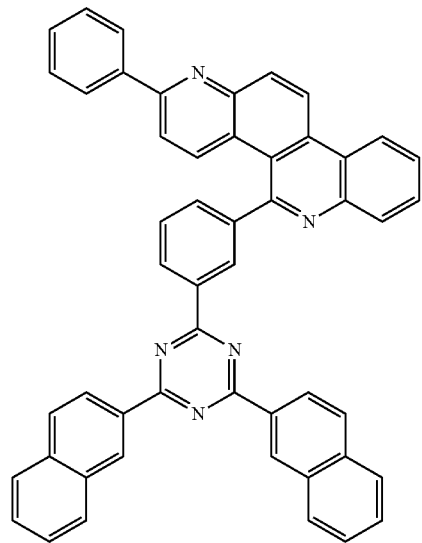
44
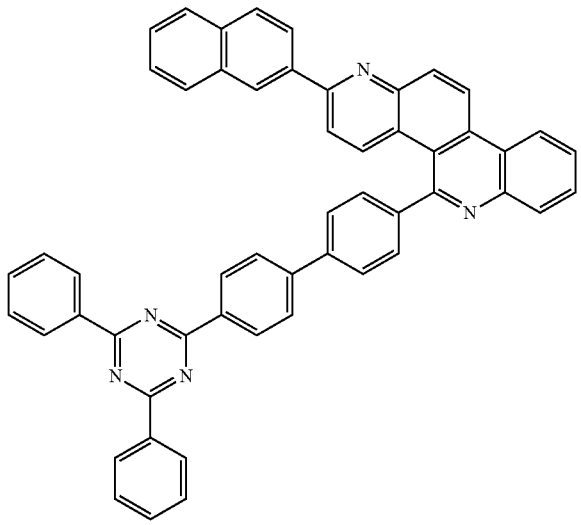

-continued
45
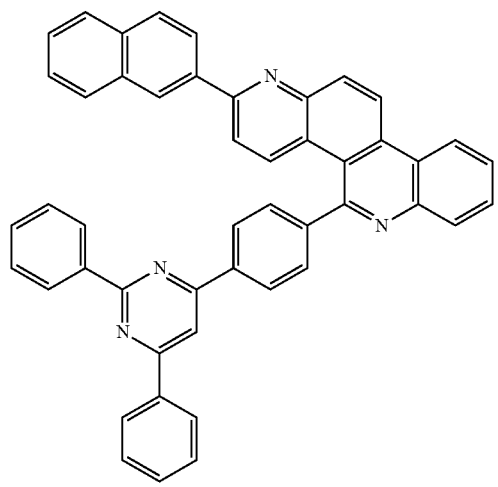
46
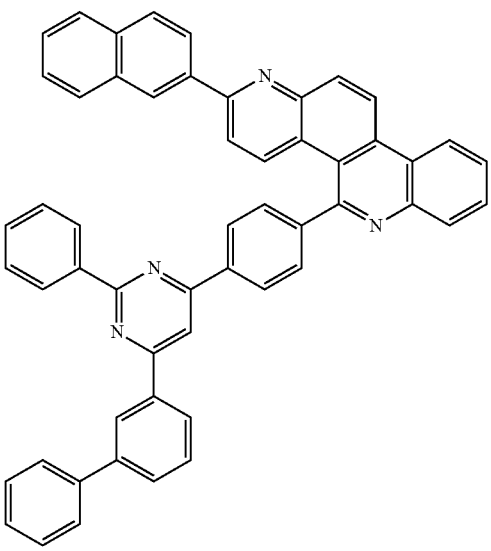
47
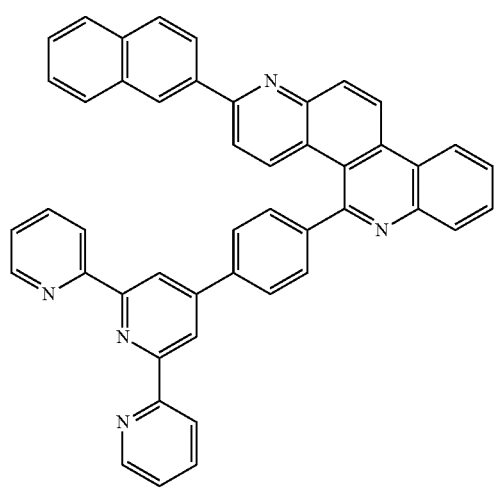
48
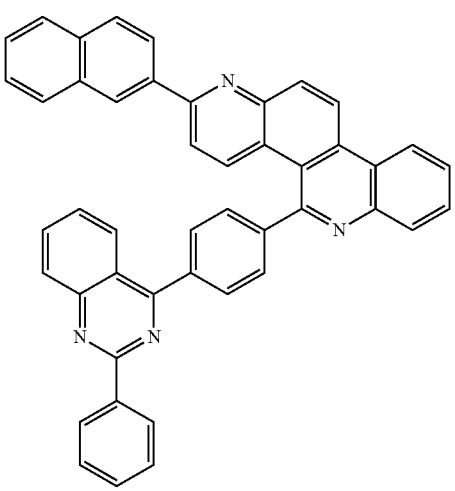
49
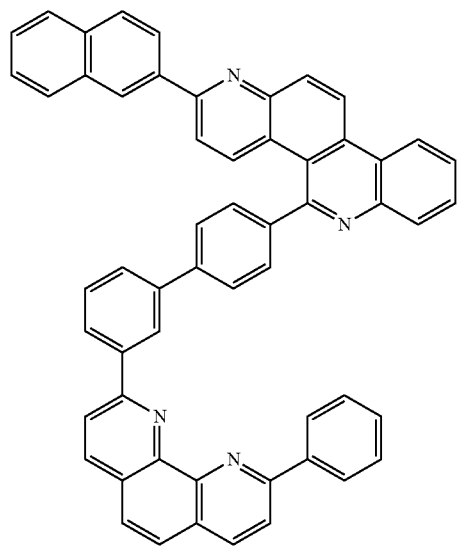
50
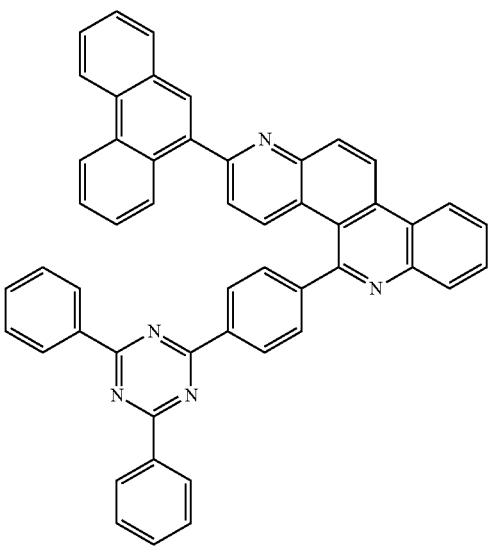

235 236
-continued
51 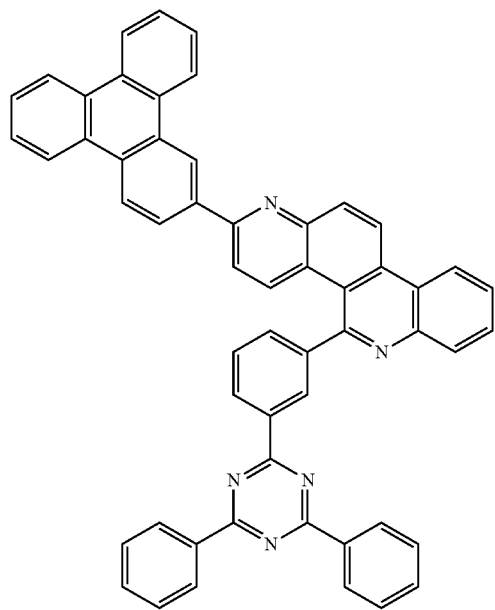 52 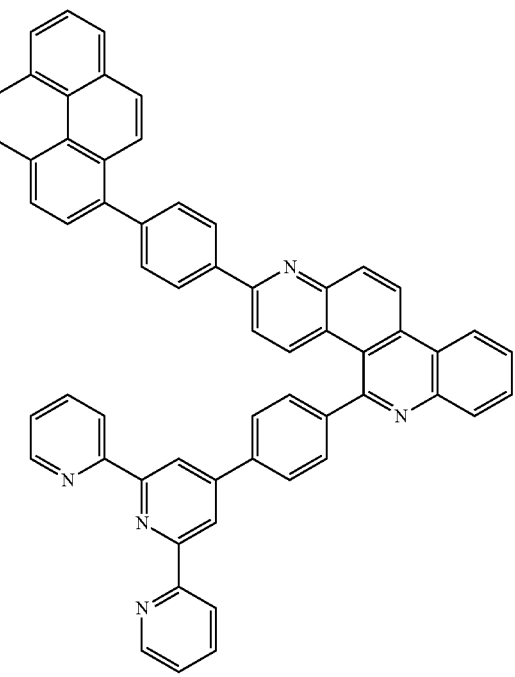
53 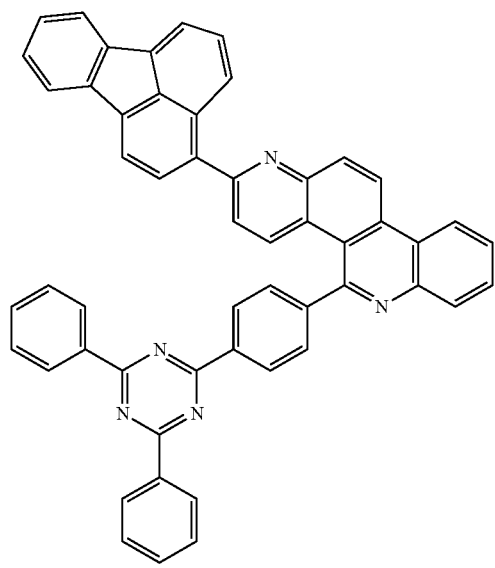 54 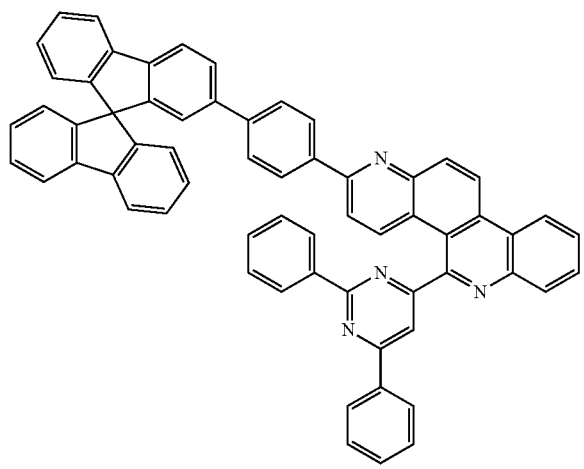

55
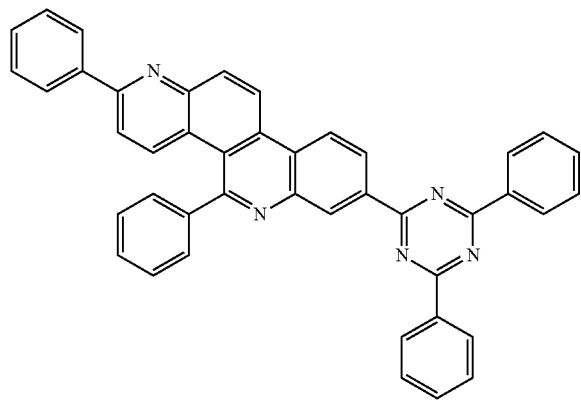
56
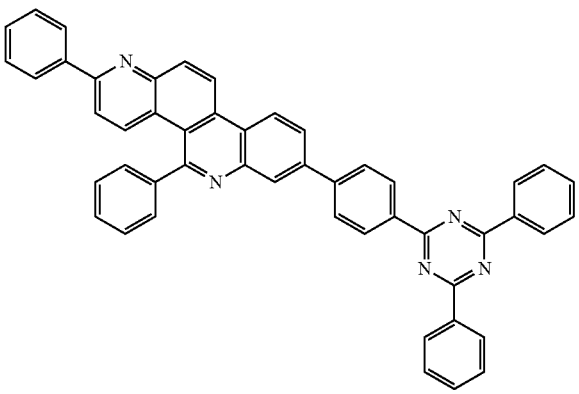
57
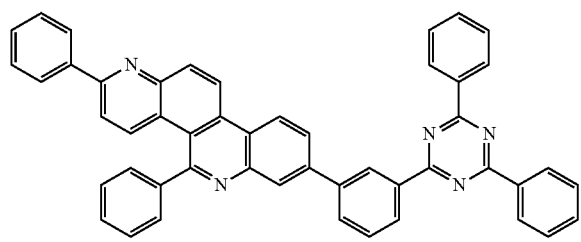
58
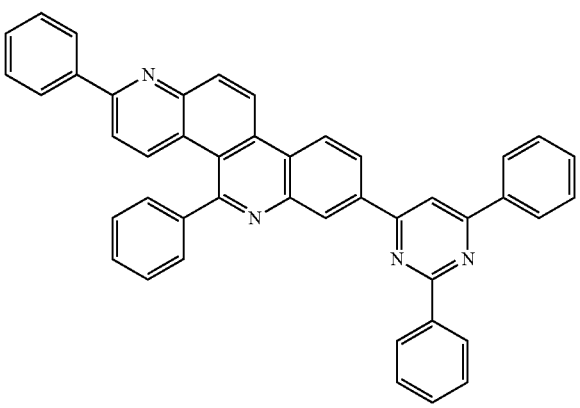
59
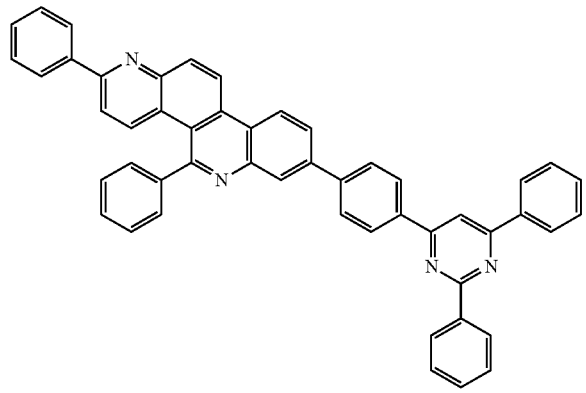
60
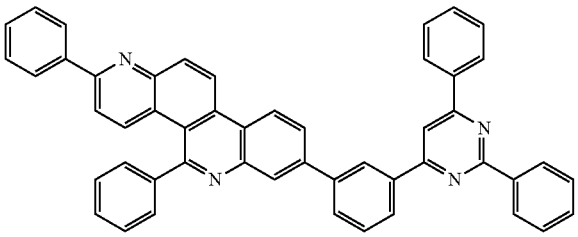

-continued
61
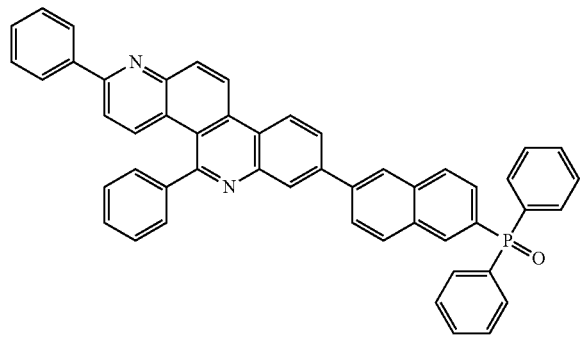
62
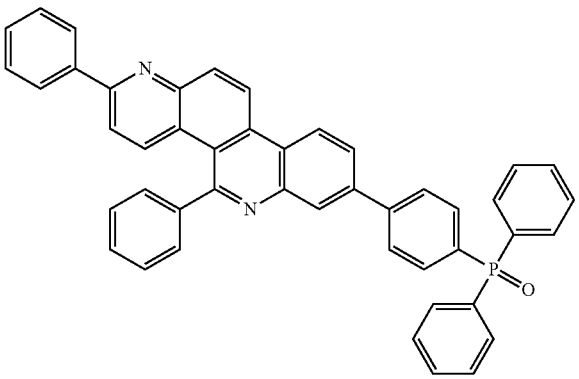
63
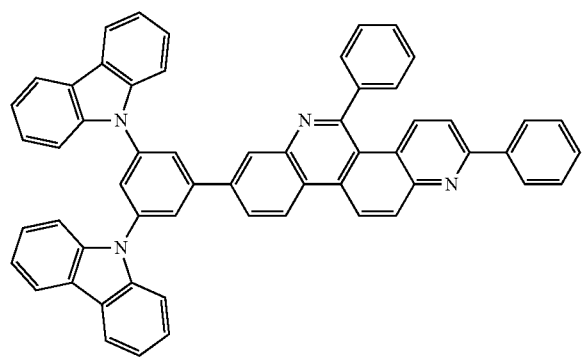
64
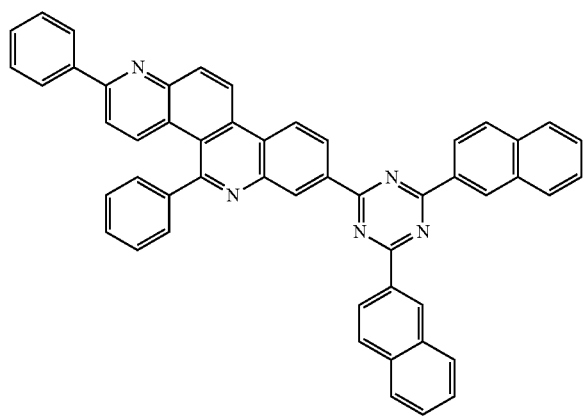
65
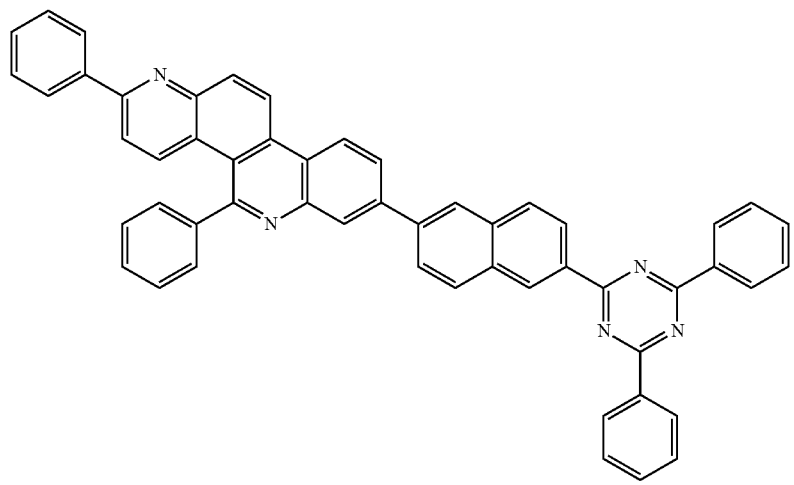

-continued
66
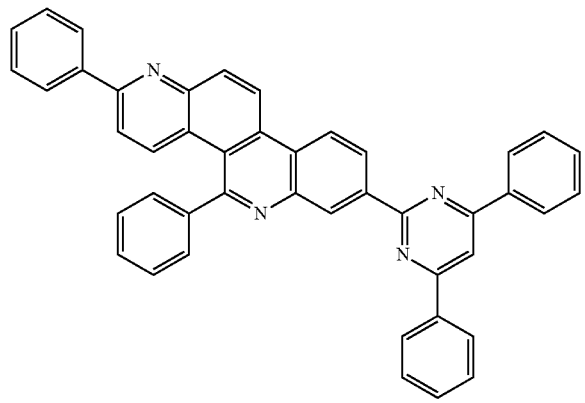
67
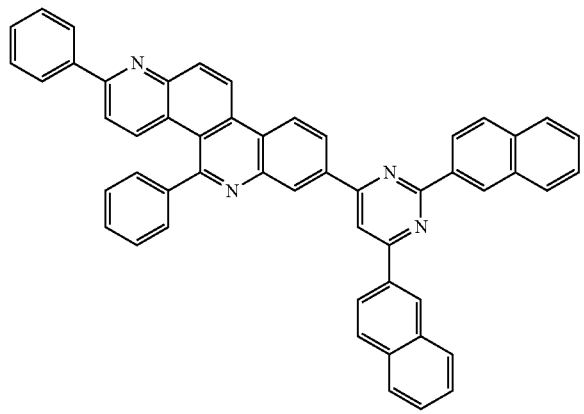
68
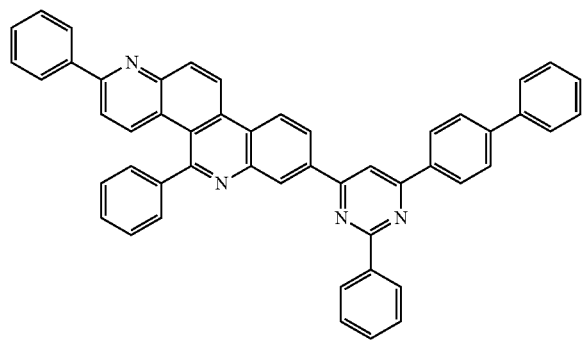
69
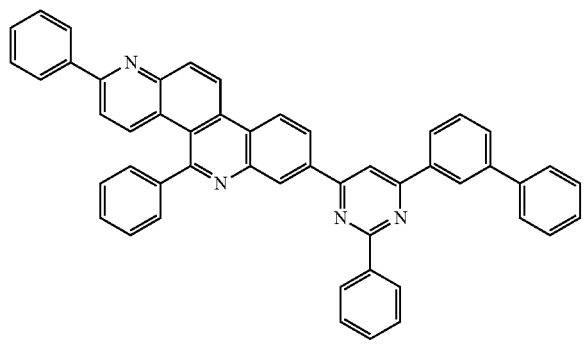
70
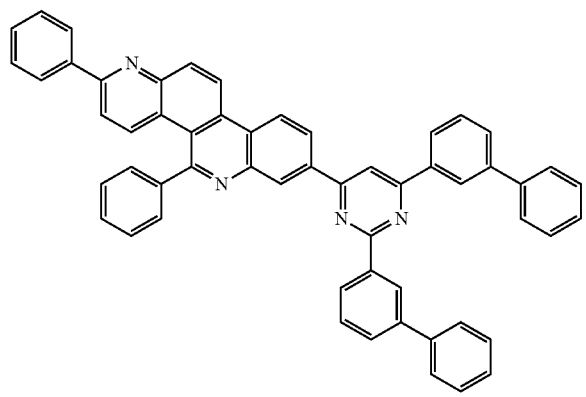
71
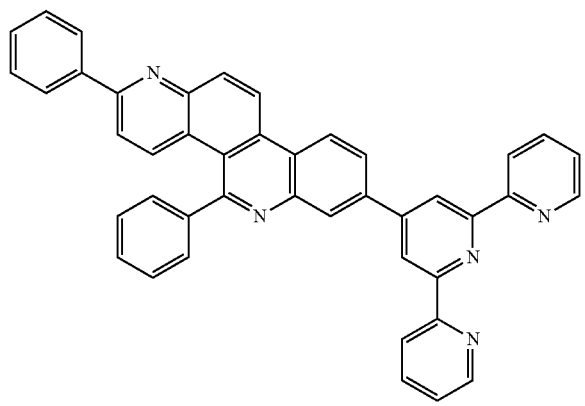

72
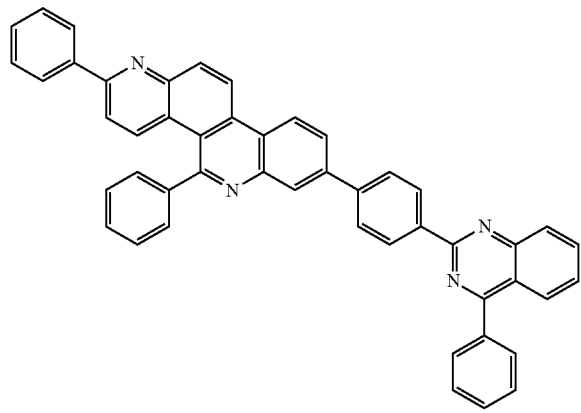
73
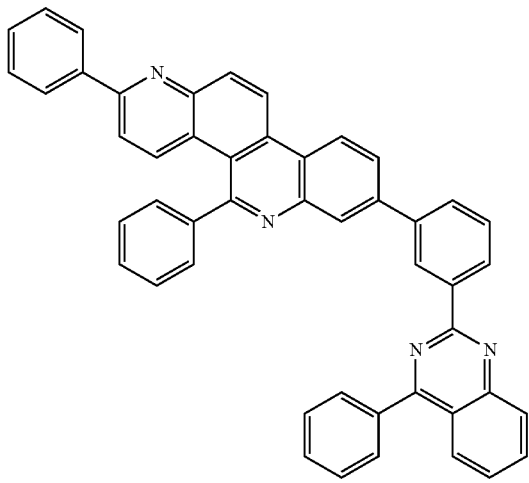
74
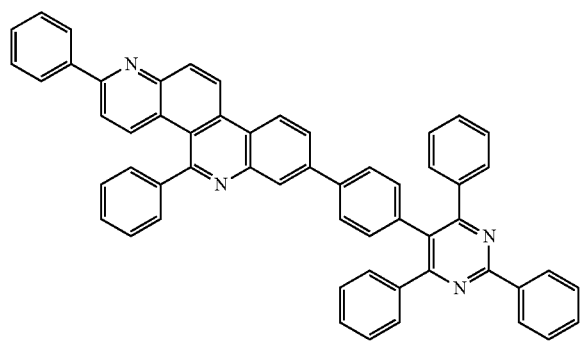
75
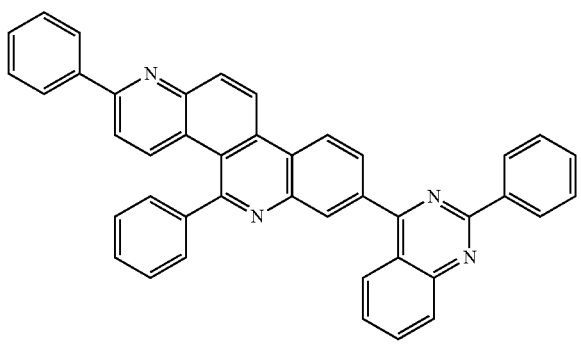
76
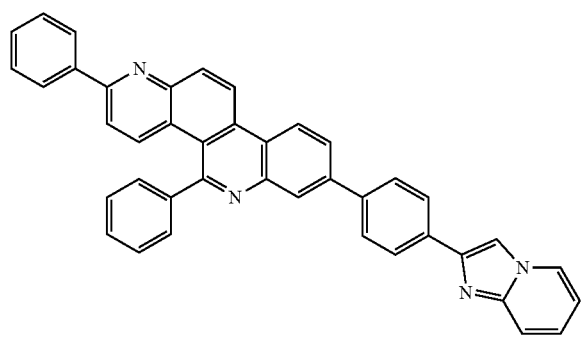
77
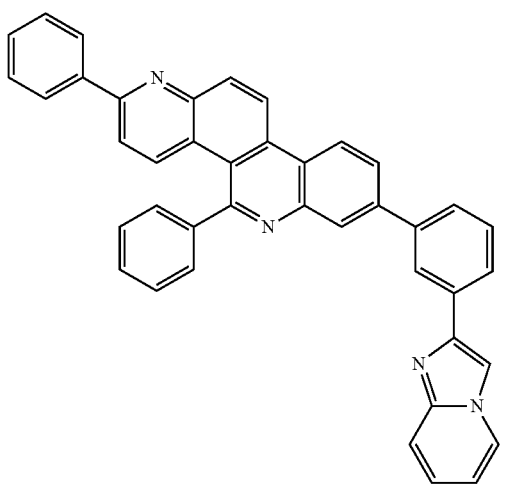

-continued
78
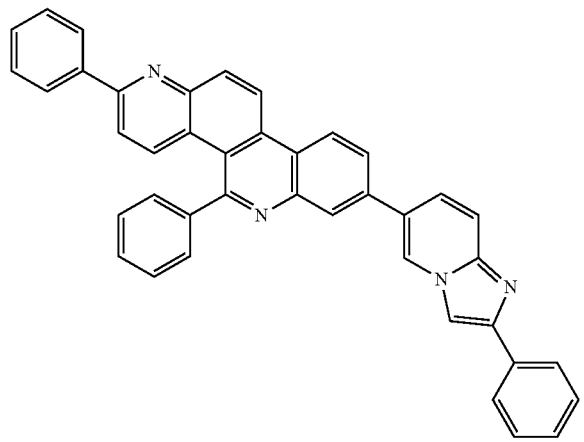
79
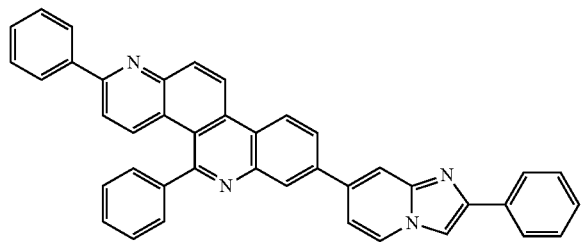
80
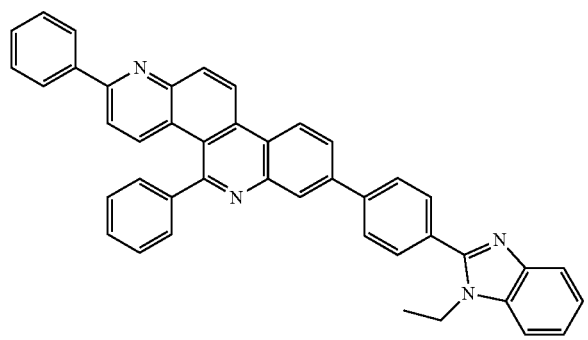
81
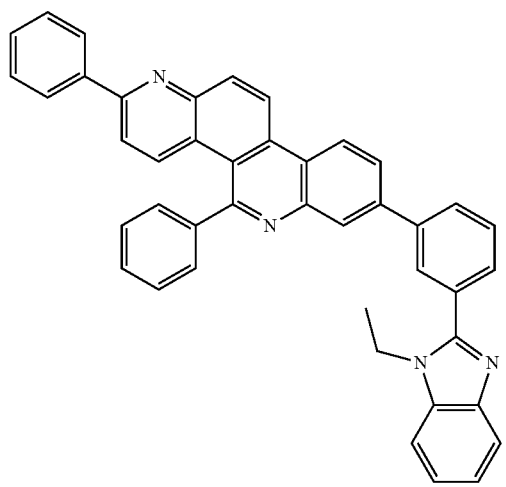
82
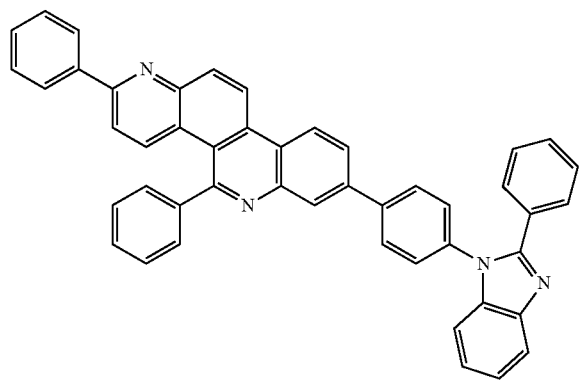
83
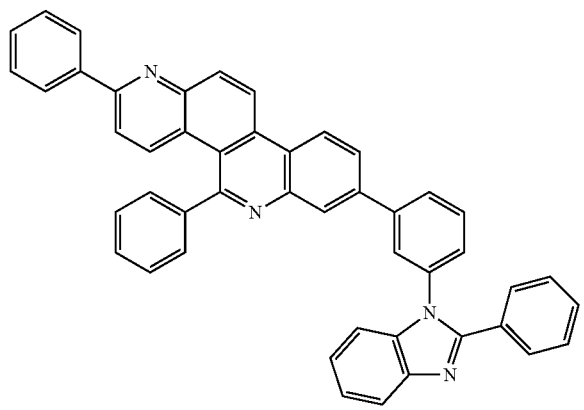

-continued
84
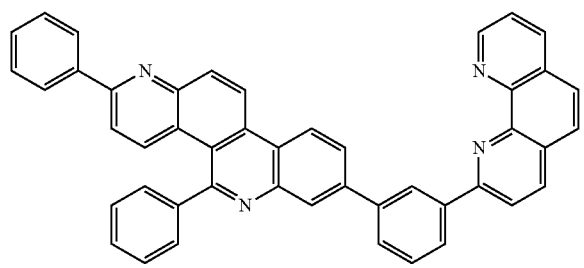
85
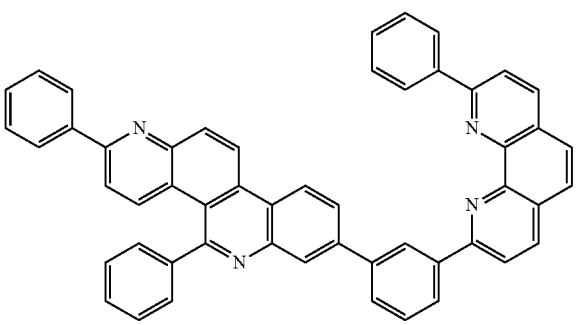
86
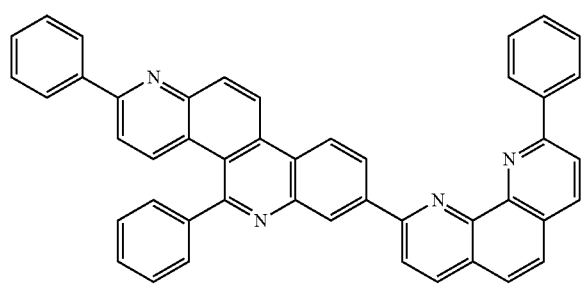
87
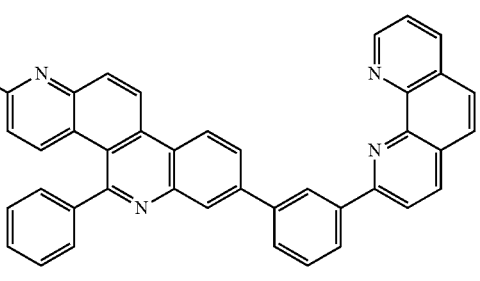
88
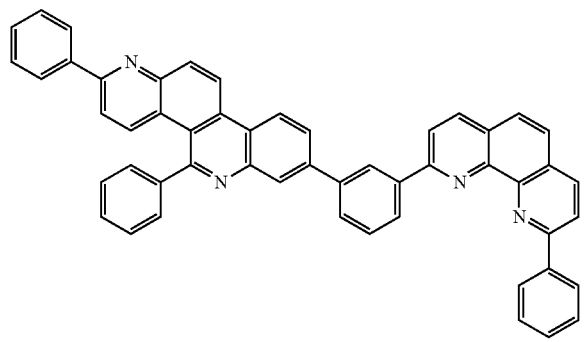
89
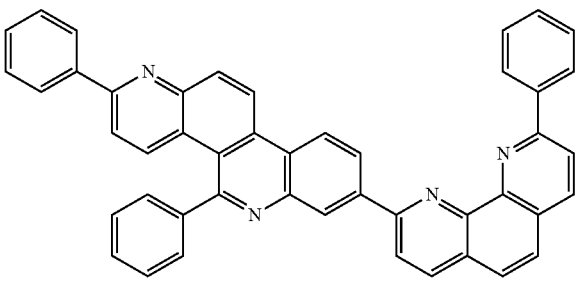
90
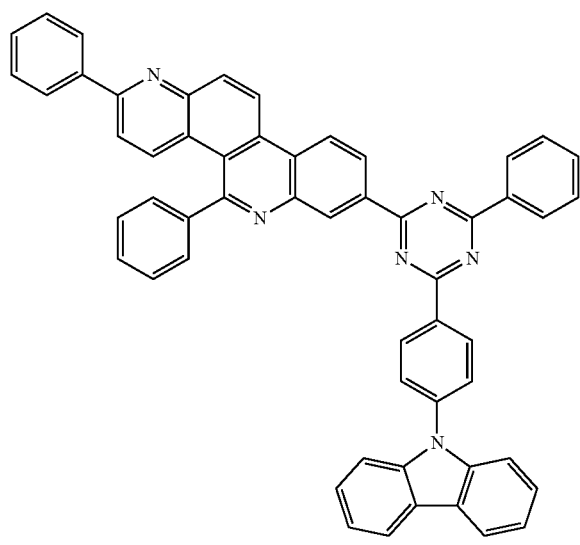
91
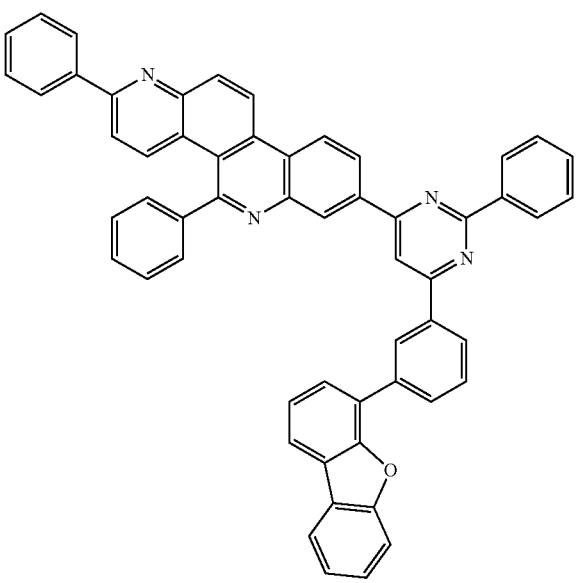

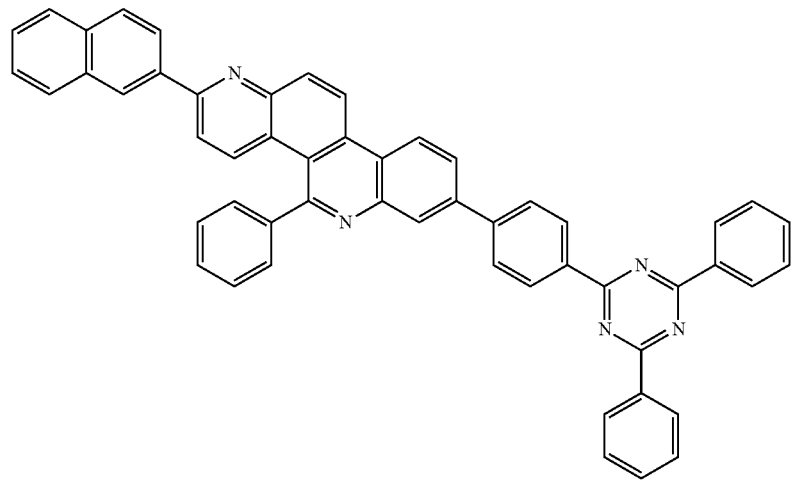
92
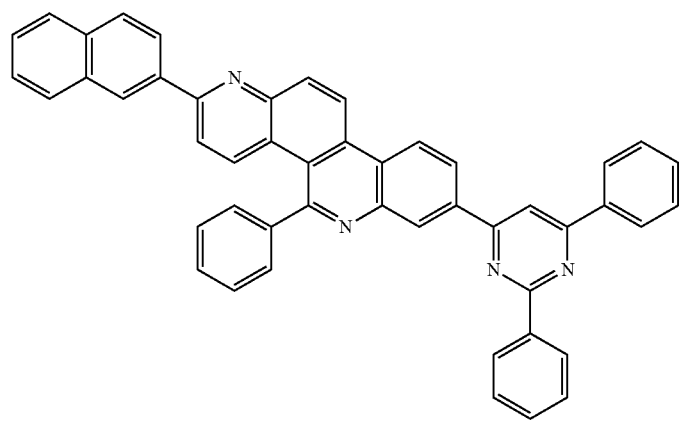
93
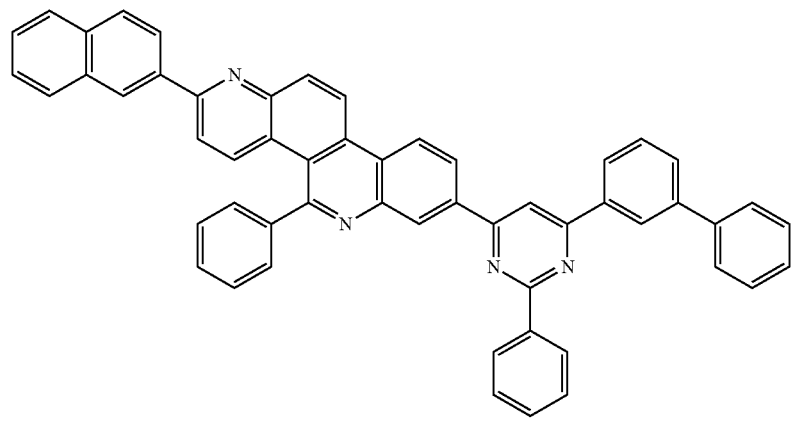
94

95
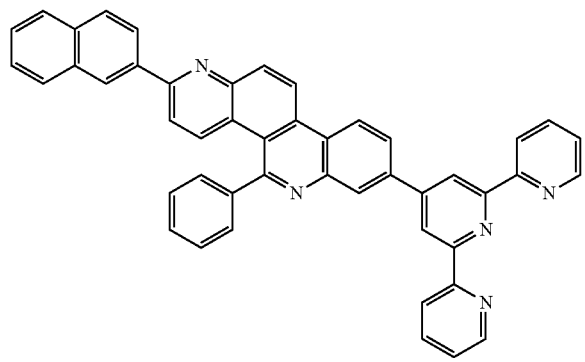
96
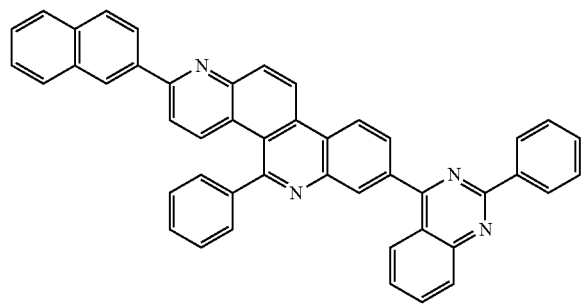
97
99
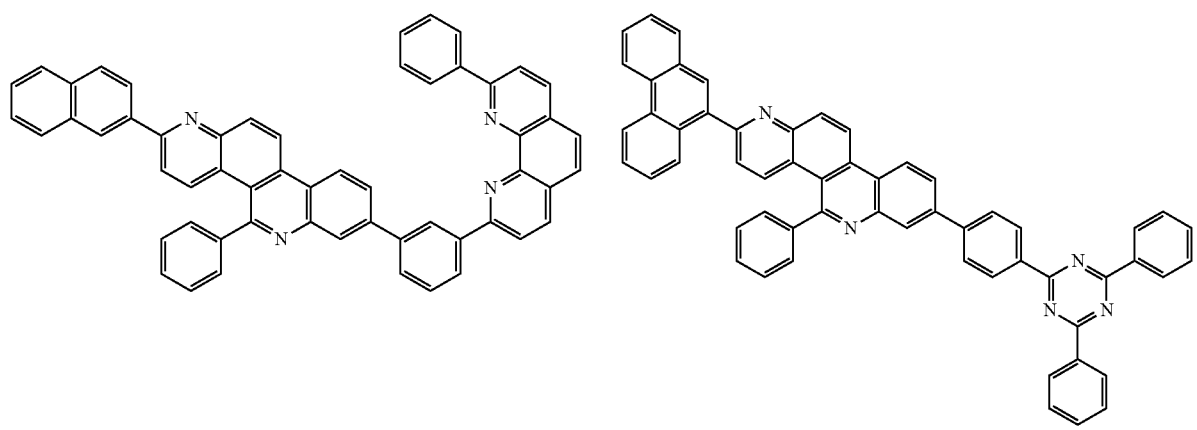
99
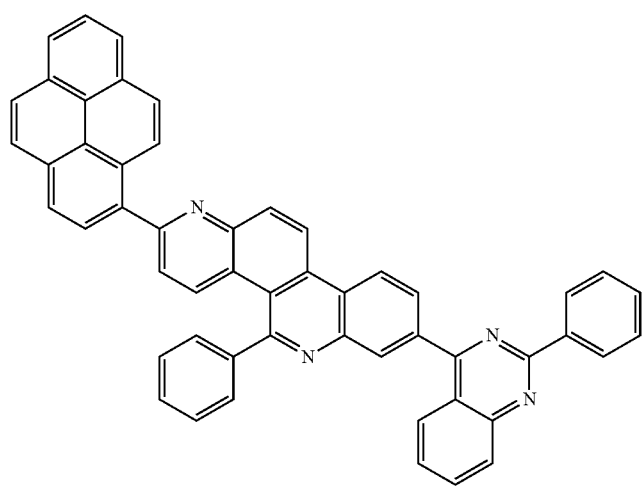

-continued
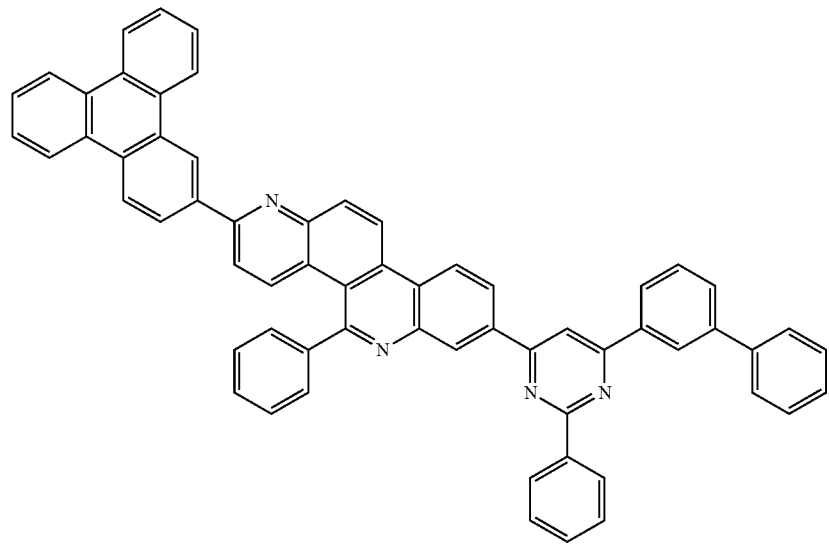
-continued
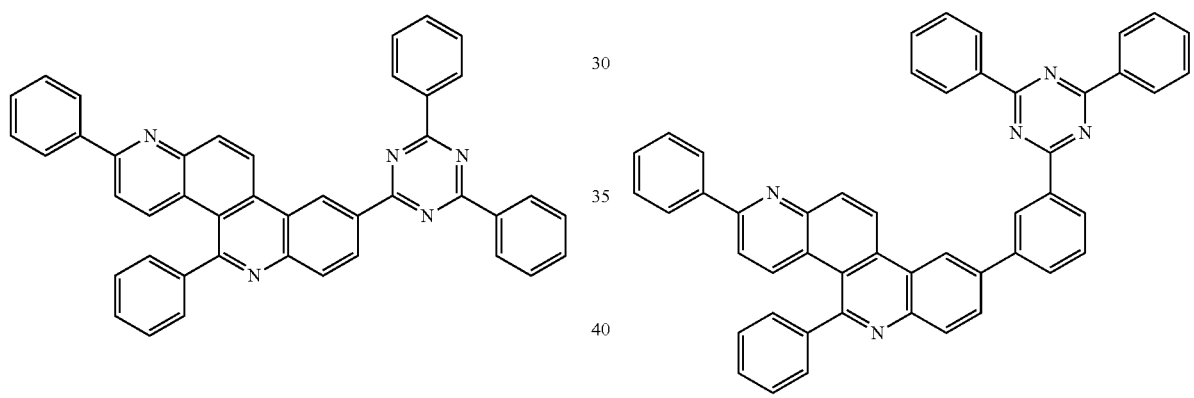
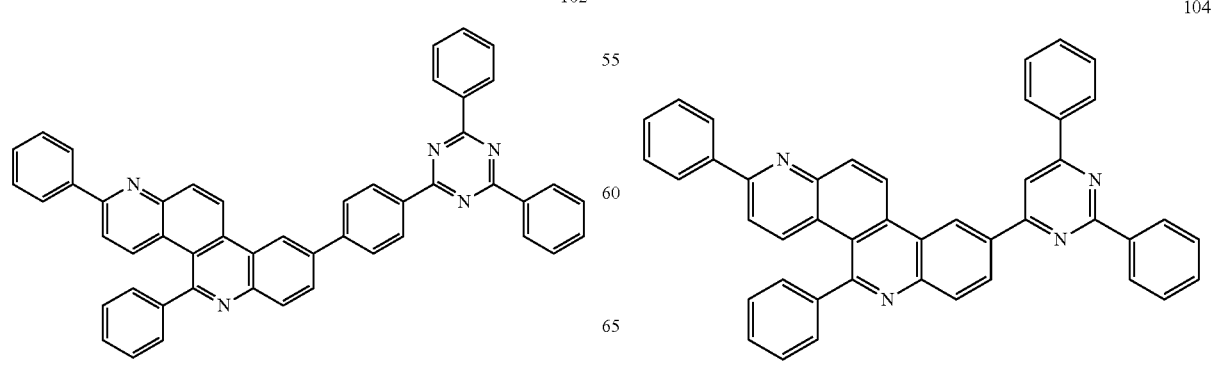

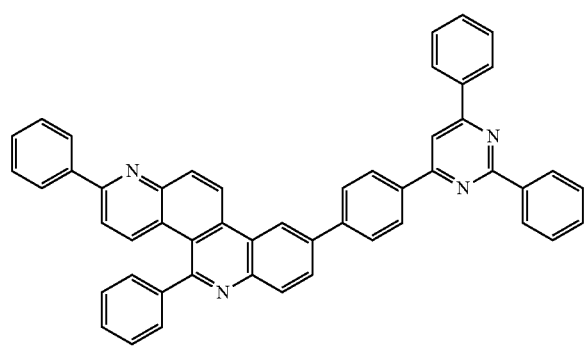
105
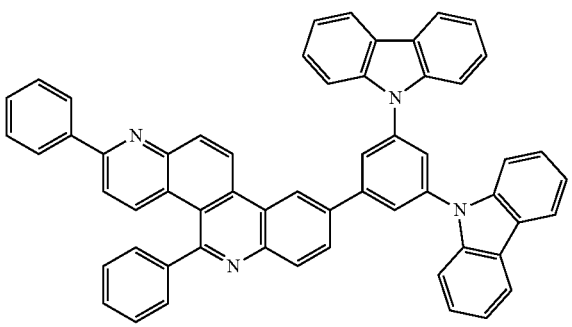
109
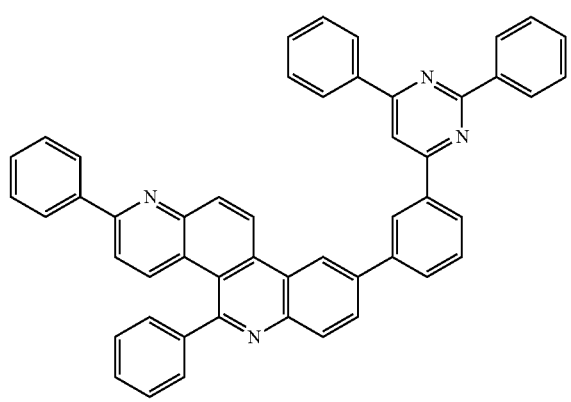
106
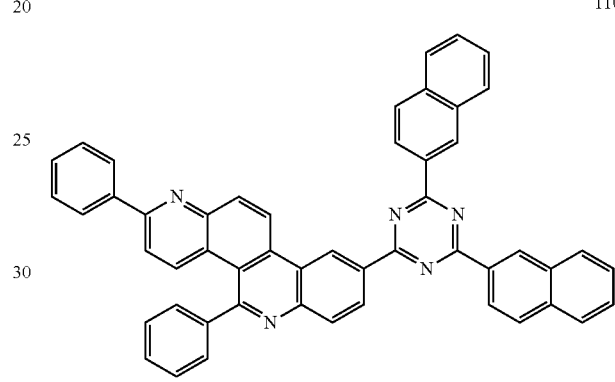
110
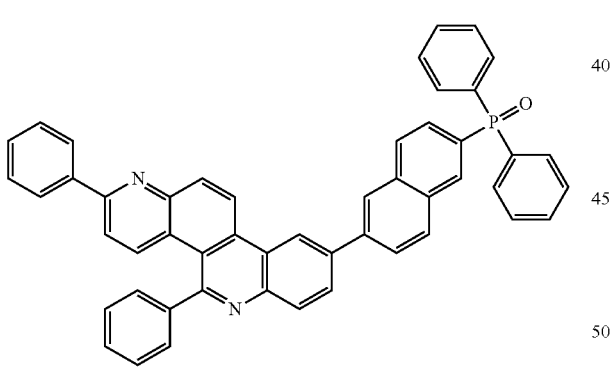
107
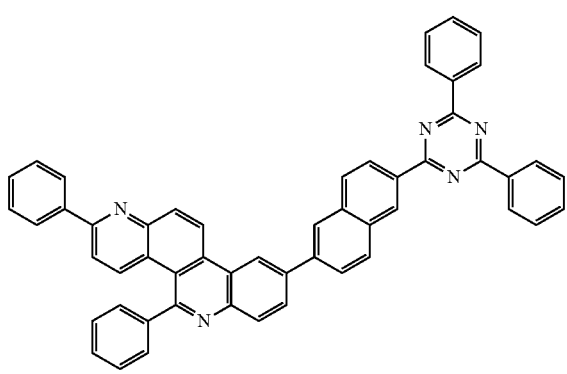
111
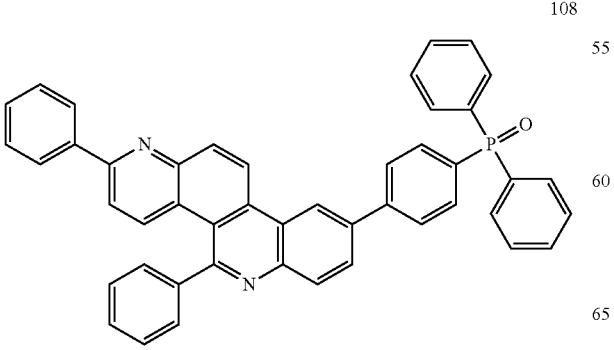
108
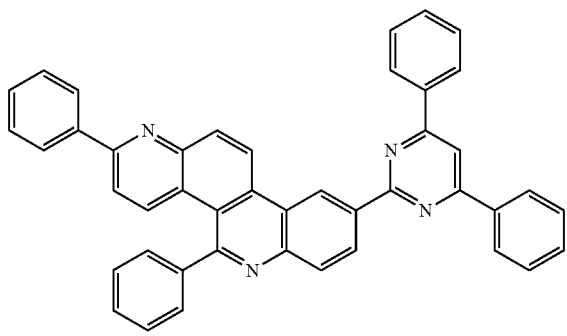
112

113
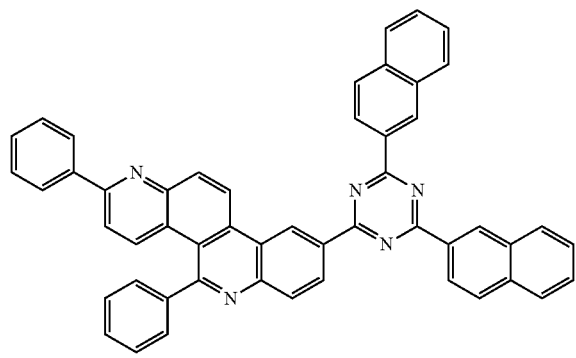
114
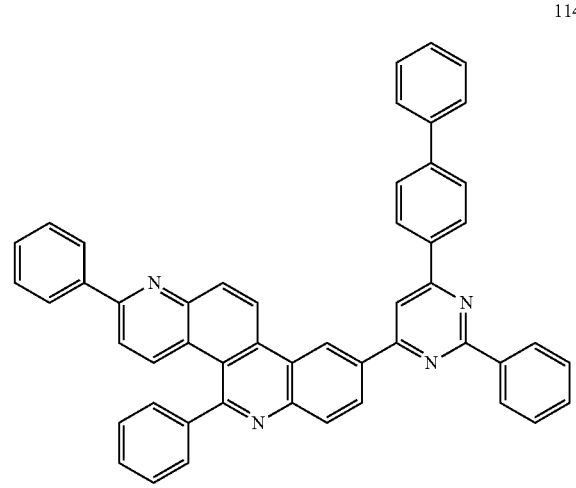
115
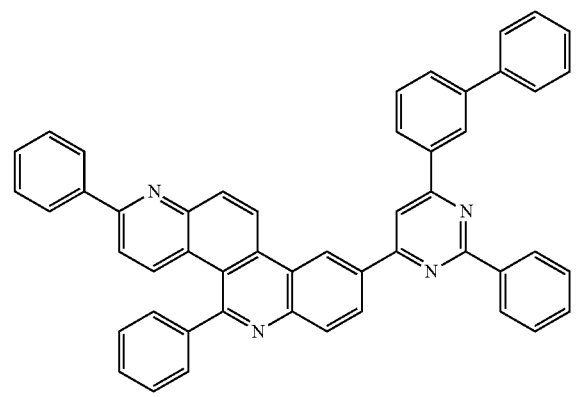
116
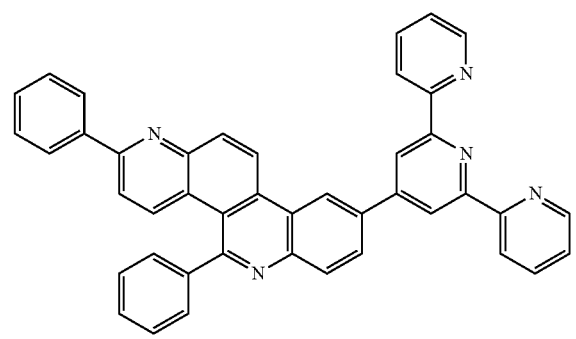
117
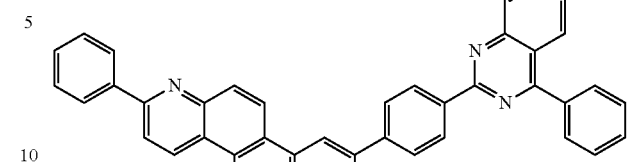
118
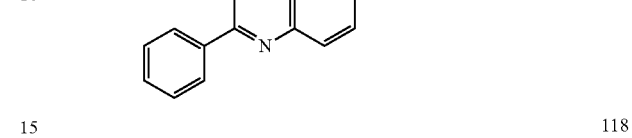
119
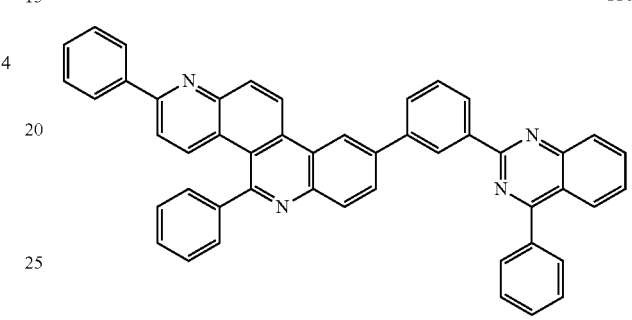
120
121
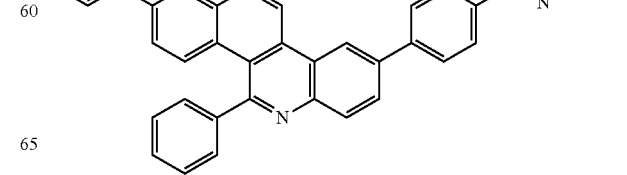

122
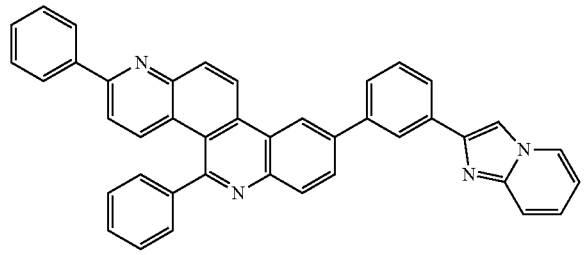
123
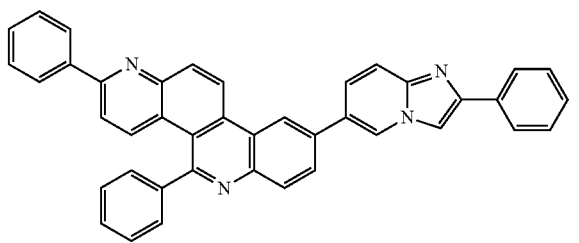
124
125
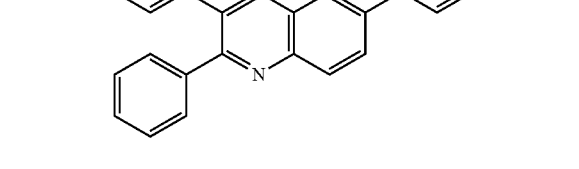
126
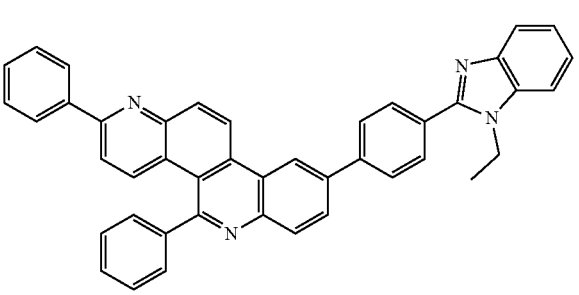
127
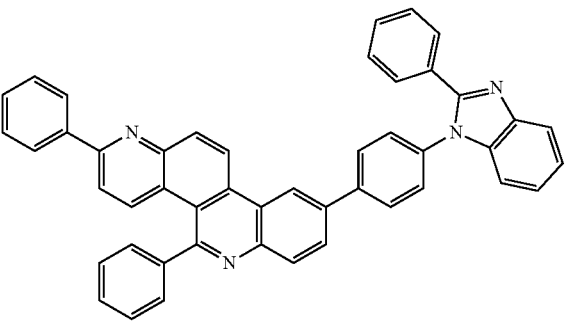
128
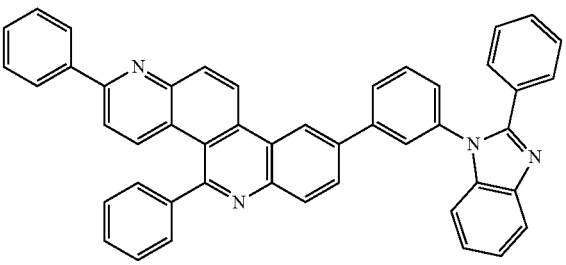
129
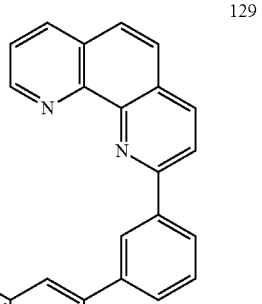
130
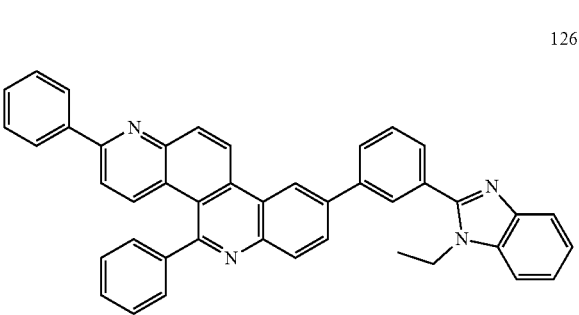

261
-continued
131
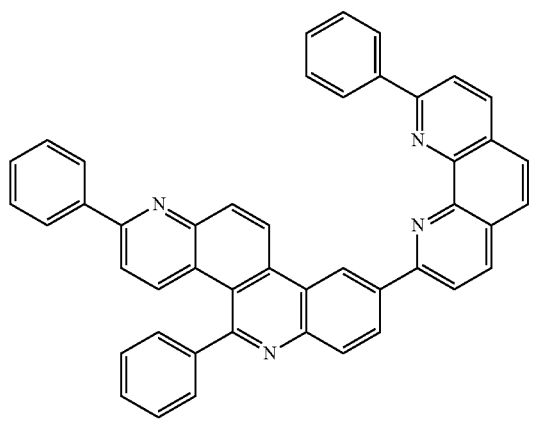
132
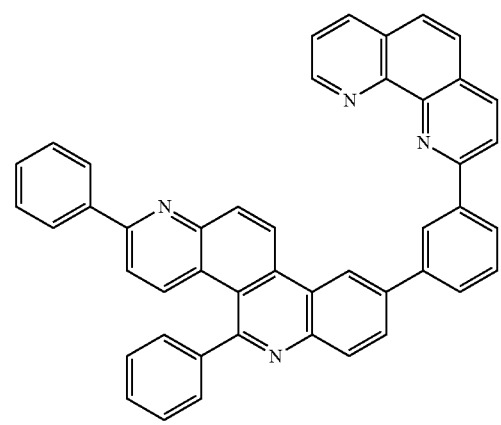
133
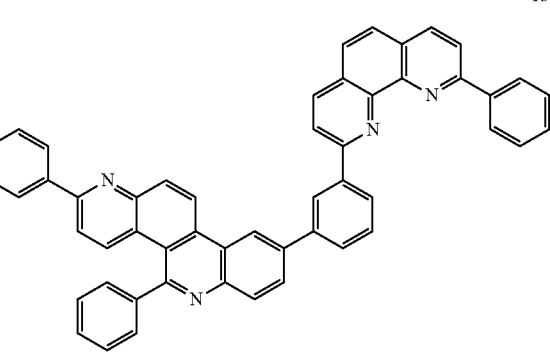
134
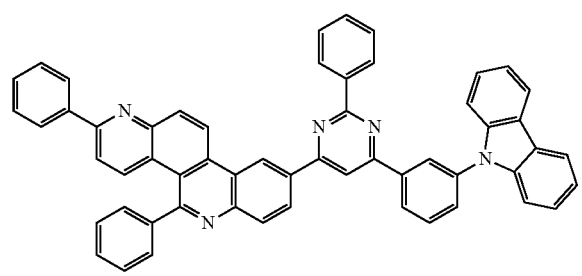
262
-continued
135
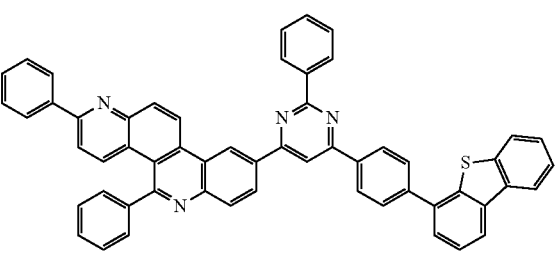
136
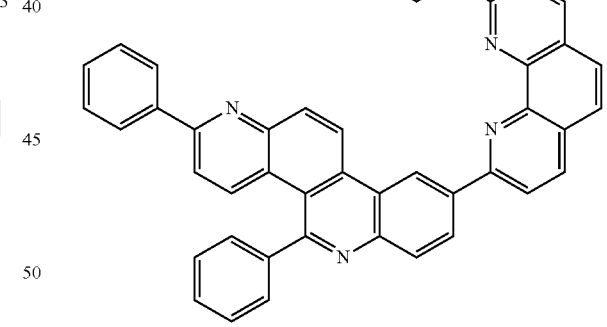
137
138
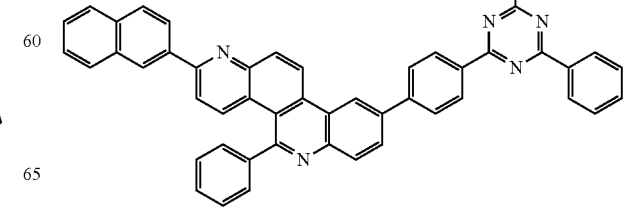

139
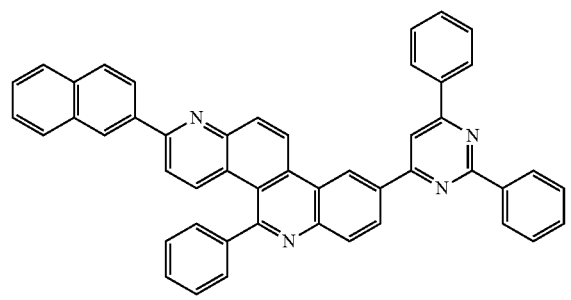
140
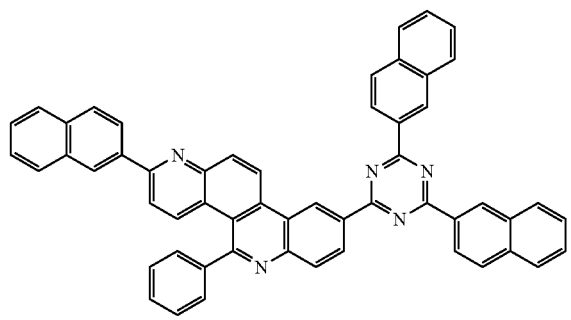
141
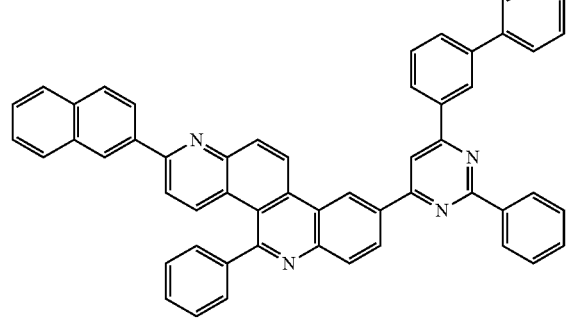
142
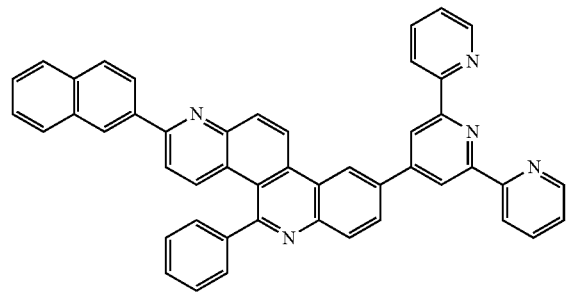
143
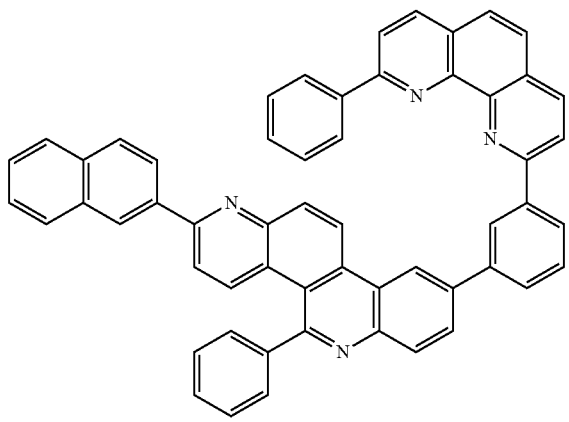
144
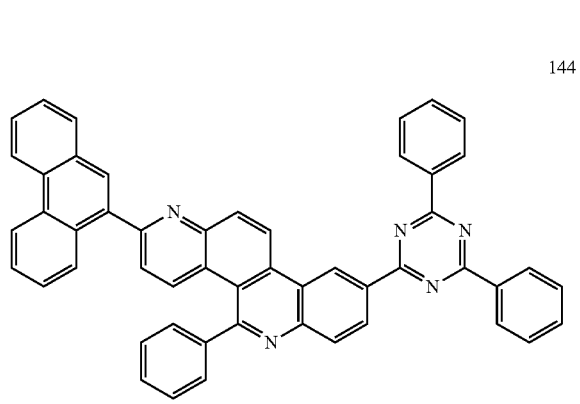
145
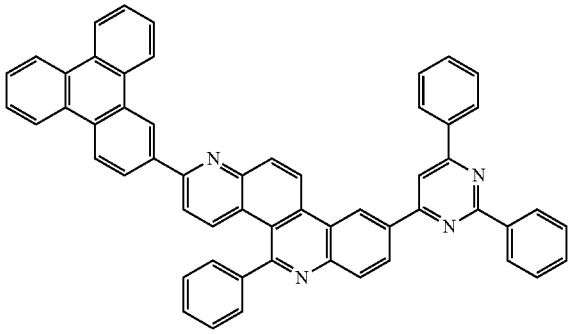
146
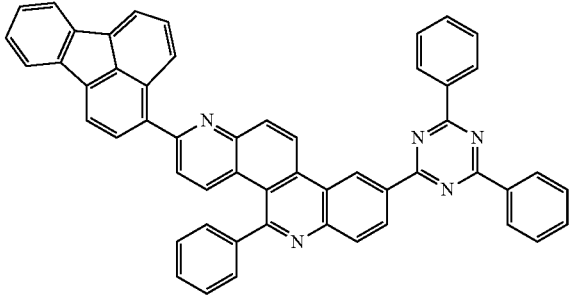

147
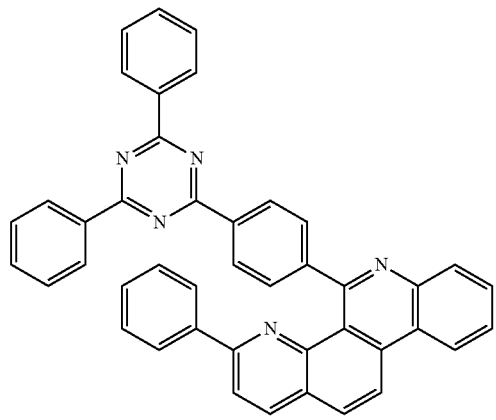
148
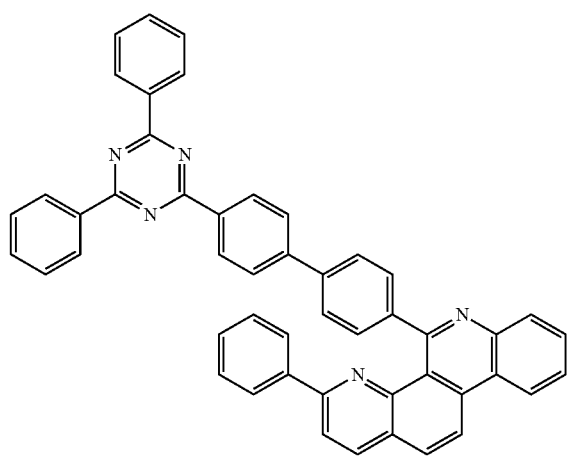
149
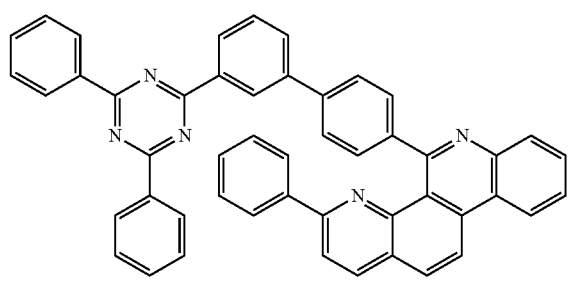
150
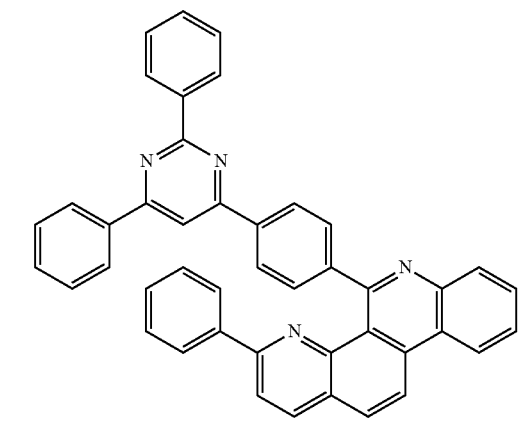
151
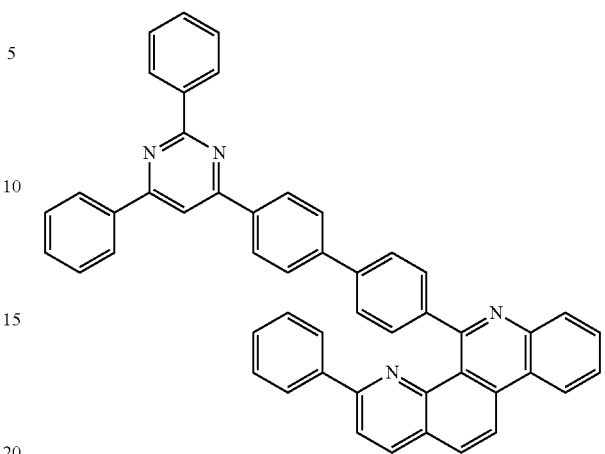
152
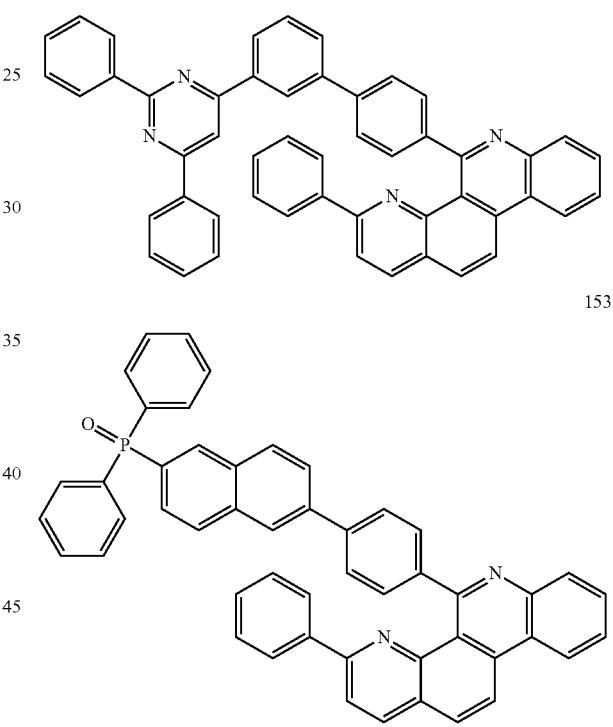
153
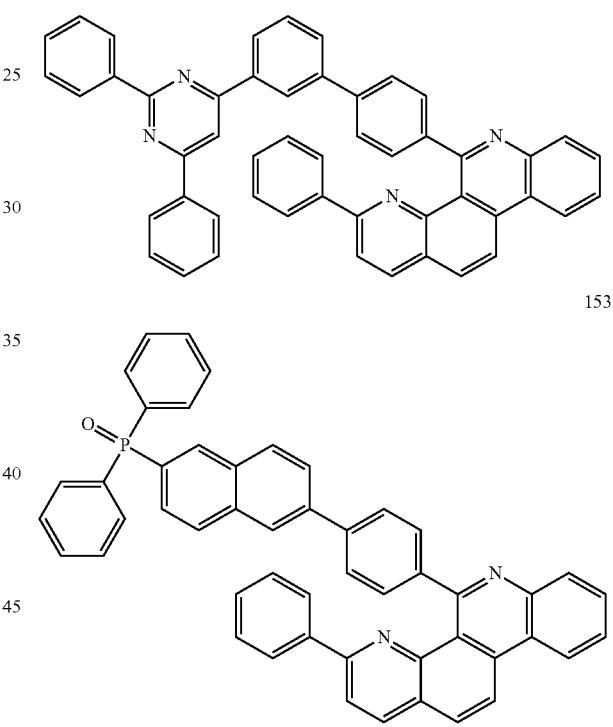
154
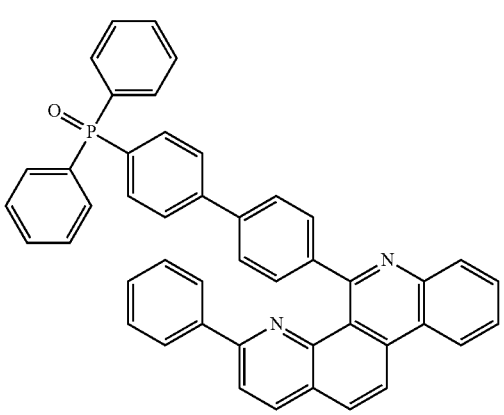

267
-continued
155
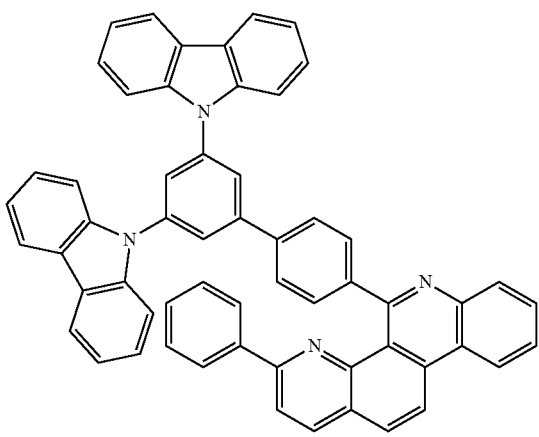
156
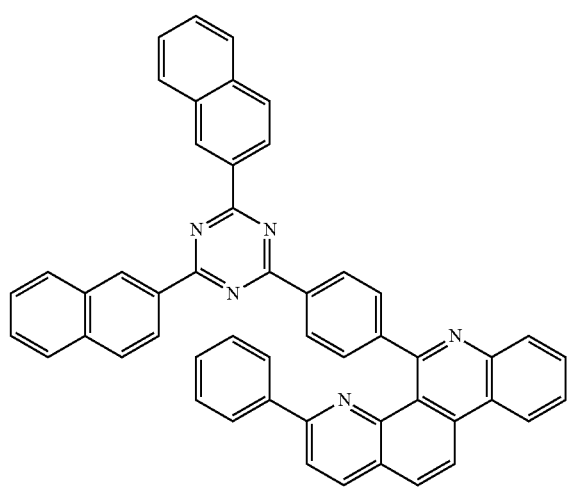
157
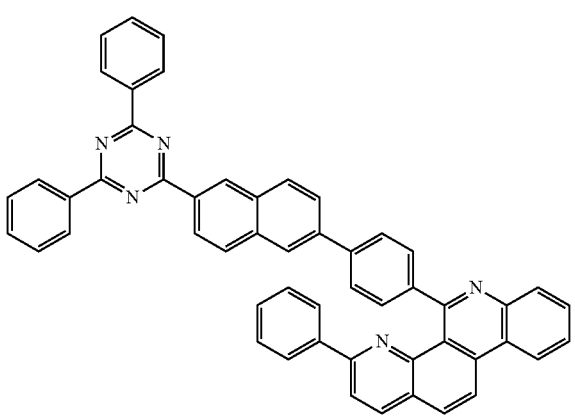
268
-continued
158
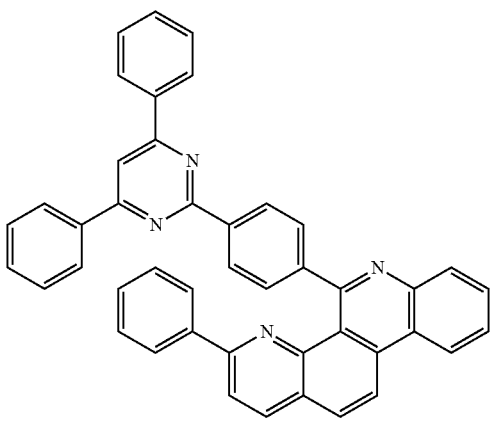
159
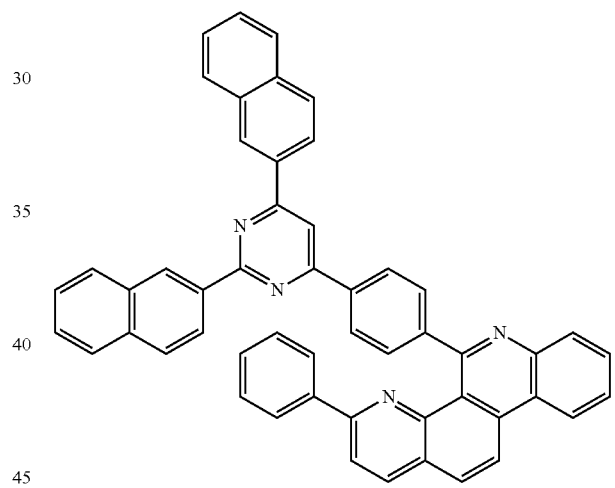
160
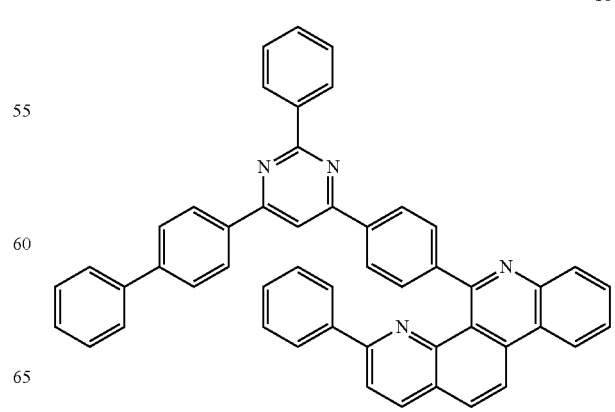

161
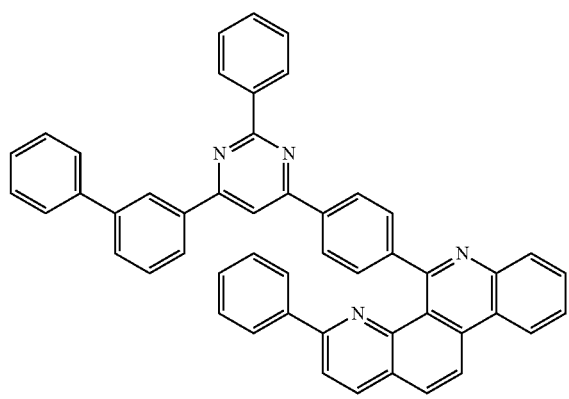
162
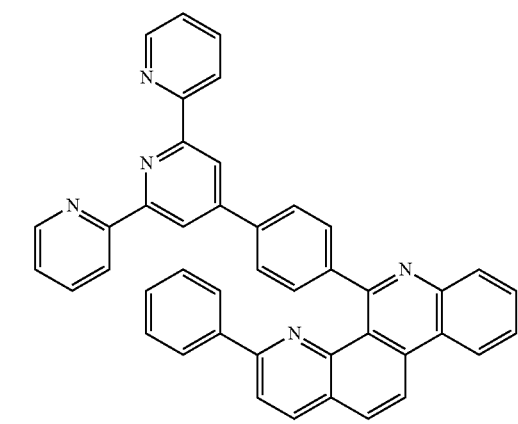
163
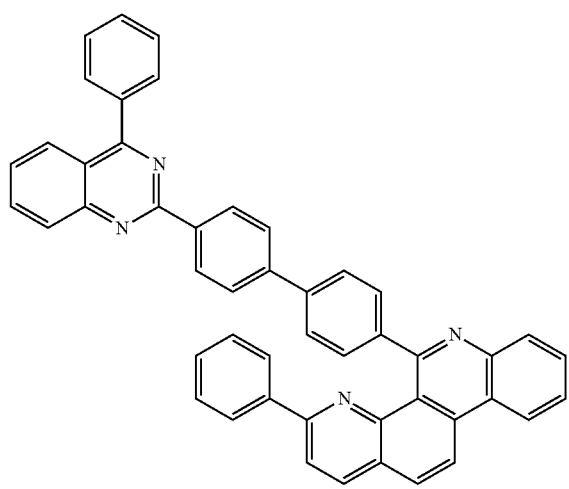
164
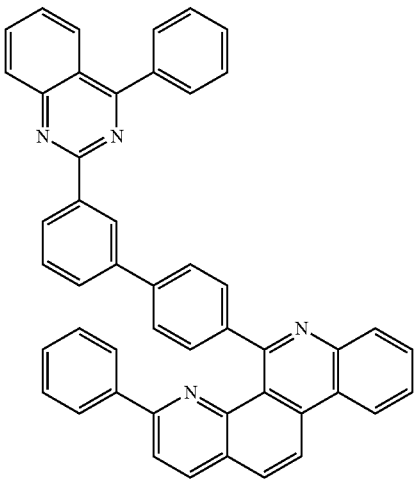
165
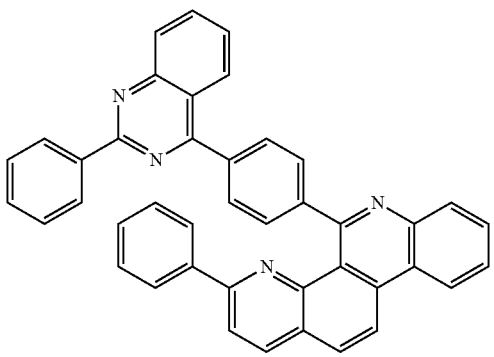
166

167
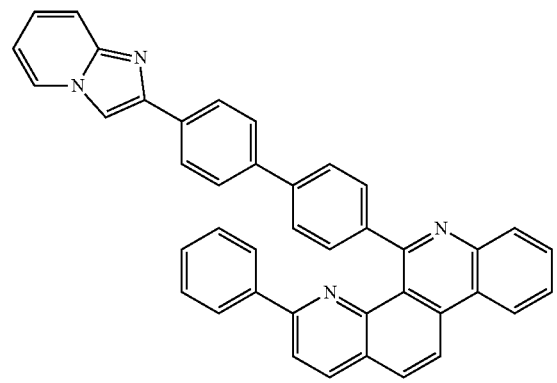
168
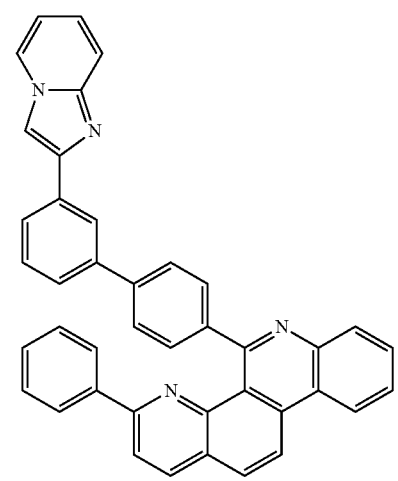
169
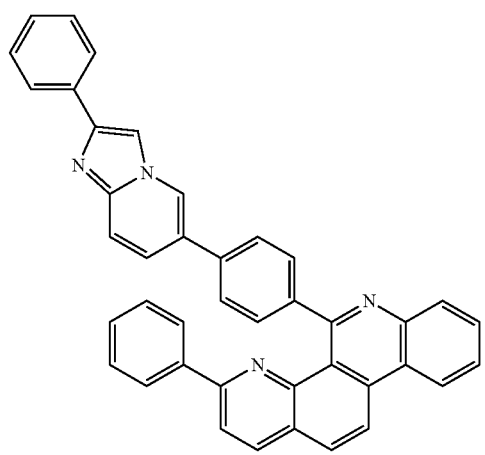
170
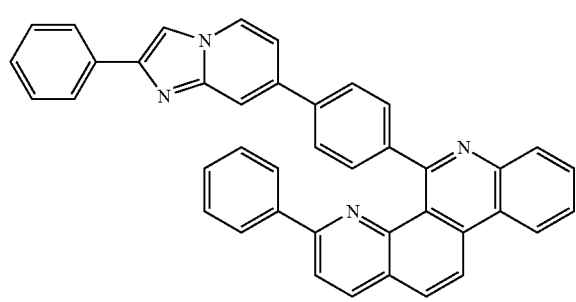
171
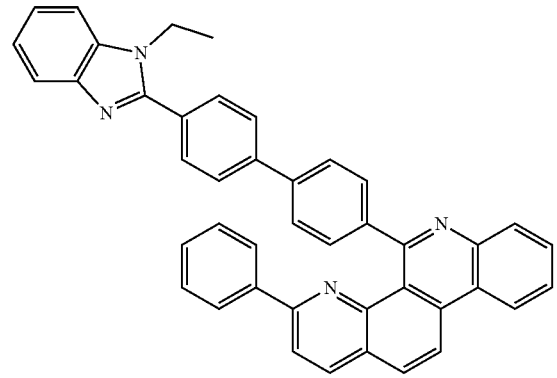
172
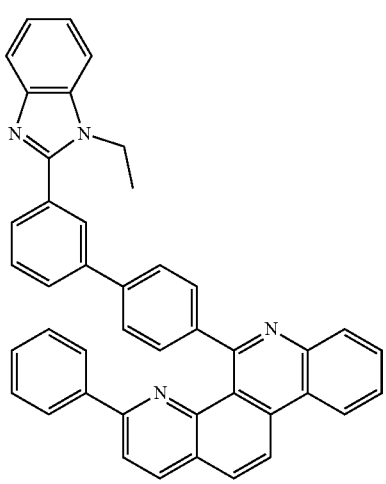
173
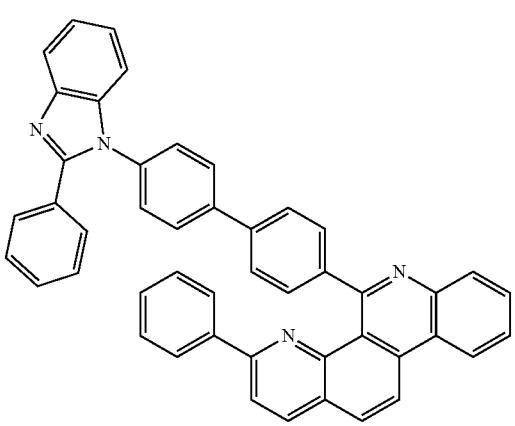

174
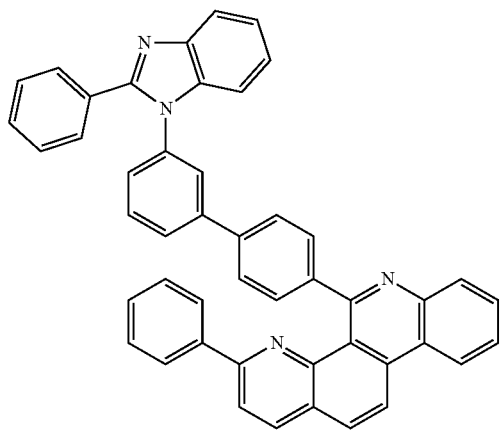
175
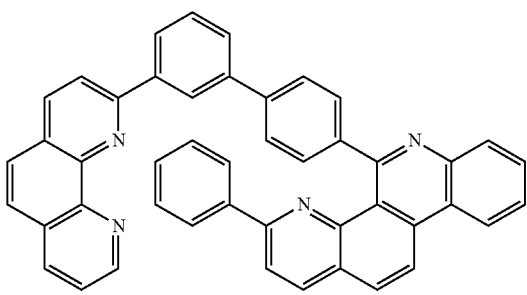
176
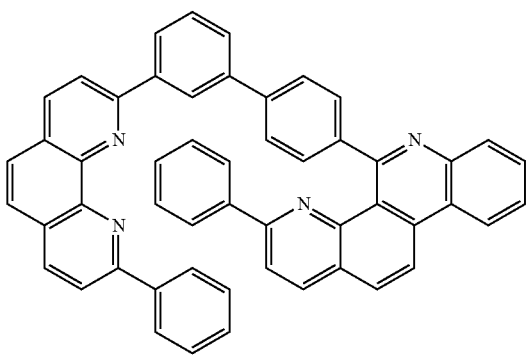
177
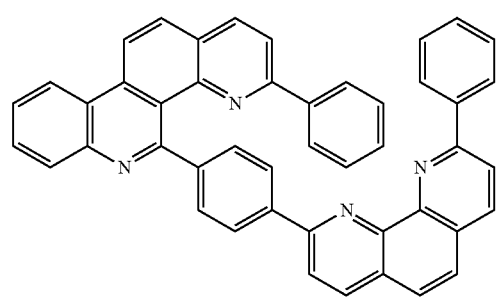
178
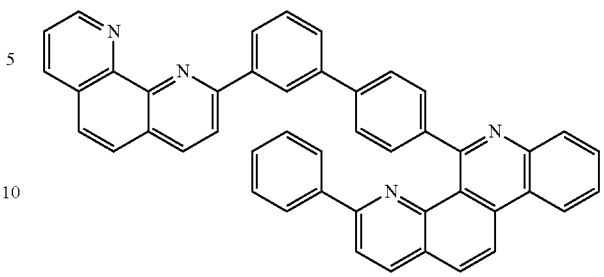
179
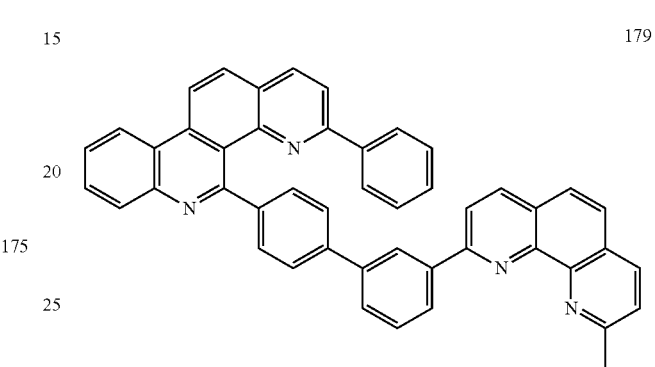
180
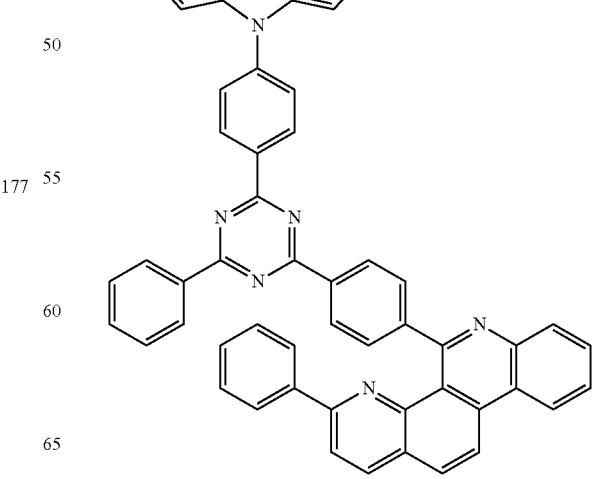
181

275
-continued
182
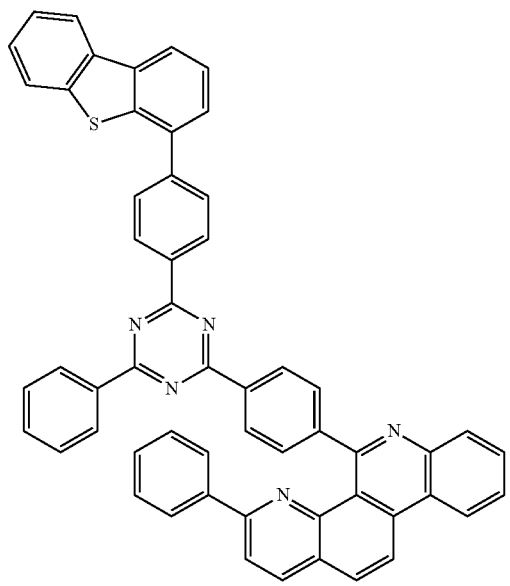
183
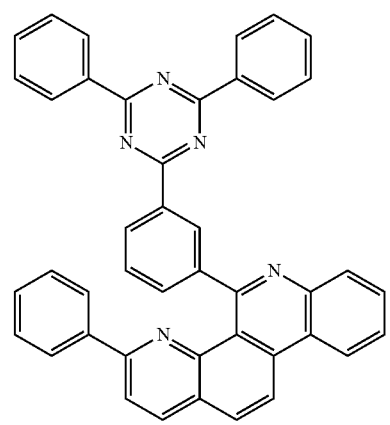
184
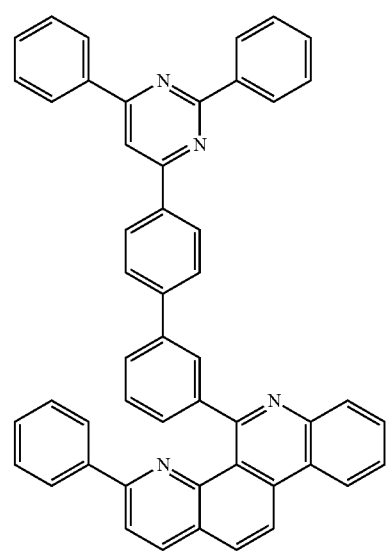
276
-continued
185
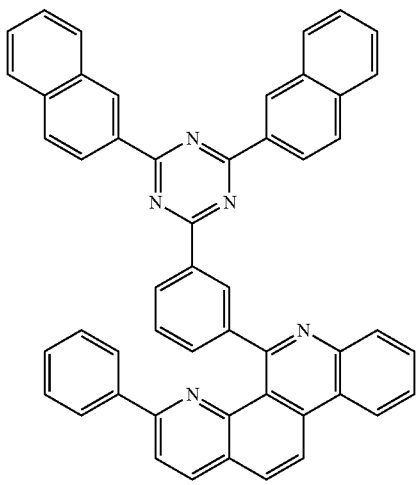
186
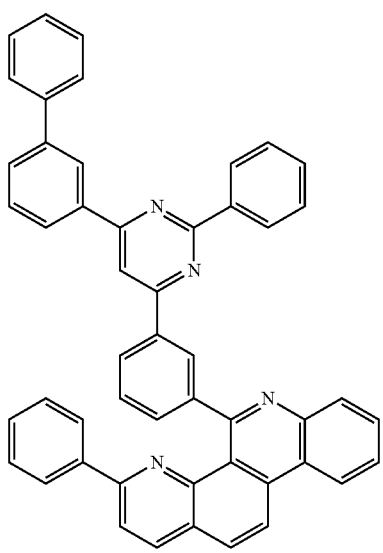
187
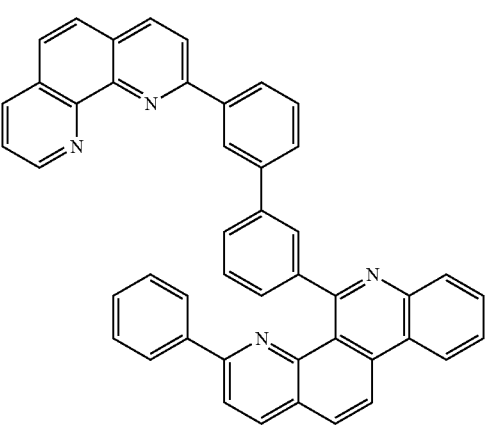

188
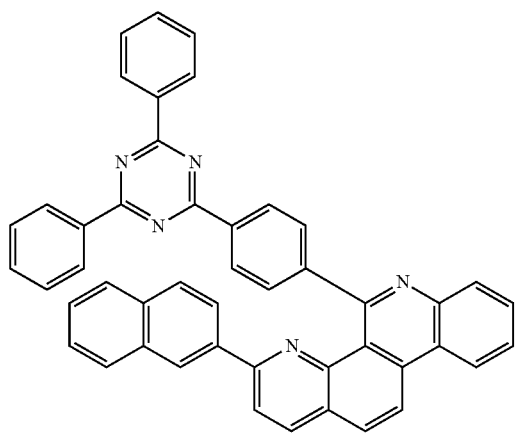
189
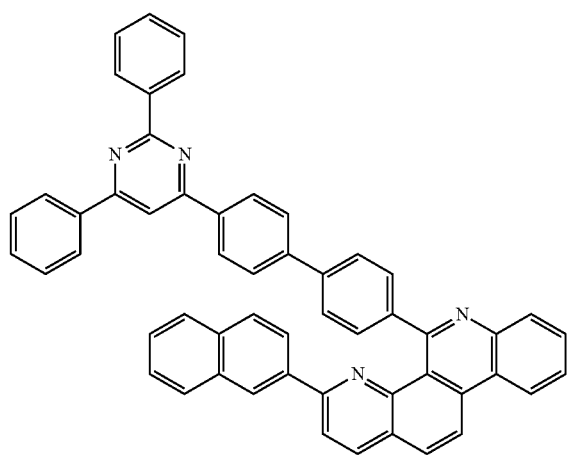
192
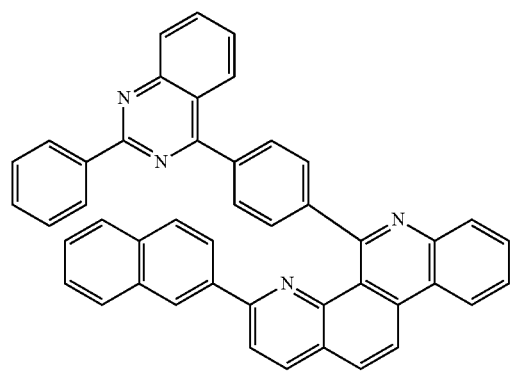
190
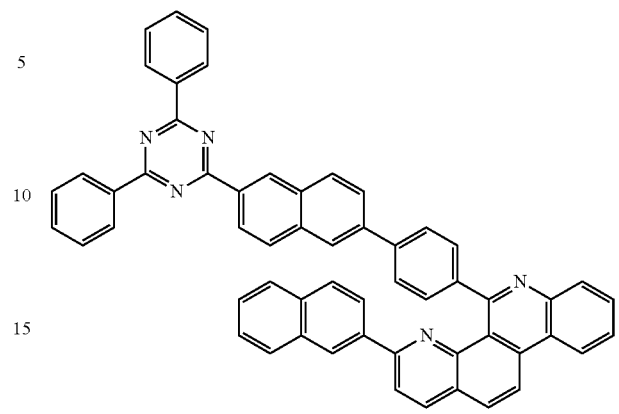
191
193
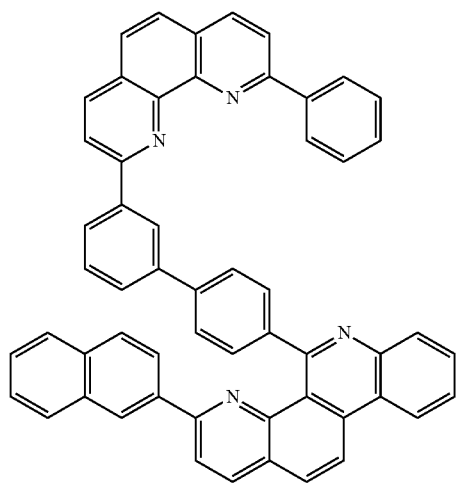

-continued
194
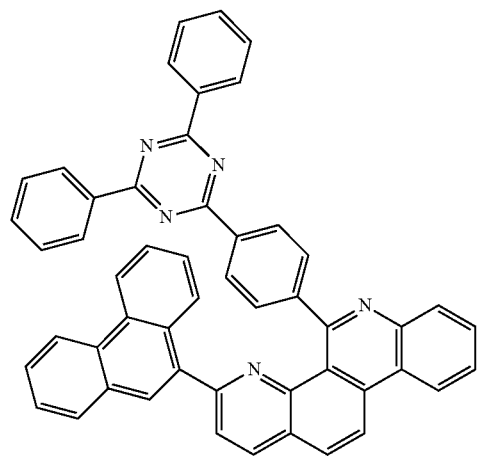
195
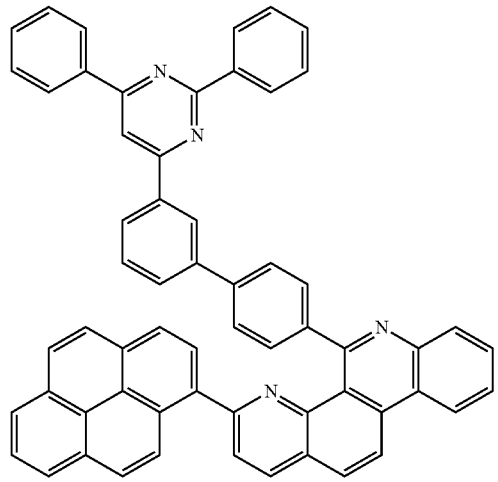
196
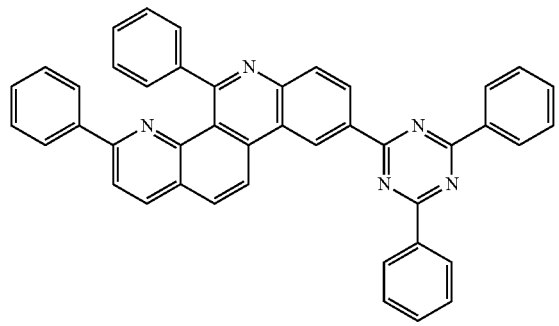
197
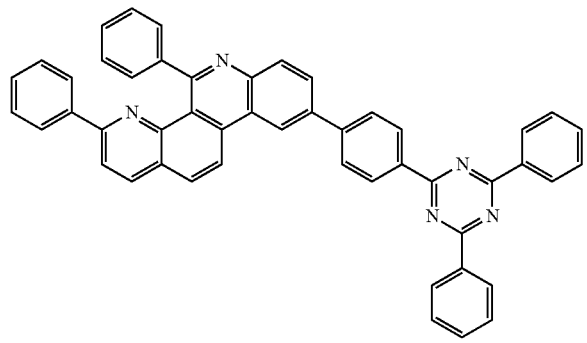
198
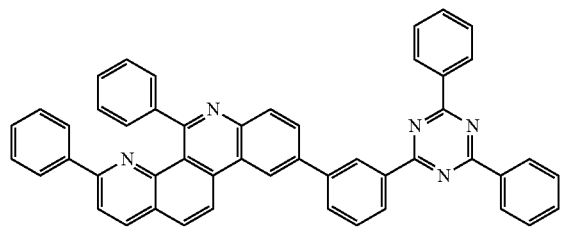
199
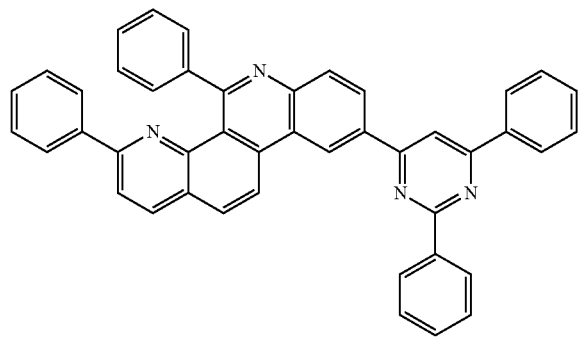
200
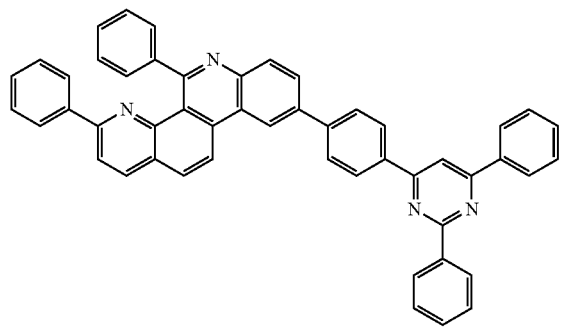
201
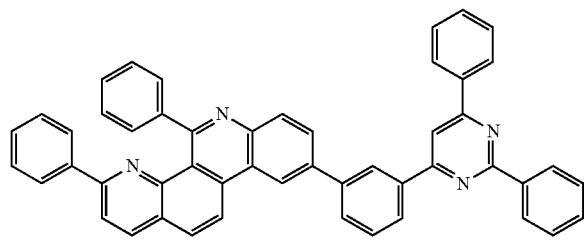

-continued
202
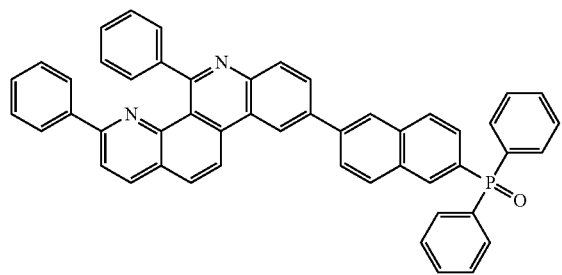
203
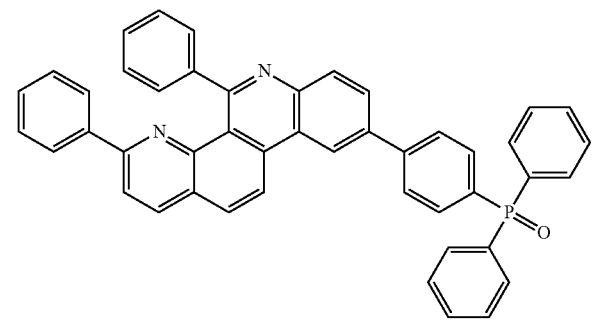
204
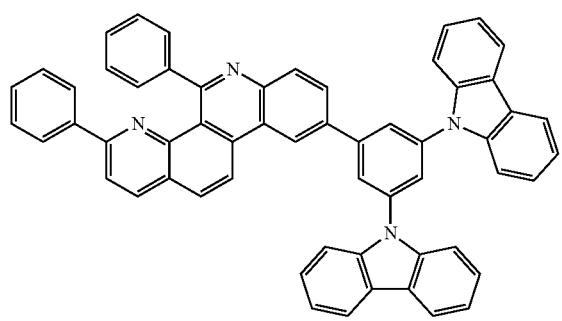
205
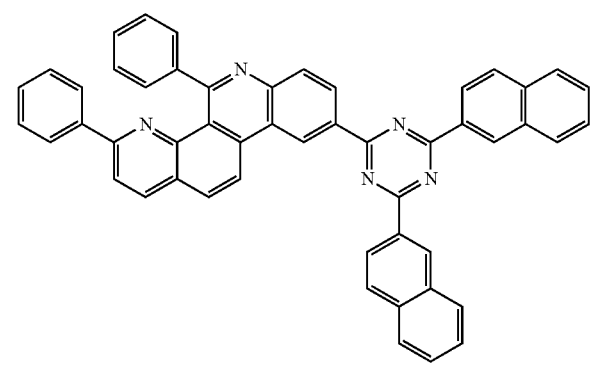
206
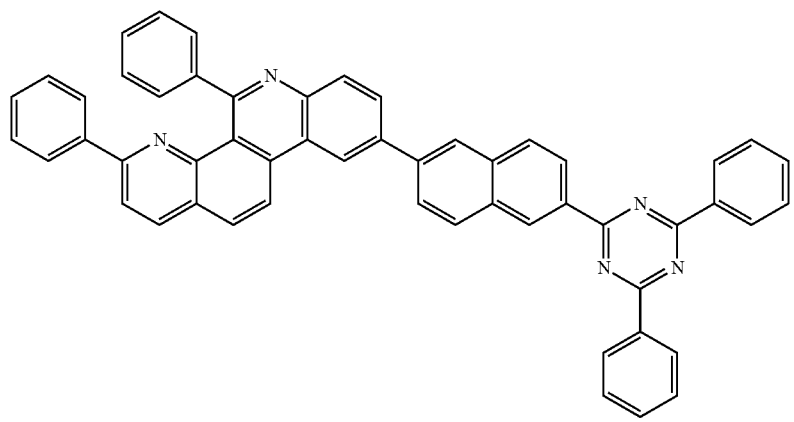
207
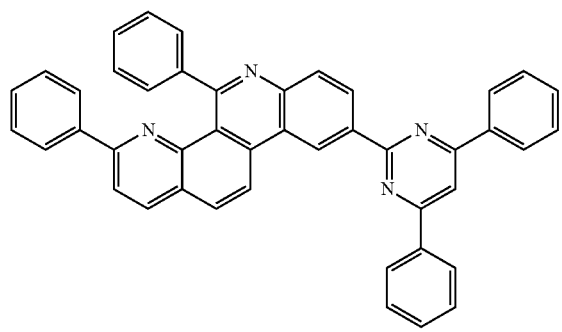
208
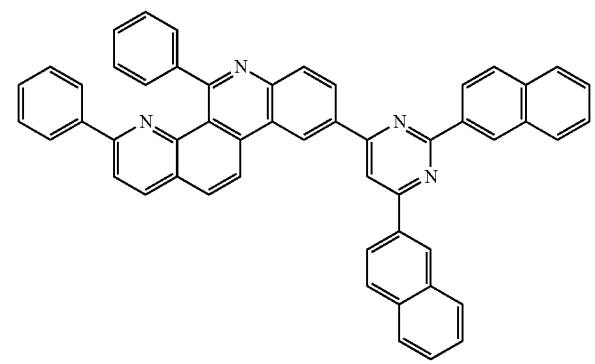

-continued
209
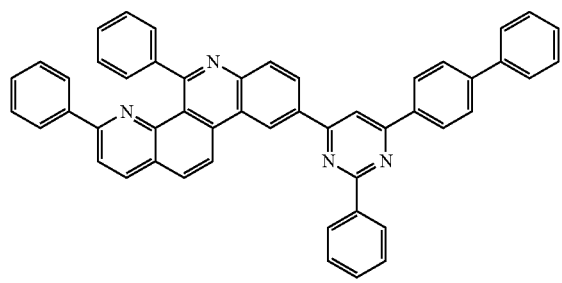
210
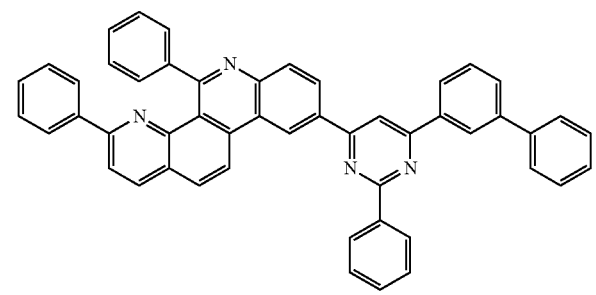
211
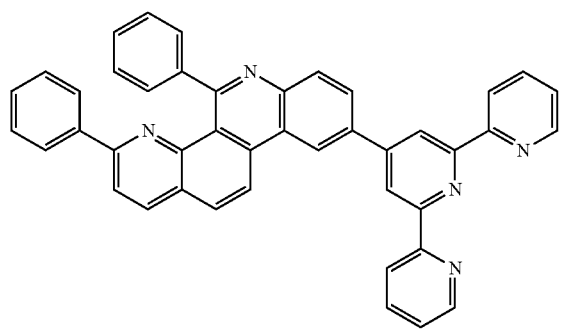
212
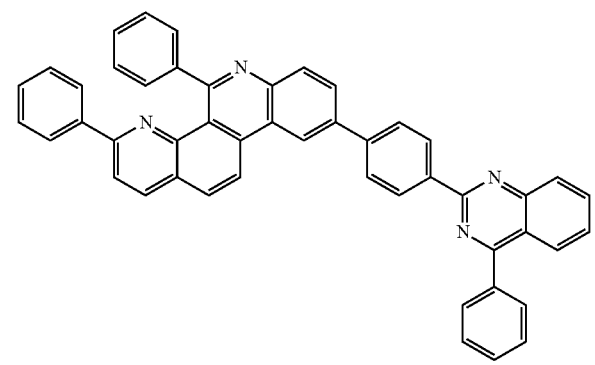
213
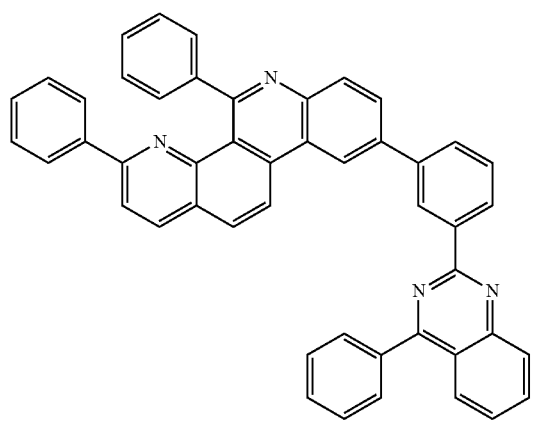
214
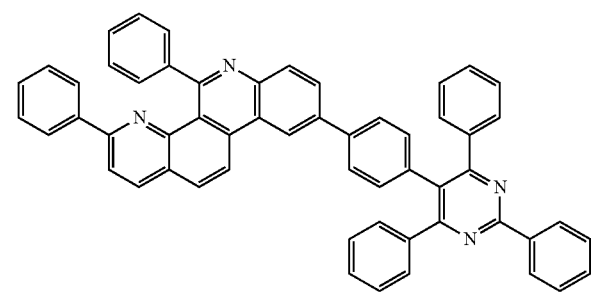
215
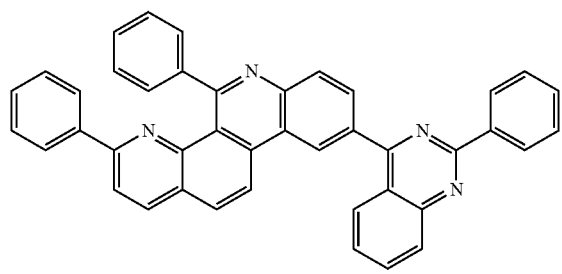
216
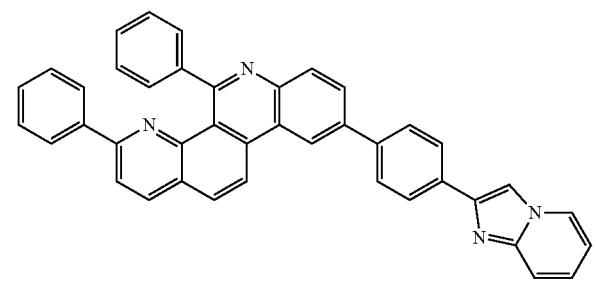

-continued
217
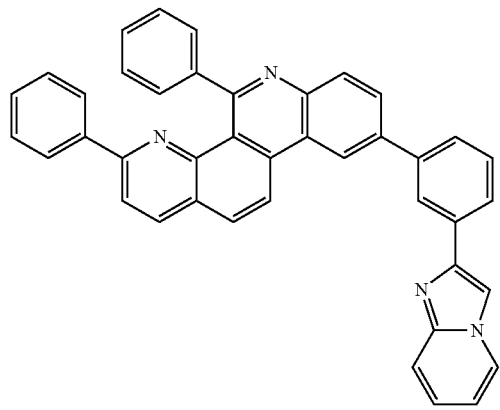
218
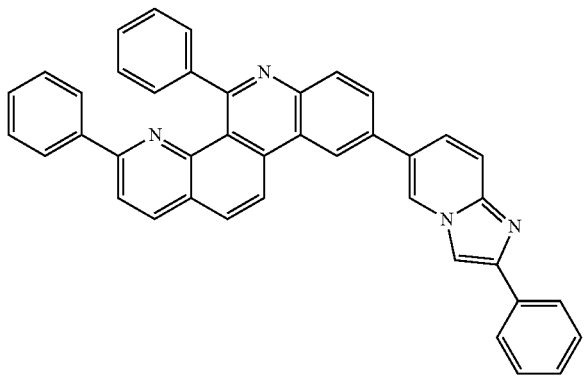
219
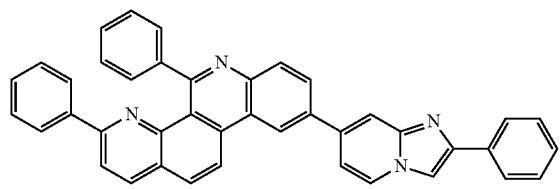
220
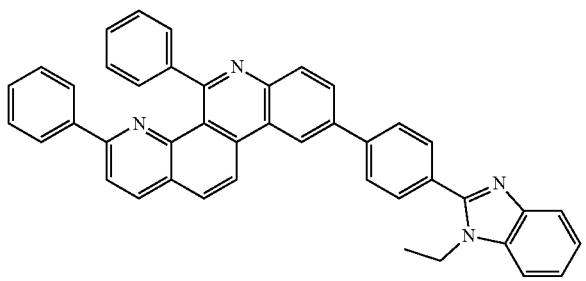
221
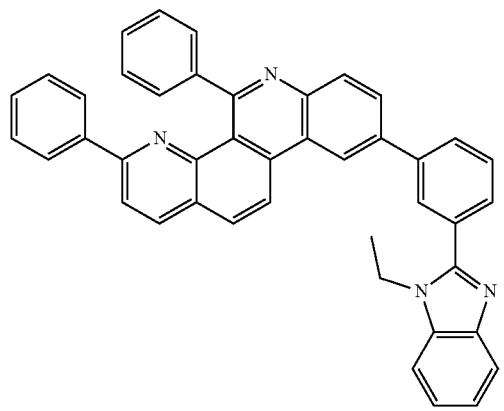
222
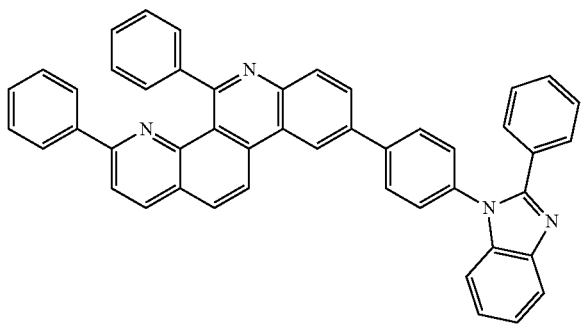
223
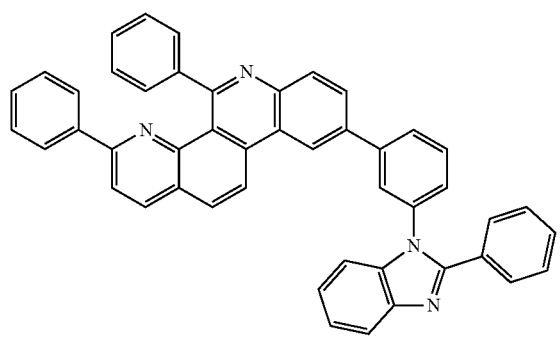
224
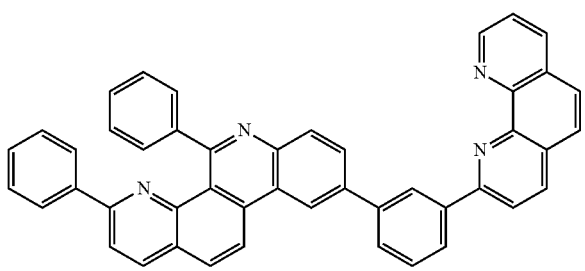

-continued
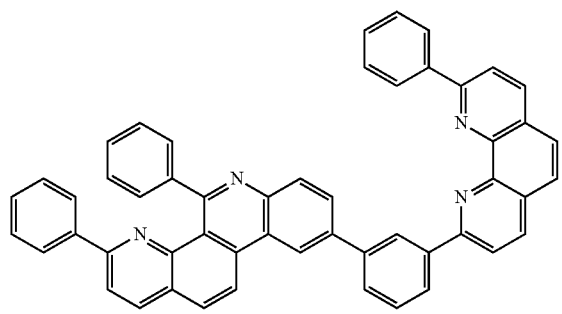
225
226
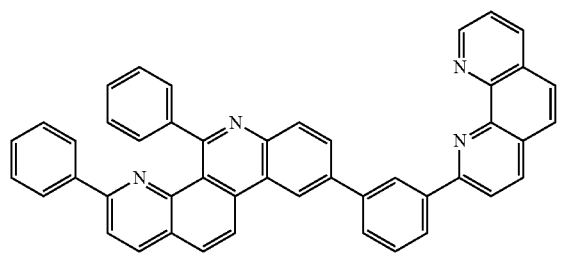
227
228
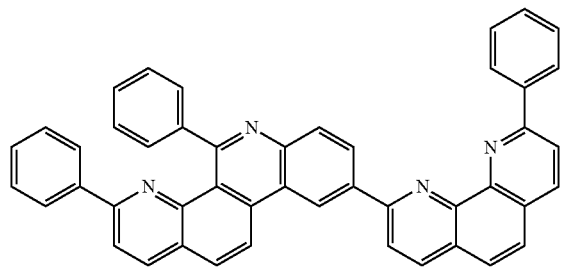
229
230
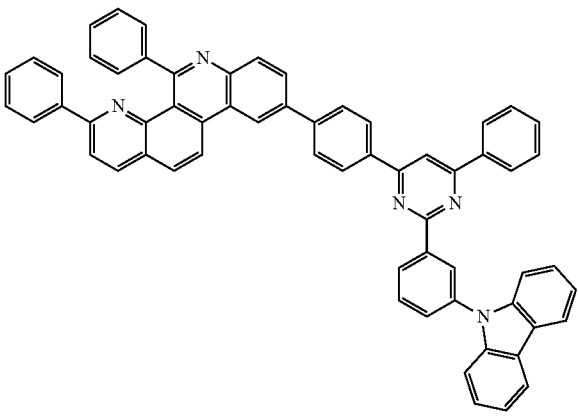
231
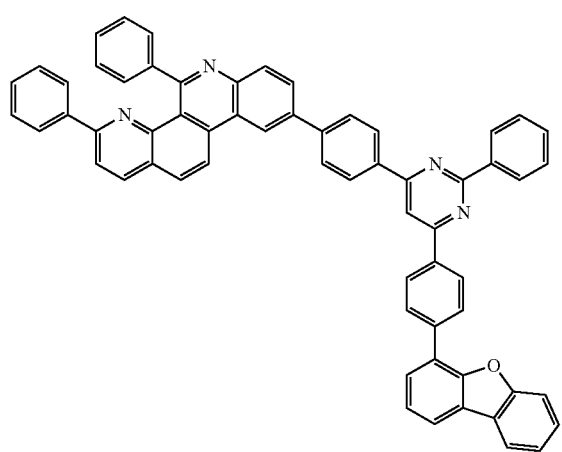

232
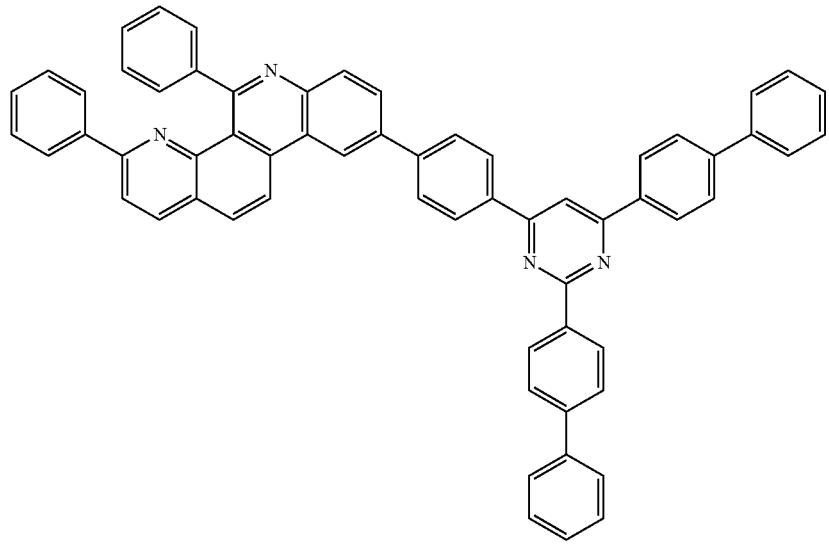
233
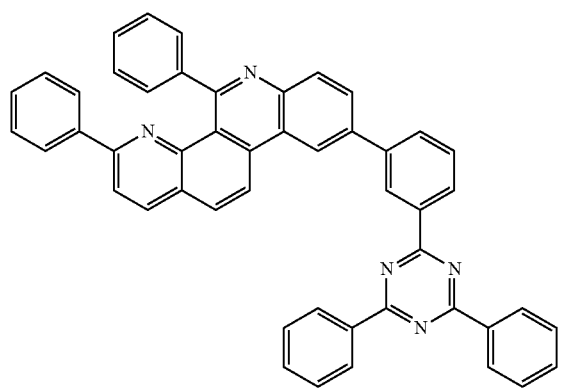
234
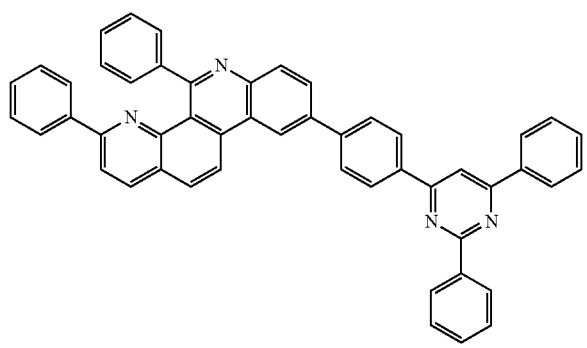
235
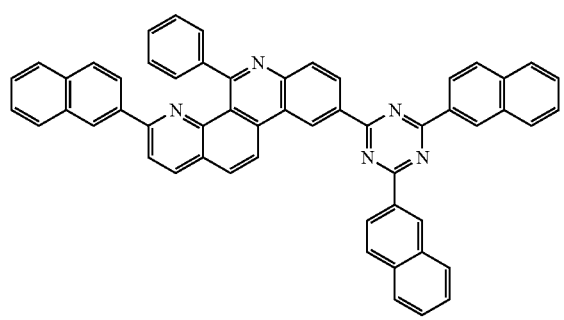
236
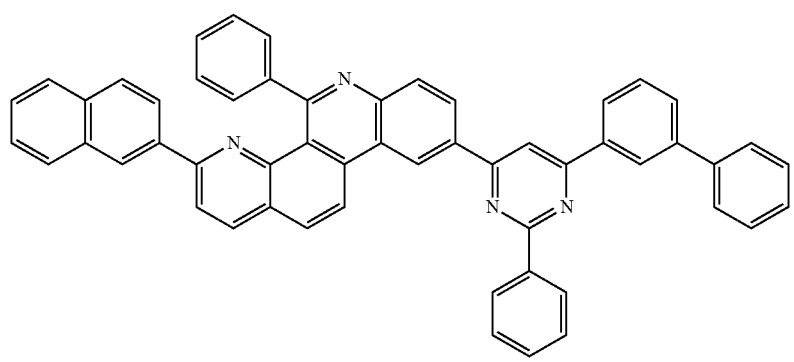

-continued
237
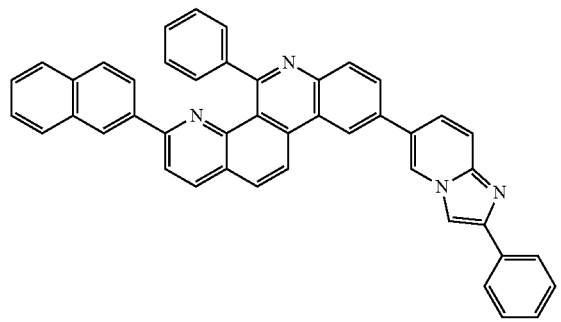
238
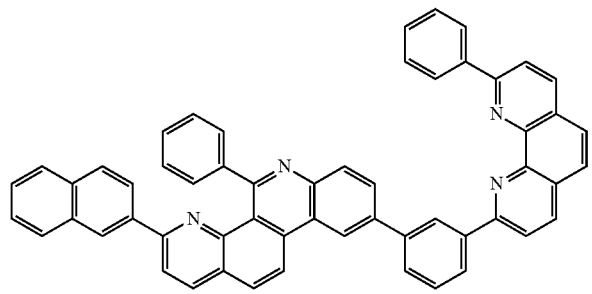
239
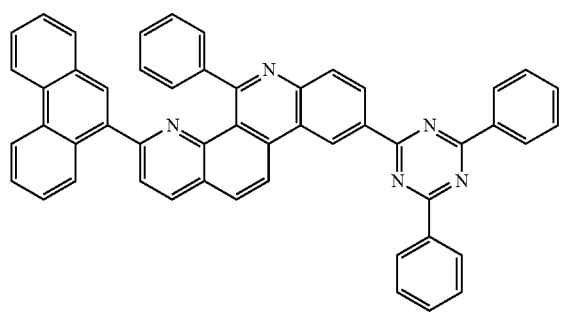
240
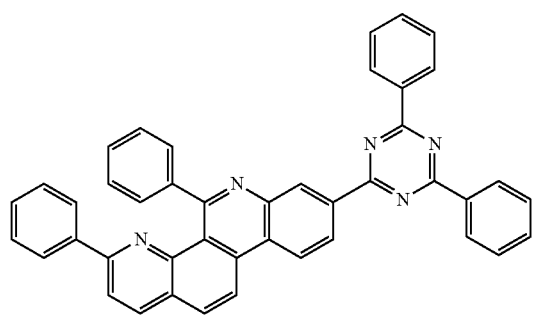
241
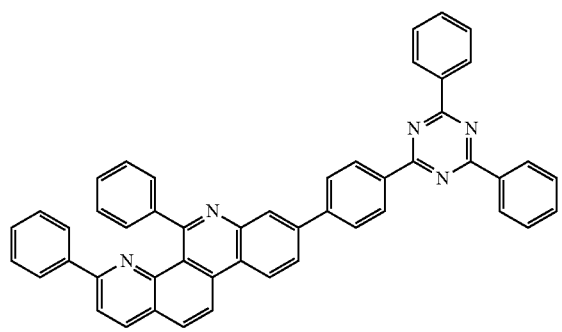
242
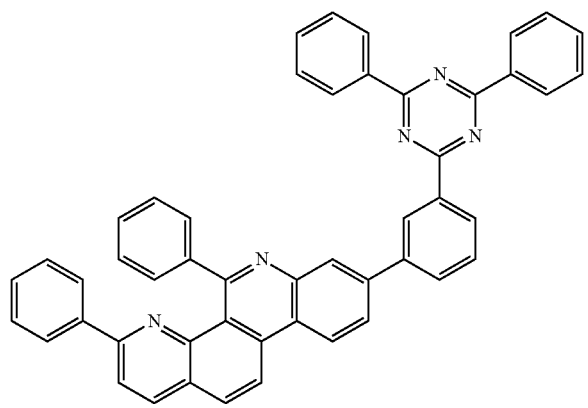
243
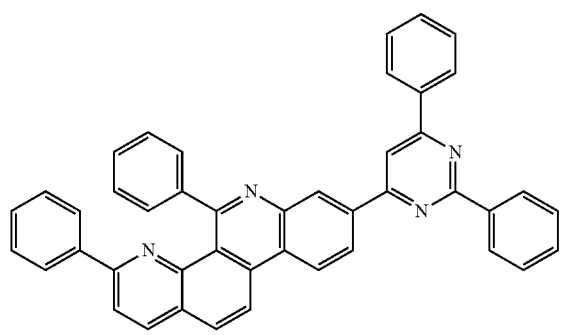
244
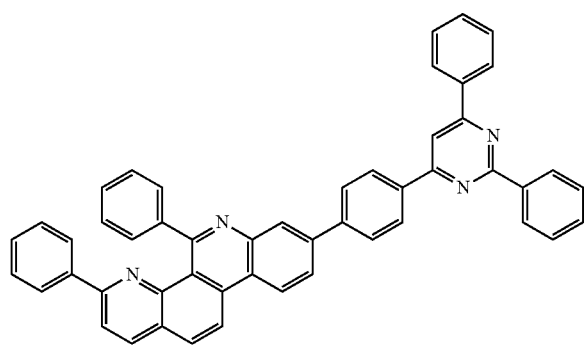

-continued
245
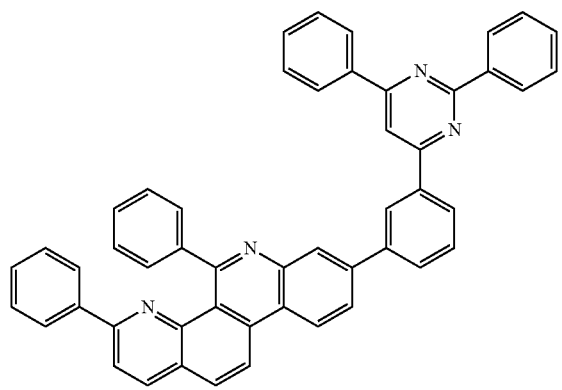
246
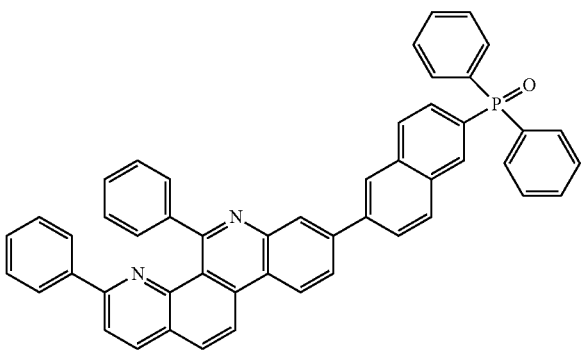
247
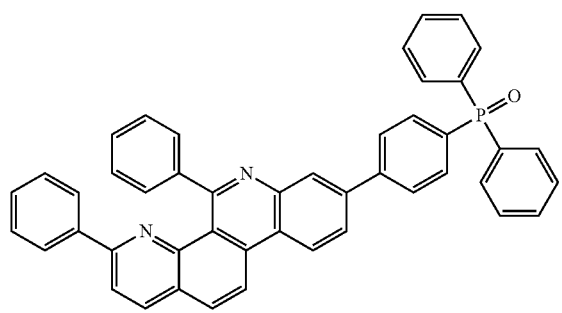
248
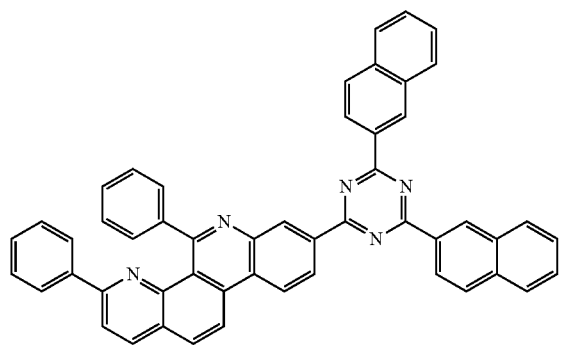
249
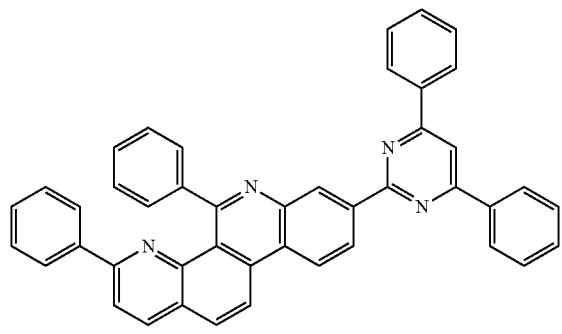
250
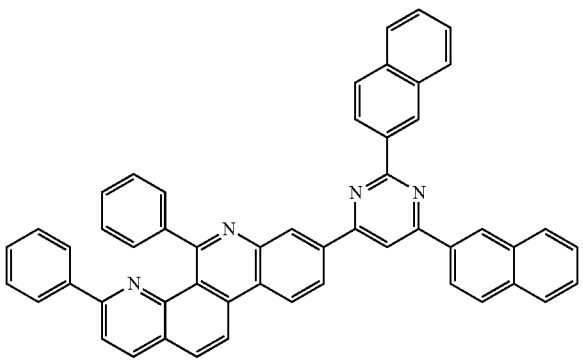
251
252

-continued
253
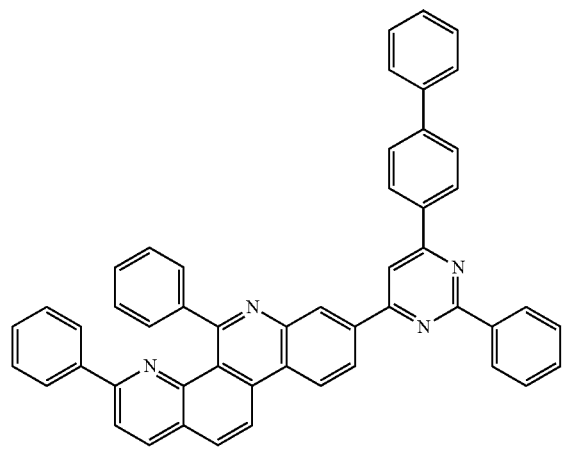
254
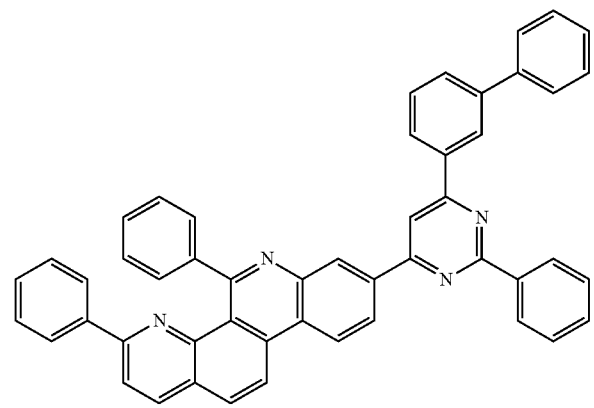
255
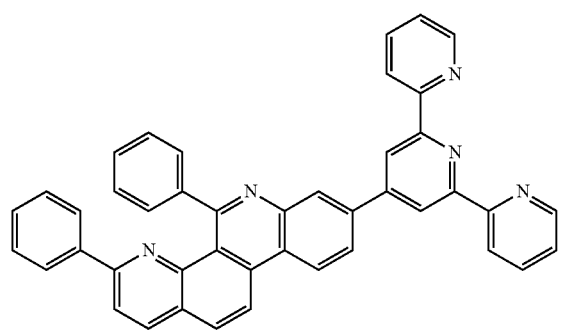
256
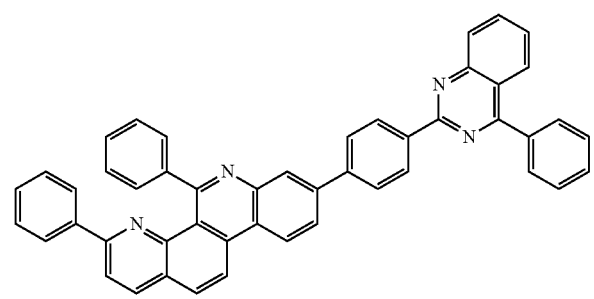
257
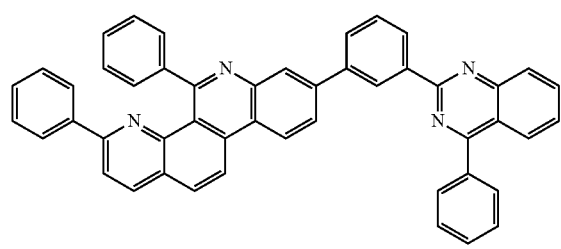
258
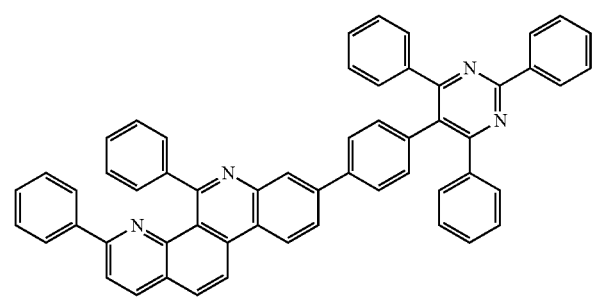
259
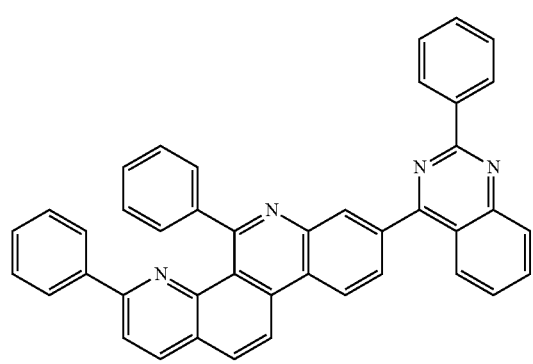
260
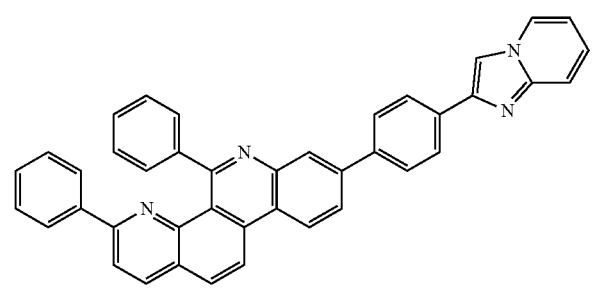

-continued
261
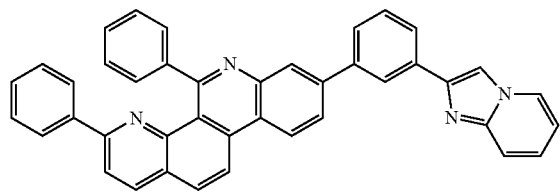
262
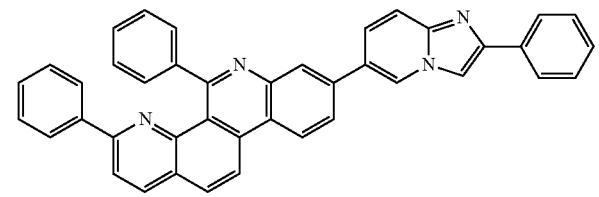
263
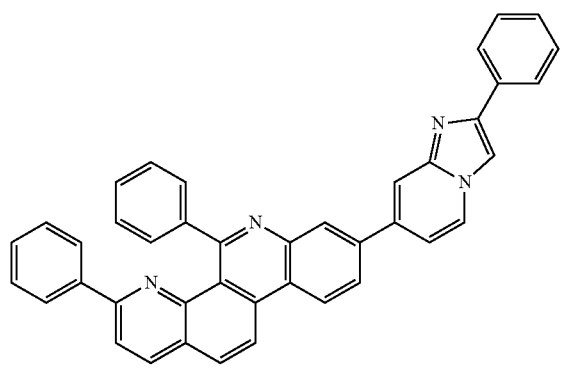
264
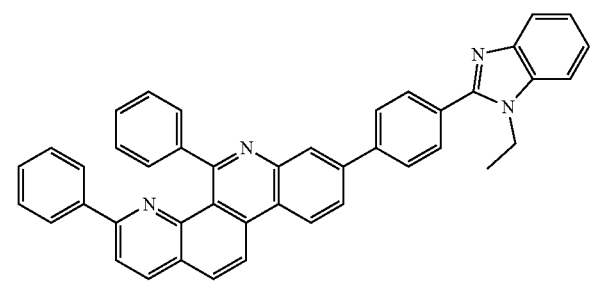
265
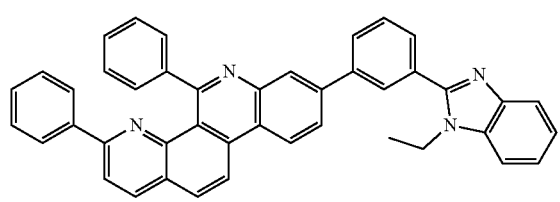
266
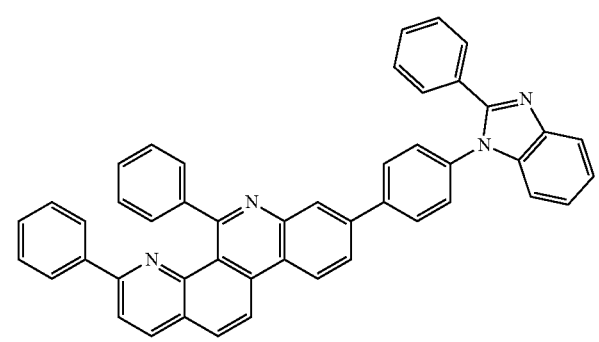
267
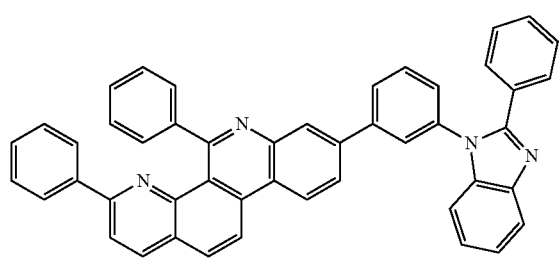
268
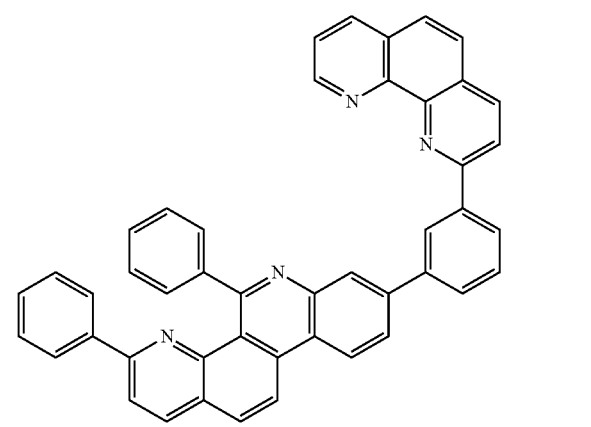

-continued
269
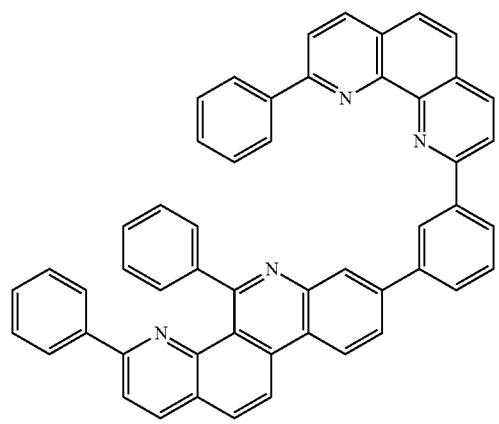
270
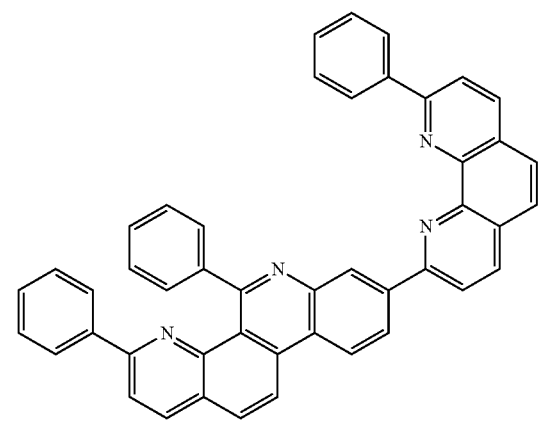
271
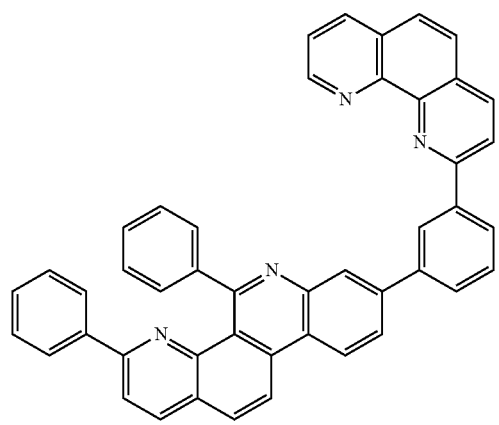
272
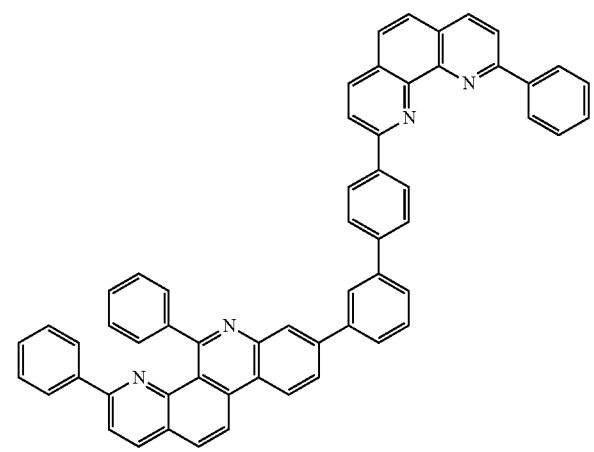
273
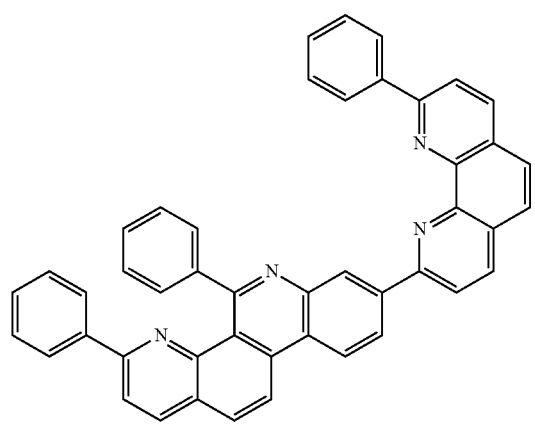

274
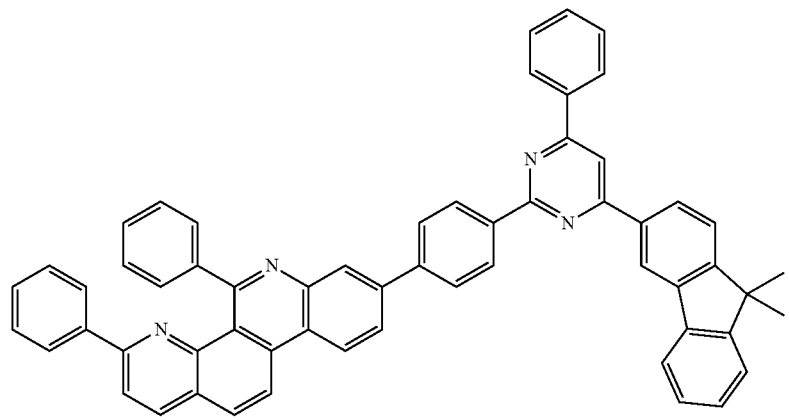
275
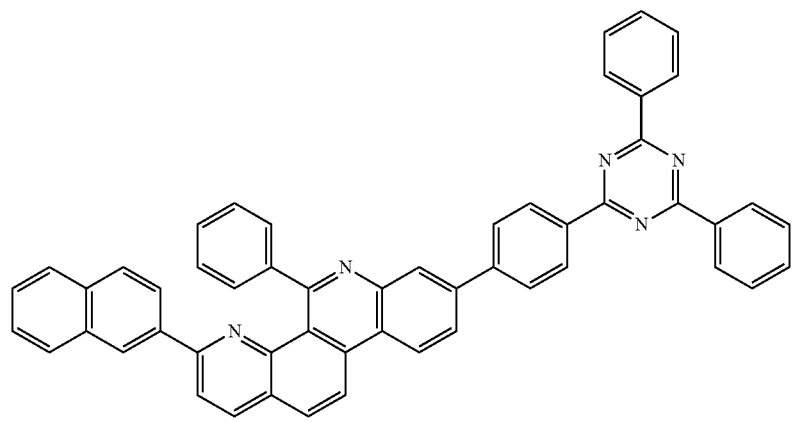
276 277
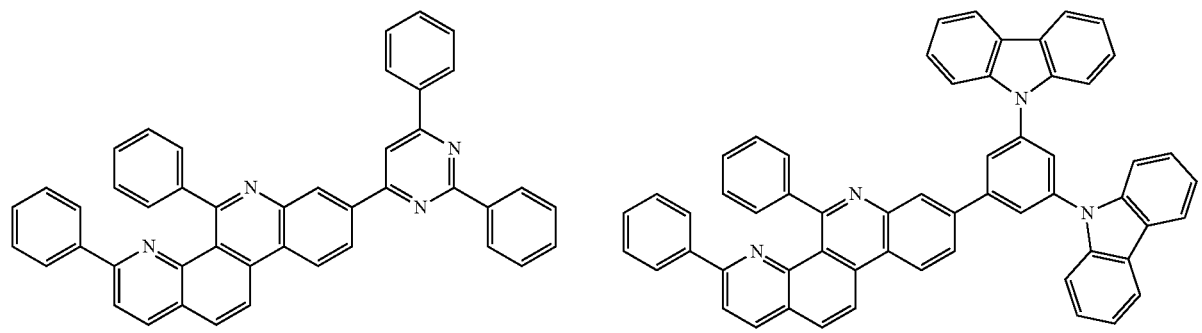
278 279
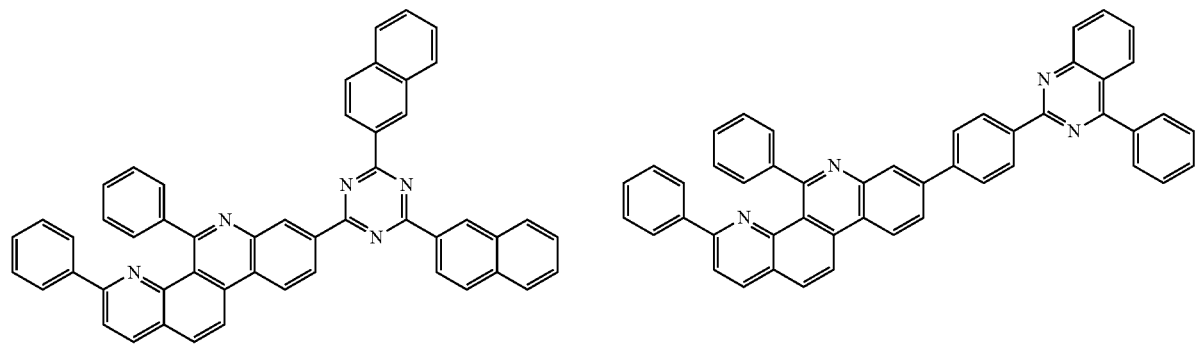

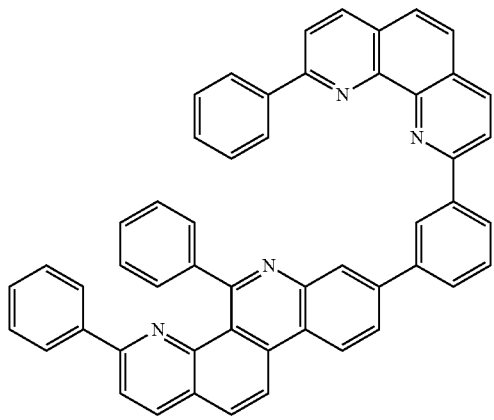
280

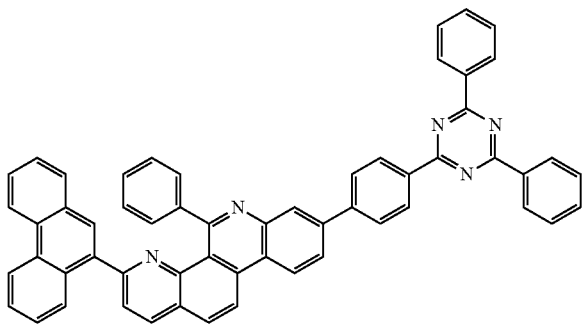
281

8. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

9. The organic light emitting device of claim 8, wherein the organic material layer comprises a light emitting layer, and the light emitting layer comprises the heterocyclic compound.

10. The organic light emitting device of claim 8, wherein the organic material layer comprises an electron injection layer or an electron transfer layer, and the electron injection layer or the electron transfer layer comprises the heterocyclic compound.

11. The organic light emitting device of claim 8, wherein the organic material layer comprises an electron blocking layer or a hole blocking layer, and the electron blocking layer or the hole blocking layer comprises the heterocyclic compound.

12. The organic light emitting device of claim 8, further comprising one, two or more layers selected from the group consisting of a light emitting layer, a hole injection layer, a hole transfer layer, an electron injection layer, an electron transfer layer, an electron blocking layer and a hole blocking layer.

13. The organic light emitting device of claim 8, comprising:
a first stack provided on the first electrode and comprising a first light emitting layer;
a charge generation layer provided on the first stack;
a second stack provided on the charge generation layer and comprising a second light emitting layer; and
the second electrode provided on the second stack.

14. The organic light emitting device of claim 13, wherein the charge generation layer comprises the heterocyclic compound.

15. The organic light emitting device of claim 13, wherein the charge generation layer is an N-type charge generation layer, and the charge generation layer comprises the heterocyclic compound.

* * * * *